US011098042B2

(12) United States Patent
Ren et al.

(10) Patent No.: US 11,098,042 B2
(45) Date of Patent: Aug. 24, 2021

(54) INHIBITORS OF INFLUENZA VIRUS REPLICATION AND USES THEREOF

(71) Applicant: SUNSHINE LAKE PHARMA CO., LTD., Guangdong (CN)

(72) Inventors: Qingyun Ren, Dongguan (CN); Changhua Tang, Dongguan (CN); Junjun Yin, Dongguan (CN); Kai Yi, Dongguan (CN); Yibo Lei, Dongguan (CN); Yejun Wang, Dongguan (CN); Yingjun Zhang, Dongguan (CN)

(73) Assignee: Sunshine Lake Pharma Co., Ltd., Guangdong (CN)

( * ) Notice: Subject to any disclaimer, the term of this patent is extended or adjusted under 35 U.S.C. 154(b) by 25 days.

(21) Appl. No.: 16/474,150

(22) PCT Filed: Jan. 4, 2018

(86) PCT No.: PCT/CN2018/071377
§ 371 (c)(1),
(2) Date: Jun. 27, 2019

(87) PCT Pub. No.: WO2018/127096
PCT Pub. Date: Jul. 12, 2018

(65) Prior Publication Data
US 2020/0339564 A1  Oct. 29, 2020

(30) Foreign Application Priority Data
Jan. 5, 2017 (CN) .......................... 201710006258.6

(51) Int. Cl.
| | |
|---|---|
| *C07D 471/04* | (2006.01) |
| *A61P 31/16* | (2006.01) |
| *A61K 35/76* | (2015.01) |
| *A61K 47/64* | (2017.01) |
| *A61K 31/404* | (2006.01) |
| *A61K 31/4172* | (2006.01) |
| *A61K 31/4965* | (2006.01) |
| *A61K 31/506* | (2006.01) |
| *A61K 31/519* | (2006.01) |
| *A61K 31/5377* | (2006.01) |
| *A61K 31/5383* | (2006.01) |
| *A61K 31/7056* | (2006.01) |
| *C07D 519/00* | (2006.01) |

(52) U.S. Cl.
CPC .......... *C07D 471/04* (2013.01); *A61K 31/404* (2013.01); *A61K 31/4172* (2013.01); *A61K 31/4965* (2013.01); *A61K 31/506* (2013.01); *A61K 31/519* (2013.01); *A61K 31/5377* (2013.01); *A61K 31/5383* (2013.01); *A61K 31/7056* (2013.01); *A61K 35/76* (2013.01); *A61K 47/646* (2017.08); *A61P 31/16* (2018.01); *C07D 519/00* (2013.01)

(58) Field of Classification Search
CPC .... C07D 471/04; C07D 519/00; A61K 35/76; A61K 31/7056; A61K 31/4965; A61K 31/506; A61K 31/5383; A61K 31/4172; A61K 31/519; A61K 31/404; A61K 31/5377; A61K 47/646; A61P 31/16
USPC .......................................................... 546/27
See application file for complete search history.

(56) References Cited

U.S. PATENT DOCUMENTS

| | | | |
|---|---|---|---|
| 8,829,007 | B2 | 9/2014 | Charifson et al. |
| 8,871,774 | B2 | 10/2014 | Charifson et al. |
| 9,051,319 | B2 | 6/2015 | Charifson et al. |
| 9,345,708 | B2 | 5/2016 | Charifson et al. |
| 9,394,302 | B2 | 7/2016 | Charifson et al. |
| 9,518,056 | B2 | 12/2016 | Charifson et al. |
| 9,908,878 | B2 | 3/2018 | Charifson et al. |
| 9,932,346 | B2 | 4/2018 | Jonckers et al. |
| 10,023,569 | B2 | 7/2018 | Tanoury et al. |
| 2012/0171245 | A1 | 7/2012 | Charifson et al. |
| 2013/0345218 | A1 | 12/2013 | Charifson et al. |
| 2014/0005197 | A1 | 1/2014 | Charifson et al. |
| 2017/0226102 | A1 | 8/2017 | Jonckers et al. |
| 2018/0065962 | A1 | 3/2018 | Farmer et al. |
| 2018/0155342 | A1 | 6/2018 | Charifson et al. |
| 2018/0258074 | A1 | 9/2018 | Jonckers et al. |
| 2018/0318301 | A1 | 11/2018 | Simone et al. |
| 2018/0346463 | A1 | 12/2018 | Zhang et al. |
| 2019/0023713 | A1 | 1/2019 | Guillemont et al. |
| 2019/0047989 | A1 | 2/2019 | Jonckers et al. |

FOREIGN PATENT DOCUMENTS

| | | |
|---|---|---|
| WO | 2013184985 A1 | 12/2013 |
| WO | 2017133657 A1 | 8/2017 |
| WO | 2017133658 A1 | 8/2017 |
| WO | 2017133664 A1 | 8/2017 |
| WO | 2017133665 A1 | 8/2017 |
| WO | 2017133667 A1 | 8/2017 |
| WO | 2017133669 A1 | 8/2017 |

(Continued)

OTHER PUBLICATIONS

ISR of PCT/CN2018/071377.

(Continued)

*Primary Examiner* — Taylor V Oh
(74) *Attorney, Agent, or Firm* — Kam Wah Law

(57) ABSTRACT

Provided herein is inhibitors of influenza virus replication and uses thereof. Specifically, provided herein a novel class of compounds as inhibitors of influenza virus replication, preparation methods thereof, pharmaceutical compositions containing these compounds, and uses of these compounds and pharmaceutical compositions thereof in the treatment of influenza.

26 Claims, No Drawings

(56) References Cited

FOREIGN PATENT DOCUMENTS

| WO | 2017133670 A1 | 8/2017 |
| WO | 2017198122 A1 | 11/2017 |
| WO | 2018033082 A1 | 2/2018 |
| WO | 2018041091 A1 | 3/2018 |
| WO | 2018041263 A1 | 3/2018 |
| WO | 2018108125 A1 | 6/2018 |

OTHER PUBLICATIONS

Written Opinion of the ISA of PCT/CN2018/071377.
Boyd, Michael J. et al, Bioorganic & Medicinal Chemistry Letters (2015), pp. 1990-1994, vol. 25(9).
Clark, Michael P. et al, Journal of Medicinal Chemistry (2014), pp. 6668-6678, vol. 57(15).
Farmer, Luc J. et al, ACS Medicinal Chemistry Letters (2017), pp. 256-260, vol. 8(2).
Bandarage, Upul K. et al, ACS Medicinal Chemistry Letters (2017), pp. 261-265, vol. 8(2).
Liang, Jianglin. et al, Organic Process Research & Development (2016), pp. 965-969, vol. 20(5).

INHIBITORS OF INFLUENZA VIRUS REPLICATION AND USES THEREOF

CROSS REFERENCE TO RELATED APPLICATIONS

This is a U.S. national stage application of the International Patent Application No. PCT/CN2018/071377, filed Jan. 4, 2018, which claims priority to Chinese Patent Application No. 201710006258.6, filed Jan. 5, 2017, both of which are incorporated herein by reference in their entirety.

FIELD

The invention belongs to the pharmaceutical field, specifically, it relates to novel compounds used as inhibitors of influenza virus replication, preparation methods thereof, pharmaceutical compositions containing these compounds, and uses of these compounds and pharmaceutical compositions thereof in the treatment of influenza. More specifically, the compounds of the invention can be used as inhibitors of influenza virus RNA polymerase.

BACKGROUND

Influenza (the following referred to as flu) is an acute respiratory infectious disease and harmful to human health, which is caused by the influenza virus and characterized by high prevalence, widespread, rapid propagation. Influenza virus can cause serious symptoms in the elderly and children with weaker immune systems, and immunocompromised patients, such as pneumonia or cardiopulmonary failure. Influenza virus was first discovered by Wilson Smith, a British, who called influenza virus as H1N1. The H denotes hemagglutinin; the N denotes neuraminidase, and the numbers represent different types. Influenza virus has caused the global pandemic for many times since the discovery, and the outbreak of influenza virus happens every decade or so, which causes enormous losses in worldwide. Influenza spreads around the world in a yearly outbreak, resulting in about 250,000 to 500,000 deaths, and about three to five million cases of severe illness, and a total of about 5% to 15% of people in worldwide are infected. Every time a pandemic was due to the emergence of new strains in humans. Usually, these new strains are caused by the spread of existing influenza virus from other animal species to humans.

Influenza viruses are RNA viruses belong to the family of orthomyxoviridae, which belong to the genus of influenza virus. According to the differences of the virion nucleoprotein (NP) and matrix protein (M) antigenic characteristics and genetic characteristics, influenza viruses are divided into three types: A, B and C. The three types of influenza viruses have similar biochemical and biological characteristics. The virus particle is 80-120 nanometers in diameter and usually roughly spherical, although filamentous forms can occur. Virus is constituted with three layers, and the inner layer is the viral nucleocapsid containing nucleoprotein (NP), P protein and RNA. NP is a soluble antigen (S antigen) with type specificity and antigenic stability. P protein (P1, P2, P3) may be polymerase required for RNA transcription and replication. Middle is a viral envelope consisting of a lipoid layer and a layer of membrane protein (MP), MP has antigenic stability and type specificity. Outer layer is a radial tuber consisting of two different glycoprotein projections, i.e., hemagglutinin (H) and neuraminidase (N). H is a tool for viral absorbtion on sensitive cell surface which can cause agglutination of erythrocyte, N is a tool for breaking away from cell surface after the completing of virus replication, which is capable of hydrolyzing mucus protein and N-acetylneuraminic acid that locates at the end of cell surface specific glycoprotein receptor. H and N both have variation characteristics, and only have the strain specific antigen, the antibody of which has a protective effect.

Influenzavirus A has one species, influenza A virus. Wild aquatic birds are the natural hosts for a large variety of influenza A. Occasionally, viruses are transmitted to other species and may then cause devastating outbreaks in domestic poultry or give rise to human influenza pandemics. The type A virus is the most virulent human pathogen among the three influenza types and cause the severest disease, and can be transmitted to other species and may then cause human influenza pandemic. The influenza A virus can be subdivided into different serotypes based on the antibody response to these viruses. The serotypes that have been confirmed in humans, ordered by the number of known human pandemic deaths, are: H1N1, which caused Spanish Flu in 1918; H2N2, which caused Asian Flu in 1957; H3N2, which caused Hong Kong Flu in 1968; H5N1, which caused pandemic threats in the influenza season of 2007-2008; H7N7, which has unusual zoonotic potential; H1N2, endemic in humans and pigs; H9N2; H7N2; H7N3; and H10N7.

Influenzavirus B has one species, influenza B virus, which causes local epidemic influenza and can not cause the global influenza pandemic. The only animals known to be susceptible to influenza B infection are humans and the seal. This type of influenza mutates at a rate 2-3 times slower than type A and consequently is less genetically diverse, with only one influenza B serotype. As a result of this lack of antigenic diversity, a degree of immunity to influenza B is usually acquired at an early age. However, influenza B mutates enough that lasting immunity is not possible. This reduced rate of antigenic change, combined with its limited host range (inhibiting cross species antigenic shift), ensures that pandemics of influenza B do not occur.

Influenzavirus C has one species, influenza C virus, which exists in sporadic form, and usually only causes mild disease in children. Influenzavirus C usually can not cause influenza pandemic, and infect humans and pigs.

Unusually for a virus, its genome is not a single piece of nucleic acid; instead, it contains seven or eight pieces of negative-sense RNA. The genome of influenza A viruses encodes 11 proteins: hemagglutinin (H), neuraminidase (N), nucleoprotein (NP), M1, M2, NS1, NS2 (NEP), PA, PB1, PB1-F2 and PB2. Hemagglutinin (H) and neuraminidase (N) are the two large glycoproteins on the outside of the viral particles. HA is a lectin that mediates binding of the virus to target cells and entry of the viral genome into the target cell, while NA is involved in the release of progeny virus from infected cells, by cleaving sugars that bind the mature viral particles. Thus, these proteins are targets for antiviral drugs. Furthermore, they are antigens to which antibodies can be raised. Influenza A viruses are classified into subtypes based on antibody responses to H and N. These different types of HA and NA form the basis of the H and N distinctions in, for example, H5N1.

Vaccination and usage of antiviral drugs are important tools for responding to influenza pandemic. Due to the high mutation rate of the flu virus antigen, the vaccine can't be produced in large scale before influenza pandemic. The two classes of antiviral drugs used against influenza are M2 protein inhibitors (amantadine and rimantadine) and neuraminidase inhibitors (oseltamivir, zanamivir, peramivir and laninamivir). However, the influenza viruses have developed drug resistance to all these drugs. Therefore, continuing demand for new anti-influenza treatment agent is existing.

Favipiravir, a new antiviral agent, having a new mechanism has been launched, which plays antiviral action by inhibiting influenza virus RNA polymerase to target the inhibition of viral gene replication, but the therapeutic effect and the drug resistance of influenza viruses still need to be proved.

Other compounds as anti-influenza agents of this mechanism are still needed to be researched.

SUMMARY

The invention provides a novel class of compounds used as inhibitors of influenza virus RNA polymerase. These compounds and compositions thereof can be used in the manufacture of a medicament for preventing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

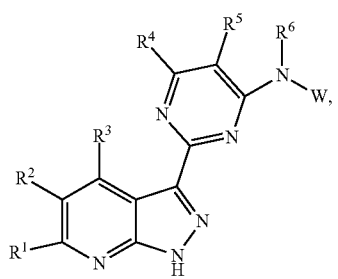

(I)

wherein $R^1$, $R^2$, $R^3$, $R^4$, $R^5$, $R^6$ and W are as defined herein.

In some embodiments, each of $R^1$, $R^2$ and $R^3$ is independently H, D, F, Cl, Br, CN, $NO_2$, —C(=O)$R^a$, —C(=O)O$R^b$, —C(=O)N$R^cR^d$, —O$R^b$, —N$R^cR^d$, $R^bO$—$C_{1-4}$ alkylene, $R^dR^cN$—$C_{1-4}$ alkylene, $C_{1-6}$ alkyl, $C_{2-6}$ alkenyl or $C_{2-6}$ alkynyl; or, $R^1$ and $R^2$, together with the carbon atoms to which they are attached, form a $C_{3-6}$ carbocyclic ring, 5- to 6-membered heterocyclic ring, $C_{6-10}$ aromatic ring or 5- to 6-membered heteroaromatic ring, and wherein each of $C_{1-6}$ alkyl, $C_{2-6}$ alkenyl, $C_{2-6}$ alkynyl, $C_{3-6}$ carbocyclic ring, 5- to 6-membered heterocyclic ring, $C_{6-10}$ aromatic ring and 5- to 6-membered heteroaromatic ring is independently unsubstituted or substituted with 1, 2, 3 or 4 substituents independently selected from D, F, Cl, Br, CN, —O$R^b$, —N$R^cR^d$, $C_{1-6}$ alkyl, $C_{1-6}$ haloalkyl, $R^bO$—$C_{1-4}$ alkylene or $R^dR^cN$—$C_{1-4}$ alkylene; $R^4$ is —O$R^b$, —N$R^cR^d$, $C_{1-6}$ alkyl, $C_{2-6}$ alkenyl, $C_{2-6}$ alkynyl, $C_{3-12}$ carbocyclyl, $C_{3-12}$ carbocyclyl-$C_{14}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each of $C_{1-6}$ alkyl, $C_{2-6}$ alkenyl, $C_{2-6}$ alkynyl, $C_{3-12}$ carbocyclyl, $C_{3-12}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl and (5- to 16-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)O$R^b$, —C(=O)N$R^cR^d$, —O$R^b$, —N$R^cR^d$, $R^bO$—$C_{1-4}$ alkylene, $R^dR^cN$—$C_{1-4}$ alkylene, $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-6}$ alkyl, $C_{2-6}$ alkenyl, $C_{2-6}$ alkynyl, $C_{3-12}$ cycloalkyl, $C_{3-12}$ cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-12}$ carbocyclic ring, 3- to 12-membered heterocyclic ring, $C_{6-10}$ aromatic ring or 5- to 10-membered heteroaromatic ring, and wherein each of $C_{3-12}$ carbocyclic ring, 3- to 12-membered heterocyclic ring, $C_{6-10}$ aromatic ring and 5- to 10-membered heteroaromatic ring is independently unsubstituted or substituted with 1, 2, 3, 4 or 5 R';

each R' is independently D, F, Cl, Br, CN, $NO_2$, —O$R^b$, —N$R^cR^d$, $R^bO$—$C_{1-4}$ alkylene, $R^dR^cN$—$C_{1-4}$ alkylene, —C(=O)$R^a$, —C(=O)O$R^b$, —C(=O)N$R^cR^d$, $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene; or, two adjacent R', together with the carbon atoms to which they are attached, form a $C_{3-6}$ carbocyclic ring, 5- to 6-membered heterocyclic ring, $C_{6-10}$ aromatic ring or 5- to 6-membered heteroaromatic ring, and wherein each of $C_{1-12}$ alkyl, $C_{1-6}$ haloalkyl, $C_{3-6}$ cycloalkyl, $C_{3-6}$ cycloalkyl-$C_{1-4}$ alkylene, 3- to 8-membered heterocyclyl, (3- to 8-membered heterocyclyl)-$C_{1-4}$ alkylene, $C_{6-10}$ aryl, $C_{6-10}$ aryl-$C_{1-4}$ alkylene, 5- to 10-membered heteroaryl, (5- to 10-membered heteroaryl)-$C_{1-4}$ alkylene, $C_{3-6}$ carbocyclic ring, 5- to 6-membered heterocyclic ring, $C_{6-10}$ aromatic ring and 5- to 6-membered heteroaromatic ring is independently unsubstituted or substituted with 1, 2, 3 or 4 substituents independently selected from D, F, Cl, Br, CN, $NO_2$, —O$R^b$, —N$R^cR^d$, $C_{1-6}$ alkyl, $C_{1-6}$ haloalkyl, $R^bO$—$C_{1-4}$ alkylene or $R^dR^cN$—$C_{1-4}$ alkylene;

$R^6$ is H, D or $C_{1-6}$ alkyl, and wherein $C_{1-6}$ alkyl is optionally substituted with 1, 2, 3 or 4 substituents independently selected from D, F, Cl, Br, CN, $NO_2$ or —O$R^b$;

W is $C_{1-8}$ alkyl, $C_{3-12}$ carbocyclyl or 3- to 12-membered heterocyclyl, and wherein each of $C_{1-8}$ alkyl, $C_{3-12}$ carbocyclyl and 3- to 12-membered heterocyclyl is independently unsubstituted or substituted with 1, 2, 3 or 4 $R^w$;

each $R^w$ is independently D, F, Cl, Br, CN, $NO_2$, —C(=O)$R^a$, —C(=O)O$R^b$, —C(=O)N$R^cR^d$, —N$R^e$C(=O)$R^a$, —N$R^e$C(=O)N$R^cR^d$, —S(=O)$_2R^f$, —S(=O)$_2$N$R^e$C(=O)$R^a$, —S(=O)$_2$N$R^cR^d$, $(R^bO)_2$P(=O)—$C_{0-2}$ alkylene, —O$R^b$, $R^bO$—$C_{1-2}$ alkylene, $R^dR^cN$—$C_{1-2}$ alkylene, $C_{1-6}$ alkyl, 5- to 6-membered heteroaryl or 5- to 6-membered heterocyclyl, and wherein each of $C_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, $N_3$, =O, $NO_2$, —O$R^b$, $C_{1-6}$ alkyl or $C_{1-6}$ haloalkyl;

each $R^a$, $R^b$, $R^c$, $R^d$, $R^e$ and $R^f$ is independently H, D, hydroxy, $C_{1-6}$ haloalkyl, $C_{1-6}$ alkyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene; wherein each of $C_{1-6}$ alkyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino;

or, $R^c$ and $R^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the invention provides a compound having Formula (II) or a stereoisomer, a tautomer, an N-oxide, a solvate, a metabolite, a pharmaceutically acceptable salt or a prodrug thereof,

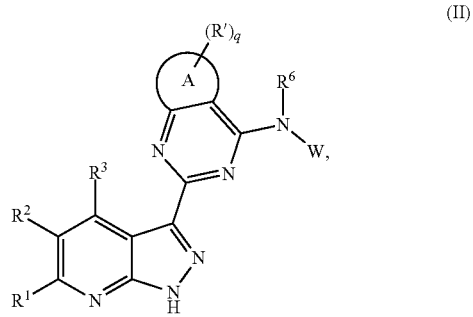

(II)

wherein A, $R^1$, $R^2$, $R^3$, R', $R^6$, q and W are as defined herein.

In other embodiments, W is $C_{1-8}$ alkyl, $C_{3-8}$ carbocyclyl or 3- to 12-membered heterocyclyl, and wherein each of $C_{1-8}$ alkyl, $C_{3-8}$ carbocyclyl and 3- to 12-membered heterocyclyl is independently unsubstituted or substituted with 1, 2, 3 or 4 $R^w$.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4, or 5.

In other embodiments, each of $R^1$, $R^2$ and $R^3$ is independently H, D, F, Cl, Br, CN, $NO_2$, —C(=O)$R^a$, —C(=O)$OR^b$, —C(=O)$NR^cR^d$, —$OR^b$, —$NR^cR^d$, methyl, ethyl, n-propyl or i-propyl; or, $R^1$ and $R^2$, together with the carbon atoms to which they are attached, form a $C_{5-6}$ carbocyclic ring, 5- to 6-membered heterocyclic ring, benzene ring or 5- to 6-membered heteroaromatic ring, and wherein each of methyl, ethyl, n-propyl i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, —$OR^b$, —$NR^cR^d$ or $C_{1-3}$ haloalkyl.

In other embodiments, $R^4$ is —$OR^b$, —$NR^cR^d$, $C_{1-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 10-membered heterocyclyl, (5- to 10-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 10-membered heterocyclyl, (5- to 10-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(=O)$R^a$, —C(=O)$OR^b$, —C(=O)$NR^cR^d$, —$OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 10-membered heteroaromatic ring, and wherein each of $C_{3-6}$ carbocyclic ring, 3- to 6-membered heterocyclic ring, $C_{6-10}$ aromatic ring and 5- to 10-membered heteroaromatic ring is independently unsubstituted or substituted with 1, 2, 3, 4 or 5 R'.

In other embodiments, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 6-membered heteroaromatic ring, and wherein each of $C_{3-6}$ carbocyclic ring, 3- to 6-membered heterocyclic ring, $C_{6-10}$ aromatic ring and 5- to 6-membered heteroaromatic ring is independently unsubstituted or substituted with 1, 2, 3, 4 or 5 R'.

In other embodiments, each R' is independently D, F, Cl, Br, CN, $NO_2$, —$OR^b$, —$NR^cR^d$, —C(=O)$R^a$, —C(=O)$OR^b$, —C(=O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl; or two adjacent R', together with the carbon atoms to which they are attached, form a $C_{5-6}$ carbocyclic ring or benzene ring, and wherein each of $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene, 5- to 6-membered heteroaryl, $C_{5-6}$ carbocyclic ring and benzene ring is independently unsubstituted or substituted with 1, 2, 3 or 4 substituents independently selected from D, F, Cl, Br, CN, $NO_2$, —$OR^b$, —$NR^cR^d$, methyl, ethyl, n-propyl or i-propyl.

In other embodiments, each R' is independently D, F, Cl, Br, CN, $NO_2$, OH, —$OCH_3$, —$OCH_2CH_3$, —$NR^cR^d$, —C(=O)$R^a$, —C(=O)OH, —C(=O)$OCH_2CH_3$, —C(=O)$OCH_3$, —C(=O)$NH_2$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, and wherein each of methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from D, F, Cl, Br, CN, $NO_2$, OH, —$NH_2$, methyl, ethyl, n-propyl or i-propyl.

In other embodiments, $R^6$ is H, D, $CF_3$, methyl, ethyl, n-propyl or i-propyl.

In other embodiments, W is $C_{1-6}$ alkyl, $C_{5-8}$ carbocyclyl or 5- to 8-membered heterocyclyl, and wherein each of $C_{1-6}$ alkyl, $C_{5-8}$ carbocyclyl and 5- to 8-membered heterocyclyl is independently unsubstituted or substituted with 1, 2, 3 or 4 $R^w$.

In other embodiments, each $R^w$ is independently D, F, Cl, Br, CN, $NO_2$, —C(=O)$OCH_3$, —C(=O)$OCH_2CH_3$, —C(=O)OH, —C(=O)$NR^cR^d$, —NHC(=O)$R^a$, —NHC(=O)$NR^cR^d$, —S(=O)$_2R^f$, —S(=O)$_2$NHC(=O)$R^a$, —S(=O)$_2NR^cR^d$, $(R^bO)_2P$(=O)—$C_{0-2}$ alkylene, —$OR^b$, methyl, ethyl, n-propyl, i-propyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidyl and 5- to 6-membered heterocyclyl is independently unsubstituted or substituted with 1, 2, 3 or 4 substituents independently selected from D, F, Cl, Br, CN, $N_3$, =O, $NO_2$, —$OCH_3$, $C_{1-3}$ alkyl or $C_{1-3}$ haloalkyl.

In other embodiments, each $R^a$, $R^b$, $R^c$, $R^d$, $R^e$ and $R^f$ is independently H, D, hydroxy, trifluoromethyl, methyl, ethyl, i-propyl, n-propyl, n-butyl, t-butyl, methoxy, ethoxy, cyclopropyl, $C_{3-6}$ carbocyclyl, 5- to 6-membered heterocyclyl, phenyl, 5- to 6-membered heteroaryl or (5- to 6-membered heteroaryl)-$C_{1-4}$ alkylene, and wherein each of methyl, ethyl, i-propyl, n-propyl, n-butyl, t-butyl, methoxy, ethoxy, cyclopropyl, $C_{3-6}$ carbocyclyl, 5- to 6-membered heterocyclyl, phenyl, 5- to 6-membered heteroaryl and (5- to 6-membered heteroaryl)-$C_{1-4}$ alkylene is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy; or, $R^c$ and $R^d$, together with the nitrogen atom to which they are attached, form 5- to 6-membered heterocyclyl or 5- to 6-membered heteroaryl, and wherein each of 5- to 6-membered heterocyclyl and 5- to 6-membered heteroaryl is independently unsubstituted or substituted with 1, 2, 3 or 4 substituents independently selected from D, F, Cl, CN, OH, $NH_2$, $C_{1-3}$ alkyl, $C_{1-3}$ haloalkyl or methoxy.

In other embodiments, A is a $C_{3-6}$ carbocyclic ring, 3- to 6-membered heterocyclic ring, $C_{6-10}$ aromatic ring or 5- to 6-membered heteroaromatic ring.

In other embodiments, $R^4$ is —$OR^b$, —$NR^cR^d$, ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imidazolyl, benzimidazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl or dibenzofuryl, and wherein each of ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imidazolyl, benzimidazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl and dibenzofuryl is independently unsubstituted or substituted with 1, 2, 3, 4 or 5 R';

$R^5$ is H, D, F, Cl, Br, CN, $NO_2$, methyl, ethyl, n-propyl or i-propyl;

or, $R^4$ and $R^5$, together with the carbon atoms to which they are attached, form benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

In other embodiments, A is a $C_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

In other embodiments, W is one of the following sub-formulae:

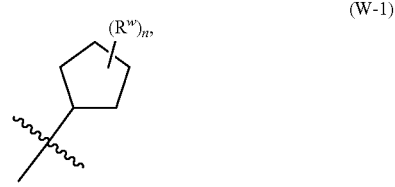

(W-1)

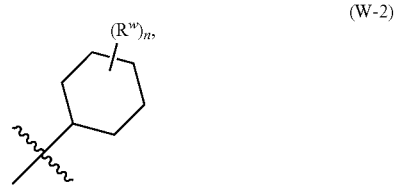

(W-2)

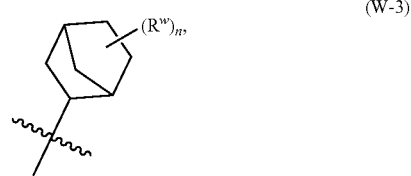

(W-3)

-continued

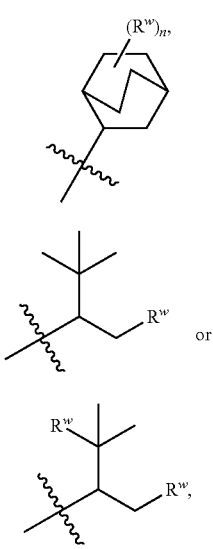

(W-4)

(W-5)

or (W-6)

wherein n is 0, 1, 2, 3 or 4, and R$^w$ is as defined herein.

In other embodiments, the invention relates to a compound having Formula (III) or a stereoisomer, a tautomer, an N-oxide, a solvate, a metabolite, a pharmaceutically acceptable salt or a prodrug thereof,

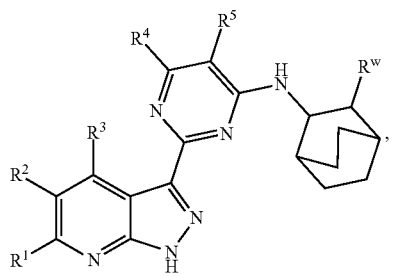

(III)

wherein R$^1$, R$^2$, R$^3$, R$^4$, R$^5$ and R$^w$ are as defined herein.

In other embodiments, the invention relates to a compound having Formula (IV) or a stereoisomer, a tautomer, an N-oxide, a solvate, a metabolite, a pharmaceutically acceptable salt or a prodrug thereof,

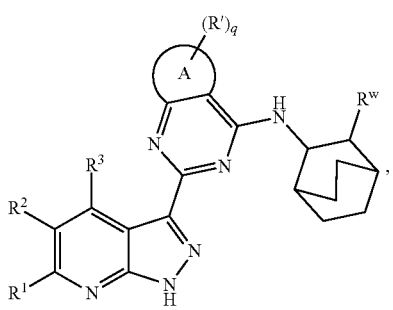

(IV)

wherein A, R$^1$, R$^2$, R$^3$, R', q and R$^w$ are as defined herein.

In other embodiments, the invention relates to a compound having Formula (V) or a stereoisomer, a tautomer, an N-oxide, a solvate, a metabolite, a pharmaceutically acceptable salt or a prodrug thereof,

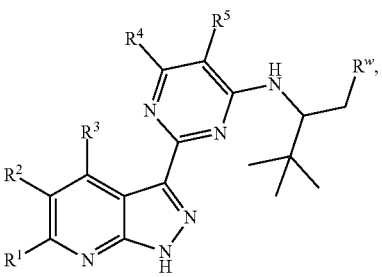

(V)

wherein R$^1$, R$^2$, R$^3$, R$^4$, R$^5$ and R$^w$ are as defined herein.

In other embodiments, the invention relates to a compound having Formula (VI) or a stereoisomer, a tautomer, an N-oxide, a solvate, a metabolite, a pharmaceutically acceptable salt or a prodrug thereof,

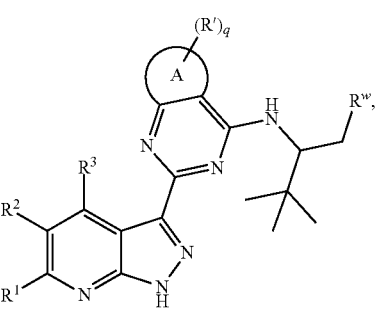

(VI)

wherein A, R$^1$, R$^2$, R$^3$, R', q and R$^w$ are as defined herein.

In other embodiments, the invention relates to a compound having Formula (VII) or a stereoisomer, a tautomer, an N-oxide, a solvate, a metabolite, a pharmaceutically acceptable salt or a prodrug thereof,

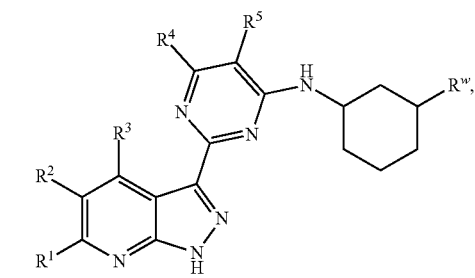

(VII)

wherein R$^1$, R$^2$, R$^3$, R$^4$, R$^5$ and R$^w$ are as defined herein.

In other embodiments, the invention relates to a compound having Formula (VIII) or a stereoisomer, a tautomer, an N-oxide, a solvate, a metabolite, a pharmaceutically acceptable salt or a prodrug thereof,

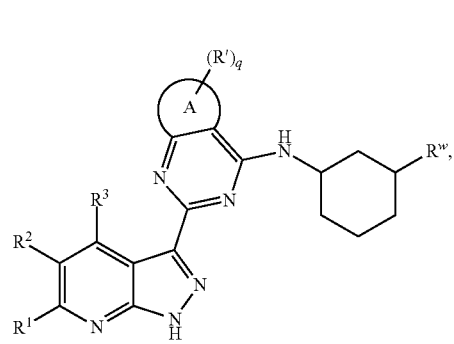

(VIII)

wherein A, $R^1$, $R^2$, $R^3$, R', q and $R^w$ are as defined herein.

In other embodiments, the invention relates to a compound having Formula (IX) or a stereoisomer, a tautomer, an N-oxide, a solvate, a metabolite, a pharmaceutically acceptable salt or a prodrug thereof,

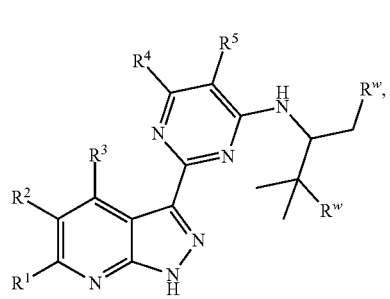

(IX)

wherein $R^1$, $R^2$, $R^3$, $R^4$, $R^5$ and $R^w$ are as defined herein.

In other embodiments, the invention relates to a compound having Formula (X) or a stereoisomer, a tautomer, an N-oxide, a solvate, a metabolite, a pharmaceutically acceptable salt or a prodrug thereof,

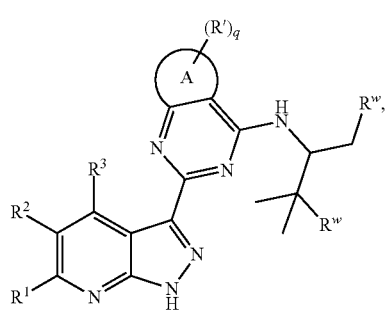

(X)

wherein A, $R^1$, $R^2$, $R^3$, R', q and $R^w$ are as defined herein.

In other embodiments, the invention relates to a compound having Formula (XI) or a stereoisomer, a tautomer, an N-oxide, a solvate, a metabolite, a pharmaceutically acceptable salt or a prodrug thereof,

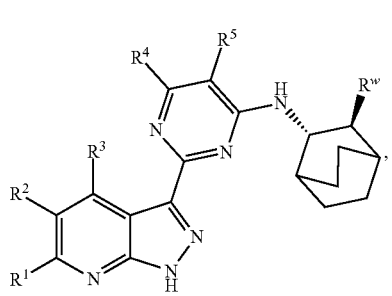

(XI)

wherein $R^1$, $R^2$, $R^3$, $R^4$, $R^5$ and $R^w$ are as defined herein.

In other embodiments, the invention relates to a compound having Formula (XII) or a stereoisomer, a tautomer, an N-oxide, a solvate, a metabolite, a pharmaceutically acceptable salt or a prodrug thereof,

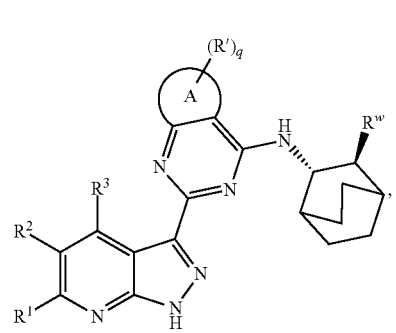

(XII)

wherein A, $R^1$, $R^2$, $R^3$, R', q and $R^w$ are as defined herein.

In other embodiments, the invention relates to a compound having Formula (XIII) or a stereoisomer, a tautomer, an N-oxide, a solvate, a metabolite, a pharmaceutically acceptable salt or a prodrug thereof,

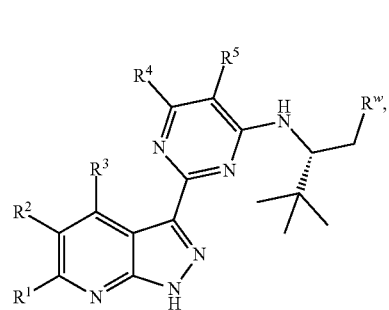

(XIII)

wherein $R^1$, $R^2$, $R^3$, $R^4$, $R^5$ and $R^w$ are as defined herein.

In other embodiments, the invention relates to a compound having Formula (XIV) or a stereoisomer, a tautomer, an N-oxide, a solvate, a metabolite, a pharmaceutically acceptable salt or a prodrug thereof,

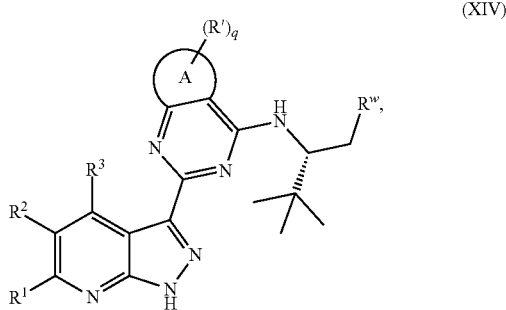

(XIV)

wherein A, R¹, R², R³, R', q and $R^w$ are as defined herein.

In another aspect, provided herein is a pharmaceutical composition comprising an effective amount of the compound disclosed herein.

In some embodiments, the pharmaceutical composition provided herein further comprises a pharmaceutically acceptable carrier, adjuvant, vehicle or a combination thereof.

In some embodiments, the pharmaceutical composition provided herein further comprises one or more other therapeutic agents.

In other embodiments, the other therapeutic agent disclosed herein is an anti-influenza virus agent or anti-influenza virus vaccine.

In other embodiments, the pharmaceutical composition is in the form of a liquid, a solid, a semi-solid, a gel or a spray.

In other embodiments, the pharmaceutical composition, wherein the other therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, S-033188, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, treating or lessening a disorder or disease caused by virus infection in a subject.

In some embodiments, the virus infection disclosed herein is influenza virus infection.

In some embodiments, the influenza virus is H1N1 A/Weiss/43.

In another aspect, provided herein is use of the compound or the pharmaceutical composition disclosed herein in the manufacture of a medicament for inhibiting virus.

In some embodiments, inhibiting virus is realized by inhibiting virus RNA polymerase.

In some embodiments, the virus is influenza virus.

In some embodiments, the influenza virus is H1N1 A/Weiss/43.

In another aspect, provided herein is the compound or the pharmaceutical composition disclosed herein for use in preventing, treating or lessening a disorder or disease caused by virus infection in a subject.

In some embodiments, the virus infection is influenza virus infection.

In another aspect, provided herein is the compound or the pharmaceutical composition disclosed herein for use in inhibiting virus.

In some embodiments, inhibiting virus is realized by inhibiting virus RNA polymerase.

In some embodiments, the virus is influenza virus.

In some embodiments, the influenza virus is H1N1 A/Weiss/43.

In another aspect, provided herein is a method of preventing, treating or lessening a disorder or disease caused by a virus infection in a subject, comprising administering to the subject a therapeutically effective amount of the compound or the pharmaceutical composition disclosed herein.

In some embodiments, the virus infection is influenza virus infection.

In another aspect, provided herein is a method of inhibiting virus in a subject, comprising administering to the subject a therapeutically effective amount of the compound or the pharmaceutical composition disclosed herein.

In some embodiments, inhibiting virus is realized by inhibiting virus RNA polymerase.

In some embodiments, the virus is influenza virus.

In some embodiments, the influenza virus is H1N1 A/Weiss/43.

Unless otherwise stated, all stereoisomers, geometric isomers, tautomers, solvates, hydrates, metabolites, salts and pharmaceutically acceptable prodrugs of the compounds disclosed herein are within the scope of the invention.

In some embodiments, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

In other embodiments, the salts are not necessarily pharmaceutically acceptable salts, and which may be useful as intermediates for preparing and/or purifying compounds of the invention and/or for separating enantiomers of compounds of the invention.

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

In other embodiments, the compound disclosed herein may contain several asymmetric centers and therefore exist in the form of racemic mixture generally described. Furthermore, it is intended that all racemic mixture, parts of the racemic mixture, and enantiomer and diastereomers purified by separation form part of the present invention.

The compounds disclosed herein may exist in the form of possible isomers, including rotamers, atropisomers, tautomer or a mixture thereof. It is intended that mixtures of isomers, including rotamers, atropisomers, tautomers, parts of the mixtures of isomers, rotamers, atropisomers, tautomers, and the isomers, including rotamers, atropisomers, tautomer purified by separation form part of the present invention.

In another aspect, the compounds of the invention include isotopically enriched compounds as defined herein, for example those into which radioactive isotopes, such as $^3H$, $^{14}C$ and $^{18}F$, or those into which non-radioactive isotopes, such as $^2H$ and $^{13}C$ are present.

In another aspect, provided herein is a method of preparing, separating or purifying the compound of Formula (I).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents which may be included within the scope of of the present invention. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application shall prevail.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

Unless otherwise defined, all technical and scientific terms used herein have the same meaning as is commonly understood by one skilled in the art to which this invention belongs. All patents and publications referred to herein are incorporated by reference in their entirety.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 th Ed. 1994. Additionally, general principles of organic chemistry are described in Sorrell et al., "*Organic Chemistry*", University Science Books, Sausalito: 1999, and "*March's Advanced Organic Chemistry*", by Michael B. Smith and Jerry March, John Wiley & Sons, New York: 2007, all of which are incorporated herein by reference in their entireties.

As used herein, the term "subject" refers to an animal. Typically the animal is a mammal. The subject also refers to primates (e.g., humans), cows, sheep, goats, horses, dogs, cats, rabbits, rats, mice, fish, birds and the like. In certain embodiments, the subject is a primate. In other embodiments, the subject is a human.

The term "subject" can be used interchangeably with "patient" in the invention. The term "subject" and "patient" refer to animals (e.g., birds such as chicken, quail or turkey, or mammals), specially mammals including non-primates (e.g., cattle, pigs, horses, sheep, rabbits, guinea pigs, rats, dogs, cats and mice) and primates (e.g., monkeys, chimpanzees and humans), more specially humans. In some embodiments, the subject is a non-human animal, such as livestock (e.g., horses, cattle, pigs or sheep) or pet (e.g., dogs, cats, guinea pigs or rabbits). In other some embodiments, the "patient" refers to a human.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{13}C$, $^{14}C$, $^{15}N$, $^{16}O$, $^{17}O$, $^{31}P$ $^{32}P$, $^{36}S$, $^{18}F$ and $^{37}Cl$, respectively.

The compounds disclosed herein containing isotopes described above or other atom isotopes and pharmaceutical salts thereof are included within the scope of the present invention. Certain isotopically-labeled compounds of the present invention, for example those into which radioactive isotopes such as $^{3}H$ or $^{14}C$ are incorporated, are useful in drug and/or substrate tissue distribution assays. Because of easy preparation and detection, isotopes such as tritiated, i.e., $^{3}H$, and carbon-14, i.e., $^{14}C$ are preferred. Further, substitution with heavier isotopes, particularly deuterium (i.e., $^{2}H$ or D) may afford certain therapeutic advantages resulting from greater metabolic stability, for example increased in vivo half-life or reduced dosage requirements. Therefore, the heavier isotopes may be preferred in somewhere.

Stereochemical definitions and conventions used herein generally follow the definition as described in S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. A specific stereoisomer may be referred to as an enantiomer, and a mixture of such stereoisomers is called an enantiomeric mixture. For a given chemical structure, these stereoisomers are identical except that they are mirror images of one another. A specific stereoisomer may be referred to as an enantiomer, and a mixture of such stereoisomers is called an enantiomeric mixture. A 50:50 mixture of enantiomers is referred to as a racemic mixture or a racemate, which may occur where there has been no stereoselection or stereospecificity in a chemical reaction or process.

Depending on the choice of the starting materials and procedures, the compounds can be present in the form of one of the possible stereoisomers or as mixtures thereof, such as racemates and diastereoisomer mixtures, depending on the number of asymmetric carbon atoms. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration.

The compounds disclosed herein may contain asymmetric or chiral centers, and therefore exist in different stereoisomeric forms. It is intended that all stereoisomeric forms of the compounds disclosed herein, including but not limited to, diastereomers, enantiomers, atropisomers and geometric (conformational) isomers as well as mixtures thereof such as racemic mixtures, form part of the present invention.

Unless otherwise specified, the Formula described herein also contain all the isomers thereof (such as, enantiomers, diastereomers, atropisomers and geometric (conformational) isomers; such as all (R) and (S) isomers, (Z) and (E) isomers around the double bond, (Z) and (E) conformational isomers. Therefore, single stereochemical isomers as well as enantiomeric, diastereomeric, or geometric mixtures of the present compounds are within the scope disclosed herein.

The term "tautomer" or "tautomeric form" refers to structural isomers of different energies which are interconvertible via a low energy barrier. Where tautomerization is possible (e.g. in solution), a chemical equilibrium of tautomers can be reached. For example, proton tautomers (also known as prototropic tautomers) include interconversions via migration of a proton, such as keto-enol and imine-enamine isomerizations. Valence tautomers include interconversions by reorganization of some of the bonding electrons. A specific example of keto-enol tautomerization is the interconversion of pentane-2,4-dione and 4-hydroxypent-3-en-2-one tautomers. Another example of tautomerization is phenol-keto tautomerization. The specific example of phenol-keto tautomerisms is pyridin-4-ol and pyridin-4(1H)-one tautomerism. Unless otherwise stated, all tautomeric forms of the compounds disclosed herein are within the scope of the invention.

An "N-oxide" refers to one or more than one nitrogen atoms oxidised to form an N-oxide or N-oxides, where a compound contains several amine functions. Particular examples of N-oxides are the N-oxides of a tertiary amine or a nitrogen atom of a nitrogen-containing heterocycle. N-oxides can be formed by treatment of the corresponding amine with an oxidizing agent such as hydrogen peroxide or a per-acid (e.g., a peroxycarboxylic acid) (See, *Advanced Organic Chemistry*, by Jerry March, 4th Edition, Wiley Interscience, pages). More particularly, N-oxides can be made by the procedure of L. W. Deady (Syn. Comm. 1977, 7, 509-514) in which the amine compound is reacted with m-chloroperoxybenzoic acid (MCPBA), for example, in an inert solvent such as dichloromethane.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

A "pharmaceutically acceptable salts" refers to organic or inorganic salts of a compound disclosed herein. Pharmaceutically acceptable salts are well known in the art. For example, S. M. Berge et al., describe pharmaceutically acceptable salts in detail in J. Pharmaceutical Sciences, 1977, 66: 1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, alginate, ascorbate, aspartate, benzenesulfonate, benzoate, bisulfate, borate, butyrate, camphanic acid salt, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oilsoluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_{1-24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, *Pro-drugs as Novel Delivery Systems*, Vol. 14 of the A.C.S. Symposium Series, Edward B. Roche, ed., *Bioreversible Carriers in Drug Design*, American Pharmaceutical Association and Pergamon Press, 1987, J. Rautio et al., Prodrugs: Design and Clinical Applications, *Nature Review Drug Discovery*, 2008, 7, 255-270, and S. J. Hecker et al., Prodrugs of Phosphates and Phosphonates, *Journal of Medicinal Chemistry*, 2008, 51, 2328-2345, all of which are incorporated herein by reference in their entireties.

Any asymmetric atom (e.g., carbon or the like) of the compound(s) disclosed herein can be present in racemic or enantiomerically enriched, for example the (R)-, (S)-, (R, R)-, (S, S)-, (S, R)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. If the compound contains a double bond, the substituent may be cis-(Z) or trans-(E) configuration.

Therefore, as the invention described, the compound disclosed herein may exist in the form of any possible isomer, such as rotational isomer, atropisomer, tautomer, or a mixture thereof, i.e., substantially pure geometric (cis- or trans-) isomer, diastereoisomer, optical isomer (enantiomer), racemate or a mixture thereof.

Any resulting mixtures of stereoisomers can be separated on the basis of the physicochemical differences of the constituents, into the pure or substantially pure geometric isomers, optical isomers, diastereoisomers, racemate, for example, by chromatography and/or fractional crystallization.

Any resulting racemates of final products or intermediates can be resolved into the optical antipodes by methods known to those skilled in the art, e.g., by separation of the diastereomeric salts thereof. Racemic products can also be resolved by chiral chromatography, e.g., high performance liquid chromatography (HPLC) using a chiral adsorbent. Preferred enantiomers can also be prepared by asymmetric syntheses. See, for example, Jacques, et al., *Enantiomers, Racemates and Resolutions* (Wiley Interscience, New York, 1981); *Principles of Asymmetric Synthesis* (2nd Ed. Robert E. Gawley, Jeffrey Aubé, Elsevier, Oxford, U K, 2012); Eliel, E. L. *Stereochemistry of Carbon Compounds* (McGraw-Hill, N Y, 1962); Wilen, S. H. *Tables of Resolving Agents and Optical Resolutions* p. 268 (E. L. Eliel, Ed., Univ. of Notre Dame Press, Notre Dame, Ind. 1972).

As described herein, compounds disclosed herein may optionally be substituted with one or more substituents, such as are illustrated generally below, or as exemplified by particular classes, subclasses, and species of the invention. It will be appreciated that the phrase "optionally substituted" is used interchangeably with the phrase "substituted or unsubstituted". The term "optional" or "optionally" refers to that a subsequently described event or circumstance may but need not occur, and that the description includes instances where the event or circumstance occurs and instances in which it does not. In general, whenever the term "optionally" is or is not before the term "substituted", the term "substituted" refers to the unreplacement or replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substitutents can be, but are not limited to, D, F, Cl, Br, CN, $N_3$, OH, $NH_2$, $NO_2$, oxo (=O), —C(=O)$R^a$, —C(=O)O$R^b$, —C(=O)N$R^cR^d$, —N$R^e$C(=O)$R^a$, —S(=O)$_2R^f$, —S(=O)$_2$N$R^e$C(=O)$R^a$, —S(=O)$_2$N$R^cR^d$, ($R^bO$)$_2$P(=O)—$C_{0-2}$ alkylene, —O$R^b$, —N$R^cR^d$, $R^bO$—$C_{1-4}$ alkylene, $R^dR^cN$—$C_{1-4}$ alkylene, $C_{1-12}$ alkyl, $C_{1-6}$ haloalkyl, $C_{1-6}$ alkoxy, $C_{1-6}$ alkylamino, $C_{2-6}$ alkenyl, $C_{2-6}$ alkynyl, $C_{3-12}$ cycloalkyl, $C_{3-12}$cycloalkyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 16-membered heteroaryl or (5- to 16-membered heteroaryl)-$C_{1-4}$ alkylene, and wherein each $R^a$, $R^b$, $R^c$, $R^d$, $R^e$ and $R^f$ is as defined herein.

Furthermore, what need to be explained is that the phrase "each . . . is independently" and "each of . . . and . . . is independently", unless otherwise stated, should be broadly understood. The specific options expressed by the same symbol are independent of each other in different groups; or the specific options expressed by the same symbol are independent of each other in same groups.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl. Term "5- to 10-membered heteroaryl" specifically refers to 5-membered heteroaryl, 6-membered heteroaryl, 7-membered heteroaryl, 8-membered heteroaryl, 9-membered heteroaryl and 10-membered heteroaryl, each of which is independently public.

At various places in the present specification, linking substituents are described. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "alkyl" or "alkyl group" refers to a saturated linear or branched-chain monovalent hydrocarbon radical of 1 to 20 carbon atoms. Unless otherwise specified, the alkyl group contains 1-20 carbon atoms. In some embodiments, the alkyl group contains 1-12 carbon atoms. In other embodiments, the alkyl group contains 1-10 carbon atoms. In other embodiments, the alkyl group contains 1-9 carbon atoms. In other embodiments, the alkyl group contains 1-8 carbon atoms. In other embodiments, the alkyl group contains 1-6 carbon atoms. In other embodiments, the alkyl group contains 1-4 carbon atoms. In still other embodiments, the alkyl group contains 1-3 carbon atoms.

Some non-limiting examples of the alkyl group include, methyl (Me, —$CH_3$), ethyl (Et, —$CH_2CH_3$), n-propyl (n-Pr, —$CH_2CH_2CH_3$), isopropyl (i-Pr, —CH($CH_3$)$_2$), n-butyl (n-Bu, —$CH_2CH_2CH_2CH_3$), isobutyl (i-Bu, —$CH_2$CH($CH_3$)$_2$), sec-butyl (s-Bu, —CH($CH_3$)$CH_2CH_3$), tert-butyl (t-Bu, —C($CH_3$)$_3$), n-pentyl (—$CH_2CH_2CH_2CH_2CH_3$), 2-pentyl (—CH($CH_3$)$CH_2CH_2CH_3$), 3-pentyl (—CH($CH_2CH_3$)$_2$), 2-methyl-2-butyl (—C($CH_3$)$_2CH_2CH_3$), 3-methyl-2-butyl (—CH($CH_3$)CH($CH_3$)$_2$), 3-methyl-1-butyl (—$CH_2CH_2$CH($CH_3$)$_2$), 2-methyl-1-butyl (—$CH_2$CH($CH_3$)$CH_2CH_3$), n-hexyl (—$CH_2CH_2CH_2CH_2CH_2CH_3$), 2-hexyl (—CH($CH_3$)$CH_2CH_2CH_2CH_3$), 3-hexyl (—CH($CH_2CH_3$)($CH_2CH_2CH_3$)), 2-methyl-2-pentyl (—C($CH_3$)$_2CH_2CH_2CH_3$), 3-methyl-2-pentyl (—CH($CH_3$)CH($CH_3$)$CH_2CH_3$), 4-methyl-2-pentyl (—CH($CH_3$)$CH_2$CH($CH_3$)$_2$), 3-methyl-3-pentyl (—C($CH_3$)($CH_2CH_3$)$_2$), 2-methyl-3-pentyl (—CH($CH_2CH_3$)CH($CH_3$)$_2$), 2,3-dimethyl-2-butyl (—C($CH_3$)$_2$CH($CH_3$)$_2$), 3,3-dimethyl-2-butyl (—CH($CH_3$)C($CH_3$)$_3$, n-heptyl and n-octyl, etc. Wherein the alkyl group can be independently unsubstituted or substituted with one or more substitutents described herein.

The term "alkyl" or the prefix "alk-" is inclusive of both straight chain and branched saturated carbon chain.

The term "alkylene" refers to a saturated divalent hydrocarbon group derived from a straight or branched chain saturated hydrocarbon by the removal of two hydrogen atoms. In some embodiments, the alkylene group contains 1-10 carbon atoms. In other embodiments, the alkylene group contains 1-6 carbon atoms. In still other embodiments, the alkylene group contains 1-4 carbon atoms. In yet other embodiments, the alkyl group contains 1-2 carbon atoms. And alkylene group is exemplified by methylene (—$CH_2$—), ethylene (—$CH_2CH_2$—), isopropylene (—CH($CH_3$)$CH_2$—), and the like. Wherein the alkylene group is independently unsubstituted or substituted with one or more substitutents disclosed herein.

The term "alkenyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "Z" and "E" orientations. Specific examples of the alkenyl group include, but are not limited to, vinyl (—CH═CH$_2$), allyl (—CH$_2$CH═CH$_2$), and the like.

The term "alkynyl" refers to a linear or branched chain monovalent hydrocarbon radical of 2 to 12 carbon atoms, or 2 to 8 carbon atoms, or 2 to 6 carbon atoms, or 2 to 4 carbon atoms, with at least one site of unsaturation, i.e., a carbon-carbon, sp triple bond, wherein the alkynyl radical may be optionally substituted independently with one or more substituents described herein. Specific examples of the alkynyl group include, but are not limited to, ethynyl (—C≡CH), propargyl (—CH$_2$C≡CH), 1-propinyl (—C≡C—CH$_3$) and the like.

The term "alkoxy" refers to an alkyl group, attached to the parent molecular moiety via an oxygen atom, wherein the alkyl group is as defined herein. Unless otherwise specified, the alkyl group contains 1-20 carbon atoms. In other embodiments, the alkyl group contains 1-10 carbon atoms. In other embodiments, the alkyl group contains 1-8 carbon atoms. In other embodiments, the alkyl group contains 1-6 carbon atoms. In still other embodiments, the alkyl group contains 1-4 carbon atoms; in yet other embodiments, the alkyl group contains 1-3 carbon atoms; and in still yet other embodiments, the alkyl group contains 1-2 carbon atoms.

Some non-limiting examples of alkoxy group include, methoxy (MeO, —OCH$_3$), ethoxy (EtO, —OCH$_2$CH$_3$), 1-propoxy (n-PrO, n-propoxy, —OCH$_2$CH$_2$CH$_3$), 2-propoxy (i-PrO, i-propoxy, —OCH(CH$_3$)$_2$), 1-butoxy (n-BuO, n-butoxy, —OCH$_2$CH$_2$CH$_2$CH$_3$), 2-methyl-1-propoxy (i-BuO, i-butoxy, —OCH$_2$CH(CH$_3$)$_2$), 2-butoxy (s-BuO, s-butoxy, —OCH(CH$_3$)CH$_2$CH$_3$), 2-methyl-2-propoxy (t-BuO, t-butoxy, —OC(CH$_3$)$_3$), 1-pentoxy (n-pentoxy, —OCH$_2$CH$_2$CH$_2$CH$_2$CH$_3$), 2-pentoxy (—OCH(CH$_3$)CH$_2$CH$_2$CH$_3$), 3-pentoxy (—OCH(CH$_2$CH$_3$)$_2$), 2-methyl-2-butoxy (—OC(CH$_3$)$_2$CH$_2$CH$_3$), 3-methyl-2-butoxy (—OCH(CH$_3$)CH(CH$_3$)$_2$), 3-methyl-1-butoxy (—OCH$_2$CH$_2$CH(CH$_3$)$_2$), 2-methyl-1-butoxy (—OCH$_2$CH(CH$_3$)CH$_2$CH$_3$), and the like. Wherein the alkoxy group is independently unsubstituted or substituted with one or more substitutents disclosed herein.

The terms "haloalkyl", "haloalkenyl" or "haloalkoxy" refer to alkyl, alkenyl or alkoxy, as the case may be, substituted with one or more halogen atoms. In some embodiments, the haloalkyl group contains 1-10 carbon atoms. In other embodiments, the haloalkyl group contains 1-8 carbon atoms. In other embodiments, the haloalkyl group contains 1-6 carbon atoms. In still other embodiments, the haloalkyl group contains 1-4 carbon atoms. In yet other embodiments, the haloalkyl group contains 1-3 carbon atoms. Some non-limiting examples of these groups include monofluoromethyl (—CH$_2$F), difluoromethyl (—CHF$_2$), trifluoromethyl (—CF$_3$), fluoroethyl (—CHFCH$_3$, —CH$_2$CH$_2$F), difluoroethyl (—CF$_2$CH$_3$, —CFHCFH$_2$, —CH$_2$CHF$_2$), perfluoroethyl, fluoropropyl (—CHFCH$_2$CH$_3$, —CH$_2$CHFCH$_3$, —CH$_2$CH$_2$CH$_2$F), difluoropropyl (—CF$_2$CH$_2$CH$_3$, —CFHCFHCH$_3$, —CH$_2$CH$_2$CHF$_2$, —CH$_2$CF$_2$CH$_3$, —CH$_2$CHFCH$_2$F), trifluoropropyl, trifluoropropyl, 1,1-dichloroethyl, 1,2-dichloropropyl, trifluoromethoxy, difluoromethyl, and the like.

The term "carbocycle", "carbocyclyl", "carbocyclic" or "carbocyclic ring" used interchangeablely herein refers to a no aromatic carbon ring system having 3 to 14 ring carbon atoms, which is saturated or contains one or more units of unsaturation, and there is no aromatic ring existing in the ring system. In some embodiments, the number of carbon atom is 3 to 12; in other embodiments, the number of carbon atom is 3 to 10; in other embodiments, the number of carbon atom is 3 to 8; in other embodiments, the number of carbon atom is 3 to 6; in other embodiments, the number of carbon atom is 5 to 6; in other embodiments, the number of carbon atom is 5 to 8; in other embodiments, the number of carbon atom is 6 to 8. The "carbocyclyl" includes a monocyclic, bicyclic, or polycyclic fused ring, spiro ring or bridged ring system. The bicyclic carbocyclyl groups includes bridged bicyclic carbocyclyl, fused bicyclic carbocyclyl and spiro bicyclic carbocyclyl group, and fused bicyclic system contains two rings which share two adjacent ring atoms. Bridged bicyclic group contains two rings which share two, three, four or five adjacent ring atoms. Spiro cyclic system contains two rings which share one ring atom. Some non-limiting examples of the carbocyclic group include cycloalkyl, cycloalkenyl and cycloalkynyl. Further examples of carbocyclyl groups include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Bridged carbocyclyl group includes, but is not limited to, bicyclo[2.2.2]octyl, bicyclo[2.2.1]heptyl, bicyclo[3.3.1]nonyl, bicyclo[3.2.3]nonyl, and the like.

The term "cycloalkyl" refers to a saturated ring having 3 to 12 ring carbon atoms as a monocyclic, bicyclic, or tricyclic ring system, which has one or more attachments attaching to the rest of the molecule. In some embodiments, the cycloalkyl group contains 3 to 10 ring carbon atoms. In other embodiments, the cycloalkyl group contains 3 to 8 ring carbon atoms. In other embodiments, the cycloalkyl group contains 5 to 8 ring carbon atoms. In still other embodiments, the cycloalkyl group contains 3 to 6 ring carbon atoms. In yet other embodiments, the cycloalkyl group contains 5 to 6 ring carbon atoms. Examples of cycloalkyl group include, but are not limited to, cyclopropyl, cyclobutyl, cyclopentyl, cyclohexyl and the like. The cycloalkyl radical is independently unsubstituted or substituted with one or more substituents described herein.

The term "heterocycle", "heterocyclyl", or "heterocyclic ring" as used interchangeably herein refers to a saturated or partially unsaturated non-aromatic monocyclic, bicyclic or tricyclic ring containing 3-12 ring atoms of which at least one ring atom is selected from nitrogen, sulfur and oxygen, wherein the heterocyclyl system is non-aromatic, and there is no aromatic ring existing in the heterocyclyl system, and of which may has one or more attachments attached to the rest of the molecule. The term "heterocyclyl" includes a monocyclic, bicyclic, or polycyclic fused, spiro, bridged heterocyclic ring system. Biheterocyclyl radical includes bridged biheterocyclyl, fused biheterocyclyl and spiro biheterocyclyl. Unless otherwise specified, the heterocyclyl group may be carbon or nitrogen linked, and a —CH$_2$— group can be optionally replaced by a —C(═O)— group. In which, the sulfur can be optionally oxygenized to S-oxide, and the nitrogen can be optionally oxygenized to N-oxide. In some embodiments, the heterocyclyl group is a 3- to 8-membered heterocyclyl group; in other embodiments, the heterocyclyl group is a 3- to 6-membered heterocyclyl group; in other embodiments, the heterocyclyl group is a 5- to 7-membered heterocyclyl group; in other embodiments, the heterocyclyl group is a 5- to 8-membered heterocyclyl group; in other embodiments, the heterocyclyl group is a 6- to 8-membered heterocyclyl group; in other embodiments, the heterocyclyl group is a 5- to 6-membered heterocyclyl group; in other embodiments, the heterocyclyl group is a 4-membered heterocyclyl group; in other embodiments, the heterocyclyl group is a 5-membered heterocyclyl group; in other embodiments, the heterocyclyl group is a 6-membered heterocyclyl group; in other embodiments, the heterocyclyl group is a 7-membered heterocyclyl group; in other embodiments, the heterocyclyl group is a 8-membered heterocyclyl group.

Some non-limiting examples of the heterocyclyl group include oxiranyl, azetidinyl, oxetanyl, thietanyl, pyrrolidinyl, 2-pyrrolinyl, 3-pyrrolinyl, pyrazolinyl, pyrazolidinyl, imidazolinyl, imidazolidinyl, tetrahydrofuranyl, dihydrofuranyl, tetrahydrothienyl, dihydrothienyl, 1,3-dioxolanyl, dithiolanyl, tetrahydropyranyl, dihydropyranyl, 2H-pyranyl, 4H-pyranyl, tetrahydrothiopyranyl, piperidinyl, morpholinyl, thiomorpholinyl, piperazinyl, dioxanyl, dithianyl, thioxanyl, homopiperazinyl, homopiperidinyl, oxepanyl, thiepanyl, and the like. Some non-limiting examples of heterocyclyl wherein —CH$_2$— group is replaced by —C(=O)— moiety include 2-oxopyrrolidinyl, oxo-1,3-thiazolidinyl, 2-piperidinonyl, 3,5-dioxopiperidinyl, pyrimidinedione-yl, and the like. Some non-limiting examples of heterocyclyl wherein the ring sulfur atom is oxidized are sulfolanyl and 1,1-dioxo-thiomorpholinyl. Some non-limiting examples of bridged heterocyclyl group includes, 2-oxabicyclo[2.2.2]octyl, 1-azabicyclo[2.2.2]octyl, 3-azabicyclo[3.2.1]octyl, and the like. The heterocyclyl group may be optionally substituted with one or more substituents disclosed herein.

The term "bridged" refers to a bond, an atom or an unbranched atoms chain connecting two different parts of a molecule. The two atoms (usually but not always two tertiary carbon atoms) linked by the bridge denotes "bridgeheads".

The term "m-membered", where m is an integer typically describes the number of ring-forming atoms in a moiety where the number of ring-forming atoms is m. For example, piperidinyl is an example of a 6 membered heterocyclyl and 1,2,3,4-tetrahydro-naphthalene is an example of a 10 membered carbocyclyl group.

The term "heteroatom" refers to O, S, N, P and Si, including any oxidized form of N, S or P; primary, secondary, tertiary or quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" refers to fluorine (F), chlorine (Cl), bromine (Br), or iodine (I).

The term "azido" or "N3" refers to an azide moiety. This radical may be attached, for example, to a methyl group to form azidomethane (methyl azide, MeN$_3$); or attached to a phenyl group to form phenyl azide (PhN$_3$).

The term "D" refers to deuteration, ie., $^2$H.

The term "aryl" used alone or as a great part of "arylalkyl", "arylalkoxy", or "aryloxyalkyl" refers to monocyclic, bicyclic and tricyclic carbocyclic ring systems having a total of 6 to 14 ring members, or 6 to 12 ring members, or 6 to 10 ring members, wherein at least one ring in the system is aromatic, wherein each ring in the system contains 3 to 7 ring members and that has a single point or multipoint of attachment to the rest of the molecule. The term "aryl" may be used interchangeably with the term "aryl ring" or "aromatic ring". Some non-limiting examples of the aryl group include phenyl, 2,3-dihydro-1H-indenyl, naphthyl and anthracene. The aryl group may be optionally unsubstituted or substituted with one or more substituents disclosed herein.

The term "heteroaryl" used alone or as a great part of "heteroarylalkyl" or "heteroarylalkoxy", refers to monocyclic, bicyclic and tricyclic ring systems having a total of five to fourteen ring members, or five to twelve ring members, or five to ten ring members; or a monocyclic ring system having a total of five to eight ring members, five to seven ring members, or five to six ring members, wherein at least one ring in the system is aromatic, and at least one ring in the system contains one or more heteroatom, and wherein each ring in the system contains 5 to 7 ring members and that has a single point or multipoint of attachment to the rest of the molecule. When there exists a —CH$_2$— group in the heteroaryl group, the —CH$_2$— group can be optionally replaced by a —C(=O)— group. The term "heteroaryl" and "heteroaromatic ring" or "heteroaromatic compound" can be used interchangeably herein. In one embodiment, the heteroaryl group is a 5- to 14-membered heteroaryl comprising 1, 2, 3 or 4 heteroatoms independently selected from O, S and N. In another embodiment, the heteroaryl group is a 5- to 12-membered heteroaryl comprising 1, 2, 3 or 4 heteroatoms independently selected from O, S and N. In another embodiment, the heteroaryl group is a 5- to 10-membered heteroaryl comprising 1, 2, 3 or 4 heteroatoms independently selected from O, S and N. In another embodiment, the heteroaryl group is a 5- to 8-membered heteroaryl comprising 1, 2, 3 or 4 heteroatoms independently selected from O, S and N. In another embodiment, the heteroaryl group is a 5- to 7-membered heteroaryl comprising 1, 2, 3 or 4 heteroatoms independently selected from O, S and N. In another embodiment, the heteroaryl group is a 5- to 6-membered heteroaryl comprising 1, 2, 3 or 4 heteroatoms independently selected from O, S and N. In another embodiment, the heteroaryl group is a 5-membered heteroaryl comprising 1, 2, 3 or 4 heteroatoms independently selected from O, S and N. In another embodiment, the heteroaryl group is a 6-membered heteroaryl comprising 1, 2, 3 or 4 heteroatoms independently selected from O, S and N.

In another embodiment, some non-limiting examples of heteroaryl group include the following monocyclic group: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5H-tetrazolyl, 2H-tetrazolyl), triazolyl (e.g., 2-triazolyl, 5-triazolyl, 4H-1,2,4-triazolyl, 1H-1,2,4-triazolyl and 1,2,3-triazolyl), 2-thienyl, 3-thienyl, pyrazolyl (e.g., 2-pyrazolyl and 3-pyrazolyl), isothiazolyl, 1,2,3-oxadiazolyl, 1,2,5-oxadiazolyl, 1,2,4-oxadiazolyl, 1,3,4-oxadiazolyl, 1,2,3-thiadiazolyl, 1,3,4-thiadiazolyl, 1,2,5-thiadiazolyl, pyrazinyl, 1,3,5-triazinyl, and the following bicycles or tricycles, but are not limited to: indolinyl, 1,2,3,4-tetrahydroisoquinolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl or 4-isoquinolinyl), phenoxathiinyl, dibenzoimidazolyl, dibenzofuryl, dibenzothienyl,

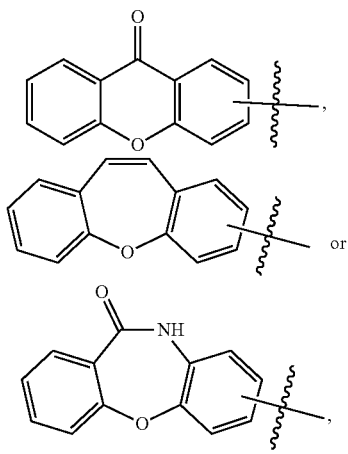

and the like. The heteroaryl group is optionally substituted with one or more substituents disclosed herein.

The terms "carboxy" or "carboxyl", whether used alone or with other terms, such as "carboxyalkyl", refer to —CO$_2$H.

The term "carbonyl", whether used alone or with other terms, such as "aminocarbonyl", "acyloxy", denotes —(C=O)—.

The term "alkylamino" refers to "N-alkylamino" and "N,N-dialkylamino" wherein amino groups are independently substituted with one alkyl radical or two alkyl radicals, respectively. In some embodiments, the alkylamino group is a lower alkylamino group having one or two $C_{1-6}$ alkyl groups attached to nitrogen atom. In other embodiments, the alkylamino group is a lower alkylamino group having 1 to 3 carbon atoms. Suitable alkylamino radical may be monoalkylamino or dialkylamino. Examples of the alkylamino radical include, but are not limited to, N-methylamino, N-ethylamino, N,N-dimethylamino, N,N-diethylamino, and the like.

The term "arylamino" refers to an amino group substituted with one or two aryl groups. Some non-limiting examples of such group include N-phenylamino. In some embodiments, the aryl group of the arylamino may be further substituted.

The term "aminoalkyl" refers to a $C_{1-10}$ linear or branched-chain alkyl group substituted with one or more amino groups. In some embodiments, the aminoalkyl is a $C_{1-6}$ lower aminoalkyl derivated from an alkyl group substituted with one or more amino groups. Some non-limiting examples of the aminoalkyl group include aminomethyl, aminoethyl, aminopropyl, aminobutyl and aminohexyl.

As described herein, a bond drawn from a substituent to the center of one ring within a ring system represents substitution of substituents at any substitutable position on the rings, and wherein the ring system includes mono-, bi- or polycyclic ring system. For example, formula a represents substitution of substituents at any substitutable position on the ring system, i.e., formula b-1 to formula b-8:

formula a

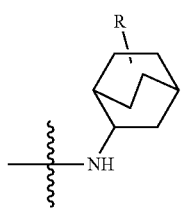

formula b-1

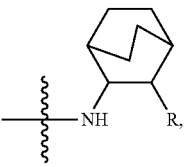

formula b-2

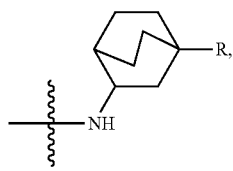

formula b-3

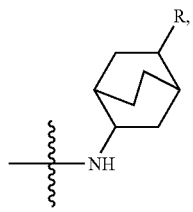

formula b-4

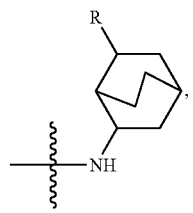

formula b-5

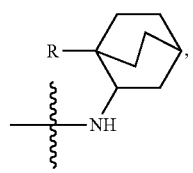

formula b-6

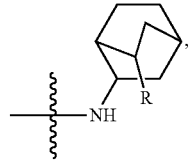

formula b-7

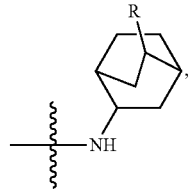

formula b-8

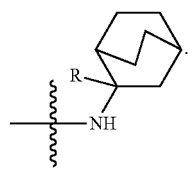

As described herein, a bond drawn from a substituent to the center of one ring within a ring system represents the bond can attach to the rest of the molecule at any attachable position on the rings. For example, formula c represents substitution of substituents at any substitutable position on the rings, i.e., formula d-1 and formula d-2.

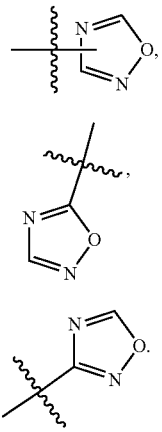

formula c formula d-1 formula d-2

As described herein, when there are two or more substituents represented by the same letter, number or symbol in one structural formula, the substituents are independent from each other. For example, in formula e, each $R^W$ is as defined herein, and each $R^W$ is independent of each other, which can be the same or different of each other.

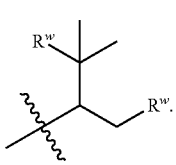

formula e

The term "unsaturated" refers to a moiety having one or more units of unsaturation.

The term "comprising" or "comprise" is meant to be open ended, including the indicated component but not excluding other elements.

As described herein, the term "pharmaceutically acceptable carrier" includes any solvents, dispersion media, coating agents, surfactants, antioxidants, preservatives (e.g., antibacterial agents, antifungal agents), isotonic agents, salt, drug stabilizers, binders, excipients, dispersants, lubricants, sweetening agents, flavoring agents, coloring agents, or a combination thereof, all of which are well known to the skilled in the art. (e.g., *Remington's Pharmaceutical Sciences*, 18th Ed. Mack Printing Company, 1990, pp. 1289-1329, all of which are incorporated herein by reference). Except any conventional carrier is incompatible with the active ingredient, the pharmaceutically acceptable carriers are effectively used in the treatment or pharmaceutical compositions.

As used herein, the term "inhibition of the replication of influenza viruses" includes both the reduction in the amount of virus replication (e.g. the reduction by at least 10%) and the complete arrest of virus replication (i.e., 100% reduction in the amount of virus replication). In some embodiments, the replication of influenza viruses are inhibited by at least 50%, at least 65%, at least 75%, at least 85%, at least 90%, or at least 95%.

As used herein, an "effective amount" refers to an amount sufficient to elicit the desired biological response. In the present invention, the desired biological response is to inhibit the replication of influenza virus, to reduce the amount of influenza viruses or to reduce or ameliorate the severity, duration, progression, or onset of a influenza virus infection, prevent the advancement of an influenza virus infection, prevent the recurrence, development, onset or progression of a symptom associated with an influenza virus infection, or enhance or improve the prophylactic or therapeutic effect(s) of another therapy used against influenza infections. The precise amount of compound administered to a subject will depend on the mode of administration, the type and severity of the infection and the characteristics of the subject, such as general health, age, sex, body weight and tolerance to drugs. The skilled artisan will be able to determine appropriate dosages depending on these and other factors. When co-administered with other anti viral agents, e.g., when co-administered with an anti-influenza medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range between approximately 0.01 to 100 mg/kg body weight/day for therapeutic or prophylactic treatment.

As used herein, the terms "treat", "treatment" and "treating" refer to both therapeutic and prophylactic treatments. For example, therapeutic treatments includes the reduction or amelioration of the progression, severity and/or duration of influenza viruses mediated conditions, or the amelioration of one or more symptoms (specifically, one or more discernible symptoms) of influenza viruses mediated conditions, resulting from the administration of one or more therapies (e.g., one or more therapeutic agents such as a compound or composition of the invention). In specific embodiments, the therapeutic treatment includes the amelioration of at least one measurable physical parameter of an influenza virus mediated condition. In other embodiments the therapeutic treatment includes the inhibition of the progression of an influenza virus mediated condition, either physically by, e.g., stabilization of a discernible symptom, physiologically by, e.g., stabilization of a physical parameter, or both. In other embodiments the therapeutic treatment includes the reduction or stabilization of influenza viruses mediated infections. Antiviral drugs can be used in the community setting to treat people who already have influenza to reduce the severity of symptoms and reduce the number of days that they are sick.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, p-toluenesulfonyl (Ts), t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfonyl)ethyl, 2-(diphenylphosphino)ethyl, nitroethyl and the like. For a general description of protecting groups and their use, see T. W. Greene, *Protective Groups in Organic Synthesis*, John Wiley & Sons, New York, 1991; and P. J. Kocienski, Protecting Groups, Thieme, Stuttgart, 2005.

DESCRIPTION OF COMPOUNDS OF THE INVENTION

The invention provides a novel class of compounds used as inhibitors of influenza virus RNA polymerase. These compounds and compositions thereof can be used in the manufacture of a medicament for preventing, treating or lessening virus infection in patients.

In one aspect, provided herein is a compound having Formula (I) or a stereoisomer, a tautomer, an N-oxide, a solvate, a metabolite, a pharmaceutically acceptable salt or a prodrug thereof,

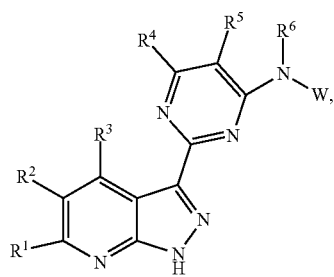

(I)

wherein $R^1$, $R^2$, $R^3$, $R^4$, $R^5$, $R^6$ and W are as defined herein.

In some embodiments, each of $R^1$, $R^2$ and $R^3$ is independently H, D, F, Cl, Br, CN, NO$_2$, —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-6}$ alkyl, C$_{2-6}$ alkenyl or C$_{2-6}$ alkynyl; or, $R^1$ and $R^2$, together with the carbon atoms to which they are attached, form a C$_{3-6}$ carbocyclic ring, 5- to 6-membered heterocyclic ring, C$_{6-10}$ aromatic ring or 5- to 6-membered heteroaromatic ring, and wherein each of C$_{1-6}$ alkyl, C$_{2-6}$ alkenyl, C$_{2-6}$ alkynyl, C$_{3-6}$ carbocyclic ring, 5- to 6-membered heterocyclic ring, C$_{6-10}$ aromatic ring and 5- to 6-membered heteroaromatic ring is independently unsubstituted or substituted with 1, 2, 3 or 4 substituents independently selected from D, F, Cl, Br, CN, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

$R^4$ is —OR$^b$, —NR$^c$R$^d$, C$_{1-6}$ alkyl, C$_{2-6}$ alkenyl, C$_{2-6}$ alkynyl, C$_{3-12}$ carbocyclyl, C$_{3-12}$ carbocyclyl-C$_{1-4}$ alkylene, 3- to 12-membered heterocyclyl, (3- to 12-membered heterocyclyl)-C$_{1-4}$ alkylene, C$_{6-10}$ aryl, C$_6$10 aryl-C$_{1-4}$ alkylene, 5- to 16-membered heteroaryl or (5- to 16-membered heteroaryl)-C$_{1-4}$ alkylene, and wherein each of C$_{1-6}$ alkyl, C$_{2-6}$ alkenyl, C$_{2-6}$ alkynyl, C$_{3-12}$ carbocyclyl, C$_{3-12}$ carbocyclyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 16-membered heteroaryl and (5- to 16-membered heteroaryl)-C$_{1-4}$ alkylene is independently unsubstituted or substituted with 1, 2, 3, 4 or 5 R';

$R^5$ is H, D, F, Cl, Br, CN, NO$_2$, —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-6}$ alkyl, C$_{2-6}$ alkenyl, C$_{2-6}$ alkynyl, C$_{3-12}$ cycloalkyl, C$_{3-12}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene, and wherein each of C$_{1-6}$ alkyl, C$_{2-6}$ alkenyl, C$_{2-6}$ alkynyl, C$_{3-12}$ cycloalkyl, C$_{3-12}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl and (5- to 10-membered heteroaryl)-C$_{1-4}$ alkylene is independently unsubstituted or substituted with 1, 2, 3, 4 or 5 R';

or, $R^4$ and $R^5$, together with the carbon atoms to which they are attached, form a C$_{3-12}$ carbocyclic ring, 3- to 12-membered heterocyclic ring, C$_{6-10}$ aromatic ring or 5- to 10-membered heteroaromatic ring, and wherein each of C$_{3-12}$ carbocyclic ring, 3- to 12-membered heterocyclic ring, C$_{6-10}$ aromatic ring and 5- to 10-membered heteroaromatic ring is independently unsubstituted or substituted with 1, 2, 3, 4 or 5 R';

each R' is independently D, F, Cl, Br, CN, NO$_2$, —OR$^b$, —NR$^c$R$^d$, R$^b$O—C$_{1-4}$ alkylene, R$^d$R$^c$N—C$_{1-4}$ alkylene, —C(=O)R$^a$, —C(=O)OR$^b$, —C(=O)NR$^c$R$^d$, C$_{1-12}$ alkyl, C$_{1-6}$ haloalkyl, C$_{3-6}$ cycloalkyl, C$_{3-6}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene; or, two adjacent R', together with the carbon atoms to which they are attached, form a C$_{3-6}$ carbocyclic ring, 5- to 6-membered heterocyclic ring, C$_{6-10}$ aromatic ring or 5- to 6-membered heteroaromatic ring, and wherein each of C$_{1-12}$ alkyl, C$_{1-6}$ haloalkyl, C$_{3-6}$ cycloalkyl, C$_{3-6}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, C$_{6-10}$ aryl-C$_{1-4}$ alkylene, 5- to 10-membered heteroaryl, (5- to 10-membered heteroaryl)-C$_{1-4}$ alkylene, C$_{3-6}$ carbocyclic ring, 5- to 6-membered heterocyclic ring, C$_{6-10}$ aromatic ring and 5- to 6-membered heteroaromatic ring is independently unsubstituted or substituted with 1, 2, 3 or 4 substituents independently selected from D, F, Cl, Br, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

$R^6$ is H, D or C$_{1-6}$ alkyl, and wherein C$_{1-6}$ alkyl is optionally substituted with 1, 2, 3 or 4 substituents independently selected from D, F, Cl, Br, CN, NO$_2$ or —OR$^b$;

W is C$_{1-8}$ alkyl, C$_{3-12}$ carbocyclyl or 3- to 12-membered heterocyclyl, and wherein each of C$_{1-8}$ alkyl, C$_{3-12}$ carbocyclyl and 3- to 12-membered heterocyclyl is independently unsubstituted or substituted with 1, 2, 3 or 4 R$^w$;

each R$^w$ is independently D, F, Cl, Br, CN, NO$_2$, —C(=O)R$^a$, —C(=O)OR$^b$, —C(=O)NR$^c$R$^d$, —NR$^c$C(=O)R$^a$, —NR$^c$C(=O)NR$^c$R$^d$, —S(=O)$_2$R$^f$, —S(=O)$_2$NR$^c$C(=O)R$^a$, —S(=O)$_2$NR$^c$R$^d$, (R$^b$O)$_2$P(=O)—C$_{0-2}$ alkylene, —OR$^b$, R$^b$O—C$_{1-2}$ alkylene, R$^d$R$^c$N—C$_{1-2}$ alkylene, C$_{1-6}$ alkyl, 5- to 6-membered heteroaryl or 5- to 6-membered heterocyclyl, and wherein each of C$_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, N$_3$, =O, NO$_2$, —OR$^b$, C$_{1-6}$ alkyl or C$_{1-6}$ haloalkyl;

each R$^a$, R$^b$, R$^c$, R$^d$, R$^e$ and R$^f$ is independently H, D, hydroxy, C$_{1-6}$ haloalkyl, C$_{1-6}$ alkyl, C$_{1-6}$ alkoxy, C$_{2-6}$ alkenyl, C$_{2-6}$ alkynyl, C$_{3-6}$ carbocyclyl, C$_{3-6}$ carbocyclyl-C$_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene; wherein each of $C_{1-6}$ alkyl, $C_{1-6}$ alkoxy, $C_{2-6}$ alkenyl, $C_{2-6}$ alkynyl, $C_{3-6}$ carbocyclyl, $C_{3-6}$ carbocyclyl-$C_{1-4}$ alkylene, 3- to 12-membered heterocyclyl, (3- to 12-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino;

or, $R^c$ and $R^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, $NH_2$, $C_{1-6}$ alkyl, $C_{1-6}$ haloalkyl, $C_{1-6}$ alkoxy or $C_{1-6}$ alkylamino.

In other embodiments, the invention provides a compound having Formula (II) or a stereoisomer, a tautomer, an N-oxide, a solvate, a metabolite, a pharmaceutically acceptable salt or a prodrug thereof,

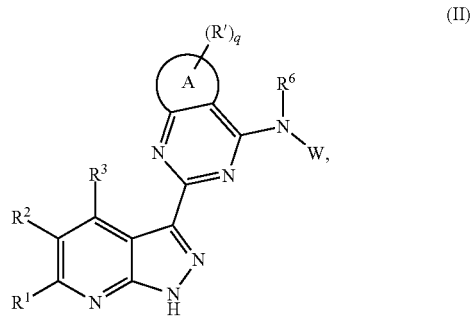

(II)

wherein A, $R^1$, $R^2$, $R^3$, R', $R^6$, q and W are as defined herein.

In other embodiments, W is $C_{1-8}$ alkyl, $C_{3-8}$ carbocyclyl or 3- to 12-membered heterocyclyl, and wherein each of $C_{1-8}$ alkyl, $C_{3-8}$ carbocyclyl and 3- to 12-membered heterocyclyl is independently unsubstituted or substituted with 1, 2, 3 or 4 $R^w$.

In other embodiments, A is a $C_{3-12}$ carbocyclic ring, 3- to 12-membered heterocyclic ring, $C_{6-10}$ aromatic ring or 5- to 10-membered heteroaromatic ring; and q is 0, 1, 2, 3, 4, or 5.

In other embodiments, each of $R^1$, $R^2$ and $R^3$ is independently H, D, F, Cl, Br, CN, $NO_2$, —C(═O)$R^a$, —C(═O)$OR^b$, —C(═O)$NR^cR^d$, —$OR^b$, —$NR^cR^d$, methyl, ethyl, n-propyl or i-propyl; or, $R^1$ and $R^2$, together with the carbon atoms to which they are attached, form a $C_6$ carbocyclic ring, 5- to 6-membered heterocyclic ring, benzene ring or 5- to 6-membered heteroaromatic ring, and wherein each of methyl, ethyl, n-propyl i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, —$OR^b$, —$NR^cR^d$ or $C_{1-3}$ haloalkyl.

In other embodiments, $R^4$ is —$OR^b$, —$NR^cR^d$, $C_{1-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 10-membered heterocyclyl, (5- to 10-membered heterocyclyl)-$C_{1-4}$ alkylene, $C_{6-10}$ aryl, $C_{6-10}$ aryl-$C_{1-4}$ alkylene, 5- to 10-membered heteroaryl or (5- to 10-membered heteroaryl)-$C_{1-4}$ alkylene, and wherein each of $C_{1-4}$ alkyl, $C_{2-4}$ alkenyl, $C_{2-4}$ alkynyl, $C_{3-6}$ carbocyclyl, $C_{3-6}$ carbocyclyl-$C_{1-4}$ alkylene, 5- to 10-membered heterocyclyl, (5- to 10-membered heterocyclyl)-$C_{1-4}$ alkylene, $C_{6-10}$ aryl, $C_{6-10}$ aryl-$C_{1-4}$ alkylene, 5- to 10-membered heteroaryl and (5- to 10-membered heteroaryl)-$C_{1-4}$ alkylene is independently unsubstituted or substituted with 1, 2, 3, 4 or 5 R';

$R^5$ is H, D, F, Cl, Br, CN, $NO_2$, —C(═O)$R^a$, —C(═O)$OR^b$, —C(═O)$NR^cR^d$, —$OR^b$, —$NR^cR^d$, $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl or (5- to 6-membered heteroaryl)-$C_{1-4}$ alkylene, and wherein each of $C_{1-3}$ alkyl, $C_{2-4}$ alkenyl, $C_{2-4}$ alkynyl, $C_{3-6}$ cycloalkyl, $C_{3-6}$ cycloalkyl-$C_{1-4}$ alkylene, 5- to 6-membered heterocyclyl, (5- to 6-membered heterocyclyl)-$C_{1-4}$ alkylene, $C_{6-10}$ aryl, $C_{6-10}$ aryl-$C_{1-4}$ alkylene, 5- to 6-membered heteroaryl and (5- to 6-membered heteroaryl)-$C_{1-4}$ alkylene is independently unsubstituted or substituted with 1, 2, 3, 4 or 5 R';

or, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 10-membered heteroaromatic ring, and wherein each of $C_{3-6}$ carbocyclic ring, 3- to 6-membered heterocyclic ring, $C_{6-10}$ aromatic ring and 5- to 10-membered heteroaromatic ring is independently unsubstituted or substituted with 1, 2, 3, 4 or 5 R'.

In other embodiments, $R^4$ and $R^5$, together with the carbon atoms to which they are attached, form a $C_{3-6}$ carbocyclic ring, 3- to 6-membered heterocyclic ring, $C_{6-10}$ aromatic ring or 5- to 6-membered heteroaromatic ring, and wherein each of $C_{3-6}$ carbocyclic ring, 3- to 6-membered heterocyclic ring, $C_{6-10}$ aromatic ring and 5- to 6-membered heteroaromatic ring is independently unsubstituted or substituted with 1, 2, 3, 4 or 5 R'.

In other embodiments, each R' is independently D, F, Cl, Br, CN, $NO_2$, —$OR^b$, —$NR^cR^d$, —C(═O)$R^a$, —C(═O)$OR^b$, —C(═O)$NR^cR^d$, $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene or 5- to 6-membered heteroaryl; or two adjacent R', together with the carbon atoms to which they are attached, form a $C_{5-6}$ carbocyclic ring or benzene ring, and wherein each of $C_{1-9}$ alkyl, $C_{1-3}$ haloalkyl, $C_{3-6}$ cycloalkyl, 5- to 6-membered heterocyclyl, phenyl, phenyl-$C_{1-2}$ alkylene, 5- to 6-membered heteroaryl, $C_{5-6}$ carbocyclic ring and benzene ring is independently unsubstituted or substituted with 1, 2, 3 or 4 substituents independently selected from D, F, Cl, Br, CN, $NO_2$, —$OR^b$, —$NR^cR^d$, methyl, ethyl, n-propyl or i-propyl.

In other embodiments, each R' is independently D, F, Cl, Br, CN, $NO_2$, OH, —$OCH_3$, —$OCH_2CH_3$, —$NR^cR^d$, —C(═O)$R^a$, —C(═O)OH, —C(═O)$OCH_2CH_3$, —C(═O)$OCH_3$, —C(═O)$NH_2$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, and wherein each of methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from D, F, Cl, Br, CN, NO$_2$, OH, —NH$_2$, methyl, ethyl, n-propyl or i-propyl.

In other embodiments, R$^6$ is H, D, CF$_3$, methyl, ethyl, n-propyl or i-propyl.

In other embodiments, W is C$_{1-6}$ alkyl, C$_{5-8}$ carbocyclyl or 5- to 8-membered heterocyclyl, and wherein each of C$_{1-6}$ alkyl, C$_{5-8}$ carbocyclyl and 5- to 8-membered heterocyclyl is independently unsubstituted or substituted with 1, 2, 3 or 4 R$^w$.

In other embodiments, each R$^w$ is independently D, F, Cl, Br, CN, NO$_2$, —C(=O)OCH$_3$, —C(=O)OCH$_2$CH$_3$, —C(=O)OH, —C(=O)NR$^c$R$^d$, —NHC(=O)R$^a$, —NHC(=O)NR$^c$R$^d$, —S(=O)$_2$R$^f$, —S(=O)$_2$NHC(=O)R$^a$, —S(=)$_2$NR$^c$R$^d$, (R$^b$O)$_2$P(=O)—C$_{0-2}$ alkylene, —OR$^b$, methyl, ethyl, n-propyl, i-propyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl, pyrimidyl and 5- to 6-membered heterocyclyl is independently unsubstituted or substituted with 1, 2, 3 or 4 substituents independently selected from D, F, Cl, Br, CN, N3, =O, NO2, —OCH$_3$, C$_{1-3}$ alkyl or C$_{1-3}$ haloalkyl.

In other embodiments, each R$^a$, R$^b$, R$^c$, R$^d$, R$^e$ and R$^f$ is independently H, D, hydroxy, trifluoromethyl, methyl, ethyl, i-propyl, n-propyl, n-butyl, t-butyl, methoxy, ethoxy, cyclopropyl, C$_{3-6}$ carbocyclyl, 5- to 6-membered heterocyclyl, phenyl, 5- to 6-membered heteroaryl or (5- to 6-membered heteroaryl)-C$_{1-4}$ alkylene, and wherein each of methyl, ethyl, i-propyl, n-propyl, n-butyl, t-butyl, methoxy, ethoxy, cyclopropyl, C$_{3-6}$ carbocyclyl, 5- to 6-membered heterocyclyl, phenyl, 5- to 6-membered heteroaryl and (5- to 6-membered heteroaryl)-C$_{1-4}$ alkylene is independently unsubstituted or substituted with 1, 2, 3 or 4 substituents independently selected from D, F, Cl, CN, OH, NH$_2$, C$_{1-3}$ alkyl, C$_{1-3}$ haloalkyl or methoxy;

or, R$^c$ and R$^d$, together with the nitrogen atom to which they are attached, form 5- to 6-membered heterocyclyl or 5- to 6-membered heteroaryl, and wherein each of 5- to 6-membered heterocyclyl and 5- to 6-membered heteroaryl is independently unsubstituted or substituted with 1, 2, 3 or 4 substituents independently selected from D, F, Cl, CN, OH, NH$_2$, C$_{1-3}$ alkyl, C$_{1-3}$ haloalkyl or methoxy.

In other embodiments, A is a C$_{3-6}$ carbocyclic ring, 3- to 6-membered heterocyclic ring, C$_{6-10}$ aromatic ring or 5- to 6-membered heteroaromatic ring.

In other embodiments, R$^4$ is —OR$^b$, —NR$^c$R$^d$, ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imidazolyl, benzimidazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl or dibenzofuryl, and wherein each of ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imidazolyl, benzimidazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl and dibenzofuryl is independently unsubstituted or substituted with 1, 2, 3, 4 or 5 R';

R$^5$ is H, D, F, Cl, Br, CN, NO$_2$, methyl, ethyl, n-propyl or i-propyl;

or, R$^4$ and R$^5$, together with the carbon atoms to which they are attached, form benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

In other embodiments, A is a C$_{3-6}$ carbocyclic ring, 3- to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

In other embodiments, W is one of the following sub-formulae:

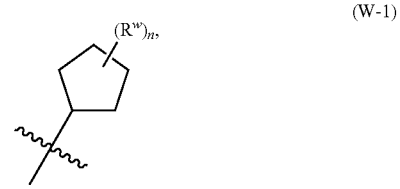

(W-1)

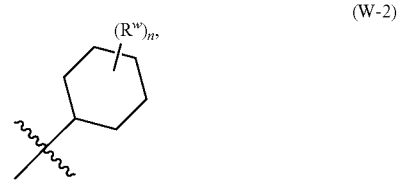

(W-2)

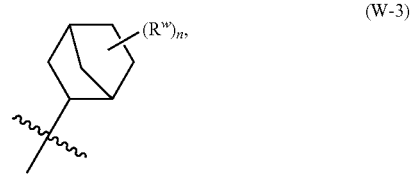

(W-3)

-continued

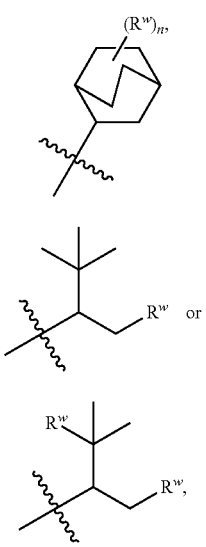

(W-4)

(W-5)

(W-6)

wherein n is 0, 1, 2, 3 or 4, and $R^w$ is as defined herein.

In other embodiments, the invention relates to a compound having Formula (III) or a stereoisomer, a tautomer, an N-oxide, a solvate, a metabolite, a pharmaceutically acceptable salt or a prodrug thereof,

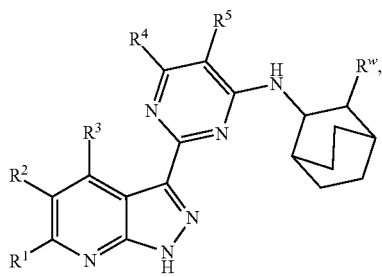

(III)

wherein $R^1$, $R^2$, $R^3$, $R^4$, $R^5$ and $R^w$ are as defined herein.

In other embodiments, the invention relates to a compound having Formula (IV) or a stereoisomer, a tautomer, an N-oxide, a solvate, a metabolite, a pharmaceutically acceptable salt or a prodrug thereof,

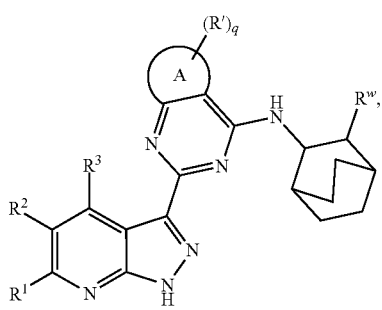

(IV)

wherein A, $R^1$, $R^2$, $R^3$, R', q and $R^w$ are as defined herein.

In other embodiments, the invention relates to a compound having Formula (V) or a stereoisomer, a tautomer, an N-oxide, a solvate, a metabolite, a pharmaceutically acceptable salt or a prodrug thereof,

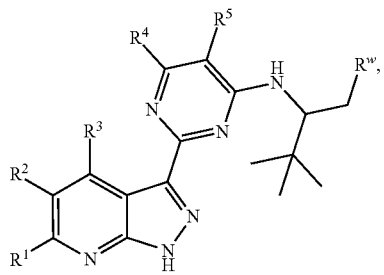

(V)

wherein $R^1$, $R^2$, $R^3$, $R^4$, $R^5$ and $R^w$ are as defined herein.

In other embodiments, the invention relates to a compound having Formula (VI) or a stereoisomer, a tautomer, an N-oxide, a solvate, a metabolite, a pharmaceutically acceptable salt or a prodrug thereof,

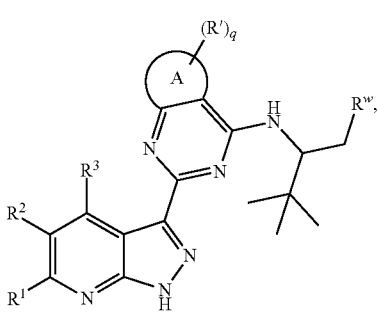

(VI)

wherein A, $R^1$, $R^2$, $R^3$, R', q and $R^w$ are as defined herein.

In other embodiments, the invention relates to a compound having Formula (VII) or a stereoisomer, a tautomer, an N-oxide, a solvate, a metabolite, a pharmaceutically acceptable salt or a prodrug thereof,

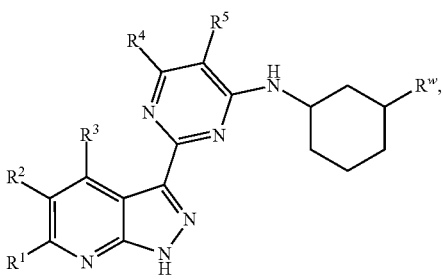

(VII)

wherein $R^1$, $R^2$, $R^3$, $R^4$, $R^5$ and $R^w$ are as defined herein.

In other embodiments, the invention relates to a compound having Formula (VIII) or a stereoisomer, a tautomer, an N-oxide, a solvate, a metabolite, a pharmaceutically acceptable salt or a prodrug thereof,

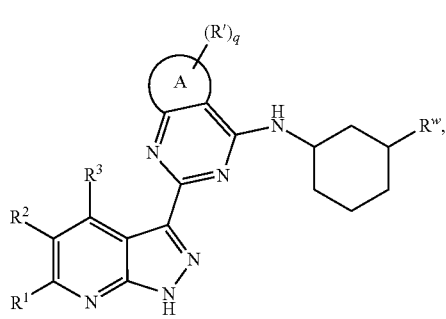

(VIII)

wherein A, R$^1$, R$^2$, R$^3$, R', q and R$^w$ are as defined herein.

In other embodiments, the invention relates to a compound having Formula (IX) or a stereoisomer, a tautomer, an N-oxide, a solvate, a metabolite, a pharmaceutically acceptable salt or a prodrug thereof,

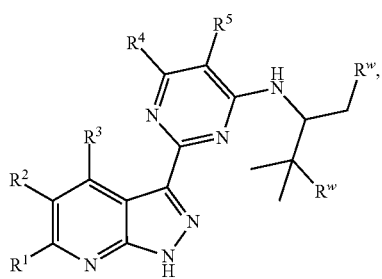

(IX)

wherein R$^1$, R$^2$, R$^3$, R$^4$, R$^5$ and R$^w$ are as defined herein.

In other embodiments, the invention relates to a compound having Formula (X) or a stereoisomer, a tautomer, an N-oxide, a solvate, a metabolite, a pharmaceutically acceptable salt or a prodrug thereof,

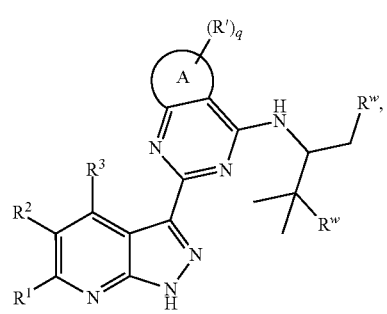

(X)

wherein A, R$^1$, R$^2$, R$^3$, R', q and R$^w$ are as defined herein.

In other embodiments, the invention relates to a compound having Formula (XI) or a stereoisomer, a tautomer, an N-oxide, a solvate, a metabolite, a pharmaceutically acceptable salt or a prodrug thereof,

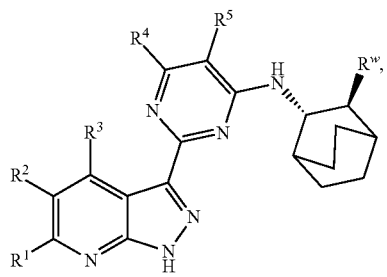

(XI)

wherein R$^1$, R$^2$, R$^3$, R$^4$, R$^5$ and R$^w$ are as defined herein.

In other embodiments, the invention relates to a compound having Formula (XII) or a stereoisomer, a tautomer, an N-oxide, a solvate, a metabolite, a pharmaceutically acceptable salt or a prodrug thereof,

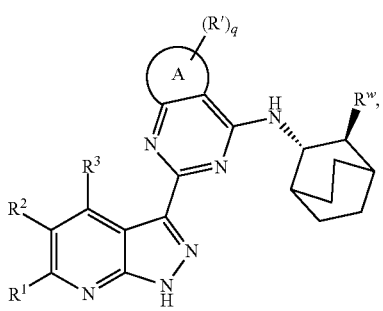

(XII)

wherein A, R$^1$, R$^2$, R$^3$, R', q and R$^w$ are as defined herein.

In other embodiments, the invention relates to a compound having Formula (XIII) or a stereoisomer, a tautomer, an N-oxide, a solvate, a metabolite, a pharmaceutically acceptable salt or a prodrug thereof,

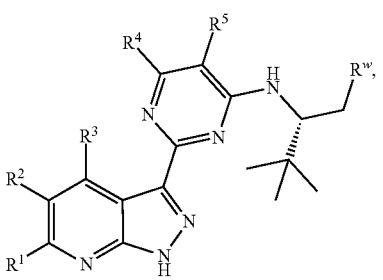

(XIII)

wherein R$^1$, R$^2$, R$^3$, R$^4$, R$^5$ and R$^w$ are as defined herein.

In other embodiments, the invention relates to a compound having Formula (XIV) or a stereoisomer, a tautomer, an N-oxide, a solvate, a metabolite, a pharmaceutically acceptable salt or a prodrug thereof,

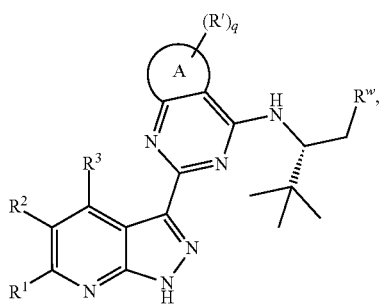
(XIV)
wherein A, R$^1$, R$^2$, R$^3$, R', q and R$^w$ are as defined herein.
In other embodiments, the invention relates to one of the following compounds, or a stereoisomer, a tautomer, an N-oxide, a solvate, a metabolite, a pharmaceutically acceptable salt or a prodrug thereof, which are not limited to,
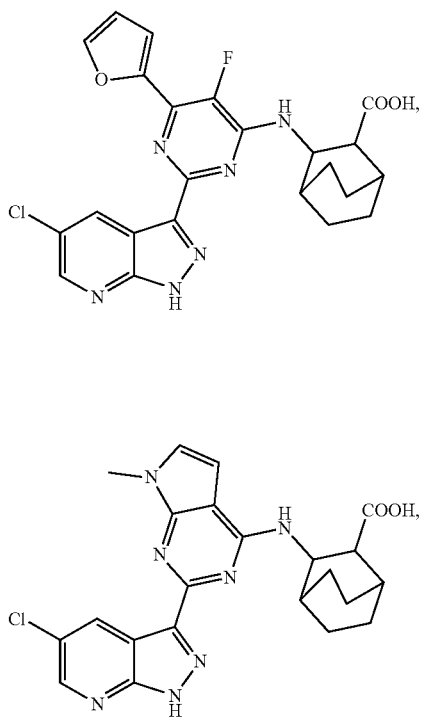
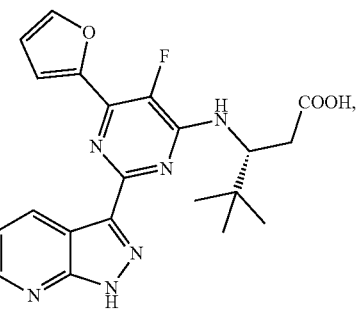
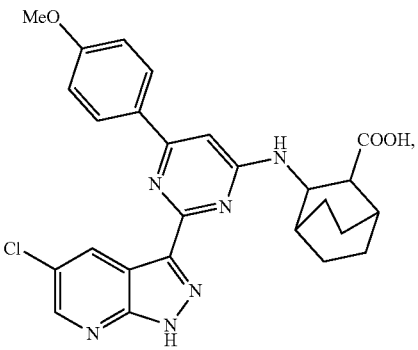
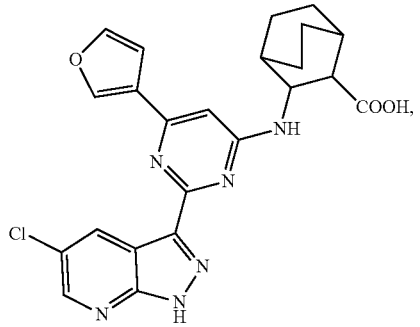
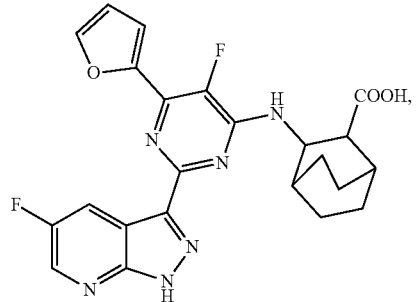
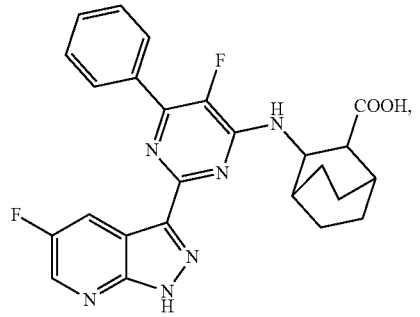

(9)
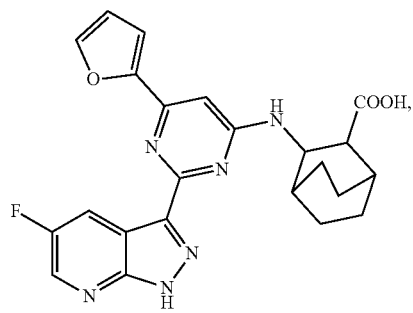
(10)
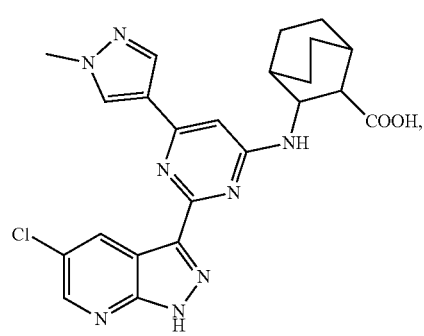
(11)
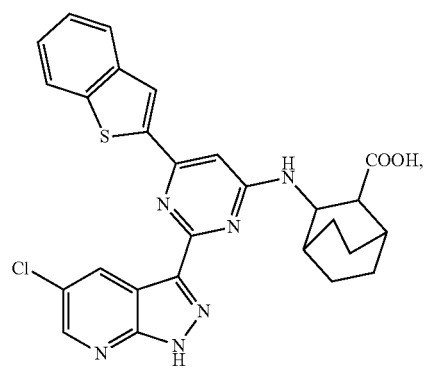
(12)
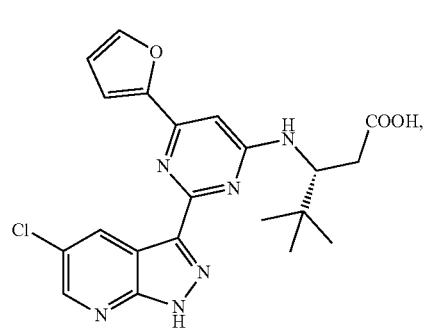
(13)
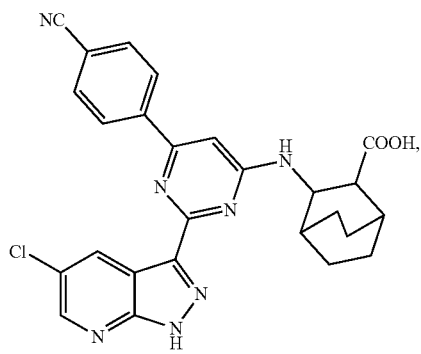
(14)
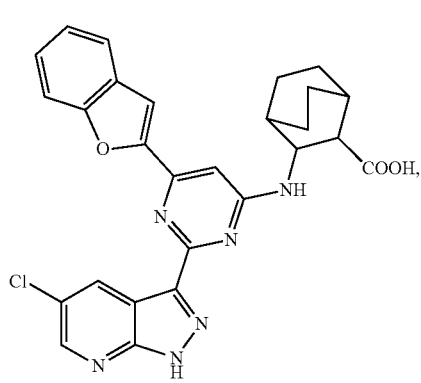
(15)
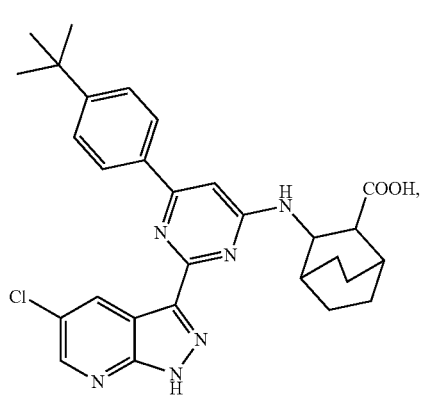
(16)
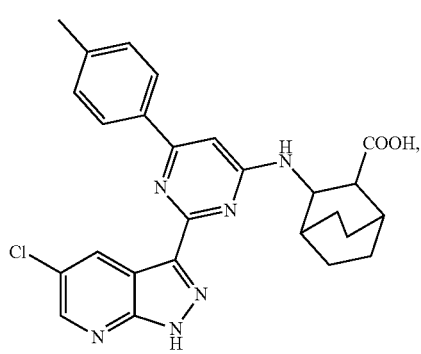

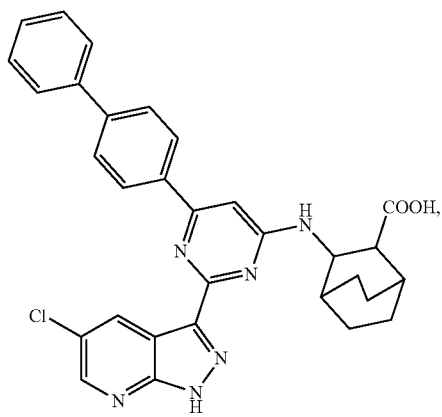
(17)
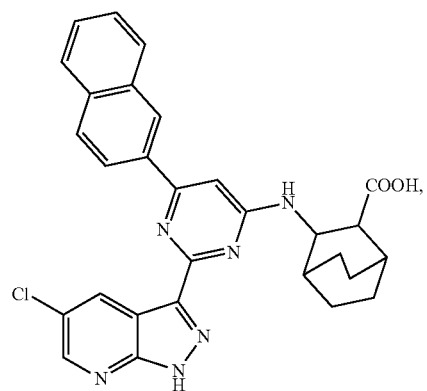
(18)
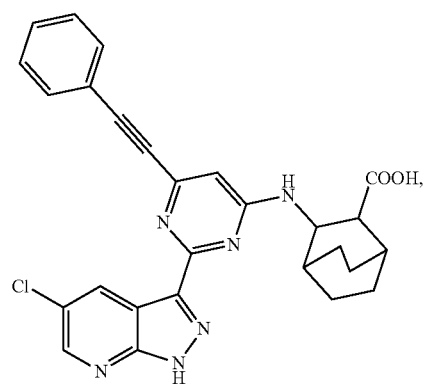
(19)
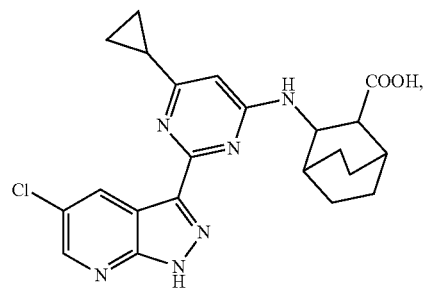
(20)
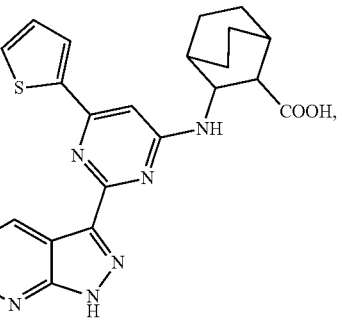
(21)
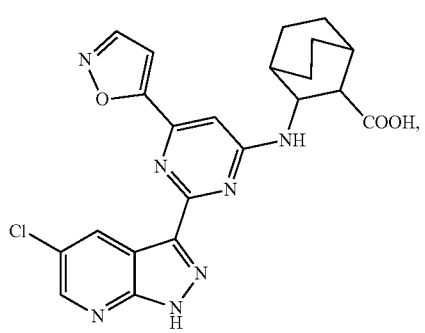
(22)
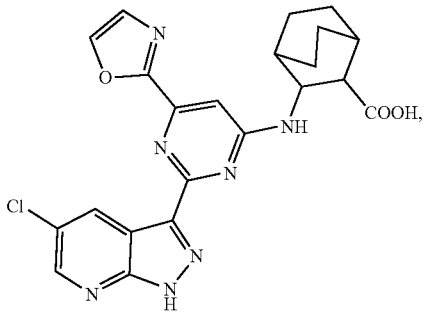
(23)
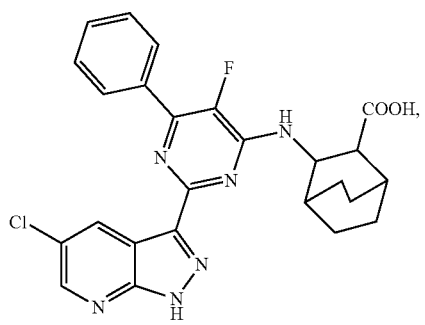
(24)
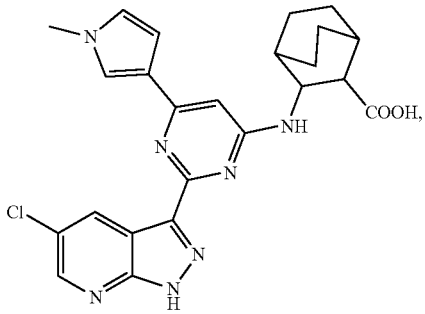
(25)

(26)
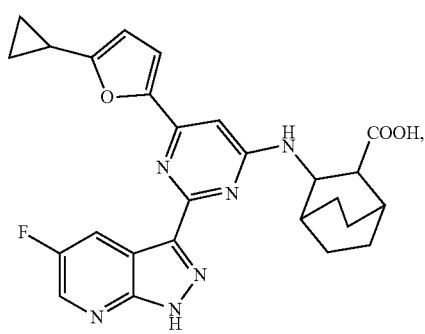
(27)
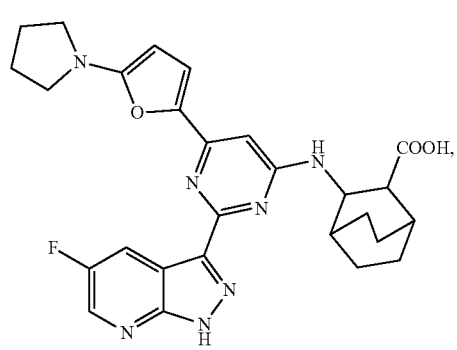
(28)
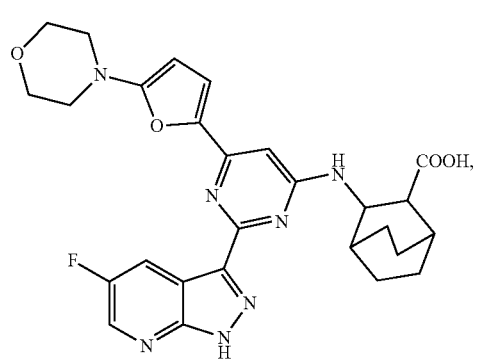
(29)
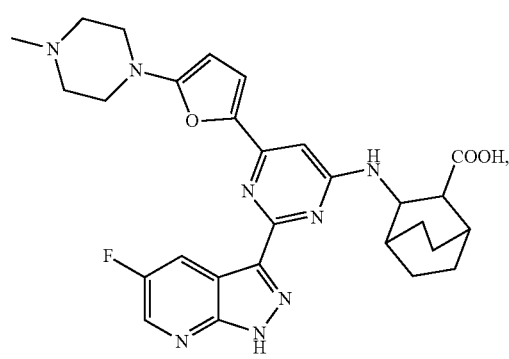
(30)
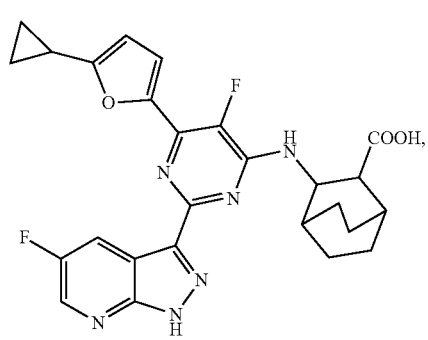
(31)
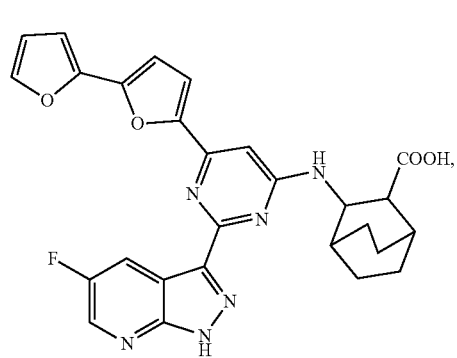
(32)
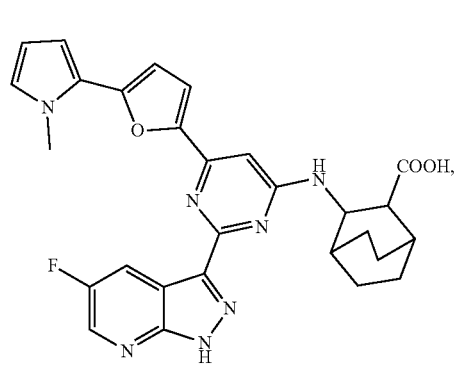
(33)
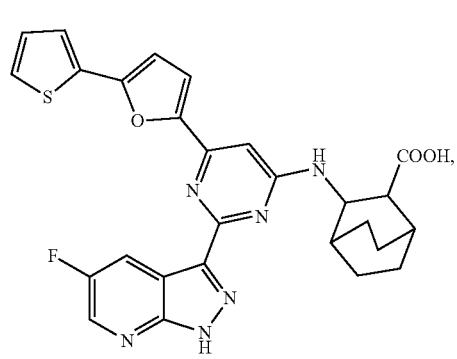

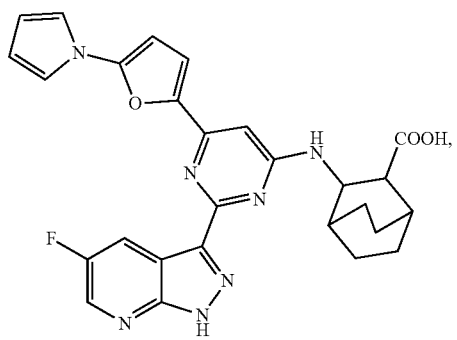
(34)
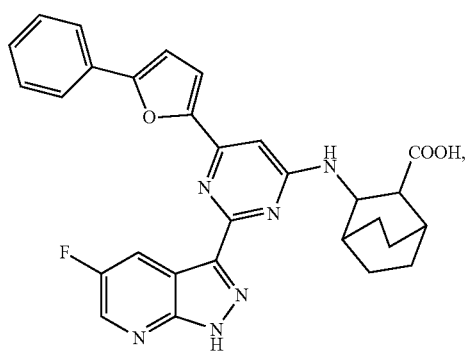
(35)
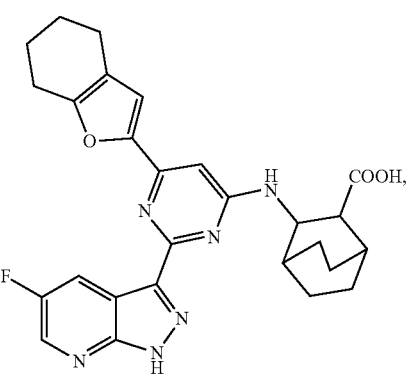
(36)
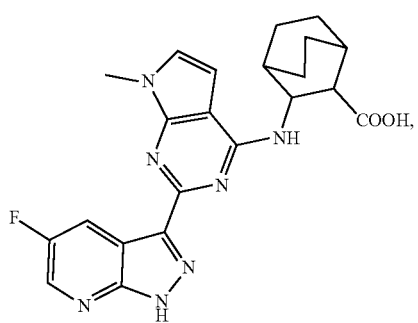
(37)
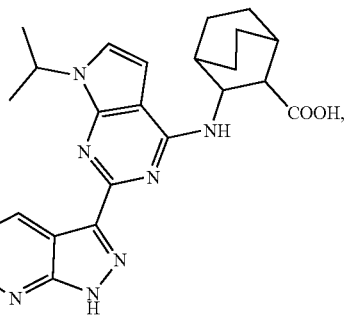
(38)
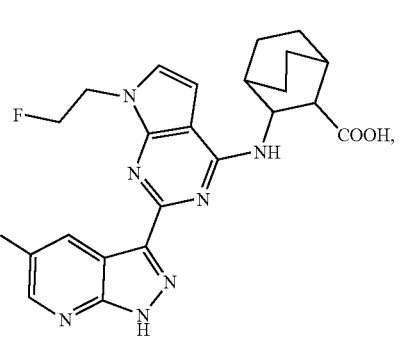
(39)
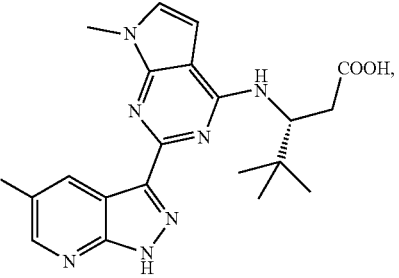
(40)
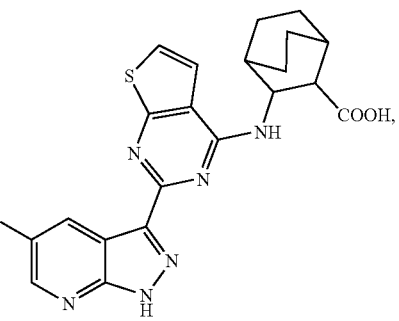
(41)
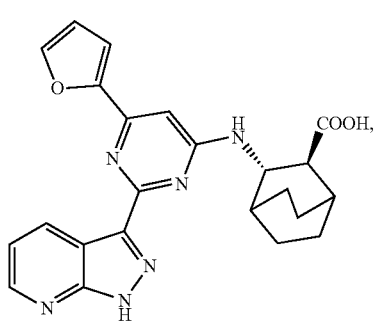
(42)

-continued
(43)
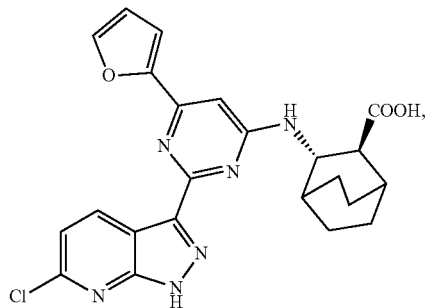
(44)
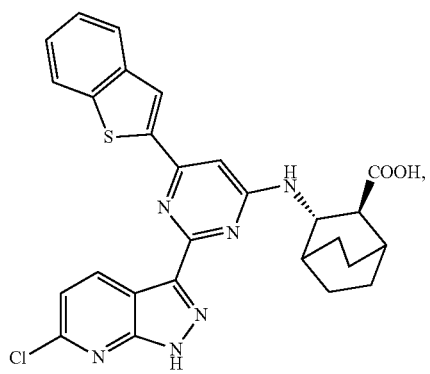
(45)
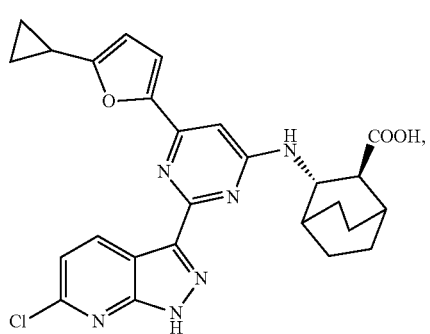
(46)
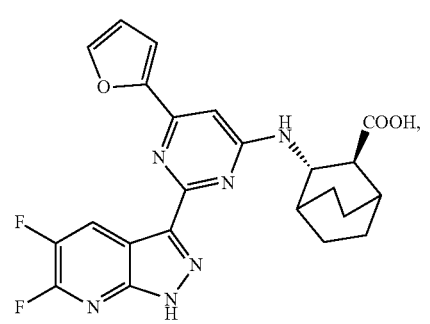
(47)
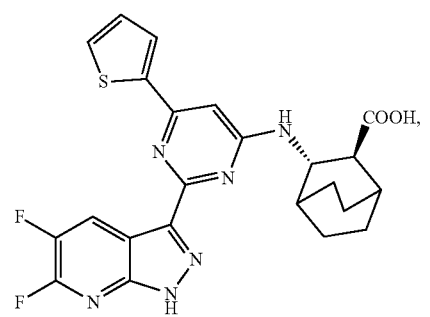
-continued
(48)
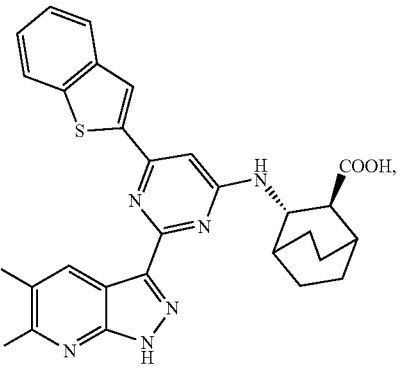
(49)
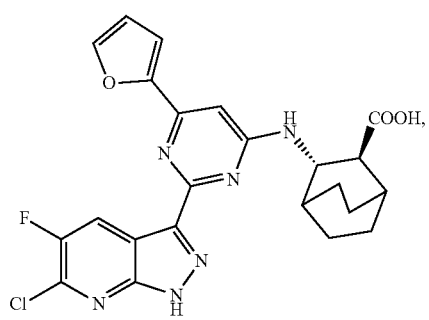
(50)
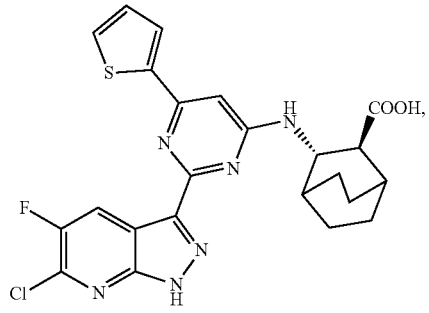
(51)
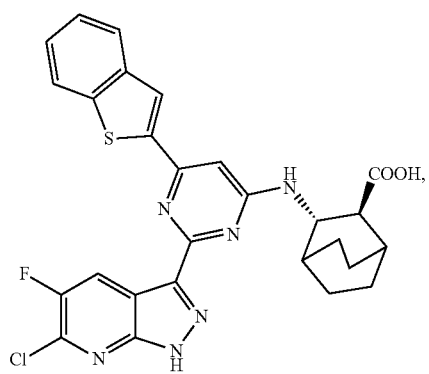

(52) 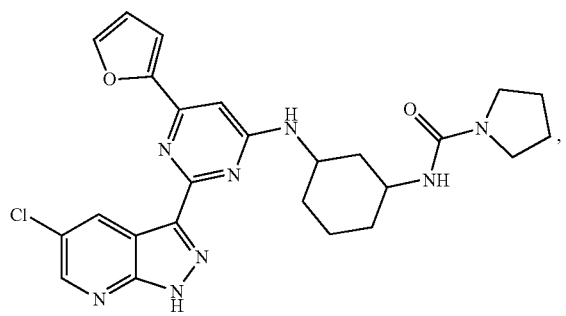
(53) 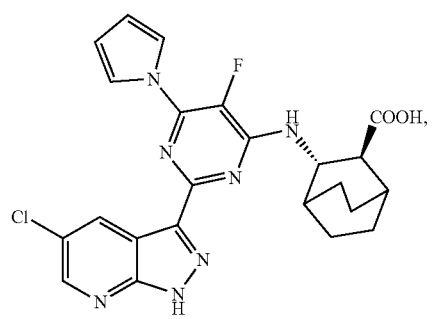
(54) 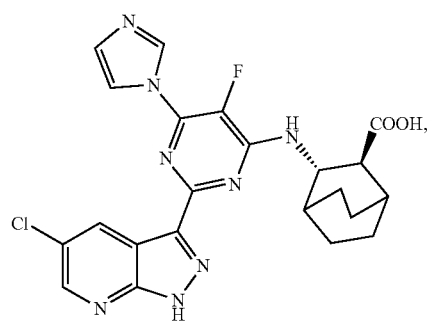
(55) 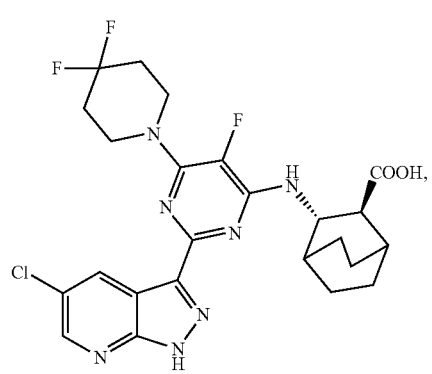
(56) 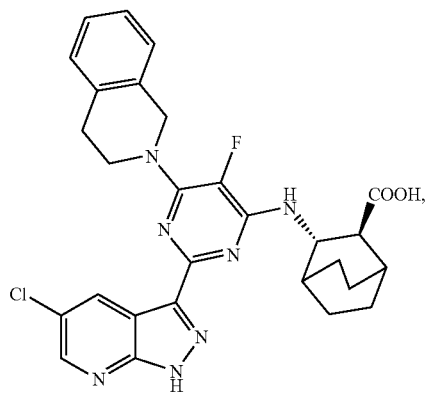
(57) 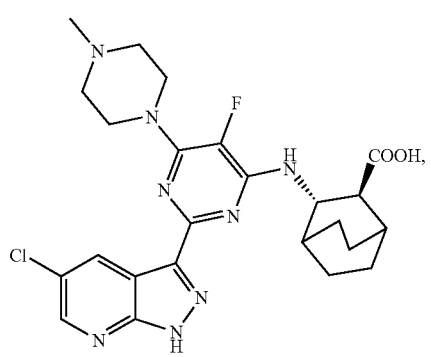
(58) 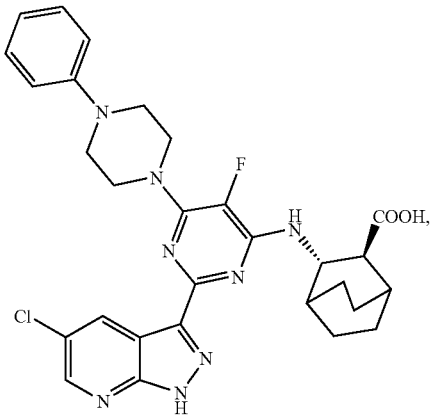
(59) 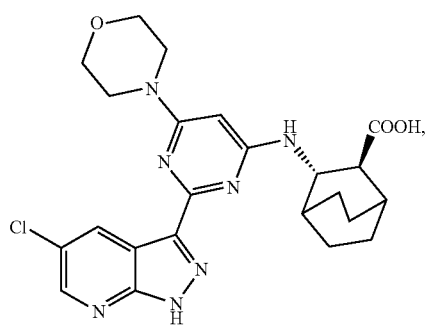

(60)
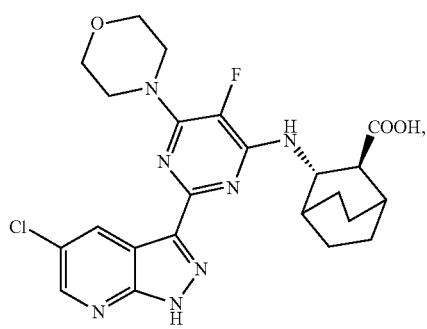
(61)
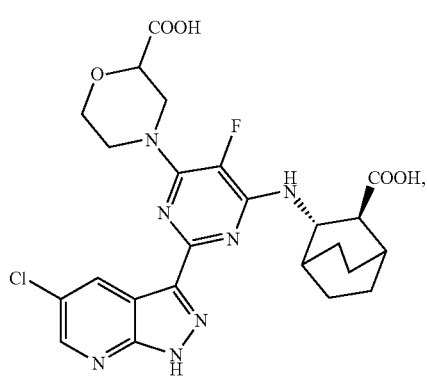
(62)
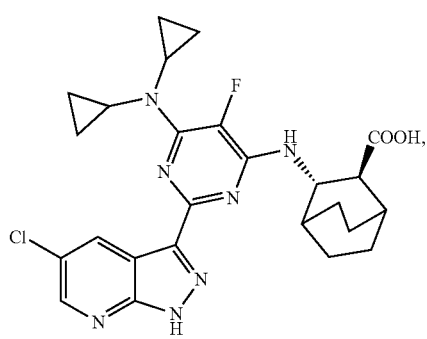
(63)
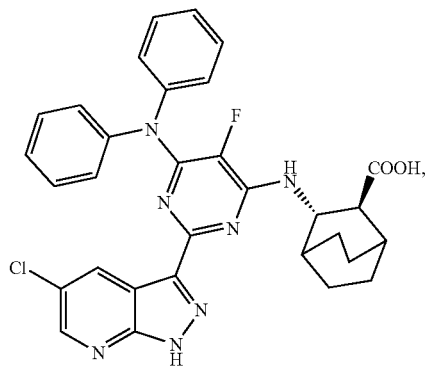
(64)
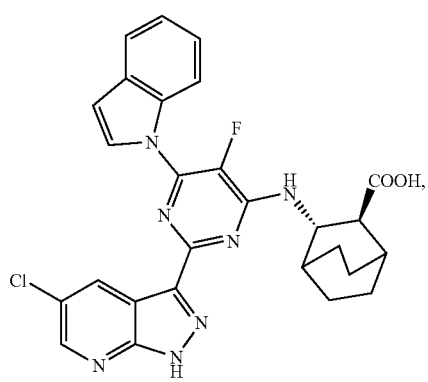
(65)
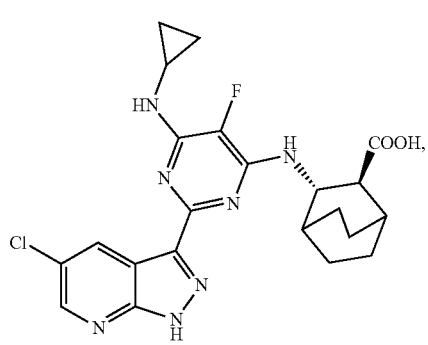
(66)
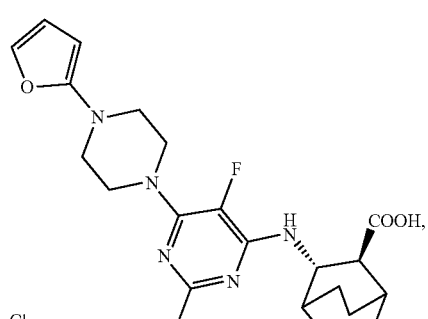
(67)
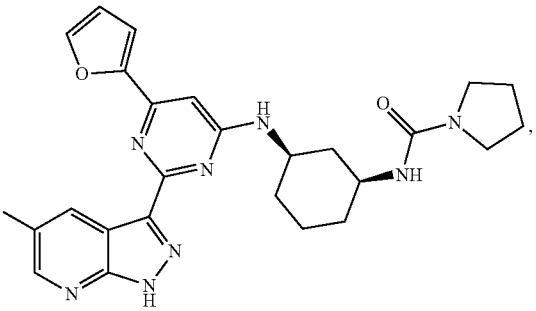

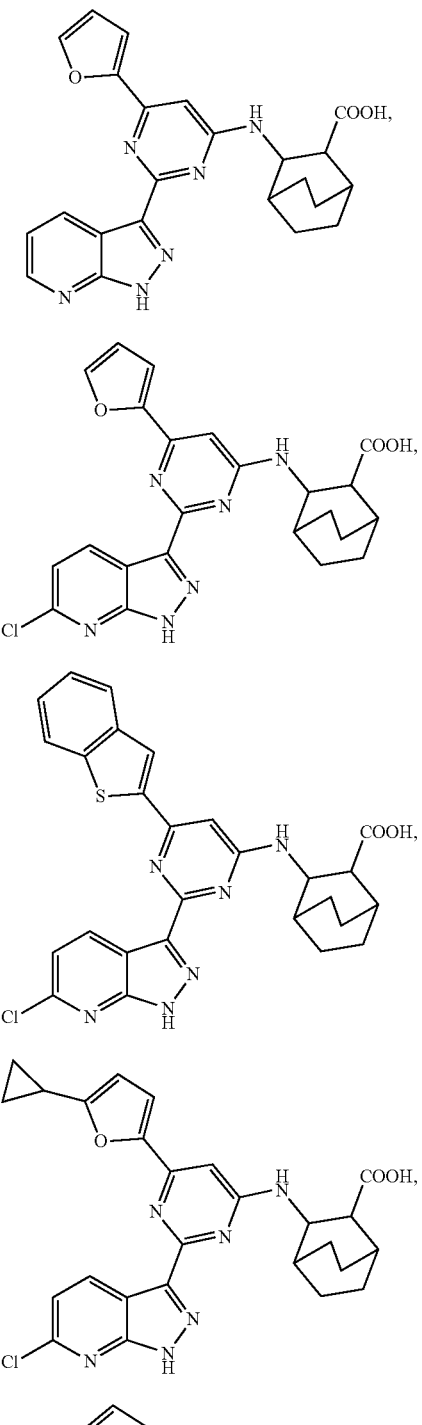
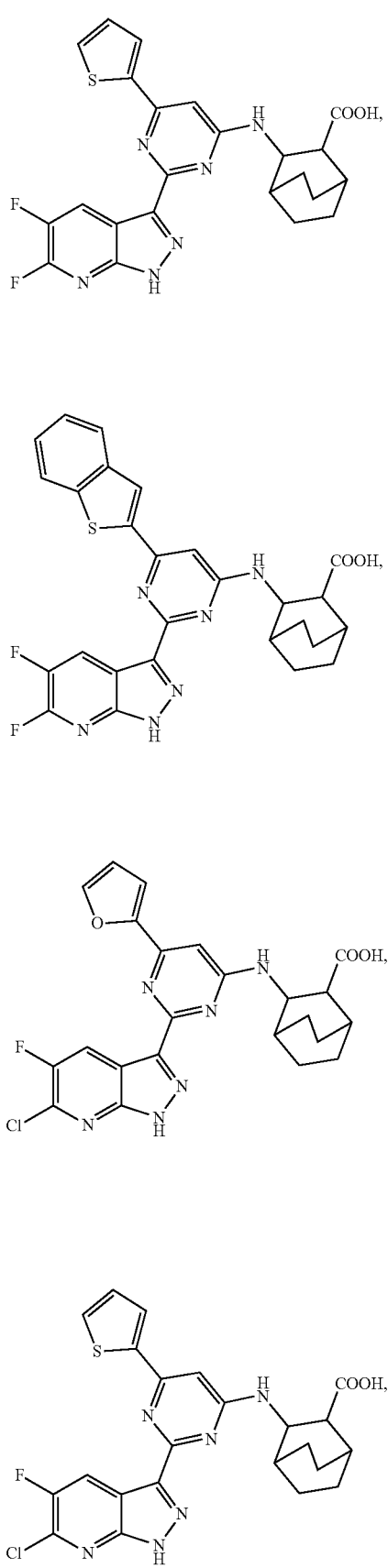

-continued
(77)
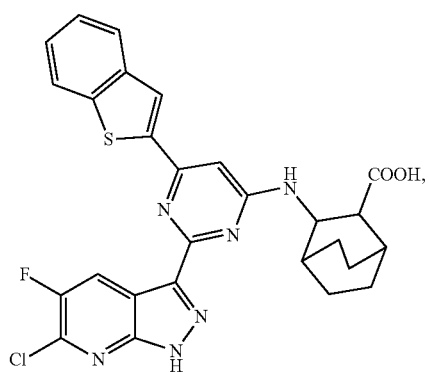
(78)
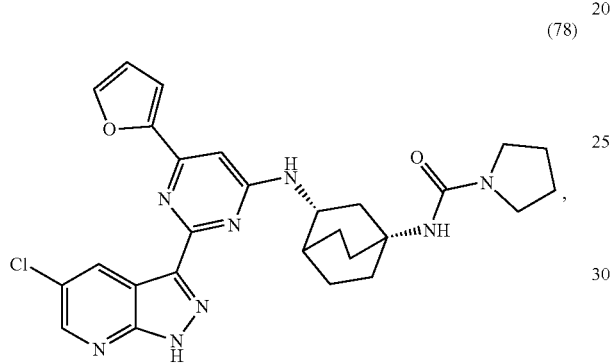
(79)
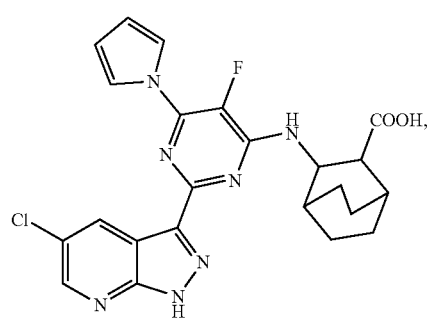
(80)
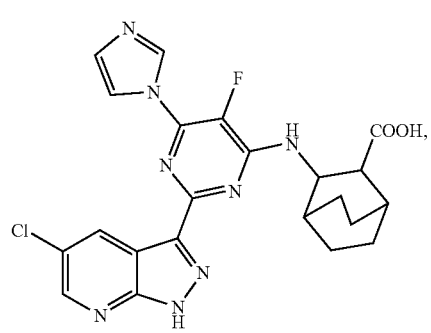
-continued
(81)
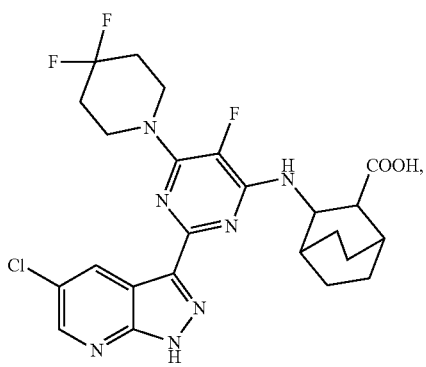
(82)
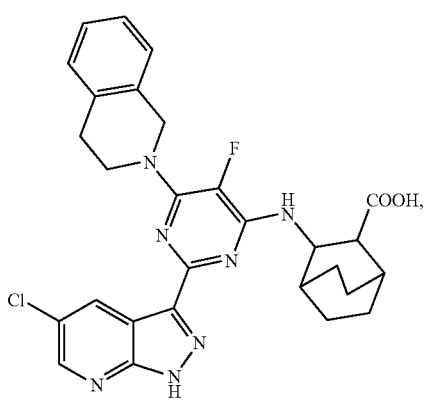
(83)
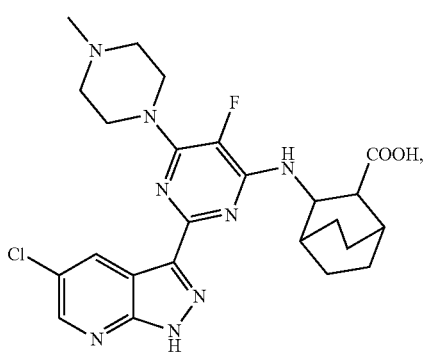
(84)
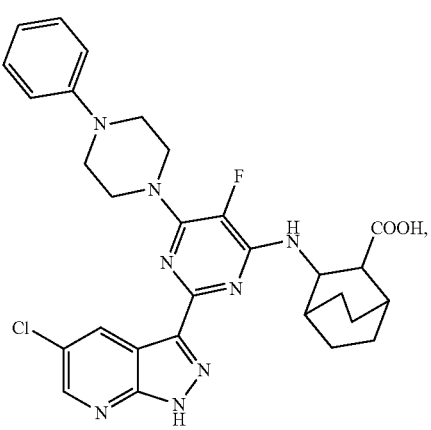

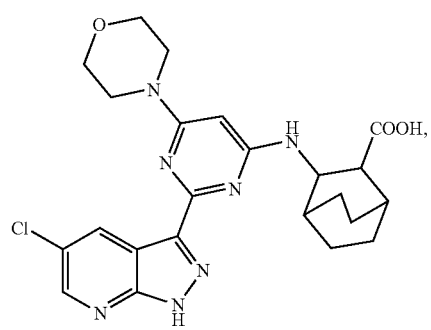
(85)
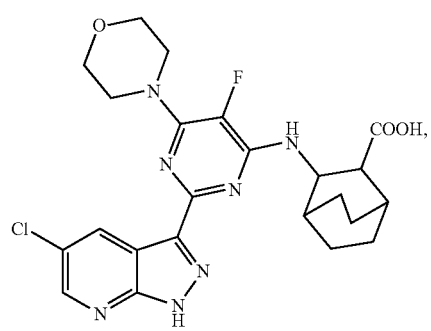
(86)
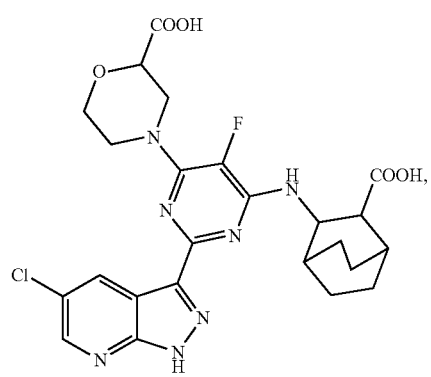
(87)
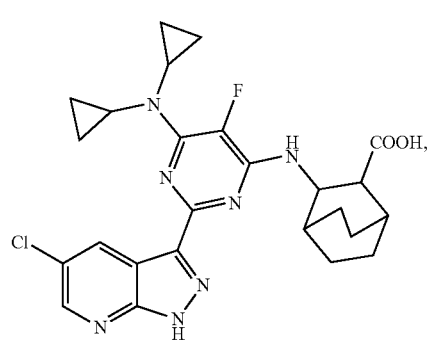
(88)
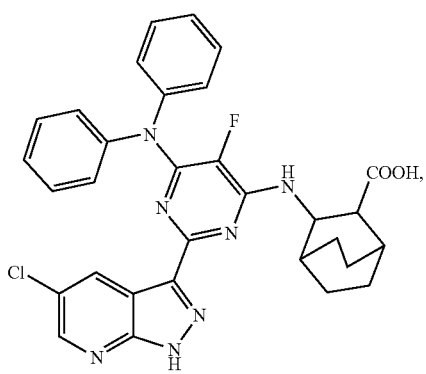
(89)
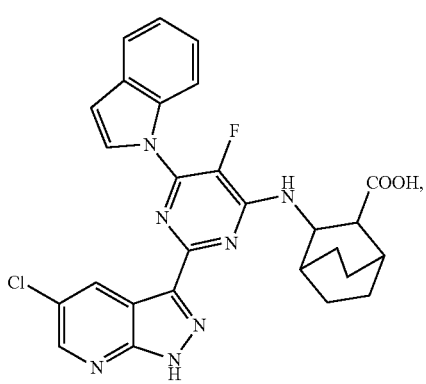
(90)
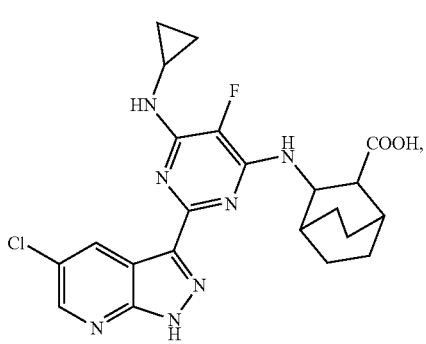
(91)
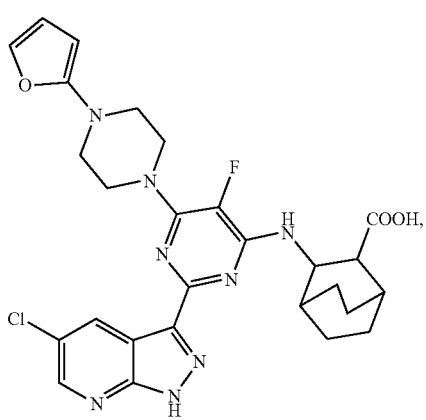
(92)

(93) 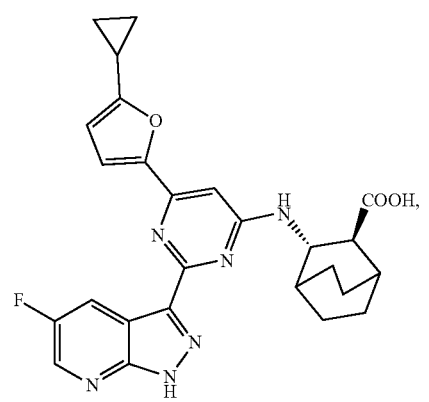
(94) 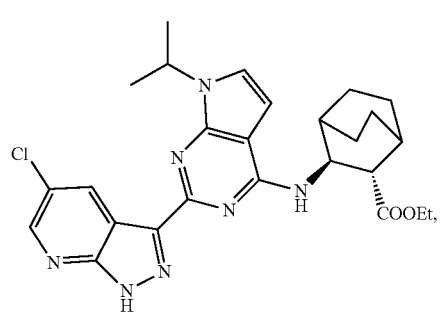
(95) 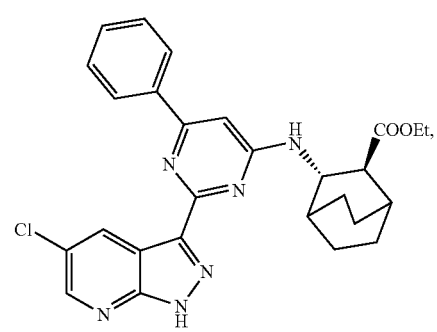
(95) 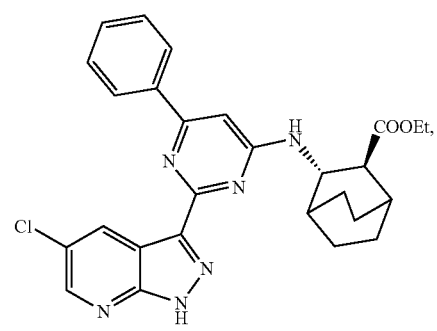
(97) 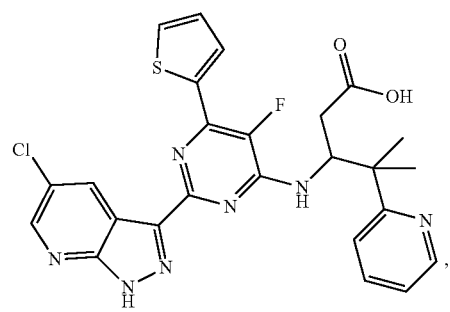
(98) 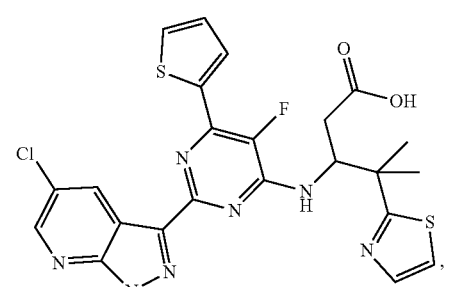
(99) 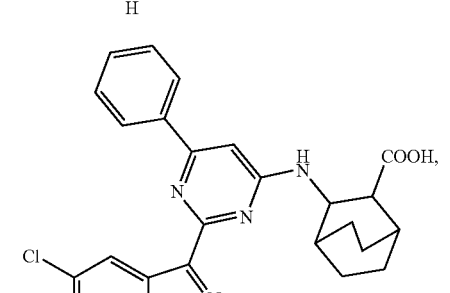
(100) 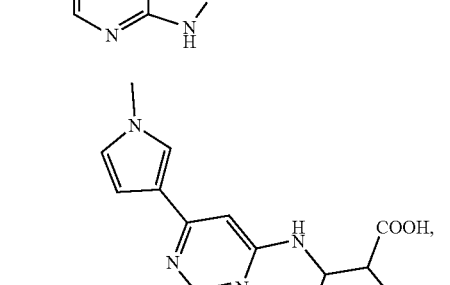
(101) 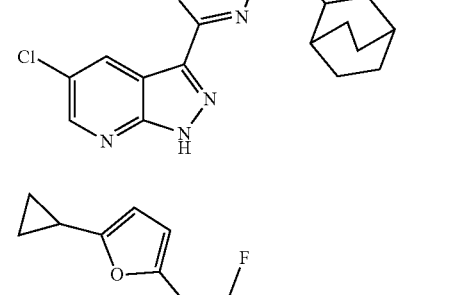

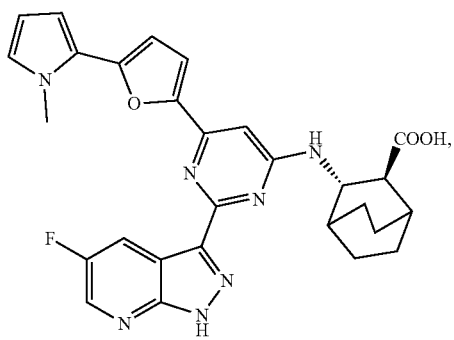
(102)

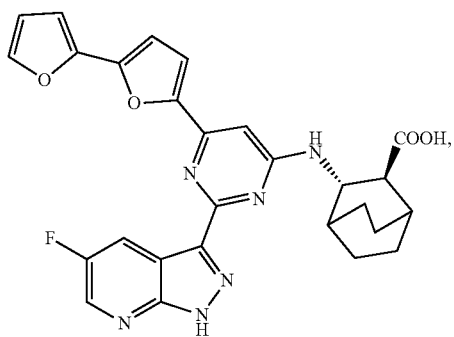
(103)

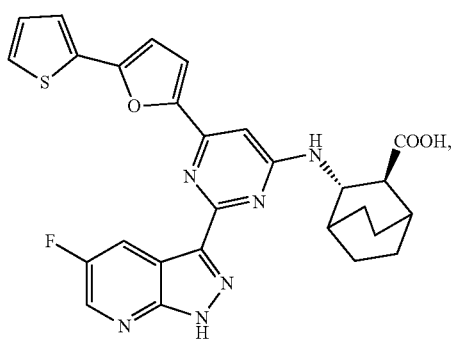
(104)

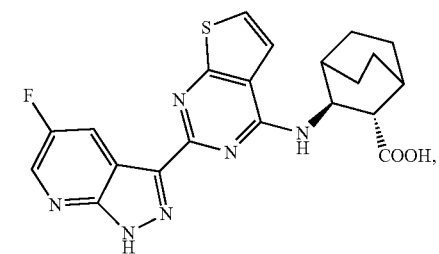
(105)

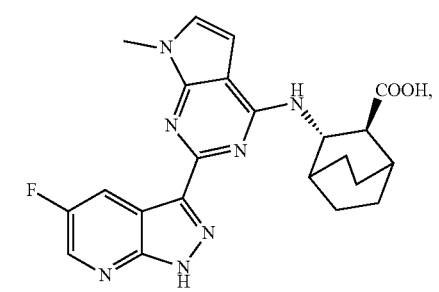
(106)

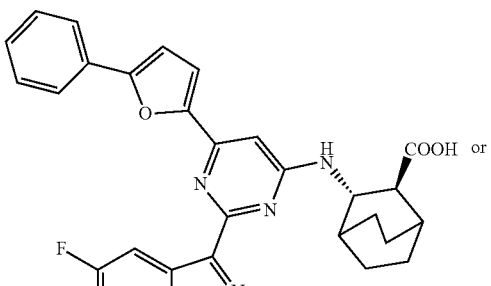
(107) or

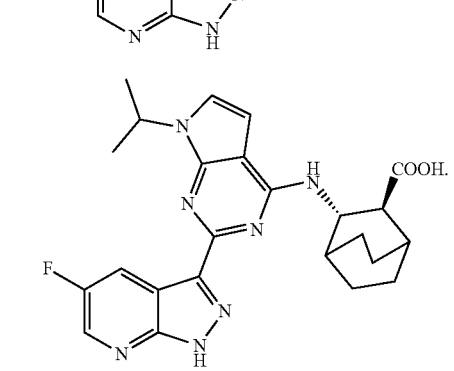
(108)

In another aspect, provided herein is a pharmaceutical composition comprising an effective amount of the compound disclosed herein.

In some embodiments, the pharmaceutical composition provided herein further comprises a pharmaceutically acceptable carrier, adjuvant, vehicle or a combination thereof.

In some embodiments, the pharmaceutical composition provided herein further comprises one or more other therapeutic agents.

In other embodiments, the other therapeutic agent disclosed herein is an anti-influenza virus agent or anti-influenza virus vaccine.

In other embodiments, the pharmaceutical composition is in the form of a liquid, a solid, a semi-solid, a gel or a spray.

In other embodiments, the pharmaceutical composition, wherein the other therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no. 1422050-75-6, JNJ-872, S-033188, an influenza vaccine (FluMist Quadrivalent®, Fluarix® Quadrivalent, Fluzone® Quadrivalent, Flucelvax® or FluBlok®) or a combination thereof.

In another aspect, provided herein is use of the compound or the pharmaceutical composition disclosed herein in the manufacture of a medicament for preventing, managing, treating or lessening a disorder or disease caused by virus infection in a patient.

In some embodiments, the virus infection disclosed herein is an influenza virus infection.

In some embodiments, the influenza virus is H1N1 A/Weiss/43.

In another aspect, provided herein is use of the compound or the pharmaceutical composition disclosed herein in the manufacture of a medicament for inhibiting virus.

In some embodiments, inhibiting virus is realized by inhibiting virus RNA polymerase In some embodiments, the virus is influenza virus.

In some embodiments, the influenza virus is H1N1 A/Weiss/43.

In some embodiments, the salt is a pharmaceutically acceptable salt. The phrase "pharmaceutically acceptable" refers to that the substance or composition must be chemically and/or toxicologically compatible with the other ingredients comprising a formulation, and/or the mammal being treated therewith.

The compound of the invention also embraces the salts thereof, and the salts are not necessarily pharmaceutically acceptable salts, and which may be useful as intermediates for preparing and/or purifying compounds of the invention and/or for separating enantiomers of compounds of the invention.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulfonate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, subsalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a basic or acidic moiety, by conventional chemical methods. Generally, such salts can be prepared by reaction free acid forms of these compounds with a stoichiometric amount of the appropriate base (such as Na, Ca, Mg, or K hydroxide, carbonate, bicarbonate or the like), or by reaction free base forms of these compounds with a stoichiometric amount of the appropriate acid. Such reactions are typically carried out in water or in an organic solvent, or in a mixture of the two. Generally, use of non-aqueous media like ethyl ether, ethyl acetate, ethanol, isopropanol, or acetonitrile is desirable, where practicable. Lists of additional suitable salts can be found, e.g., in "*Remington's Pharmaceutical Sciences*", 20th ed., Mack Publishing Company, Easton, Pa., (1985); and in "*Handbook of Pharmaceutical Salts: Properties, Selection, and Use*" by Stahl and Wermuth (Wiley-VCH, Weinheim, Germany, 2002).

Furthermore, the compounds disclosed herein, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms.

Any formula given herein is also intended to represent isotopically unenriched forms as well as isotopically enriched forms of the compounds. Isotopically enriched compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, sulfur, fluorine, and chlorine, such as $^{2}H$, $^{3}H$, $^{11}C$, $^{13}C$, $^{14}C$, $^{15}N$, $^{18}F$, $^{31}P$, $^{32}P$, $^{36}S$, $^{37}Cl$, $^{125}I$, respectively.

In another aspect, the compounds of the invention include isotopically enriched compounds as defined herein, for example those into which radioactive isotopes, such as $^{3}H$, $^{14}C$ and $^{18}F$, or those into which non-radioactive isotopes, such as $^{2}H$ and $^{13}C$ are present. Such isotopically enriched compounds are useful in metabolic studies (with $^{14}C$), reaction kinetic studies (with, for example $^{2}H$ or $^{3}H$), detection or imaging techniques, such as positron emission tomography (PET) or single-photon emission computed tomography (SPECT) including drug or substrate tissue distribution assays, or in radioactive treatment of patients. In particular, an $^{18}F$-enriched compound may be particularly desirable for PET or SPECT studies. Isotopically-enriched compounds of Formula (I) can generally be prepared by conventional techniques known to those skilled in the art or by processes analogous to those described in the accompanying examples and preparations using an appropriate isotopically-labeled reagent in place of the non-labeled reagent previously employed.

Further, substitution with heavier isotopes, particularly deuterium (i.e., $^{2}H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound of Formula (I). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Pharmaceutically acceptable solvates in accordance with the invention include those wherein the solvent of crystallization may be isotopically substituted, e.g. $D_2O$, acetone-$d_6$, DMSO-$d_6$.

Pharmaceutical Composition of the Compound of the Invention and Preparations and Administration The invention provides a pharmaceutical composition containing a compound of the invention or a stereoisomer thereof, racemic mixture or non-racemic mixture of the stereoisomer thereof. In one embodiment, the pharmaceutical composition further comprises at least one pharmaceutically acceptable carrier, diluent, adjuvant or excipient, and optionally other treating and/or preventing ingredients. In one embodiment, the pharmaceutical composition comprises an effective amount of at least one pharmaceutically acceptable carrier, diluent, adjuvant or vehicle.

A pharmaceutically acceptable carrier may contain inert ingredients which do not unduly inhibit the biological activity of the compound(s) described herein. The pharmaceutically acceptable carriers should be biocompatible, i.e., non-toxic, non-inflammatory, non-immunogenic and devoid of other undesired reactions upon the administration to a subject. Standard pharmaceutical formulation techniques can be employed.

As described above, the pharmaceutically acceptable compositions disclosed herein further comprise a pharmaceutically acceptable carrier, an adjuvant, or a vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. *Remington: The Science and Practice of Pharmacy,* 21st edition, 2005, ed. D. B. Troy, Lippincott Williams & Wilkins, Philadelphia, and Encyclopedia of Pharmaceutical Technology, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium incompatible with the compounds disclosed herein, such as by producing any undesirable biological effect or otherwise interacting in a deleterious manner with any other components of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, methyl cellulose, hydroxypropyl methyl cellulose, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compounds or pharmaceutically acceptable compositions can be administered to humans and other animals orally, rectally, parenterally, intracisternally, intravaginally, intraperitoneally, topically (as by powders, ointments or drops), bucally, as an oral or nasal spray, or the like, depending on the severity of the infection being treated.

Liquid formulations for oral administration include, but are not limited to, pharmaceutically acceptable emulsions, micro-emulsion, solution, suspension, syrup and elixir. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Addition to inert diluents, the oral compositions can also contain adjuvants such as wetting agents, emulsifiers or suspending agent, sweeteners, flavorings and fragrances.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are specifically suppositories which can be prepared by mixing the compounds described herein with suitable non-irritating excipients or carriers such as cocoa butter, polyethylene glycol or a suppository wax which are solid at ambient temperature but liquid at body temperature and therefore melt in the rectum or vaginal cavity and release the active compound.

The solid dosage forms for oral administration include capsules, tablets, pills, powders and granules. In such solid dosage forms, the active compounds are mixed with at least one pharmaceutically acceptable inert excipients or carrier, such as sodium citrate or dicalcium phosphate and/or (a) fillers or swelling agents such as starch, lactose, sucrose, glucose, mannitol and silicic acid; (b) adhesives such as carboxymethylcellulose, alginates, gelatin, polyethylene pyrrole ketone, sucrose and gum arabic; (c) moisturizing agents such as glycerol; (d) disintegrating agents such as agar, calcium carbonate, potato starch or tapioca starch, alginic acid, certain silicates and sodium carbonate; (e) blocker solution, such as paraffin; (f) absorption promoter such as quaternary ammonium compounds; (g) wetting agents such as cetyl alcohol and glycerol monostearate; (h) absorbents such as kaolin and bentonite, (i) lubricants such as talc, calcium stearate, magnesium stearate, solid polyethylene glycol, laurylsodium sulfate, and mixtures thereof. In the case of capsules, tablets and pills, the pharmaceutical compositions may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, controlled release coatings and other coatings well known in the pharmaceutical formulating art. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the pharmaceutical compositions may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions described herein may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Specifically, the compositions are administered orally, intraperitoneally or intravenously. Specifically, the compositions are administered orally, intraperitoneally or intravenously.

Sterile injectable forms of the compositions described herein may be aqueous or oleaginous suspension. These suspensions may be formulated according to techniques known in the art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil can be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions described herein may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions described herein may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions described herein may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, specifically, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The compounds for use in the methods of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

Use of the Compounds and Pharmaceutical Compositions

The compounds and pharmaceutical compositions provided herein can be used in the manufacture of medicaments for preventing, treating or lessening a disorder or disease caused by virus infection in a patient. In some embodiment, the virus infection is influenza virus infection.

Also provided herein are the uses of the compounds and pharmaceutical compositions described above in the manufacture of medicaments which are inhibitors of influenza virus RNA polymerase.

Provided herein is a method of treating, preventing or delaying the infections caused by viruses, and wherein the method comprises administering to the subject in need of treatment a therapeutically effective amount of the compound or the pharmaceutical composition described herein. Wherein the virus is an influenza virus. And, the compounds or pharmaceutical compositions thereof can be co-administered with other therapies or therapeutic agents. The co-administration can be performed simultaneously, sequentially, or in a certain time interval.

Doses of the compound or pharmaceutical composition needed for implementing functions such as treating, preventing or delaying usually depend on the particular compound to be administered, patient, specific disease or disorder and severity thereof, route and frequency of administration and so on, and need to be determined by the attending doctor in accordance with specific conditions. For example, when the compound or pharmaceutical composition of the present invention is administrated intravenously, the administration may be once a week or even longer intervals.

As described above, the present invention provides a novel class of compounds, and wherein the compounds can be used as inhibitors of the influenza virus RNA polymerase. The compounds of the invention are suitable for preparing medicaments as various dosage forms, which can be used for treating seasonal flu, avian flu, swine flu as well as tamiflu-resistant influenza virus mutants.

Besides being useful for human treatment, these compounds are also useful for veterinary treatment of animals such as companion animals, exotic animals and farm animals. In other embodiments, the animals disclosed herein include horses, dogs, and cats. As used herein, the compounds disclosed herein include the pharmaceutically acceptable derivatives thereof.

General Synthetic Procedures

For the purpose of describing the invention, the following examples are listed. It should be understood that, the invention is not limited to these examples, and the present invention only provide the method to practice the invention.

Generally, the compounds disclosed herein may be prepared by methods described herein, wherein the substituents are as defined for Formula (I), except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua Reagent Chemical Factory Co. Ltd., Guangzhou Reagent Chemical Factory, Tianjin YuYu Fine Chemical Ltd., Tianjing Fuchen Chemical Reagent Factory, Wuhan XinHuayuan technology development co., LTD., Qingdao Tenglong Reagent Chemical Ltd., Qingdao Ocean Chemical Factory, Beijin Ouhe Technology Co., Ltd., Shanghai Topbiochem Technology Co., Ltd, and Accela ChemBio Co., Ltd.

Anhydrous THF, 1,4-dioxane, toluene, and ether were obtained by refluxing the solvent with sodium. Anhydrous $CH_2Cl_2$ and $CHCl_3$ were obtained by refluxing the solvent with CaH2. EtOAc, PE, hexane, N,N-dimethylacetamide and DMF were treated with anhydrous $Na_2SO_4$ prior use.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted using a silica gel column. Silica gel (300-400 mesh) was purchased from Qingdao Ocean Chemical Factory.

$^1$H NMR spectra were recorded with a Bruker 400 MHz or 600 MHz spectrometer using $CDCl_3$, DMSO-$d_6$, $CD_3OD$ or acetone-$d_6$ as solvent (reported in ppm), and using TMS (0 ppm) or chloroform (7.26 ppm) as the reference standard. When peak multiplicities were reported, the following abbreviations were used: s (singlet), d (doublet), t (triplet), m (multiplet), br (broadened), dd (doublet of doublets), and dt (doublet of triplets). Coupling constants J, when given, are reported in Hertz (Hz).

Low-resolution mass spectral (MS) data were determined on an Agilent 6120 Quadrupole HPLC-MS spectrometer equipped with an Agilent Zorbax SB-C18 (2.1×30 mm, 3.5 µm). The flow rate was 0.6 mL/min; the mobile phases consisted of a combination of A (0.1% formic acid in $CH_3CN$) and B (0.1% formic acid in $H_2O$) in gradient mode (5% to 95%), and an ESI source was used, the peak of HPLC was recorded with UV-Vis detection at 210/254 nm.

Purification of compound by preparative chromatography was implemented on Agilent 1260 Series high performance liquid chromatography (Pre-HPLC) or Calesep Pump 250 Series high performance liquid chromatography (Pre-HPLC) with UV detection at 210/254 nm (NOVASEP, 50/80 mm. DAC).

The following abbreviations are used throughout the specification:
AcOH, HAc, HOAc, $CH_3COOH$ acetic acid
AcOK, KOAc, $CH_3COOK$ potassium acetate
BnOH phenylcarbinol
$Bu_4NF$ tetrabutylammonium fluoride
BOC, Boc tert-butoxycarbonyl
$(Boc)_2O$ di-tert-butyl dicarbonate ester
n-BuOH n-butyl alcohol
$CHCl_3$ chloroformCDCl3 chloroform-d
$CD_3OD$ deuterated methyl alcohol
DCM, $CH_2Cl_2$ dichloromethane
$CH_3CN$, MeCN acetonitrile
$CH_3Cl$ chloromethane
$CH_3I$ iodomethane
$CH_2SO_2Cl$, MsCl methylsufonyl chloride
Cbz benzyloxycarbonyl
DIAD diisopropyl azodicarboxylate
DIEA, DIPEA, $iPr_2Net$ N,N-diisopropylethylamine
DMF N,N-dimethylformamide, dimethylformamide
DME dimethyl ether
DMAP 4-dimethylaminopyridine
DMSO dimethylsulfoxide
DMSO-$d_6$ dimethyl sulfoxide-$d_6$
DPPA diphenylphosphoryl azide
$EC_{50}$ half effective concentration
EA, EtOAc ethyl acetate
$Et_3N$, TEA triethylamine
$Et_2O$ ethyl ether
EtOH ethyl alcohol
$Et_3SiH$ triethyl silicane
$Et_3SiCl$ triethylchlorosilicane
g gram
h hour, hours
$H_2$ hydrogen
$H_2O$ water
HCl hydrogen chloride
Hexane n-hexane
$H_2O_2$ hydrogen peroxide
$H_3PO_4$ phosphoric acid
$H_2SO_4$ sulfuric acid
$HNO_3$ nitric acid
HCOOK potassium formate
$HCOONH_4$ ammonium formate
HPLC high performance liquid chromatography
HPTLC high performance thin layer chromatography
HRMS high-resolution mass spectrometry
$I_2$ iodine
Fe iron
2-MeTHF 2-methyltetrahydrofuran
LDA Lithium diisopropylamide
LiOH Lithium hydroxide
$MgSO_4$ magnesium sulfate
$CH_3OH$, MeOH methanol
MeI, $CH_3I$ iodomethane
mL, ml milliliter
min minute, minutes
M mol/L
$N_2$ nitrogen
$NH_3$ ammonia
NMP N-methylprrolidone
$NaHCO_3$ sodium bicarbonate
$NaBH_4$ sodium borohydride
$NaBH_3CN$ sodium cyanoborohydride
NaOMe, $NaOCH_3$, $CH_3ONa$ sodium methoxide
NaOH sodium hydroxide
NaCl sodium chloride
$NaH_2PO_4$ sodium dihydrogen phosphate
NaH sodium hydride
NaI sodium iodide
$Na_2SO_4$ sodium sulfate
$Na_2S_2O_3$ sodium thiosulfate
NBS N-bromosuccinimide
NFSI N-fluorobenzenesulfonimide
NIS N-iodosuccinimide
NCS N-chlorosuccinimide
$NH_4Cl$ ammonium chloride
$NH_2OH$—HCl hydroxylamine hydrochloride
psi pound per square inch Pd/C Palladium on activated carbon
Pd(OAc)$_2$ Palladium diacetate
Pd(OH)$_2$ palladium hydroxide
Pd(PPh$_3$)$_4$ tetrakis(triphenylphosphine)palladium
Pd(PPh$_3$)$_2$C$_2$ bis(triphenylphosphine)palladium(II) chloride
Pd(dppf)Cl$_2$, PdCl$_2$(dppf) [1,1'-bis(diphenylphosphino)ferrocene]dichloropalladium(II)
Pd(dppf)Cl$_2$.CH$_2$C$_2$ 1,1'-bis(diphenylphosphino)ferrocene-palladium(II)dichloride dichloromethane complex
Pd$_2$(dba)$_3$ tris(dibenzylideneacetone)dipalladium
P(t-Bu)$_3$ tri-tert-butylphosphine
Pd(dtbpf)Cl$_2$ 1,1'-bis (di-t-butylphosphino)ferrocene palladium dichloride
PE petroleum ether (60-90° C.)
POCl$_3$ phosphorus oxychloride
Ph$_3$CCl triphenylchloromethane
K$_2$CO$_3$ potassium carbonate
K$_3$PO$_4$ potassium phosphate
KOH potassium hydroxide
RT, rt, r.t. room temperature
Rt retention time
SOCl$_2$ thionyl chloride
SI therapeutic index
t-BuOK potassium tert-butoxide
THF tetrahydrofuran
TFA trifluoroacetic acid
TFAA trifluoroacetic anhydride
TBAI tetrabutylammonium iodide
TBS tris(hydroxymethyl)aminomethane saline buffer
TsCl tosyl chloride
Ts Tosyl
ZnCl$_2$-TMEDA dichloro(N,N,N,N-tetramethylethylenediamine)zinc
X-Phos 2-(dicyclohexylphosphino)-2',4',6'-tri-i-propyl-1,1'-biphenyl
Vss apparent volume of distribution
Zn zinc
μL microliter The following schemes list the synthetic steps of the compounds of the invention, wherein R$^1$, R$^2$, R$^3$, R$^4$, R$^5$, R', q and A are as defined herein.

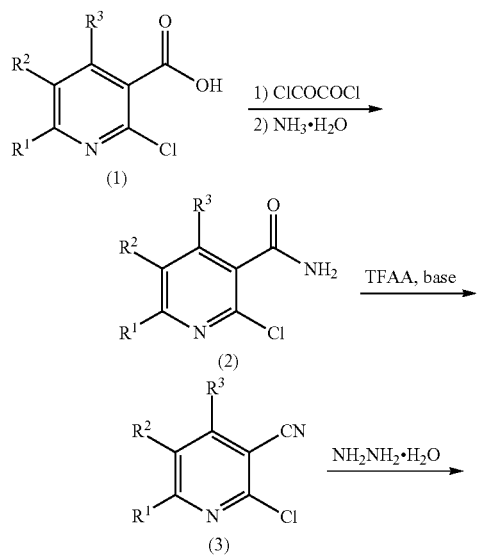

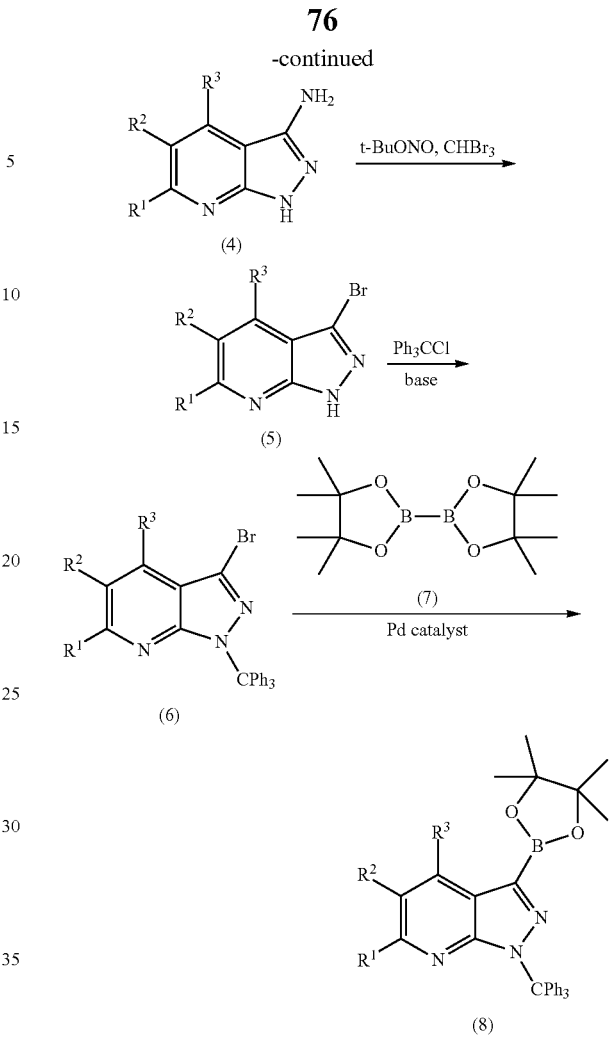

The intermediate having Formula (8) can be prepared by the process illustrated in scheme 1. Firstly, compound (1) can react with oxalyl chloride to give a product which can react directly with strong aqua ammonia to give amide compound (2). Compound (2) can react in the presence of trifluoroacetic anhydride (TFAA) and a base (such as triethylamine) to give compound (3). Compound (3) can react with hydrazine hydrate to give compound (4). Then, compound (4) can react with tert-butyl nitrite (t-BuONO) and bromoform to give compound (5). Compound (5) can react with Ph$_3$CCl under an alkaline condition to give compound (6). Lastly, compound (6) can react with compound (7) undergoing coupling reaction to give intermediate (8).

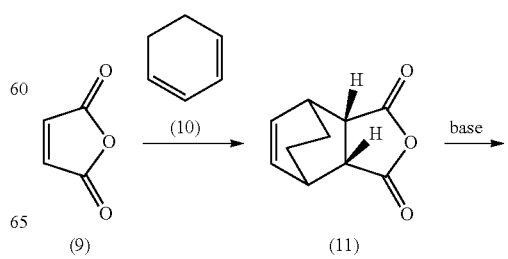

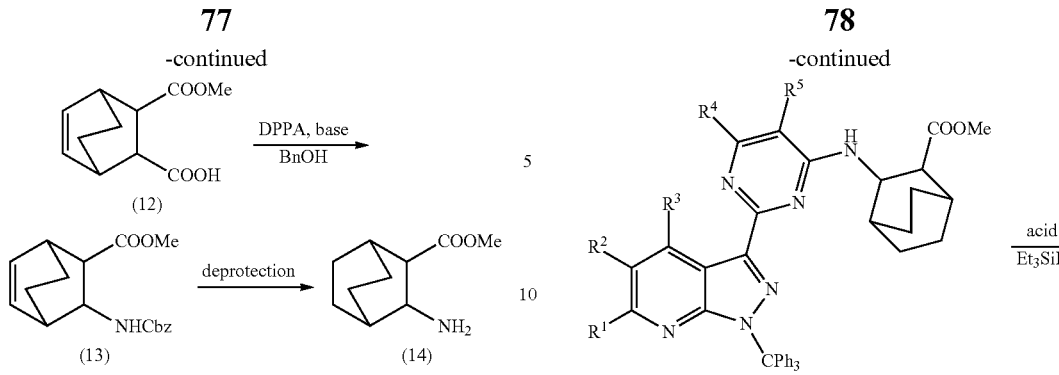

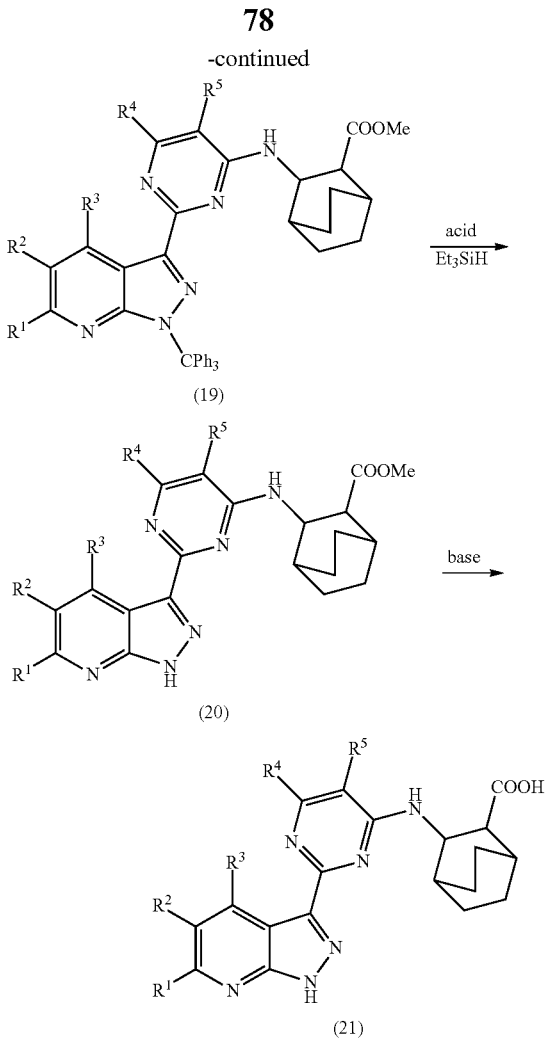

The intermediate having Formula (14) can be prepared by the process illustrated in scheme 2. Compound (9) can react with compound (10) in the absence of light to give compound (11). Then compound (11) can undergo ring-opening reaction in the presence of a base (such as sodium methoxide, etc.) to give compound (12). Then, compound (12) with DPPA and benzyl alcohol can undergo rearrangement reaction under an alkaline condition to give compound (13). Lastly, the amino-protecting group of compound (13) can be removed under a reduction condition to give compound (14).

Scheme 3

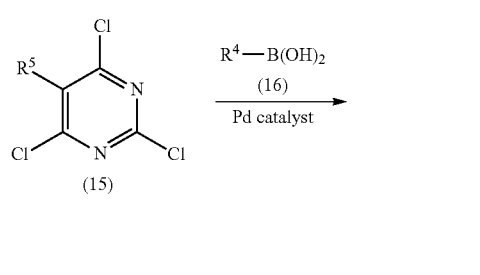

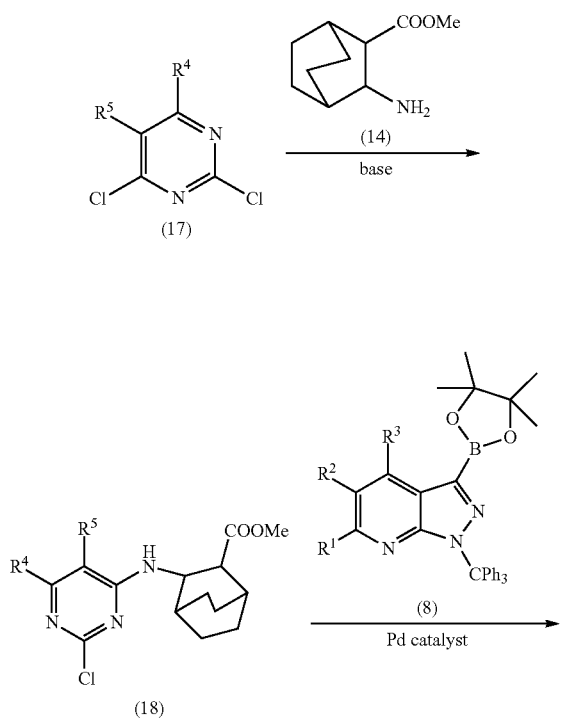

Compound having Formula (20) or Formula (21) can be prepared by the process illustrated in scheme 3. Firstly, compound (15) with a boric acid derivative (16) can undergo Suzuki coupling reaction to give compound (17). Then, compound (17) can react with compound under an alkaline condition to give compound (18). Nextly, compound (18) with compound (8) can undergo Suzuki coupling reaction in the presence of a Pd catalyst to give compound (19). The amino-protecting group of compound (19) can be removed in the presence of an acid and Et$_3$SiH to give compound (20). Lastly, the carboxy-protecting group of compound (20) can be removed in the presence of a base to give compound (21).

Scheme 4

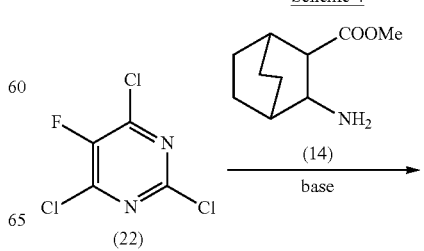

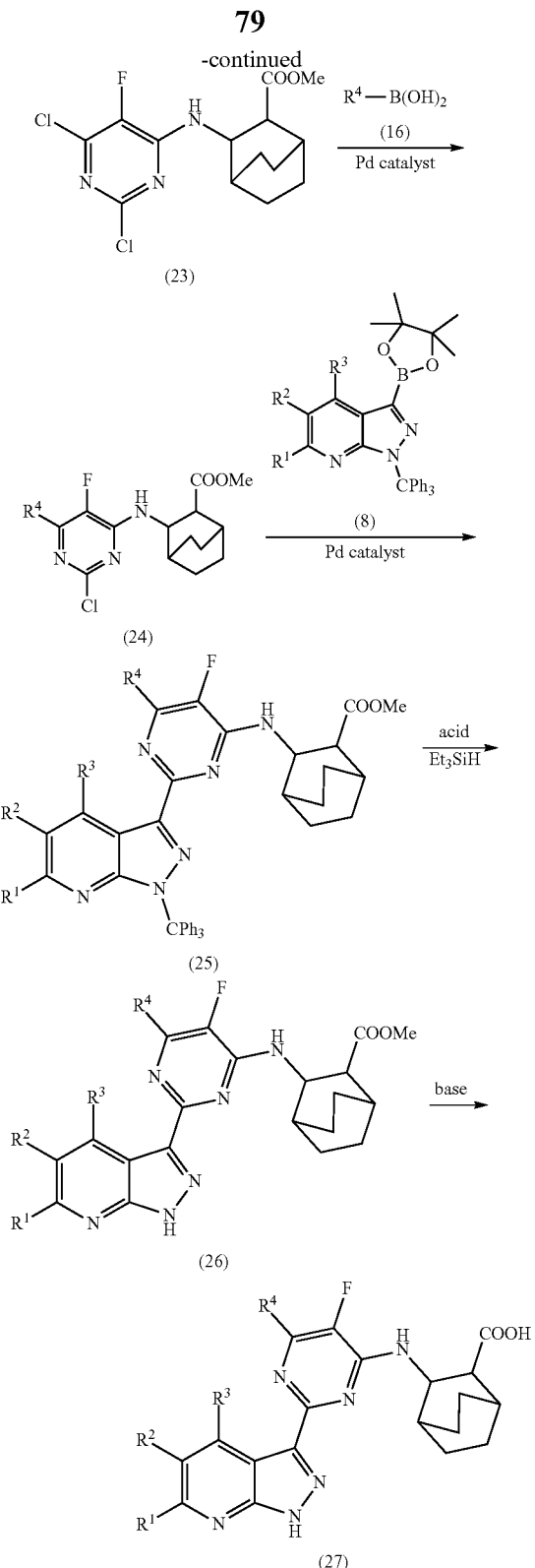

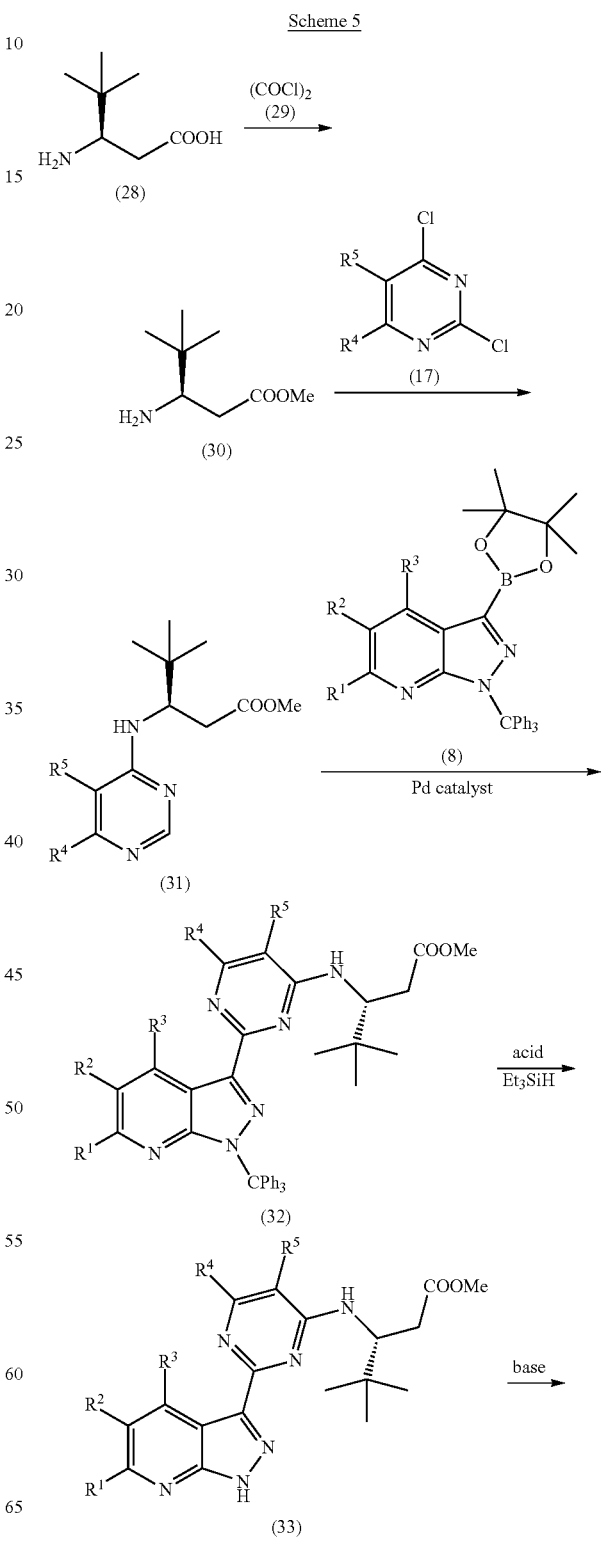

tion in the presence of a Pd catalyst to give compound (25). The amino-protecting group of compound (25) can be removed in the presence of an acid and Et₃SiH to give compound (26). Lastly, the carboxy-protecting group of compound can be removed in the presence of a base to give compound (27).

Compound having Formula (26) or Formula (27) can be prepared by the process illustrated in scheme 4. Firstly, Compound (22) can react with compound (14) under an alkaline condition to give compound (23). Then, compound (23) with a boric acid derivative (16) can undergo Suzuki coupling reaction to give compound (24). Nextly, compound (24) with compound (8) can undergo Suzuki coupling reac-

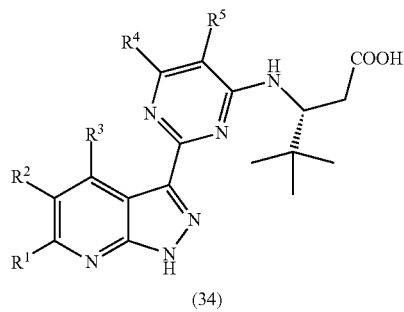

(34)

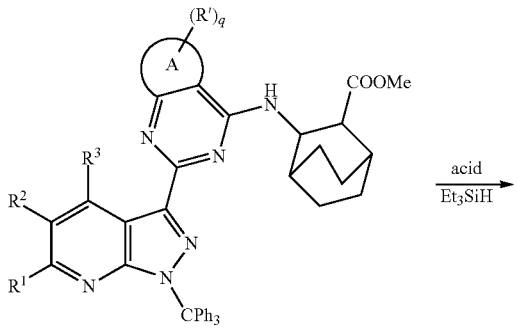

(37)

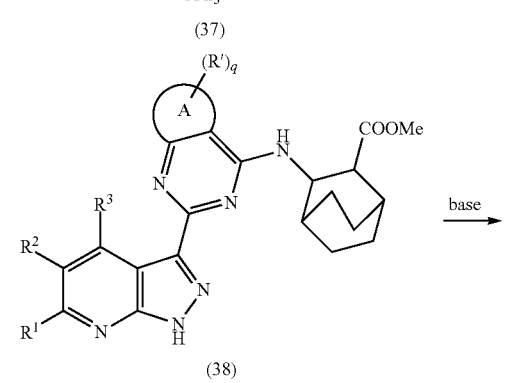

(38)

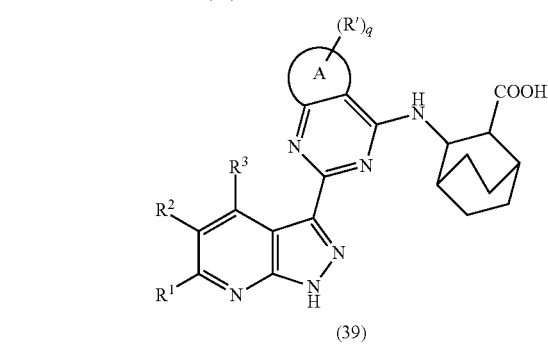

(39)

Compound having Formula (33) or Formula (34) can be prepared by the process illustrated in scheme 5. Firstly, Compound (28) can react with compound (29) to give compound (30). Then, compound (30) with compound (17) can undergo condensation reaction to give compound (31). Nextly, compound (31) with compound (8) can undergo Suzuki coupling reaction in the presence of a Pd catalyst to give compound (32). The amino-protecting group of compound (32) can be removed in the presence of an acid and $Et_3SiH$ to give compound (33). Lastly, the carboxy-protecting group of compound (33) can be removed in the presence of a base to give compound (34).

Scheme 6

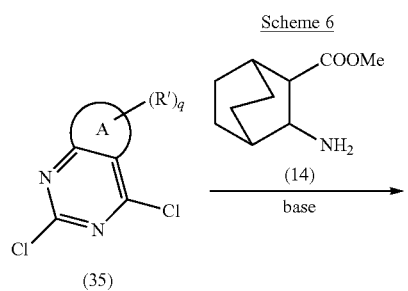

(35)

Compound having Formula (38) or Formula (39) can be prepared by the process illustrated in scheme 6. Firstly, compound (35) can react with compound (14) under an alkaline condition to give compound (3). Compound (36) with compound (8) can undergo Suzuki coupling reaction in the presence of a Pd catalyst to give compound (37). Then the amino-protecting group of compound (37) can be removed in the presence of an acid and $Et_3SiH$ to give compound (38). Lastly, the carboxy-protecting group of compound (38) can be removed in the presence of a base to give compound (39).

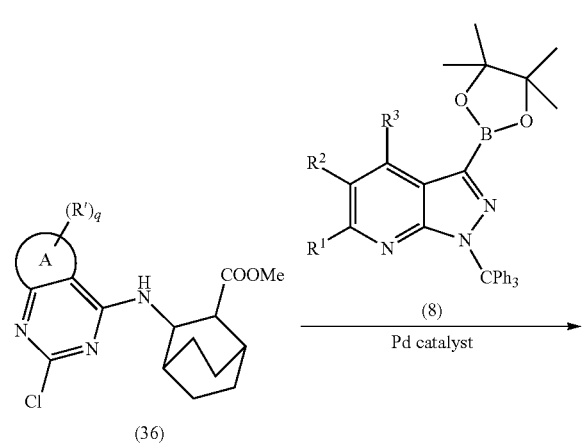

(36)

Scheme 7

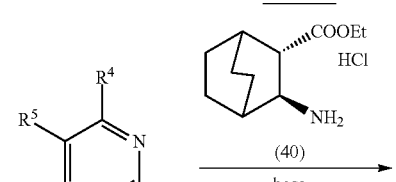

(17)

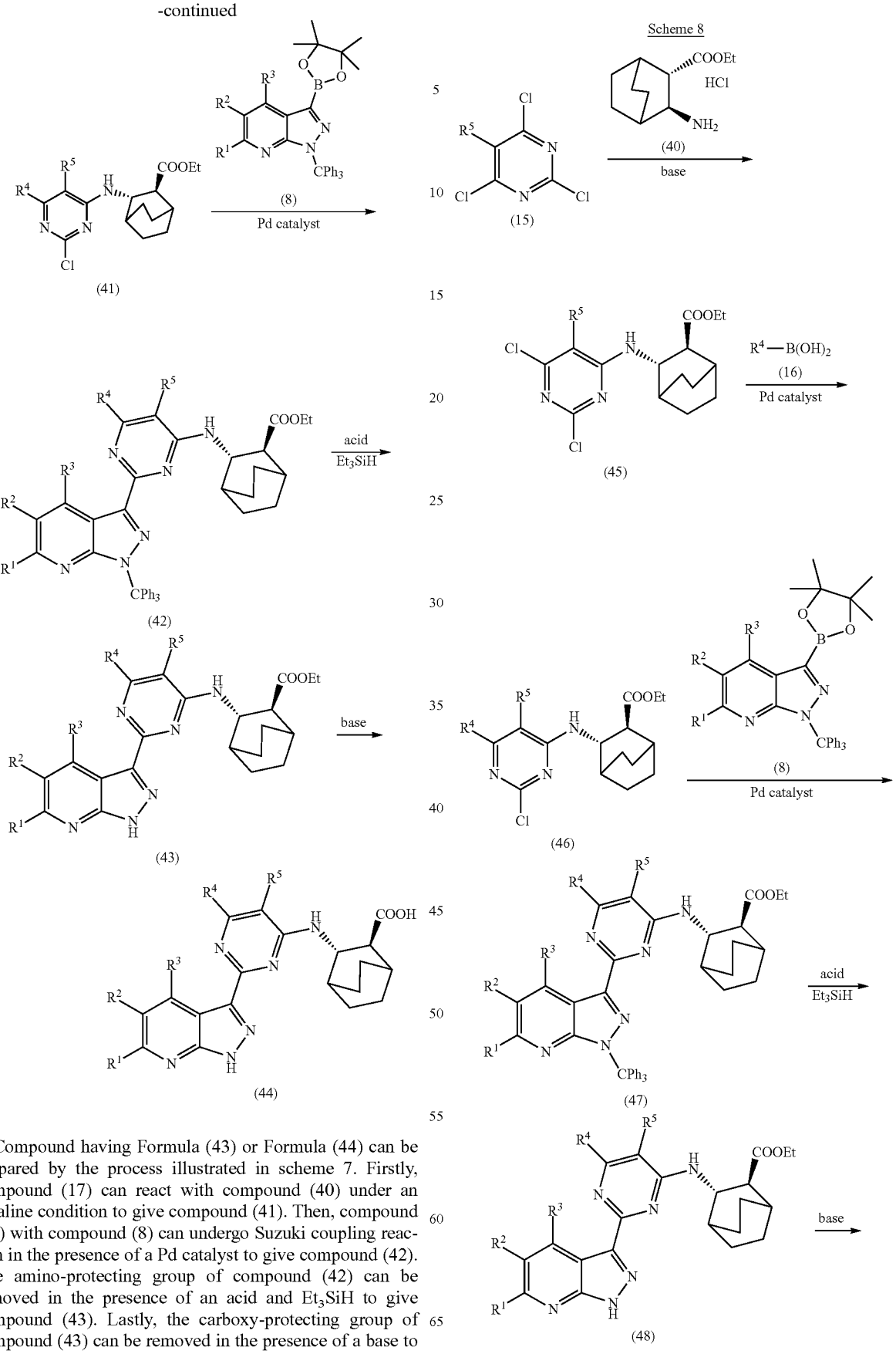

Compound having Formula (43) or Formula (44) can be prepared by the process illustrated in scheme 7. Firstly, compound (17) can react with compound (40) under an alkaline condition to give compound (41). Then, compound (41) with compound (8) can undergo Suzuki coupling reaction in the presence of a Pd catalyst to give compound (42). The amino-protecting group of compound (42) can be removed in the presence of an acid and $Et_3SiH$ to give compound (43). Lastly, the carboxy-protecting group of compound (43) can be removed in the presence of a base to give compound (39).

-continued

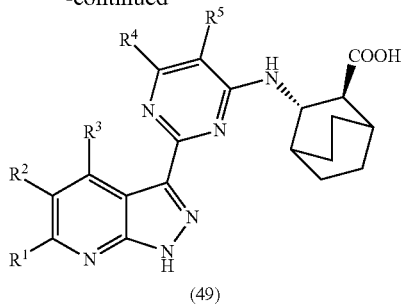

(49)

Compound having Formula (48) or Formula (49) can be prepared by the process illustrated in scheme 8. Firstly, compound (15) can react with compound (40) under an alkaline condition to give compound (45). Then, compound (45) with a boric acid derivative (16) can undergo Suzuki coupling reaction to give compound (46). Then compound (46) with compound can undergo Suzuki coupling reaction in the presence of a Pd catalyst to give compound (47). The amino-protecting group of compound (47) can be removed in the presence of an acid and Et$_3$SiH to give compound (48). Lastly, the carboxy-protecting group of compound (48) can be removed in the presence of a base to give compound (49).

Scheme 9

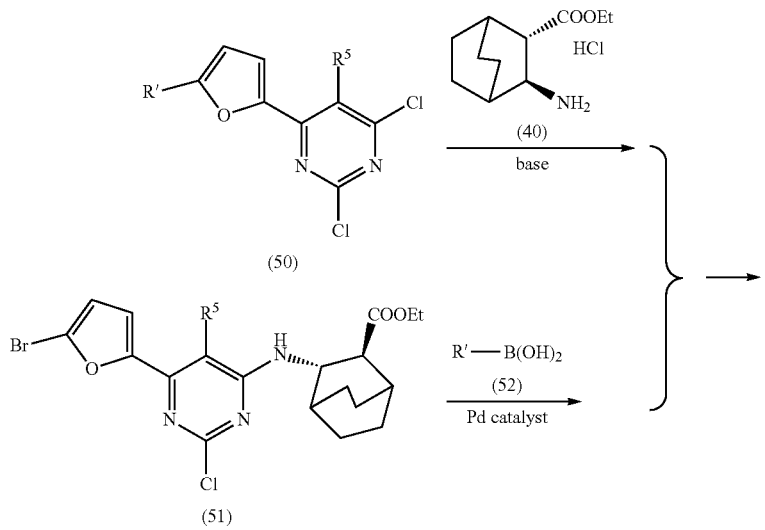

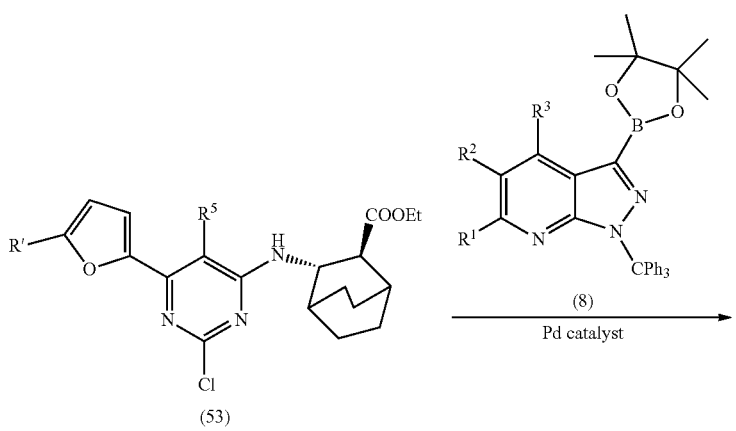

87

-continued

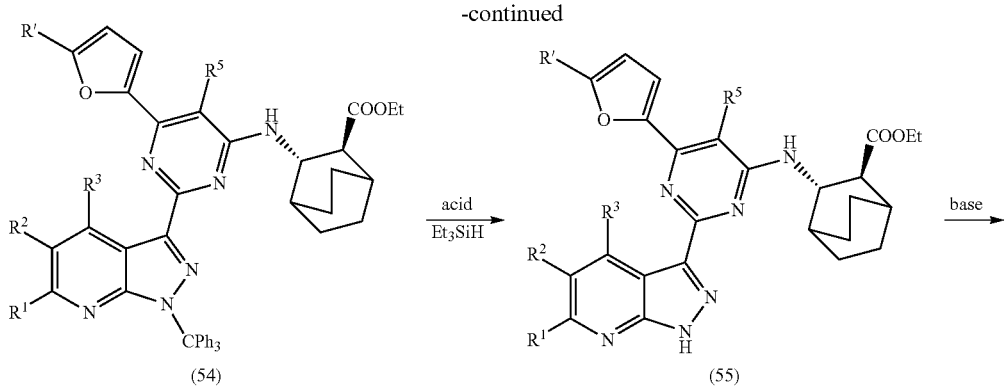

(54) → (55)

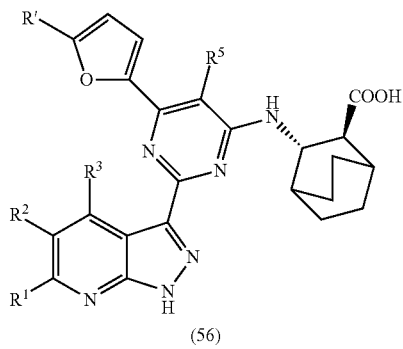

(56)

Compound having Formula (55) or Formula (56) can be prepared by the process illustrated in scheme 9. Firstly, compound (50) can react with compound (40) under an alkaline condition to give compound (5; or compound (5 with a boric acid derivative (52) can undergo Suzuki coupling reaction to give compound (53). Then, compound (53) with compound can undergo Suzuki coupling reaction in the presence of a Pd catalyst to give compound (54). The amino-protecting group of compound (54) can be removed in the presence of an acid and $Et_3SiH$ to give compound (55). Lastly, the carboxy-protecting group of compound (55) can be removed in the presence of a base to give compound (56).

Scheme 10

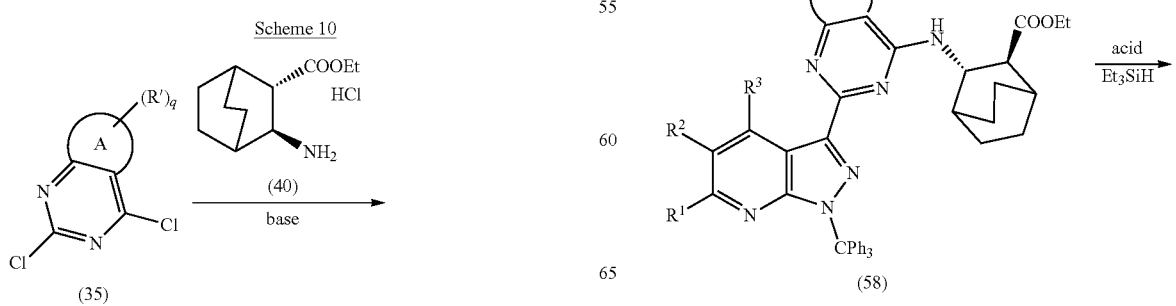

-continued

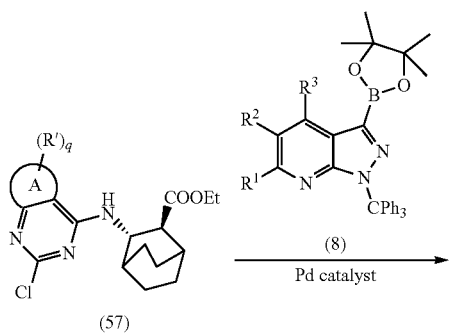

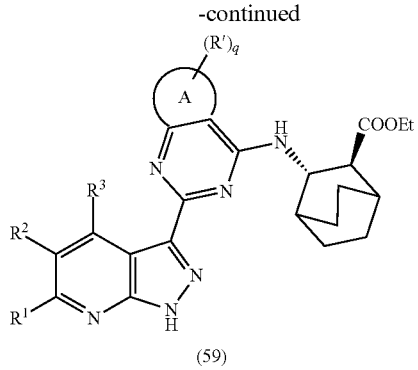

(59)

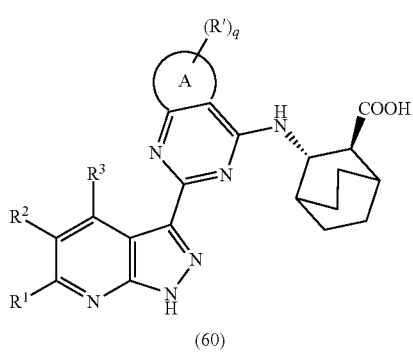

(60)

Compound having Formula (59) or Formula (60) can be prepared by the process illustrated in scheme 10. Firstly, compound (35) can react with compound (40) under an alkaline condition to give compound (57). Then, compound (with compound (8) can undergo Suzuki coupling reaction in the presence of a Pd catalyst to give compound (58). Nextly, the amino-protecting group of compound (58) can be removed in the presence of an acid and Et₃SiH to give compound (59). Lastly, the carboxy-protecting group of compound (59) can be removed in the presence of a base to give compound (60).

Scheme 11

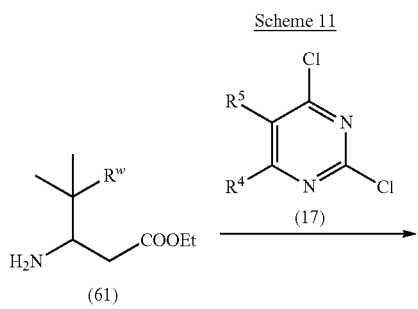

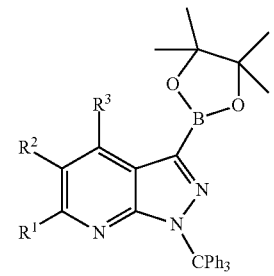

(62)

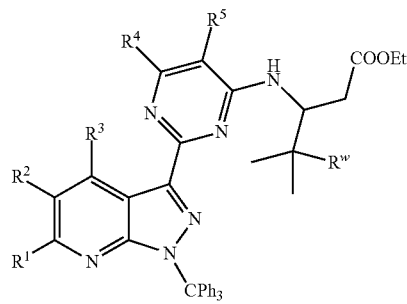

(63)

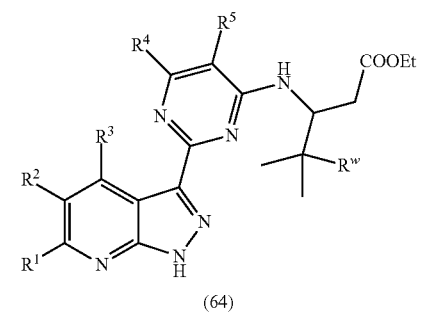

(64)

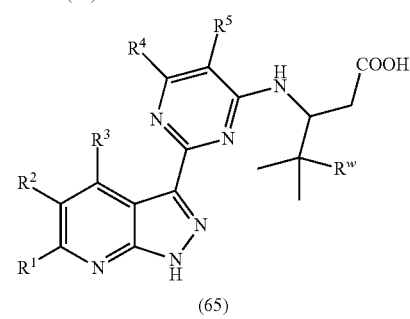

(65)

Compound having Formula (64) or Formula (65) can be prepared by the process illustrated in scheme 11. Firstly, compound (61) with compound (17) can undergo condensation reaction to give compound (62). Then, compound (with compound (8) can undergo Suzuki coupling reaction in the presence of a Pd catalyst to give compound (63). Nextly, the amino-protecting group of compound (63) can be removed in the presence of an acid and Et₃SiH to give compound (64). Lastly, the carboxy-protecting group of compound (64) can be removed in the presence of a base to give compound (65).

DESCRIPTION OF THE PREFERRED EMBODIMENTS

The following examples are used for illustrating the invention, but can not be construed to limit the scope of the invention.

Preparation Examples

Using parts of the compounds of the invention as examples, the preparations of the compounds of the present invention have been described in detail in the following examples.

Example 1: (+/−)-trans-3-((2-(5-chloro-1H-pyrazolo[3,4-b]pyridin-3-yl)-6-(furan-2-yl) pyrimidin-4-yl)amino)bicyclo[2.2.2]octane-2-carboxylic Acid

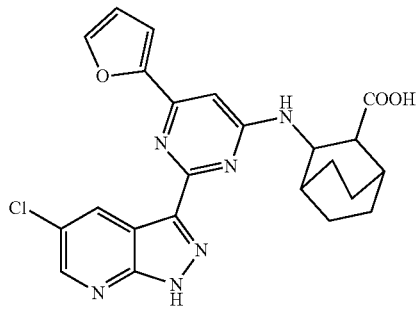 [SMILES: O=C(O)C1C2CCC(CC2)C1Nc1cc(-c2ccco2)nc(-c2n[nH]c3ncc(Cl)cc23)n1]

Step 1: meso-endo-tetrahydro-4,7-ethanoisobenzofuran-1,3-dione

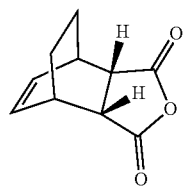

To a 2000 mL dried flask were added maleic anhydride (100 g, 1.02 mol) and chloroform (1000.0 mL) in turn, then the mixture was cooled to 0° C., and 1,3-cyclohexadiene (112.5 mL, 1.12 mol) was added dropwise. After the addition, the mixture was warmed to rt, and stirred overnight in the absence of light. After the reaction was completed, the mixture was concentrated in vacuo to remove the solvent. To the residue was added methanol (700.0 mL), and the resulting mixture was heated to 50° C. and stirred for 10 min. then cooled to 0° C. and stirred for 30 min. The mixture was filtered by suction, and the filter cake was dried in vacuo at 45° C. to give the title compound as a white solid (147 g, 81%).

MS (ESI, pos. ion) m/z: 179.1 [M+H]$^+$;

$^1$H NMR (400 MHz, DMSO-d$_6$) δ (ppm): 6.28 (dd, J=4.2, 3.4 Hz, 2H), 3.29 (s, 2H), 3.04 (s, 2H), 1.61 (d, J=7.9 Hz, 2H), 1.22 (d, J=7.6 Hz, 2H).

Step 2: (+/−)-trans-3-(methoxycarbonyl)bicyclo[2.2.2]oct-5-ene-2-carboxylic Acid

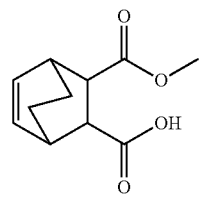

To a dried flask was added meso-endo-tetrahydro-4,7-ethanoisobenzofuran-1,3-dione (33.50 g, 188.01 mmol), then a solution of sodium methoxide in methanol (5 M, 300.8 mL) was added dropwise at 0° C. After the addition, the mixture was warmed to rt and stirred for 4 days, then concentrated in vacuo to remove part of the methanol (about 120 mL). The residue was added slowly into 0° C. aqueous hydrochloric acid solution (277 mL, 18%), and there was a white solid precipitated out. The mixture was concentrated in vacuo to remove methanol, and the residue was stirred at 0° C. for 30 min, then filtered by suction. The filter cake was washed with water three times and dried in vacuo to give the title compound as a white solid (37.19 g, 94%).

MS (ESI, ne.g. ion) m/z: 209.0 [M−H]$^-$;

$^1$H NMR (600 MHz, DMSO-d$_6$) δ (ppm): 12.28 (s, 1H), 6.34 (s, 1H), 6.17 (s, 1H), 3.65 (s, 3H), 2.94 (s, 1H), 2.91 (d, J=4.4 Hz, 1H), 2.86 (d, J=2.4 Hz, 1H), 2.72 (s, 1H), 1.48-1.58 (m, 1H), 1.34-1.44 (m, 1H), 1.26-1.16 (m, 1H), 1.09-0.99 (m, 1H).

Step 3: (+/−)-trans-methyl 3-(((benzyloxy)carbonyl)amino)bicyclo[2.2.2]oct-5-ene-2-carboxylate

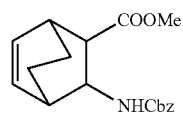

A solution of (+/−)-trans-3-(methoxycarbonyl)bicyclo[2.2.2]oct-5-ene-2-carboxylic acid (6.0 g, 29 mmol) in toluene (50 mL) was degassed and filled with nitrogen for three times, then diphenyl azidophosphate (7.0 mL, 32 mmol) and triethylamine (4.0 mL, 29 mmol) were added in turn by syringe. The mixture was heated to 90° C. and stirred for 2 hours, then phenylcarbinol (3.0 mL, 29 mmol) was added dropwise by syringe. The mixture was stirred for further 3 days maintaining at this temperature. The reaction mixture was cooled to rt, and ethyl acetate (60 mL) was added to dilute the mixture. The resulting mixture was washed with saturated aqueous sodium bicarbonate (60 mL×2) and saturated brine (50 mL) in turn, and the organic layer was dried over anhydrous sodium sulfate, filtered, then the filtrate concentrated in vacuo. The residue was purified by silica gel column chromatography (PE/EtOAc (v/v)=8/1) to give the title compound as yellow oil (8.25 g, 92%).

MS (ESI, pos. ion) m/z: 316.1 [M+H]$^+$.

Step 4: (+/−)-trans-methyl 3-aminobicyclo[2.2.2] octane-2-carboxylate

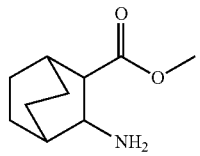

To an autoclave were added (+/−)-trans-methyl 3-(((benzyloxy)carbonyl)amino) bicyclo[2.2.2]oct-5-ene-2-carboxylate (8.21 g, 26.0 mmol), tetrahydrofuran (20 mL) and methanol (20 mL) in turn. To the solution was added Pd/C (10%, 1.40 g), and the mixture was stirred at rt overnight under a hydrogen pressure of 40 psi. The reaction mixture was filtered through a celite pad to remove the catalyst, then the filter cake was washed with methanol (20 mL) and ethyl acetate (20 mL) in turn. The combined filtrates were concentrated in vacuo to give colourless oil, which was purified by silica-gel column chromatography (DCM/MeOH (v/v)= 20/1-10/1) to give the title compound as colourless oil (3.95 g, 83%).

MS (ESI, neg. ion) m/z: 184.2 [M−H]$^-$;
$^1$H NMR (400 MHz, CDCl$_3$) δ (ppm): 3.68 (s, 3H), 3.31 (d, J=6.7 Hz, 1H), 2.11 (d, J=6.7 Hz, 1H), 1.98-1.91 (m, 1H), 1.83-1.71 (m, 1H), 1.60-1.33 (m, 10H).

Step 5: 2,4-dichloro-6-(furan-2-yl)pyrimidine

To a solution of 2,4,6-trichloropyrimidine (100 mg, 0.55 mmol) in tertrahydrofuran (4 mL) were added tetrakis (triphenylphosphine)palladium (43 mg, 0.05 mmol), furan-2-ylboronic acid (61 mg, 0.55 mol) and aqueous sodium bicarbonate solution (1 M, 1.64 mL, 1.64 mmol). The mixture was stirred at 80° C. overnight. The reaction mixture was diluted with water (50 mL), and the resulting mixture was extracted with EtOAc (50 mL×3). The combined organic layers were washed with saturated brine (50 mL), dried over anhydrous Na$_2$SO$_4$, and filtered. The filtrate was concentrated in vacuo, and the residue was purified by silica gel column chromatography (PE) to give the title compound as a yellow solid (42 mg, 36%).

MS (ESI, pos. ion) m/z: 215.0 [M+H]$^+$;
$^1$H NMR (400 MHz, CDCl$_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 6: (+/−)-trans-methyl 3-((2-chloro-6-(furan-2-yl)pyrimidin-4-yl)amino)bicyclo[2.2.2]octane-2-carboxylate To a solution of (+/−)-trans-methyl 3-aminobicyclo[2.2.2] octane-2-carboxylate (429 mg, 2.34 mmol) and 2,4-dichloro-6-(furan-2-yl)pyrimidine (420 mg, 1.95 mmol) in DMF (6 mL) was added potassium carbonate (809 mg, 5.86 mmol), and the mixture was stirred at rt overnight. To the reaction mixture was added water (40 mL), and the resulting mixture was extracted with ethyl acetate (40 mL×3). The combined organic layers were washed with saturated brine (80 mL), dried over anhydrous sodium sulfate and filtered. The filtrate was concentrated in vacuo to dry and the residue was purified by silica gel column chromatography (PE/EtOAc (v/v)=8/1) to give the title compound as a white solid (383 mg, 54%).

MS (ESI, pos. ion) m/z: 362.1 [M+H]$^+$;
$^1$H NMR (400 MHz, CDCl$_3$) δ (ppm): 7.56 (s, 1H), 7.22 (s, 1H), 6.93 (s, 1H), 6.55 (d, J=1.6 Hz, 1H), 5.47 (d, J=5.5 Hz, 1H), 4.44 (s, 1H), 3.70 (s, 3H), 2.44-2.33 (m, 1H), 1.96 (d, J=2.5 Hz, 1H), 1.88 (s, 1H), 1.84-1.58 (m, 8H).

Step 7: 2,5-dichloronicotinamide

To a solution of 2,5-dichloronicotinic acid (810.30 mg, 4.22 mmol) in dichloromethane (8.0 mL) was added oxalyl chloride (0.80 mL, 9.50 mmol), then DMF (0.03 mL, 0.40 mmol) was added dropwise slowly to the reaction mixture. The resulting mixture was stirred for 2 h at rt. Then, the reaction mixture was concentrated at 30° C. to remove DCM, and to the residue was added THF (5 mL). The mixture was cooled to 0° C. under an ice-bath condition. To the mixture was added strong aqua ammonia (6.2 mL, 26%), and the resulting mixture was stirred at rt for 2 h. Ethyl acetate (20 mL) was added to dilute the reaction mixture, and the resulting mixture was extracted with EtOAc (80 mL×3). The combined organic phases were washed with saturated brine (150 mL), dried over anhydrous Na$_2$SO$_4$, filtered, and the filtrate was concentrated in vacuo. The residue was purified by silica gel chromatograph (PE/EtOAc (v/v)=4/1) to give the title compound as a white solid (780 mg, 97%).

MS (ESI, pos. ion) m/z: 191.1 [M+H]$^+$;
$^1$H NMR (400 MHz, CDCl$_3$) δ (ppm) 8.56 (d, J=2.6 Hz, 1H), 8.12 (d, J=2.6 Hz, 2H), 7.87 (s, 1H).

Step 8: 2,5-dichloronicotinonitrile

To a solution of 2,5-dichloronicotinamide (180 mg, 0.94 mmol) in DCM (8.0 mL) were added TFAA (0.16 mL, 1.20 mmol) and Et$_3$N (0.30 mL, 2.20 mmol) in turn. The mixture was stirred at rt for 1.5 h. After the reaction was completed, the reaction mixture was added into water (50 mL). And the reaction mixture was extracted with dichloromethane (80 mL×3). The combined organic layers were washed with saturated brine (150 mL), dried over anhydrous sodium sulfate, filtered, and the filtrate was concentrated in vacuo. The residue was purified by silica gel chromatograph (PE/EtOAc (v/v)=4/1) to give the title compound as a white solid (155 mg, 95%).

MS (ESI, pos. ion) m/z: 196.1 [M+Na]$^+$;
$^1$H NMR (400 MHz, CDCl$_3$) δ (ppm): 8.58 (d, J=2.5 Hz, 1H), 8.01 (d, J=2.5 Hz, 1H).

Step 9: 5-chloro-1H-pyrazolo[3,4-b]pyridin-3-amine

To a solution of 2,5-dichloronicotinonitrile (160 mg, 0.92 mmol) in n-butanol (15.0 mL) was added hydrazine hydrate (0.4 mL, 15 mmol). The mixture was stirred at 120° C. for 7 h. The reaction mixture was concentrated in vacuo to remove the solvent, and the residue was purified by silica gel column chromatography (PE/EtOAc (v/v)=4/1) to give the title compound as a white solid (86 mg, 55%).

MS (ESI, pos. ion) m/z: 169.0 [M+H]$^+$;
$^1$H NMR (400 MHz, CDCl$_3$) δ (ppm): 8.33 (s, 1H), 8.29 (s, 1H), 5.69 (s, 2H).

Step 10: 3-bromo-5-chloro-1H-pyrazolo[3,4-b]pyridine

To a solution of 5-chloro-1H-pyrazolo[3,4-b]pyridin-3-amine (694 mg, 4.12 mmol) in bromoform (5 mL) was added tert-butyl nitrite (1.2 mL, 10.0 mmol). The mixture was stirred at 61° C. for 1 h, then heated to 90° C. and stirred for further 1 h. The reaction was stopped, and the reaction mixture was concentrated in vacuo to remove bromoform. The residue was dissolve in ethyl acetate and then the mixture was concentrated. The resulting residue was purified by silica gel column chromatography (PE/EtOAc (v/v) =4/1) to give the title compound as yellow powder (471 mg, 49%).

MS (ESI, pos. ion) m/z: 233.9 [M+H]$^+$;

$^1$H NMR (400 MHz, DMSO-d$_6$) δ (ppm): 14.03 (d, J=206.4 Hz, 1H), 8.61 (dd, J=18.1, 1.7 Hz, 1H), 8.28 (dd, J=10.7, 2.0 Hz, 1H).

Step 11: 3-bromo-5-chloro-1-trityl-1H-pyrazolo[3,4-b]pyridine

To a solution of 3-bromo-5-chloro-1H-pyrazolo[3,4-b]pyridine (471 mg, 2.03 mmol) in DMF (5 mL) was added K$_2$CO$_3$ (98 mg, 6.11 mmol) at 0° C. Then the reaction mixture was stirred for 30 min at 0° C. Triphenylchloromethane (677 mg, 2.43 mmol) was added and the reaction mixture was stirred at rt overnight. Water (50 mL) was added to quench the reaction, and the resulting mixture was extracted with EtOAc (80 mL×2). The combined organic phases were washed with saturated brine (80 mL×3), dried over anhydrous Na$_2$SO$_4$, filtered, and the filtrate was concentrated in vacuo. The residue was purified by silica gel chromatograph (PE/EtOAc (v/v)=4/1) to give the title compound as a yellow solid (425 mg, 44%).

$^1$H NMR (400 MHz, CDCl$_3$) δ (ppm): 8.38 (d, J=2.3 Hz, 1H), 8.26 (d, J=2.3 Hz, 1H), 7.31-7.19 (m, 15H).

Step 12: 5-chloro-3-(4,4,5,5-tetramethyl-1,3,2-dioxaborolan-2-yl)-1-trityl-1H-pyrazolo[3,4-b]pyridine The air in a suspension of 3-bromo-5-chloro-1-trityl-1H-pyrazolo[3,4-b]pyridine (500 mg, 1.05 mmol), Pd(dppf)Cl$_2$ (158 mg, 0.21 mmol) and KOAc (310 mg, 3.16 mmol) in DME (10 mL) was exchanged with nitrogen and then to the suspension was added bis(pinacolato)diboron (401 mg, 1.58 mmol). The mixture was stirred at 105° C. for 2 h under nitrogen protection. The reaction mixture was cooled to rt, and ethyl acetate (20 mL) was added. The resulting mixture was filtered through a celite pad, and the filter cake was washed with ethyl acetate (20 mL). The filtrate was concentrated in vacuo to give the title compound as brown thickness oil (335 mg, 61%), which was used in the next step without further purification.

Step 13: (+/−)-trans-methyl 3-((2-(5-chloro-1-trityl-1H-pyrazolo[3,4-b]pyridin-3-yl)-6-(furan-2-yl)pyrimidin-4-yl)amino)bicyclo[2.2.2]octane-2-carboxylate To 1,4-dioxane (5 mL) were added 5-chloro-3-(4,4,5,5-tetramethyl-1,3,2-dioxaborolan-2-yl)-1-trityl-1H-pyrazolo[3,4-b]pyridine (428 mg, 0.41 mmol, 50%), K$_2$CO$_3$ (160 mg, 1.13 mmol), PdCl$_2$(dppf) (30 mg, 0.04 mmol) and (+/−)-trans-methyl 3-((2-chloro-6-(furan-2-yl)pyrimidin-4-yl)amino)bicyclo[2.2.2]octane-2-carboxylate (136 mg, 0.38 mmol). Then H$_2$O (1 mL) was added to the mixture, and the air in the mixture was exchanged with nitrogen by bubbling for 10 min. The mixture in a sealed tub was stirred for 1.5 h at 110° C. by heating. The mixture was filtered to remove the solid impurity, and the filtrate was concentrated to remove the solvent. The residue was purified by silica gel column chromatography (PE/EtOAc (v/v)=10/1-5/1) to give the title compound as a white solid (235 mg, 87%).

Step 14: (+/−)-trans-methyl 3-((2-(5-chloro-1H-pyrazolo[3,4-b]pyridin-3-yl)-6-(furan-2-yl) pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(furan-2-yl)pyrimidin-4-yl)amino)bicyclo[2.2.2]octane-2-carboxylate (150 mg, 0.21 mmol) in DCM (5 mL) were added trifluoroacetic acid (200 mg, 2.08 mmol) and triethyl silicane (200 mg, 2.08 mmol). The mixture was stirred at rt overnight. The reaction mixture was added into saturated aqueous sodium carbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (61 mg, 61%).

MS (ESI, pos. ion) m/z: 479.2 [M+H]$^+$.

Step 15: (+/−)-trans-3-((2-(5-chloro-1H-pyrazolo[3,4-b]pyridin-3-yl)-6-(furan-2-yl)pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(furan-2-yl)pyrimidin-4-yl)amino)bicyclo[2.2.2]octane-2-carboxylate (61 mg, 0.13 mmol) in THF/MeOH (v/v=5 mL/5 mL) was added a solution of NaOH (56 mg, 1.27 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (36 mg, 61%).

MS (ESI, pos. ion) m/z: 465.2 [M+H]$^+$;

HRMS (ESI, pos. ion) m/z: 465.1434[M+H]$^+$, (C$_{23}$H$_{22}$ClN$_6$O$_3$)[M+H]$^+$ theoretical value: 465.1442;

$^1$H NMR (400 MHz, DMSO-d$_6$) δ (ppm): 14.23 (s, 1H), 8.92 (s, 1H), 8.62 (s, 1H), 7.91 (s, 1H), 7.78 (s, 1H), 7.21 (s, 1H), 6.77 (s, 1H), 6.72 (s, 1H), 4.72 (s, 1H), 2.02 (s, 1H), 1.54 (m, 11H).

Example 2: (+/−)-trans-3-((2-(5-chloro-1H-pyrazolo[3,4-b]pyridin-3-yl)-5-fluoro-6-(furan-2-yl)pyrimidin-4-yl)amino)bicyclo[2.2.2]octane-2-carboxylic Acid

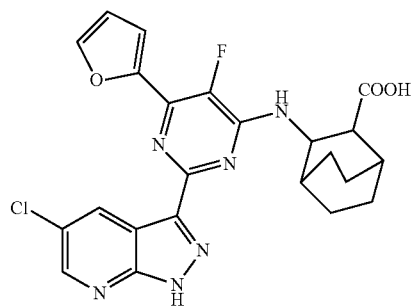 [SMILES: O=C(O)C1C2CCC(CC2)C1Nc1nc(-c2n[nH]c3ncc(Cl)cc23)nc(-c2ccco2)c1F]

Step 1: (+/−)-trans-methyl 3-((2,6-dichloro-5-fluoropyrimidin-4-yl)amino)bicyclo[2.2.2]octane-2-carboxylate A suspension of 2,4,6-trichloro-5-fluoropyrimidine (2.21 g, 8.78 mmol), (+/−)-trans-methyl 3-aminobicyclo[2.2.2]octane-2-carboxylate (1.75 g, 8.78 mmol) and $K_2CO_3$ (2.43 g, 17.60 mmol) in DMF (5 mL) was stirred at rt overnight. $H_2O$ (100 mL) was added to quench the reaction, and the resulting mixture was extracted with EtOAc (50 mL×3). The combined organic layers were washed with saturated brine (80 mL×3), dried over anhydrous sodium sulfate, filtered, and the filtrate was concentrated in vacuo. The residue was purified by silica gel chromatograph (PE/EtOAc (v/v)=5/1) to give the title compound as a white solid (2.71 g, 89%).
MS (ESI, pos. ion) m/z: 348.0 [M+H]$^+$.

Step 2: (+/−)-trans-methyl 3-((2-chloro-5-fluoro-6-(furan-2-yl)pyrimidin-4-yl)amino) bicyclo[2.2.2]octane-2-carboxylate To 1,4-dioxane (8 mL) were added furan-2-ylboronic acid (0.22 g, 1.00 mmol), $K_2CO_3$ (160 mg, 1.13 mmol), $PdCl_2$(dppf) (30 mg, 0.04 mmol) and (+/−)-trans-methyl 3-((2,6-dichloro-5-fluoropyrimidin-4-yl)amino)bicyclo[2.2.2]octane-2-carboxylate (500 mg, 1.44 mmol). Then $H_2O$ (0.5 mL) was added to the mixture, and the air in the mixture was exchanged with nitrogen by bubbling for 10 min. The mixture in sealed tub was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (423 mg, 66%).
MS (ESI, pos. ion) m/z: 380.1 [M+H]$^+$;
$^1$H NMR (400 MHz, CDCl$_3$) δ (ppm): 7.66 (s, 1H), 7.19-7.14 (m, 1H), 6.59 (dd, J=3.4, 1.7 Hz, 1H), 5.33 (s, 1H), 4.51 (s, 1H), 3.78 (s, 3H), 2.43 (d, J=5.7 Hz, 1H), 2.02 (d, J=2.1 Hz, 1H), 1.91 (s, 1H), 1.84 (t, J=11.7 Hz, 1H), 1.69 (dd, J=18.2, 10.0 Hz, 5H), 1.46 (t, J=10.7 Hz, 1H), 1.28 (s, 1H).

Step 3: (+/−)-trans-methyl 3-((2-(5-chloro-1-trityl-1H-pyrazolo[3,4-b]pyridin-3-yl)-5-fluoro-6-(furan-2-yl)pyrimidin-4-yl)amino)bicyclo[2.2.2]octane-2-carboxylate To 1,4-dioxane (5 mL) were added 5-chloro-3-(4,4,5,5-tetramethyl-1,3,2-dioxaborolan-2-yl)-1-trityl-1H-pyrazolo[3,4-b]pyridine (160 mg, 0.30 mmol), $K_2CO_3$ (120 mg, 0.81 mmol), $PdCl_2$(dppf) (30 mg, 0.03 mmol) and (+/−)-trans-methyl 3-((2-chloro-5-fluoro-6-(furan-2-yl)pyrimidin-4-yl)amino)bicyclo[2.2.2]octane-2-carboxylate (102 mg, 0.27 mmol). Then $H_2O$ (1 mL) was added to the mixture, and the air in the mixture was exchanged with nitrogen by bubbling for 10 min. The mixture in a sealed tub was stirred for 1.5 h at 110° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (166 mg, 84%).

Step 4: (+/−)-trans-methyl 3-((2-(5-chloro-1H-pyrazolo[3,4-b]pyridin-3-yl)-5-fluoro-6-(furan-2-yl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-5-fluoro-6-(furan-2-yl)pyrimidin-4-yl)amino)bicyclo[2.2.2]octane-2-carboxylate (166 mg, 0.22 mmol) in DCM (5 mL) was added trifluoroacetic acid (0.15 mL, 1.65 mmol) and triethyl silicane (0.30 mL, 1.65 mmol). The mixture was stirred at rt overnight, then added into saturated aqueous sodium bicarbonate (100 mL). The resulting mixture was extracted with dichoromethane (50 mL×3). The combined organic layers were washed with saturated brine (100 mL), dried over anhydrous sodium sulfate and filtered. The filtrate was concentrated in vacuo to remove the solvent and the residue was purified by silica gel column chromatography (DCM/MeOH (v/v)=10/1) to give the title compound as a white solid (96 mg, 86%).
MS (ESI, pos. ion) m/z: 497.3 [M+H]$^+$.

Step 5: (+/−)-trans-3-((2-(5-chloro-1H-pyrazolo[3,4-b]pyridin-3-yl)-5-fluoro-6-(furan-2-yl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-5-fluoro-6-(furan-2-yl)pyrimidin-4-yl)amino)bicyclo[2.2.2]octane-2-carboxylate (96 mg, 0.19 mmol) in THF/MeOH (v/v=5 mL/5 mL) was added a solution of NaOH (80 mg, 1.93 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-/1) to give the title compound as a white solid (53 mg, 57%).
MS (ESI, pos. ion) m/z: 483.2 [M+H]$^+$;
HRMS (ESI, pos. ion) m/z: 483.1392 [M+H]$^+$, ($C_{23}H_{21}ClFN6O_3$)[M+H]$^+$ theoretical value: 483.1348;
$^1$H NMR (400 MHz, DMSO-d$_6$) δ (ppm): 14.26 (s, 1H), 8.89 (s, 1H), 8.62 (s, 1H), 8.03 (s, 1H), 7.91 (d, J=6.4 Hz, 1H), 7.25 (s, 1H), 6.79 (s, 1H), 4.78 (s, 1H), 2.93 (d, J=6.5 Hz, 1H), 2.04 (s, 1H), 1.96 (s, 1H), 1.85-1.35 (m, 9H).
$^{13}$C NMR (101 MHz, DMSO-d$_6$) δ (ppm): 175.89, 152.83, 152.73, 151.68, 148.03, 145.97, 141.21, 138.58, 137.60, 131.04, 130.06, 124.97, 114.95, 112.84, 51.21, 47.90, 28.96, 28.78, 25.69, 25.40, 24.42, 21.57, 19.48.

Example 3: (+/−)-trans-3-((2-(5-chloro-1H-pyrazolo[3,4-b]pyridin-3-yl)-7-methyl-7H-pyrrolo[2,3-d]pyrimidin-4-yl)amino)bicyclo[2.2.2]octane-2-carboxylic Acid

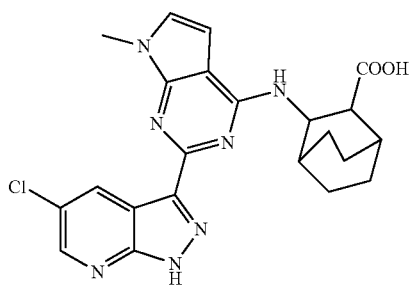 [SMILES: Cn1ccc2c(NC3C4CCC(CC4)C3C(=O)O)nc(-c3n[nH]c4ncc(Cl)cc34)nc21]

Step 1: 2,4-dichloro-7-methyl-7H-pyrrolo[2,3-d]pyrimidine

A solution of 2,4-dichloro-7H-pyrrolo[2,3-d]pyrimidine (1.00 g, 5.32 mmol) in THF (8 mL) was stirred at 0° C. for 5 min. Then sodium hydride (255 mg, 6.38 mmol) was added. The resulting mixture was stirred for 15 min, then iodomethane (8.50 g, 53.20 mmol) was added. The reaction mixture was warmed to rt and stirred overnight. $H_2O$ (100 mL) was added to quench the reaction, and the resulting mixture was extracted with EtOAc (50 mL×3). The combined organic phases were washed with brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a white solid (1.00 g, 93%).

MS (ESI, pos. ion) m/z: 203.0 $[M+H]^+$.

Step 2: (+/−)-trans-methyl 3-((2-chloro-7-methyl-7H-pyrrolo[2,3-d]pyrimidin-4-yl)amino) bicyclo[2.2.2]octane-2-carboxylate To a solution of (+/−)-trans-methyl 3-aminobicyclo[2.2.2]octane-2-carboxylate (200 mg, 1.09 mmol) and 2,4-dichloro-7-methyl-7H-pyrrolo[2,3-d]pyrimidine (200 mg, 0.99 mmol) in DMF (5 mL) was added potassium carbonate (273 mg, 1.98 mmol), and the mixture was stirred at 80° C. overnight. The reaction mixture was added into water to quench the reaction, and the resulting mixture was extracted with ethyl acetate (50 mL×3). The combined organic layers were washed with saturated brine (50 mL×3), dried over anhydrous sodium sulfate and filtered. The filtrate was concentrated in vacuo to dry, and the residue was purified by silica gel column chromatography (PE/EA (v/v)=5/1-2/1) to give the title compound as a white solid (144 mg, 42%).

MS (ESI, pos. ion) m/z: 350.1 $[M+H]^+$.

Step 3: (+/−)-trans-methyl 3-((2-(5-chloro-1-trityl-1H-pyrazolo[3,4-b]pyridin-3-yl)-7-methyl-7H-pyrrolo[2,3-d]pyrimidin-4-yl)amino)bicyclo[2.2.2]octane-2-carboxylate To 1,4-dioxane (5 mL) were added 5-chloro-3-(4,4,5,5-tetramethyl-1,3,2-dioxaborolan-2-yl)-1-trityl-1H-pyrazolo[3,4-b]pyridine (173 mg, 0.32 mmol), $K_2CO_3$ (120 mg, 0.86 mmol), $PdCl_2(dppf)$ (25 mg, 0.03 mmol) and (+/−)-trans-methyl 3-((2-chloro-7-methyl-7H-pyrrolo[2,3-d]pyrimidin-4-yl)amino)bicyclo[2.2.2]octane-2-carboxylate (100 mg, 0.29 mmol). Then $H_2O$ (1 mL) was added to the mixture, and the air in the mixture was exchanged with nitrogen by bubbling for 10 min. The mixture in a sealed tub was stirred for 1.5 h at 110° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (53 mg, 47%).

Step 4: (+/−)-trans-methyl 3-((2-(5-chloro-1H-pyrazolo[3,4-b]pyridin-3-yl)-7-methyl-7H-pyrrolo[2,3-d]pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-7-methyl-7H-pyrrolo[2,3-d]pyrimidin-4-yl)amino)bicyclo[2.2.2]octane-2-carboxylate (105 mg, 0.15 mmol) in DCM (5 mL) were added trifluoroacetic acid (180 mg, 1.48 mmol) and triethyl silicane (200 mg, 1.48 mmol). The mixture was stirred at rt overnight, then added into saturated aqueous sodium bicarbonate (100 mL). The resulting mixture was extracted with dichoromethane (50 mL×3). The combined organic layers were washed with saturated brine (100 mL), dried over anhydrous sodium sulfate and filtered. The filtrate was concentrated in vacuo to remove the solvent and the residue was purified by silica gel column chromatography (PE/EtOAc (v/v)=10/1) to give the title compound as a white solid (38 mg, 55%).

MS (ESI, pos. ion) m/z: 467.1 $[M+H]^+$.

Step 5: (+/−)-trans-3-((2-(5-chloro-1H-pyrazolo[3,4-b]pyridin-3-yl)-7-methyl-7H-pyrrolo[2,3-d]pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-7-methyl-7H-pyrrolo[2,3-d]pyrimidin-4-yl)amino)bicyclo[2.2.2]octane-2-carboxylate (38 mg, 0.08 mmol) in THF/MeOH (v/v=5 mL/5 mL) was added a solution of NaOH (36 mg, 0.82 mmol) in water (1 mL). The mixture was stirred at rt overnight, then diluted with water (10 mL). The resulting mixture was acidified with hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (22 mg, 60%).

MS (ESI, pos. ion) m/z: 453.1 $[M+H]^+$;
HRMS (ESI, pos. ion) m/z: 452.1615 $[M+H]^+$, $(C_{22}H_{23}ClN_7O_2)[M+H]^+$ theoretical value: 452.1602;
$^1H$ NMR (600 MHz, DMSO-$d_6$) δ (ppm): 14.08 (s, 1H), 9.04 (s, 1H), 8.59 (s, 1H), 7.48 (s, 1H), 7.21 (s, 1H), 6.69 (s, 1H), 4.90 (s, 1H), 3.79 (s, 3H), 2.77 (d, J=6.3 Hz, 1H), 2.04 (s, 1H), 1.99 (s, 1H), 1.90 (s, 1H), 1.78 (s, 2H), 1.68-1.35 (m, 6H).

Example 4: (R)-3-((2-(5-chloro-1H-pyrazolo[3,4-b]pyridin-3-yl)-5-fluoro-6-(furan-2-yl) pyrimidin-4-yl)amino)-4,4-dimethylpentanoic Acid

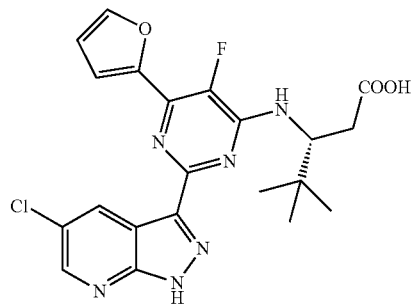 [SMILES: CC(C)(C)[C@@H](CC(=O)O)Nc1nc(-c2n[nH]c3ncc(Cl)cc23)nc(-c2ccco2)c1F]

Step 1: (R)-methyl 3-amino-4,4-dimethylpentanoate

To a 0° C. solution of (R)-3-amino-4,4-dimethylpentanoic acid (1.01 g, 6.96 mmol) in methanol (60 mL) was added dropwise slowly oxalyl chloride (0.9 mL. 10 mmol). The mixture was stirred at 0° C. for 1 h, then heated to 65° C. and stirred for further 2 h. The reaction mixture was concentrated in vacuo to dry and the residue was washed with toluene (30 mL×3), then the mixture was filtered by suction to give the title compound as a white solid (1.11 g, 99%).

MS (ESI, pos. ion) m/z: 160.3 [M+H]$^+$.

Step 2: (R)-3-((2,6-dichloro-5-fluoropyrimidin-4-yl)amino)-4,4-dimethylpentanoate 2,4,6-Trichloro-5-fluoropyrimidine (0.71 g, 3.80 mmol) and (R)-methyl 3-amino-4,4-dimethylpentanoate (1.13 g, 4.20 mmol) were dissolved in DMF (20 mL), then to the mixture was added potassium carbonate (1.63 g, 12.00 mmol). The resulting mixture was stirred at rt overnight. To the reaction mixture was added water (40 mL), and the mixture was extracted with ethyl acetate (50 mL×3). The combined organic layers were washed with saturated brine (150 mL), dried over anhydrous sodium sulfate and filtered. The filtrate was concentrated in vacuo to dry and the residue was purified by silica gel column chromatography (PE/EtOAc (v/v)=10/1) to give the title compound as a light yellow solid (0.98 g, 79%).

MS (ESI, pos. ion) m/z: 324.2 [M+H]$^+$.

Step 3: (R)-methyl 3-((2-chloro-5-fluoro-6-(furan-2-yl)pyrimidin-4-yl)amino)-4,4-dimethylpentanoate To a sealed tube were added (R)-3-((2,6-dichloro-5-fluoropyrimidin-4-yl)amino)-4,4-dimethylpentanoate (0.93 g, 2.90 mmol), furan-2-boric acid (0.33 g, 2.90 mmol), PdCl$_2$(dppf) (0.23 g, 0.29 mmol) and K$_2$CO$_3$ (1.25 g, 8.60 mmol), then to the mixture were added THF (20 mL) and water (1 mL). The air in the mixture was exchanged with nitrogen, and the mixture in the tube was sealed. Then the mixture was stirred at 100° C. for 3 h. After the reaction, the mixture was filtered to remove the solid impurities. The filtrate was concentrated in vacuo and the residue was purified by silica gel column chromatography (PE/EtOAc (v/v)=10/1) to give the title compound as light yellow oil (390 mg, 38%).

MS (ESI, pos. ion) m/z: 356.1 [M+H]$^+$;
$^1$H NMR (400 MHz, CDCl$_3$) δ (ppm): 7.66 (s, 1H), 7.19-7.13 (m, 1H), 6.60-6.57 (m, 1H), 5.64 (d, J=9.3 Hz, 1H), 3.65 (s, 3H), 3.56 (s, 1H), 2.76-2.44 (m, 3H), 1.01 (s, 9H).

Step 4: (R)-methyl 3-((2-(5-chloro-1-trityl-1H-pyrazolo[3,4-b]pyridin-3-yl)-5-fluoro-6-(furan-2-yl)pyrimidin-4-yl)amino)-4,4-dimethylpentanoate To 1,4-dioxane (10 mL) were added 5-chloro-3-(4,4,5,5-tetramethyl-1,3,2-dioxaborolan-2-yl)-1-trityl-1H-pyrazolo[3,4-b]pyridine (1.0 g, 0.96 mmol, 50%), K$_2$CO$_3$ (98 mg, 0.67 mmol), PdCl$_2$(dppf) (51 mg, 0.07 mmol) and (R)-methyl 3-((2-chloro-5-fluoro-6-(furan-2-yl)pyrimidin-4-yl)amino)-4,4-dimethylpentanoate (120 mg, 0.34 mmol). Then H$_2$O (0.5 mL) was added to the mixture, and the air in the mixture was exchanged with nitrogen by bubbling for 10 min. The mixture in a sealed tub was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as colorless oil (155 mg, 64%).

Step 5: (R)-methyl 3-((2-(5-chloro-1H-pyrazolo[3,4-b]pyridin-3-yl)-5-fluoro-6-(furan-2-yl) pyrimidin-4-yl)amino)-4,4-dimethylpentanoate To a solution of (R)-methyl 3-((2-(5-chloro-1-trityl-1H-pyrazolo[3,4-b]pyridin-3-yl)-5-fluoro-6-(furan-2-yl)pyrimidin-4-yl)amino)-4,4-dimethylpentanoate (150 mg, 0.21 mmol) in DCM (10 mL) were added Et$_3$SiH (0.40 mL, 2.52 mmol) and TFA (0.20 mL, 2.70 mmol). The mixture was stirred at rt overnight. The reaction was stopped, and the mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 473.2 [M+H]$^+$.

Step 6: (R)-3-((2-(5-chloro-1H-pyrazolo[3,4-b]pyridin-3-yl)-5-fluoro-6-(furan-2-yl)pyrimidin-4-yl)amino)-4,4-dimethylpentanoic Acid To a solution of (R)-methyl 3-((2-(5-chloro-1H-pyrazolo[3,4-b]pyridin-3-yl)-5-fluoro-6-(furan-2-yl)pyrimidin-4-yl)amino)-4,4-dimethylpentanoate (110 mg, 0.23 mmol) in THF/MeOH/H$_2$O (v/v/v=4 mL/4 mL/4 mL) was added NaOH (100 mg, 2.50 mmol). The mixture was stirred at rt overnight, then saturated brine (10 mL) was added. The resulting mixture was acidified with diluted hydrochloric acid (1 M) to pH about 6. The resulting mixture was extracted with 2-methyl tetrahydrofuran (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (35 mg, yield of step 5 and step 6: 33%).

MS (ESI, pos. ion) m/z: 459.1 [M+H]$^+$;
HRMS (ESI, pos. ion) m/z: 459.1344 [M+H]$^+$, (C$_{21}$H$_{21}$ClFN$_6$O$_3$)[M+H]$^+$ theoretical value: 459.1348;
$^1$H NMR (600 MHz, DMSO-d$_6$) δ (ppm): 14.24 (s, 1H), 12.14 (s, 1H), 9.02 (s, 1H), 8.63 (d, J=1.7 Hz, 1H), 8.04 (s, 1H), 7.73 (d, J=9.0 Hz, 1H), 7.25 (s, 1H), 6.79 (s, 1H), 4.85 (s, 1H), 2.65 (dt, J=15.6, 11.9 Hz, 2H), 0.99 (s, 9H);
$^{13}$C NMR (151 MHz, DMSO-d$_6$) δ (ppm): 173.76, 154.77, 153.81, 153.73, 151.44, 147.93, 145.98, 141.77, 140.33, 138.57, 137.73, 131.29, 124.99, 114.94, 112.90, 55.93, 36.03, 35.57, 27.02.

Example 5: (+/−)-trans-3-((2-(5-chloro-1H-pyrazolo[3,4-b]pyridin-3-yl)-6-(4-methoxy phenyl)pyrimidin-4-yl)amino)bicyclo[2.2.2]octane-2-carboxylic Acid

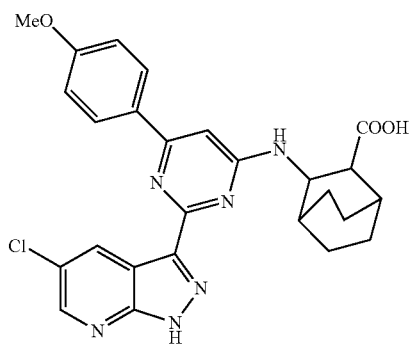 [SMILES: COc1ccc(-c2cc(NC3C4CCC(CC4)C3C(=O)O)nc(-c3n[nH]c4ncc(Cl)cc34)n2)cc1]

Step 1: 2,4-dichloro-6-(4-methoxyphenyl)pyrimidine

To a solution of 2,4,6-trichloropyrimidine (5.5 mL, 48.0 mmol) in THF (70 mL) were added palladium acetate (0.147 g, 0.64 mmol), triphenylphosphine (353 mg, 1.28 mmol), 4-methoxybenzeneboronic acid (5.01 g, 31.9 mmol) and aqueous sodium carbonate solution (1 M, 64 mL, 64 mmol). The mixture was stirred at 60° C. for 6 h under nitrogen protection. The reaction mixture was cooled to rt and concentrated in vacuo to remove the solvent. To the residue was added water (100 mL), and the resulting mixture was extracted with ethyl acetate (100 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a white solid (5.58 g, 68%).

MS (ESI, pos. ion) m/z: 255.0 [M+H]$^+$;
$^1$H NMR (400 MHz, CDCl$_3$) δ (ppm): 8.07 (dd, J=9.4, 2.4 Hz, 2H), 7.60 (s, 1H), 7.08-6.99 (m, 2H), 3.91 (s, 3H).

Step 2: (+/−)-trans-methyl 3-((2-chloro-6-(4-methoxyphenyl)pyrimidin-4-yl)amino) bicyclo[2.2.2]octane-2-carboxylate To a solution of 2,4-dichloro-6-(4-methoxyphenyl)pyrimidine (1.01 g, 3.92 mmol) and (+/−)-trans-methyl 3-aminobicyclo[2.2.2]octane-2-carboxylate (1.02 g, 5.88 mmol) in DMF (20 mL) was added potassium carbonate (0.81 g, 5.88 mmol), and the mixture was stirred at 50° C. overnight. To the reaction mixture was added water (70 mL), and the resulting mixture was extracted with ethyl acetate (100 mL×3). The combined organic layers were washed with saturated brine (150 mL), dried over anhydrous sodium sulfate and filtered. The filtrate was concentrated in vacuo to dry and the residue was purified by silica gel column chromatography (n-hexane/EtOAc (v/v)=20/1-5/1) to give the title compound as a white solid (1.01 g, 64%).

MS (ESI, pos. ion) m/z: 402.2 [M+H]$^+$;
$^1$H NMR (400 MHz, CDCl$_3$) δ (ppm): 7.98 (d, J=8.7 Hz, 2H), 6.98 (d, J=8.9 Hz, 2H), 6.72 (s, 1H), 5.46 (d, J=6.3 Hz, 1H), 4.32 (s, 1H), 3.88 (s, 4H), 3.74 (s, 3H), 2.39 (d, J=5.1 Hz, 1H), 2.08 (s, 1H), 1.90-1.84 (m, 1H), 1.78-1.71 (m, 2H), 1.70-1.63 (m, 4H), 1.58 (d, J=10.2 Hz, 2H).

Step 3: (+/−)-trans-methyl 3-((2-(5-chloro-1-trityl-1H-pyrazolo[3,4-b]pyridin-3-yl)-6-(4-methoxyphenyl)pyrimidin-4-yl)amino)bicyclo[2.2.2]octane-2-carboxylate To 1,4-dioxane (10 mL) were added 5-chloro-3-(4,4,5,5-tetramethyl-1,3,2-dioxaborolan-2-yl)-1-trityl-1H-pyrazolo[3,4-b]pyridine (1.00 g, 0.96 mmol, 50%), K$_2$CO$_3$ (105 mg, 0.75 mmol), Pd(dppf)Cl$_2$ (55 mg, 0.07 mmol) and (+/−)-trans-methyl 3-((2-chloro-6-(4-methoxyphenyl)pyrimidin-4-yl)amino)bicyclo[2.2.2]octane-2-carboxylate (150 mg, 0.37 mmol). Then H$_2$O (0.5 mL) was added to the mixture, and the air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as colorless oil (301 mg, 100%).

Step 4: (+/−)-trans-methyl 3-((2-(5-chloro-1H-pyrazolo[3,4-b]pyridin-3-yl)-6-(4-methoxyphenyl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(4-methoxyphenyl)pyrimidin-4-yl)amino)bicyclo[2.2.2]octane-2-carboxylate (301 mg, 0.40 mmol) in DCM (10 mL) were added Et$_3$SiH (0.80 mL, 5.00 mmol) and TFA (0.40 mL, 5.40 mmol). The mixture was stirred at rt overnight. The reaction was stopped, and the mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 519.3 [M+H]$^+$.

Step 5: (+/−)-trans-3-((2-(5-chloro-1H-pyrazolo[3,4-b]pyridin-3-yl)-6-(4-methoxyphenyl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(4-methoxyphenyl)pyrimidin-4-yl)amino)bicyclo[2.2.2]octane-2-carboxylate (215 mg, 0.43 mmol) in THF/MeOH/H$_2$O (v/v/v=4 mL/4 mL/4 mL) was added NaOH (173 mg, 4.26 mmol). The mixture was stirred at rt overnight, then saturated brine (10 mL) was added. The resulting mixture was acidified with diluted hydrochloric acid (1 M) to pH about 6. The resulting mixture was extracted with 2-methyl tetrahydrofuran (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (6 mg, the total yield of step 4 and step 5: 3%).

HRMS (ESI, pos. ion) m/z: 505.1741 [M+H]$^+$, (C$_{26}$H$_{26}$ClN$_6$O$_3$)[M+H]$^+$ theoretical value: 505.1755;
MS (ESI, pos. ion) m/z: 505.1 [M+H]$^+$;
$^1$H NMR (400 MHz, DMSO-d$_6$) δ (ppm): 14.22 (s, 1H), 8.95 (s, 1H), 8.62 (s, 1H), 8.08 (s, 2H), 7.67 (s, 1H), 7.11 (d, J=8.5 Hz, 2H), 6.84 (s, 1H), 4.72 (s, 1H), 3.85 (s, 3H), 1.99 (s, 1H), 1.80 (m, 4H), 1.57 (s, 3H), 1.43 (m, 2H).

Example 6: (+/−)-trans-3-((2-(5-chloro-1H-pyrazolo[3,4-b]pyridin-3-yl)-6-(furan-3-yl) pyrimidin-4-yl)amino)bicyclo[2.2.2]octane-2-carboxylic Acid

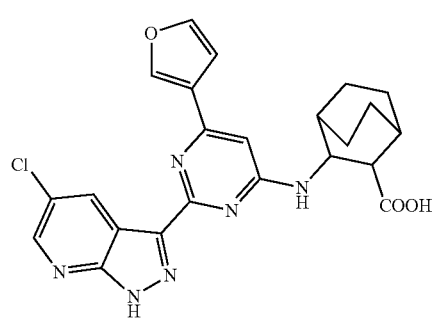 [SMILES: O=C(O)C1C2CCC(CC2)C1Nc1cc(-c2ccoc2)nc(-c2n[nH]c3ncc(Cl)cc23)n1]

Step 1: 2,4-dichloro-6-(furan-3-yl)pyrimidine

To a solution of 2,4,6-trichloropyrimidine (500 mg, 2.73 mmol) in glycol dimethyl ether (32 mL) were added tetrakis (triphenylphosphine)palladium (317 mg, 0.27 mmol), furan-3-ylboric acid (308 mg, 2.75 mmol) and aqueous sodium carbonate (1 M, 8.18 mL, 8.18 mmol). The mixture was stirred at 80° C. under nitrogen protection for 4 h, then water (30 mL) was added. The resulting mixture was extracted with ethyl acetate (30 mL×3). The combined organic layers were washed with saturated brine (30 mL), dried over anhydrous sodium sulfate, and filtered. The filtrate was concentrated in vacuo to dry, and the residue was purified by silica gel column chromatography (PE) to give the title compound as a white solid (317 mg, 31%).

$^1$H NMR (400 MHz, CDCl$_3$) δ (ppm): 8.26 (s, 1H), 7.57 (s, 1H), 7.36 (s, 1H), 6.89 (s, 1H).

Step 2: (+/−)-trans-methyl 3-((2-chloro-6-(furan-3-yl)pyrimidin-4-yl)amino)bicyclo[2.2.2]octane-2-carboxylate (+/−)-trans-Methyl 3-aminobicyclo[2.2.2]octane-2-carboxylate (324 mg, 1.77 mmol) and 2,4-dichloro-6-(furan-3-yl)pyrimidine (317 mg, 1.47 mmol) were dissolved in DMF (6 mL), then potassium carbonate (611 mg, 4.42 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (353 mg, 66%).

MS (ESI, pos. ion) m/z: 362.1 [M+H]$^+$.

Step 3: (+/−)-trans-methyl 3-((2-(5-chloro-1-trityl-1H-pyrazolo[3,4-b]pyridin-3-yl)-6-(furan-3-yl)pyrimidin-4-yl)amino)bicyclo[2.2.2]octane-2-carboxylate To 1,4-dioxane (8 mL) were added 5-chloro-3-(4,4,5,5-tetramethyl-1,3,2-dioxaborolan-2-yl)-1-trityl-1H-pyrazolo[3,4-b]pyridine (500 mg, 0.96 mmol), K$_2$CO$_3$ (53 mg, 0.38 mmol), PdCl$_2$(dppf) (30 mg, 0.04 mmol) and (+/−)-trans-methyl 3-((2-chloro-6-(furan-3-yl) pyrimidin-4-yl)amino)bicyclo[2.2.2]octane-2-carboxylate (68 mg, 0.19 mmol). Then H$_2$O (0.3 mL) was added to the mixture, and the air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as colorless oil (133 mg, 98%).

Step 4: (+/−)-trans-methyl 3-((2-(5-chloro-1H-pyrazolo[3,4-b]pyridin-3-yl)-6-(furan-3-yl) pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(furan-3-yl)pyrimidin-4-yl)amino)bicyclo[2.2.2]octane-2-carboxylate (133 mg, 0.18 mmol) in DCM (4 mL) were added Et$_3$SiH (0.40 mL, 2.50 mmol) and TFA (0.20 mL, 2.70 mmol). The mixture was stirred at rt overnight. The reaction was stopped, and the mixture was added into saturated aqueous sodium bicarbonate (10 mL). The resulting mixture was extracted with dichloromethane (10 mL×3). The combined organic layers were washed with saturated brine (30 mL), dried over anhydrous sodium sulfate, and filtered. The filtrate was concentrated in vacuo to remove the solvent to give the title compound as black oil, which was used in the next step without further purification.

MS (ESI, pos. ion) m/z: 479.3 [M+H]$^+$.

Step 5: (+/−)-trans-3-((2-(5-chloro-1H-pyrazolo[3,4-b]pyridin-3-yl)-6-(furan-3-yl)pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(furan-3-yl)pyrimidin-4-yl)amino)bicyclo[2.2.2]octane-2-carboxylate (150 mg, 0.32 mmol) in THF/MeOH/H$_2$O (v/v/v=2 mL/2 mL/2 mL) was added NaOH (131 mg, 3.23 mmol). The mixture was stirred at rt overnight, then saturated brine (10 mL) was added. The resulting mixture was acidified with diluted hydrochloric acid (1 M) to pH about 6. The resulting mixture was extracted with 2-methyl tetrahydrofuran (15 mL×3). The combined organic layers were washed with saturated brine, dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (14 mg, the total yield of step 4 and step 5: 9%).

HRMS (ESI, pos. ion) m/z: 465.1437 [M+H]$^+$, (C$_{23}$H$_{22}$ClN$_6$O$_3$)[M+H]$^+$ theoretical value: 465.1442;

MS (ESI, pos. ion) m/z: 465.0 [M+H]$^+$;

$^1$H NMR (400 MHz, DMSO-d$_6$) δ (ppm): 14.26 (d, J=11.9 Hz, 1H), 12.39 (s, 1H), 8.92 (s, 1H), 8.62 (s, 1H), 8.38 (s, 1H), 7.84 (s, 1H), 6.98 (s, 1H), 6.67 (s, 1H), 4.71 (s, 1H), 3.51 (s, 1H), 2.69 (m, 1H), 1.99 (m, 2H), 1.89-1.70 (m, 3H), 1.65-1.50 (m, 3H), 1.43 (m, 2H).

Example 7: (+/−)-trans-3-((5-fluoro-2-(5-fluoro-1H-pyrazolo[3,4-b]pyridin-3-yl)-6-(furan-2-yl)pyrimidin-4-yl)amino)bicyclo[2.2.2]octane-2-carboxylic Acid

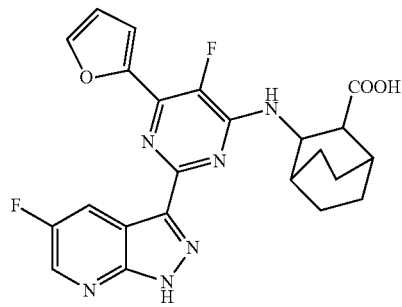 [SMILES: O=C(O)C1C2CCC(CC2)C1Nc1nc(-c2n[nH]c3ncc(F)cc23)nc(-c2ccco2)c1F]

Step 1: 5-fluoro-1H-pyrazolo[3,4-b]pyridin-3-amine

To a solution of 2-chloro-5-fluoronicotinonitrile (1.95 g, 12.50 mmol) in n-butanol (30 mL) was added hydrazine hydrate (80%, 8 mL, 125 mmol). The mixture was heated to 120° C. and stirred for 6 h, then cooled to rt and there was a little solid precipitated out. The mixture was placed in an ice-bath for 1 h, and there was a lot of solid precipitated out. Then the mixture was filtered by suction. The filter cake was washed with 0° C. water (20 mL) and dried in vacuo to give the title compound as a light yellow solid (1.36 g, 73%).

$^1$H NMR (400 MHz, CDCl$_3$) δ (ppm): 12.07 (s, 1H), 8.38 (dd, J=2.5, 1.8 Hz, 1H), 7.97 (dd, J=8.8, 2.7 Hz, 1H), 5.55 (s, 2H).

Step 2: 3-bromo-5-fluoro-1H-pyrrolo[3,4-b]pyridine

A solution of 5-fluoro-1H-pyrazolo[3,4-b]pyridin-3-amine (1.87 g, 12.30 mmol) in bromoform (20 mL) was stirred at rt, then tert-butyl nitrite (5.3 mL, 49.20 mmol) was added. The mixture was heated to 60° C. and stirred for 1 h, then heated to 90° C. for 2 h. The reaction was stopped, then the mixture was cooled to rt and concentrated in vacuo. The residue was purified by silica gel column chromatography (PE/EA (v/v)=10/1) to give the title compound as a creamy white solid (1.45 g, 55% yield).

MS (ESI, pos. ion) m/z: 216.1 [M+H]$^+$;
$^1$H NMR (400 MHz, DMSO-d$_6$) δ (ppm): 11.36 (s, 1H), 8.56 (d, J=1.7 Hz, 1H), 7.71 (dd, J=7.3, 2.6 Hz, 1H).

Step 3: 3-bromo-5-fluoro-1-trityl-1H-pyrazolo[3,4-b]pyridine

To a −15° C. solution of 3-bromo-5-fluoro-1H-pyrrolo[3,4-b]pyridine (1.48 g, 6.85 mmol) in anhydrous DMF (5 mL) was added slowly NaH (0.33 g, 8.30 mmol, 60%). The mixture was stirred at −15° C. for 30 min, then triphenylchloromethane (2.31 g, 8.29 mmol) was added. The mixture was stirred at rt for 1 h, and diluted hydrochloric acid (100 mL, 1 M) was added to quench the reaction. The resulting mixture was extracted with EtOAc (100 mL×2). The combined organic phases were washed with saturated brine (200 mL), dried over anhydrous Na$_2$SO$_4$, filtered, and the filtrate was concentrated in vacuo. The residue was purified by silica gel chromatograph (PE/EtOAc (v/v)=20/1-15/1) to give the title compound as a light yellow solid (1.09 g, 35%).

$^1$H NMR (600 MHz, DMSO-d$_6$) δ (ppm): 8.41 (s, 1H), 8.03 (dd, J=7.9, 2.6 Hz, 1H), 7.30-7.20 (m, 15H).

Step 4: 5-fluoro-3-(4,4,5,5-tetramethyl-1,3,2-dioxaborolan-2-yl)-1-trityl-1H-pyrazolo[3,4-b]pyridine To a microwave tube were added 3-bromo-5-fluoro-1-trityl-1H-pyrazolo[3,4-b]pyridine (1.09 g, 2.44 mmol), bis(pinacolato)diboron (0.95 g, 3.67 mmol), potassium acetate (0.73 g, 7.33 mmol), Pd(dppf)Cl$_2$ (0.37 g, 0.49 mmol) and DME (15 mL), then the air in the mixture was removed by bubbling with nitrogen for 10 min and then the mixture was stirred at 105° C. for 2 h with microwave heating. The mixture was filtered to remove insoluble substance, and the filter cake was washed with ethyl acetate (20 mL×2). The combined filtrates were concentrated in vacuo to give the title compound as brown thickness oil (1.24 g) which was used in the next step without further purification.

Step 5: (+/−)-trans-methyl 3-((2,6-dichloro-5-fluoropyrimidin-4-yl)amino) bicyclo[2.2.2]octane-2-carboxylate A suspension of 2,4,6-trichloro-5-fluoropyrimidine (2.21 g, 8.78 mmol), (+/−)-trans-methyl 3-aminobicyclo[2.2.2]octane-2-carboxylate (1.75 g, 8.78 mmol) and K$_2$CO$_3$ (2.43 g, 17.60 mmol) in DMF (5 mL) was stirred at rt overnight. H$_2$O (100 mL) was added to quench the reaction, and the resulting mixture was extracted with EtOAc (50 mL×3). The combined organic layers were washed with saturated brine (80 mL×3), dried over anhydrous sodium sulfate, filtered, and the filtrate was concentrated in vacuo. The residue was purified by silica gel chromatograph (PE/EtOAc (v/v)=5/1) to give the title compound as a white solid (2.71 g, two steps yield of step 4 and step 5: 89%).

MS (ESI, pos. ion) m/z: 348.0 [M+H]$^+$.

Step 6: (+/−)-trans-methyl 3-((2-chloro-5-fluoro-6-(furan-2-yl)pyrimidin-4-yl)amino) bicyclo[2.2.2]octane-2-carboxylate To a mixed solvent of 1,4-dioxane (8 mL) and H$_2$O (0.5 mL) were added furan-2-ylboronic acid (0.22 g, 1.00 mmol, 50%), K$_2$CO$_3$ (0.63 g, 4.00 mmol), Pd(dppf) C12 (0.12 g, 0.10 mmol) and (+/−)-trans-methyl 3-((2,6-dichloro-5-fluoropyrimidin-4-yl)amino)bicyclo[2.2.2]octane-2-carboxylate (500 mg, 1.44 mmol). The air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (423 mg, 66%).

MS (ESI, pos. ion) m/z: 380.1 [M+H]$^+$;
$^1$H NMR (400 MHz, CDCl$_3$) δ (ppm): 7.66 (s, 1H), 7.19-7.14 (m, 1H), 6.59 (dd, J=3.4, 1.7 Hz, 1H), 5.33 (s, 1H), 4.51 (s, 1H), 3.78 (s, 3H), 2.43 (d, J=5.7 Hz, 1H), 2.02 (d, J=2.1 Hz, 1H), 1.91 (s, 1H), 1.84 (t, J=11.7 Hz, 1H), 1.69 (dd, J=18.2, 10.0 Hz, 5H), 1.46 (t, J=10.7 Hz, 1H), 1.28 (s, 1H).

Step 7: (+/−)-trans-methyl 3-((5-fluoro-2-(5-fluoro-1-trityl-1H-pyrazolo[3,4-b]pyridin-3-yl)-6-(furan-2-yl)pyrimidin-4-yl)amino)bicyclo[2.2.2]octane-2-carboxylate To a mixed solvent of 1,4-dioxane (10 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (698 mg, 0.69 mmol, 50%), K$_2$CO$_3$ (73 mg, 0.53 mmol), PdCl$_2$(dppf) (40 mg, 0.05 mmol) and (+/−)-trans-methyl 3-((2-chloro-5-fluoro-6-(furan-2-yl)pyrimidin-4-yl)amino)bicyclo[2.2.2]octane-2-carboxylate (105 mg, 0.26 mmol). Then the air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (192 mg, 96%).

Step 8: (+/−)-trans-methyl 3-((5-fluoro-2-(5-fluoro-1H-pyrazolo[3,4-b]pyridin-3-yl)-6-(furan-2-yl)pyrimidin-4-yl)amino)bicyclo[2.2.2]octane-2-carboxylate To a solution of (+/−)-trans-methyl 3-((5-fluoro-2-(5-fluoro-1-trityl-1H-pyrazolo[3,4-b]pyridin-3-yl)-6-(furan-2-yl)pyrimidin-4-yl)amino)bicyclo[2.2.2]octane-2-carboxylate (200 mg, 0.28 mmol) in DCM (4 mL) were added Et$_3$SiH (0.55 mL, 3.40 mmol) and TFA (0.25 mL, 3.40 mmol). The mixture was stirred at rt overnight. The reaction was stopped, and the mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 481.3 [M+H]$^+$.

Step 9: (+/−)-trans-3-((5-fluoro-2-(5-fluoro-1H-pyrazolo[3,4-b]pyridin-3-yl)-6-(furan-2-yl) pyrimidin-4-yl)amino)bicyclo[2.2.2]octane-2-carboxylic Acid To a solution of (+/−)-trans-methyl 3-((5-fluoro-2-(5-fluoro-1H-pyrazolo[3,4-b]pyridin-3-yl)-6-(furan-2-yl)pyrimidin-4-yl)amino)bicyclo[2.2.2]octane-2-carboxylate (195 mg, 0.42 mmol) in THF/MeOH/H$_2$O (v/v/v=2 mL/2 mL/2 mL) was added NaOH (0.16 g, 4.18 mmol). The mixture was stirred at rt overnight, then saturated brine (10 mL) was added. The resulting mixture was acidified with diluted hydrochloric acid (1 M) to pH about 6. The resulting mixture was extracted with ethyl acetate (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (14 mg, yield in two steps of step 8 and step 9: 7%).

MS (ESI, pos. ion) m/z: 467.2 [M+H]$^+$;
HRMS (ESI, pos. ion) m/z: 467.1649 [M+H]$^+$, ($C_{23}H_{21}F_2N_6O_3$) [M+H]$^+$ theoretical value: 467.1643;
$^1$H NMR (400 MHz, DMSO-d$_6$) δ (ppm): 14.20 (s, 1H), 8.65 (s, 1H), 8.58 (d, J=8.4 Hz, 1H), 8.04 (s, 1H), 7.88 (d, J=6.9 Hz, 1H), 7.26 (s, 1H), 6.78 (s, 1H), 4.77 (s, 1H), 2.92 (d, J=6.0 Hz, 1H), 2.03 (s, 1H), 1.96 (s, 1H), 1.78 (s, 3H), 1.65-1.34 (m, 6H).

Example 8: (+/−)-trans-3-((5-fluoro-2-(5-fluoro-1H-pyrazolo[3,4-b]pyridin-3-yl)-6-phenylpyrimidin-4-yl)amino)bicyclo[2.2.2]octane-2-carboxylic Acid

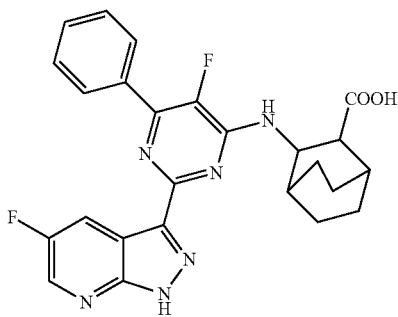 [SMILES: O=C(O)C1C2CCC(CC2)C1Nc1nc(-c2n[nH]c3ncc(F)cc23)nc(-c2ccccc2)c1F]

Step 1: (+/−)-trans-methyl 3-((2-chloro-5-fluoro-6-phenylpyrimidin-4-yl)amino) bicyclo[2.2.2]octane-2-carboxylate To acetonitrile (100 mL) were added phenylboronic acid (0.70 g, 5.74 mmol), AcOK (1.70 g, 17.20 mmol), PdCl$_2$(dppf) (0.50 g, 0.57 mmol) and methyl 3-((2,6-dichloro-5-fluoropyrimidin-4-yl)amino)bicyclo[2.2.2]octane-2-carboxylate (2.00 g, 5.74 mmol). Then to the mixture was added H$_2$O (0.5 mL). The resulting mixture was stirred at 80° C. for 12 h under nitrogen protection. The mixture was filtered to remove the solid impurity, and the filtrate was concentrated to remove the solvent. The residue was purified by silica gel column chromatography (PE/EtOAc (v/v)=20/1) to give the title compound as a white solid (424 mg, 19%).

MS (ESI, pos. ion) m/z: 390.1 [M+H]$^+$.

Step 2: (+/−)-trans-methyl 3-((5-fluoro-2-(5-fluoro-1-trityl-1H-pyrazolo[3,4-b]pyridin-3-yl)-6-phenylpyrimidin-4-yl)amino)bicyclo[2.2.2]octane-2-carboxylate To a mixed solvent of 1,4-dioxane (10 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (698 mg, 0.69 mmol, 50%), K$_2$CO$_3$ (73 mg, 0.51 mmol), PdCl$_2$(dppf) (40 mg, 0.05 mmol) and (+/−)-trans-methyl 3-((2-chloro-5-fluoro-6-phenylpyrimidin-4-yl)amino)bicyclo[2.2.2]octane-2-carboxylate (105 mg, 0.26 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (186 mg, 94%).

Step 3: (+/−)-trans-methyl 3-((5-fluoro-2-(5-fluoro-1H-pyrazolo[3,4-b]pyridin-3-yl)-6-phenyl pyrimidin-4-yl)amino)bicyclo[2.2.2]octane-2-carboxylate To a solution of (+/−)-trans-methyl 3-((5-fluoro-2-(5-fluoro-1-trityl-1H-pyrazolo[3,4-b]pyridin-3-yl)-6-benzylpyrimidin-4-yl)amino)bicyclo[2.2.2]octane-2-carboxylate (188 mg, 0.26 mmol) in DCM (4 mL) were added Et$_3$SiH (0.50 mL, 3.10 mmol) and TFA (0.25 mL, 3.40 mmol). The mixture was stirred at rt overnight. The reaction was stopped, and the mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 491.2 [M+H]$^+$.

Step 4: (+/−)-trans-3-((5-fluoro-2-(5-fluoro-1H-pyrazolo[3,4-b]pyridin-3-yl)-6-phenylpyrimidin-4-yl)amino)bicyclo[2.2.2]octane-2-carboxylic Acid To a solution of (+/−)-trans-methyl 3-((5-fluoro-2-(5-fluoro-1H-pyrazolo[3,4-b]pyridin-3-yl)-6-phenylpyrimidin-4-yl)amino)bicyclo[2.2.2]octane-2-carboxylate (178 mg, 0.37 mmol) in THF/MeOH/H$_2$O (v/v/v=2 mL/2 mL/2 mL) was added NaOH (145 mg, 3.74 mmol). The mixture was stirred at rt overnight. To the reaction mixture was added saturated brine (10 mL), and the mixture was acidified with hydrochloric acid (1 M) to pH about 6. The resulting mixture was extracted with EtOAc (15 mL×3). The combined organic layers were washed with saturated brine, dried over anhydrous sodium sulfate, and filtered. The filtrate was concentrated in vacuo to remove the solvent, and the residue was purified by silica gel column chromatography (DCM/MeOH (v/v)=15/1) to give the title compound as a light yellow solid (14 mg, two steps yield of step 3 or step 4: 8%).

HRMS (ESI, pos. ion) m/z: 477.1865[M+H]$^+$, ($C_{25}H_{23}F_2N_6O_2$)[M+H]$^+$ theoretical value: 477.1851;
MS (ESI, pos. ion) m/z: 477.1 [M+H]$^+$;
$^1$H NMR (400 MHz, DMSO-d$_6$) δ (ppm): 14.13 (s, 1H), 8.65 (s, 1H), 8.55 (dd, J=8.7, 2.4 Hz, 1H), 8.05 (d, J=7.3 Hz, 2H), 7.85 (d, J=6.1 Hz, 1H), 7.63-7.53 (m, 3H), 4.80 (s, 1H), 2.90 (d, J=4.9 Hz, 1H), 2.01 (m, 3H), 1.68-1.32 (m, 7H).

Example 9: (+/−)-trans-3-((2-(5-fluoro-1H-pyrazolo[3,4-b]pyridin-3-yl)-6-(furan-2-yl) pyrimidin-4-yl)amino)bicyclo[2.2.2]octane-2-carboxylic Acid

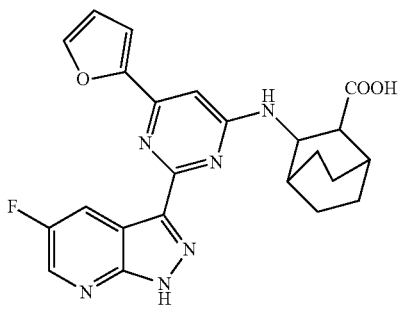 [SMILES: O=C(O)C1C2CCC(CC2)C1Nc1cc(-c2ccco2)nc(-c2n[nH]c3ncc(F)cc23)n1]

Step 1: 2,4-dichloro-6-(furan-2-yl)pyrimidine

To a solution of 2,4,6-trichloropyrimidine (100 mg, 0.55 mmol) in THF (4 mL) were added tetrakis(triphenylphosphine)palladium (43 mg, 0.05 mmol), furan-2-ylboronic acid (61 mg, 0.55 mol) and aqueous sodium bicarbonate solution (1 M, 64 mL, 64 mmol). The mixture was stirred at 80° C. overnight under nitrogen protection. To the reaction mixture was added water (10 mL), and the resulting mixture was extracted with ethyl acetate (15 mL×3). The combined organic layers were washed with saturated brine (30 mL), dried over anhydrous sodium sulfate and filtered. The filtrate was concentrated in vacuo and the residue was purified by silica gel column chromatography (PE) to give the title compound as a green solid (42 mg, 36%).
MS (ESI, pos. ion) m/z: 215.0 [M+H]$^+$;
$^1$H NMR (400 MHz, CDCl$_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 2: (+/−)-trans-methyl 3-((2-chloro-6-(furan-2-yl)pyrimidin-4-yl)amino)bicyclo[2.2.2]octane-2-carboxylate (+/−)-trans-Methyl 3-aminobicyclo[2.2.2]octane-2-carboxylate (429 mg, 2.34 mmol) and 2,4-dichloro-6-(furan-2-yl)pyrimidine (420 mg, 1.95 mmol) were dissolved in DMF (6 mL), then potassium carbonate (809 mg, 5.86 mmol) was added. The mixture was stirred at rt overnight. To the reaction mixture was added water (30 mL), and the resulting mixture was extracted with ethyl acetate (30 mL×3). The combined organic layers were washed with saturated brine (60 mL), dried over anhydrous sodium sulfate and filtered. The filtrate was concentrated in vacuo and the residue was purified by silica gel column chromatography (PE/EtOAc (v/v)=5/1) to give the title compound as a white solid (383 mg, 54%).
MS (ESI, pos. ion) m/z: 362.1 [M+H]$^+$;

$^1$H NMR (400 MHz, CDCl$_3$) δ (ppm): 7.56 (s, 1H), 7.22 (s, 1H), 6.93 (s, 1H), 6.55 (d, J=1.6 Hz, 1H), 5.47 (d, J=5.5 Hz, 1H), 4.44 (s, 1H), 3.70 (s, 3H), 2.44-2.33 (m, 1H), 1.96 (d, J=2.5 Hz, 1H), 1.88 (s, 1H), 1.84-1.58 (m, 8H).

Step 3: (+/−)-trans-methyl 3-((2-(5-fluoro-1-trityl-1H-pyrazolo[3,4-b]pyridin-3-yl)-6-(furan-2-yl) pyrimidin-4-yl)amino)bicyclo[2.2.2]octane-2-carboxylate To a mixed solvent of 1,4-dioxane (10 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (698 mg, 0.69 mmol, 50%), K$_2$CO$_3$ (78 mg, 0.55 mmol), Pd(dppf)Cl$_2$ (42 mg, 0.06 mmol) and (+/−)-trans-methyl 3-((2-chloro-6-(furan-2-yl)pyrimidin-4-yl)amino)bicyclo[2.2.2]octane-2-carboxylate (105 mg, 0.28 mmol). The air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (186 mg, 91%).

Step 4: (+/−)-trans-methyl 3-((2-(5-fluoro-1H-pyrazolo[3,4-b]pyridin-3-yl)-6-(furan-2-yl) pyrimidin-4-yl)amino)bicyclo[2.2.2]octane-2-carboxylate To a solution of (+/−)-trans-methyl 3-((2-(5-fluoro-1-trityl-1H-pyrazolo[3,4-b]pyridin-3-yl)-6-(furan-2-yl)pyrimidin-4-yl)amino)bicyclo[2.2.2]octane-2-carboxylate (186 mg, 0.26 mmol) in DCM (4 mL) were added Et$_3$SiH (0.65 mL, 4.10 mmol) and TFA (0.30 mL, 4.00 mmol). The mixture was stirred at rt overnight. The reaction was stopped, and the mixture was added into saturated aqueous sodium bicarbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.
MS (ESI, pos. ion) m/z: 463.2 [M+H]$^+$.

Step 5: (+/−)-trans-3-((2-(5-fluoro-1H-pyrazolo[3,4-b]pyridin-3-yl)-6-(furan-2-yl) pyrimidin-4-yl)amino) bicyclo[2.2.2]octane-2-carboxylic Acid To a solution of (+/−)-trans-methyl 3-((2-(5-fluoro-1H-pyrazolo[3,4-b]pyridin-3-yl)-6-(furan-2-yl)pyrimidin-4-yl)amino)bicyclo[2.2.2]octane-2-carboxylate (147 mg, 0.33 mmol) in THF/MeOH/H$_2$O (v/v/v=2 mL/2 mL/2 mL) was added NaOH (0.15 g, 3.28 mmol). The mixture was stirred at rt overnight, then saturated brine (20 mL) was added. The resulting mixture was acidified with diluted hydrochloric acid (1 M) to pH about 6. The resulting mixture was extracted with ethyl acetate (20 mL×3). The combined organic layers were washed with saturated brine (50 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (10 mg, two steps yield of step 4 and step 5: 7%).
MS (ESI, pos. ion) m/z: 449.3 [M+H]$^+$;

HRMS (ESI, pos. ion) m/z: 449.1737 [M+H]$^+$, (C$_{23}$H$_{22}$FN$_6$O$_3$) [M+H]$^+$ theoretical value: 449.1738;

$^1$H NMR (400 MHz, DMSO-d$_6$) δ (ppm): 14.16 (s, 1H), 8.63 (d, J=16.0 Hz, 2H), 7.91 (s, 1H), 7.79 (s, 1H), 7.23 (s, 1H), 6.77 (s, 1H), 6.72 (s, 1H), 4.73 (s, 1H), 1.99 (d, J=21.3 Hz, 2H), 1.74 (s, 3H), 1.63-1.34 (m, 6H).

Example 10: (+/−)-trans-3-((2-(5-chloro-1H-pyrazolo[3,4-b]pyridin-3-yl)-6-(1-methyl-1H-pyrazol-4-yl)pyrimidin-4-yl)amino)bicyclo[2.2.2]octane-2-carboxylic Acid

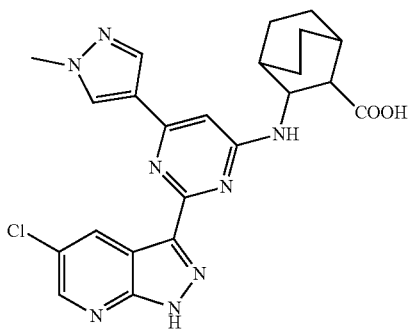 [SMILES: Cn1cc(-c2cc(NC3C4CCC(CC4)C3C(=O)O)nc(-c3n[nH]c4ncc(Cl)cc34)n2)cn1]

Step 1: 2,4-dichloro-6-(1-methyl-1H-pyrazol-4-yl) pyrimidine

To a solution of 2,4,6-trichloropyrimidine (0.81 g, 4.40 mmol) in tetrahydrofuran (10 mL) were added tetrakis (triphenylphosphine)palladium (0.49 g, 0.44 mmol), (1-methyl-1H-pyrazol-4-yl)boronic acid (0.52 g, 4.00 mmol), sodium bicarbonate (1.03 g, 12.00 mmol) and water (0.5 mL) under nitrogen protection. The mixture was stirred at 80° C. for 6 h under nitrogen protection, then filtered to remove solid impurity. The filtrate was concentrated in vacuo and the residue was purified by silica gel column chromatography (PE/EtOAc (v/v)=5/1) to give the title compound as a white solid (0.78 g, 82%).

MS (ESI, pos. ion) m/z: 229.0 [M+H]$^+$;

$^1$H NMR (400 MHz, CDCl$_3$) δ (ppm): 8.12 (s, 1H), 8.02 (s, 1H), 7.34 (s, 1H), 4.00 (s, 3H).

Step 2: (+/−)-trans-methyl 3-((2-chloro-6-(1-methyl-1H-pyrazol-4-yl)pyrimidin-4-yl)amino) bicyclo[2.2.2]octane-2-carboxylate To a solution of 2,4-dichloro-6-(1-methyl-1H-pyrazol-4-yl)pyrimidine (0.48 g, 2.10 mmol) and (+/−)-trans-methyl 3-aminobicyclo[2.2.2]octane-2-carboxylate (0.43 g, 2.30 mmol) in DMF (10 mL) was added potassium carbonate (0.61 g, 4.20 mmol), and the mixture was stirred at rt overnight. To the reaction mixture was added water (30 mL), and the resulting mixture was extracted with ethyl acetate (30 mL×3). The combined organic layers were washed with saturated brine (80 mL×3), dried over anhydrous sodium sulfate and filtered. The filtrate was concentrated in vacuo and the residue was purified by silica gel column chromatography (PE/EtOAc (v/v)=20/1) to give the title compound as a light yellow solid (0.29 g, 37%).

MS (ESI, pos. ion) m/z: 376.3 [M+H]$^+$;

$^1$H NMR (400 MHz, CDCl$_3$) δ (ppm): 8.02 (s, 1H), 7.94 (s, 1H), 6.52 (s, 1H), 5.42 (s, 1H), 4.28 (s, 1H), 3.96 (s, 3H), 3.75 (s, 3H), 3.36 (d, J=6.7 Hz, 1H), 2.38 (d, J=4.7 Hz, 1H), 1.62-1.53 (m, 5H), 1.49 (t, J=9.9 Hz, 3H), 1.43 (s, 1H).

Step 3: (+/−)-trans-methyl 3-((2-(5-chloro-1-trityl-1H-pyrazolo[3,4-b]pyridin-3-yl)-6-(1-methyl-1H-pyrazol-4-yl)pyrimidin-4-yl)amino)bicyclo[2.2.2]octane-2-carboxylate To a mixed solvent of 1,4-dioxane (10 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (997 mg, 0.96 mmol, 50%), K$_2$CO$_3$ (111 mg, 0.80 mmol), PdCl$_2$(dppf) (59 mg, 0.08 mmol) and (+/−)-trans-methyl 3-((2-chloro-6-(1-methyl-1H-pyrazol-4-yl)pyrimidin-4-yl)amino) bicyclo[2.2.2]octane-2-carboxylate (151 mg, 0.40 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=4/1) to give the title compound as a colorless oil (133 mg, 45%).

Step 4: (+/−)-trans-methyl 3-((2-(5-chloro-1H-pyrazolo[3,4-b]pyridin-3-yl)-6-(1-methyl-1H-pyrazol-4-yl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(1-methyl-1H-pyrazol-4-yl)pyrimidin-4-yl)amino)bicyclo[2.2.2]octane-2-carboxylate (130 mg, 0.18 mmol) in DCM (6 mL) were added Et$_3$SiH (0.40 mL, 2.50 mmol) and TFA (0.16 mL, 2.20 mmol). The mixture was stirred at rt overnight. The reaction was stopped, and the mixture was added into saturated aqueous sodium bicarbonate (15 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 493.3 [M+H]$^+$.

Step 5: (+/−)-trans-3-((2-(5-chloro-1H-pyrazolo[3,4-b]pyridin-3-yl)-6-(1-methyl-1H-pyrazol-4-yl)pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(1-methyl-1H-pyrazol-4-yl)pyrimidin-4-yl)amino)bicyclo[2.2.2]octane-2-carboxylate (135 mg, 0.28 mmol) in THF/MeOH (v/v/v=4 mL/4 mL) was added a solution of NaOH (110 mg, 2.82 mmol) in H$_2$O (4 m). The mixture was stirred at rt overnight, then acidified with diluted hydrochloric acid (1 M) to pH about 6, and saturated brine (10 mL) was added. The resulting mixture was extracted with 2-methyl tetrahydrofuran (15 mL×3). The combined organic layers were washed with saturated brine (30 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (7 mg, two-step yield of step 4 and step 5: 5%).

MS (ESI, pos. ion) m/z: 479.3 [M+H]$^+$;

HRMS (ESI, pos. ion) m/z: 479.1711 [M+H]$^+$, (C$_{23}$H$_{24}$ClN$_8$O$_2$) [M+H]$^+$ theoretical value: 479.1701;

$^1$H NMR (400 MHz, DMSO-d$_6$) δ (ppm): 14.18 (s, 1H), 8.93 (s, 1H), 8.61 (s, 1H), 8.33 (s, 1H), 7.99 (s, 1H), 7.58 (d, J=6.2 Hz, 1H), 6.59 (s, 1H), 4.69 (s, 1H), 3.93 (s, 3H), 2.64 (m, 1H), 2.43-2.22 (m, 1H), 1.85 (s, 2H), 1.74 (s, 2H), 1.56 (s, 3H), 1.47 (s, 3H).

Example 11: (+/−)-trans-3-((6-(benzo[b]thiophen-2-yl)-2-(5-chloro-1H-pyrazolo[3,4-b]pyridin-3-yl)pyrimidin-4-yl)amino)bicyclo[2.2.2]octane-2-carboxylic Acid

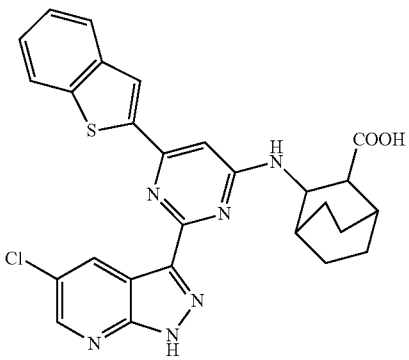 [SMILES: O=C(O)C1C2CCC(CC2)C1Nc1cc(-c2cc3ccccc3s2)nc(-c2n[nH]c3ncc(Cl)cc23)n1]

Step 1: 4-(benzo[b]thiophen-2-yl)-2,6-dichloropyrimidine

To a solution of 2,4,6-trichloropyrimidine (50 mg, 0.27 mmol) in a mixed solvent of toluene (3 mL) and ethanol (1 mL) were added tetrakis(triphenylphosphine)palladium (31 mg, 0.03 mmol), benzo[b]thiophen-2-ylboronic acid (49 mg, 0.28 mmol) and aqueous sodium carbonate solution (1 M, 0.82 mL, 0.82 mmol). The mixture was stirred at 85° C. for 4 h under nitrogen protection. To the reaction mixture was added water (20 mL), and the resulting mixture was extracted with ethyl acetate (20 mL×3). The combined organic layers were washed with saturated brine (40 mL), dried over anhydrous sodium sulfate and filtered. The filtrate was concentrated in vacuo and the residue was purified by silica gel column chromatography (PE) to give the title compound as a white solid (24 mg, 31%).

MS (ESI, pos. ion) m/z: 280.9 [M+H]$^+$;

$^1$H NMR (400 MHz, CDCl$_3$) δ (ppm): 8.17 (s, 1H), 7.91 (t, J=6.4 Hz, 2H), 7.64 (s, 1H), 7.51-7.43 (m, 2H).

Step 2: (+/−)-trans-methyl 3-((6-(benzo[b]thiophen-2-yl)-2-chloropyrimidin-4-yl)amino) bicyclo[2.2.2]octane-2-carboxylate (+/−)-trans-Methyl 3-aminobicyclo[2.2.2]octane-2-carboxylate (409 mg, 2.23 mmol) and 4-(benzo[b]thiophen-2-yl)-2,6-dichloropyrimidine (523 mg, 1.86 mmol) were dissolved in DMF (5 mL), then potassium carbonate (771 mg, 5.58 mmol) was added. The mixture was stirred at rt overnight. To the reaction mixture was added water (40 mL), and the resulting mixture was extracted with ethyl acetate (40 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=20/1) to give the title compound as a white solid (357 mg, 45%).

MS (ESI, pos. ion) m/z: 428.2 [M+H]$^+$;

$^1$H NMR (400 MHz, CDCl$_3$) δ (ppm): 8.05 (s, 1H), 7.91-7.81 (m, 2H), 7.43-7.36 (m, 2H), 6.80 (s, 1H), 5.50 (s, 1H), 4.35 (s, 1H), 3.78 (s, 3H), 2.41 (d, J=4.9 Hz, 1H), 2.10 (s, 1H), 1.90 (d, J=2.6 Hz, 1H), 1.84-1.63 (m, 6H), 1.58-1.43 (m, 2H).

Step 3: (+/−)-trans-methyl 3-((6-(benzo[b]thiophen-2-yl)-2-(5-chloro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (10 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (366 mg, 0.35 mmol, 50%), K$_2$CO$_3$ (47 mg, 0.34 mmol), PdCl$_2$(dppf) (25 mg, 0.03 mmol) and (+/−)-trans-methyl 3-((6-(benzo[b]thiophen-2-yl)-2-chloropyrimidin-4-yl)amino)bicyclo[2.2.2]octane-2-carboxylate (70 mg, 0.16 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as a colorless oil (112 mg, 89%).

$^1$H NMR (400 MHz, DMSO-d$_6$) δ (ppm): 8.35 (s, 1H), 8.06 (s, 1H), 7.96 (d, J=3.2 Hz, 1H), 7.93 (s, 1H), 7.88 (d, J=7.4 Hz, 1H), 7.45 (dd, J=5.8, 3.0 Hz, 2H), 7.39-7.13 (m, 16H), 4.66 (s, 1H), 3.93 (s, 3H), 3.65 (s, 1H), 3.58 (s, 1H), 1.84-1.61 (m, 4H), 1.56 (s, 3H), 1.49-1.33 (m, 4H).

Step 4: (+/−)-trans-methyl 3-((6-(benzo[b]thiophen-2-yl)-2-(5-chloro-1H-pyrazolo[3,4-b]pyridin-3-yl)pyrimidin-4-yl)amino)bicyclo[2.2.2]octane-2-carboxylate To a solution of (+/−)-trans-methyl 3-((6-(benzo[b]thiophen-2-yl)-2-(5-chloro-1-trityl-1H-pyrazolo[3,4-b]pyridin-3-yl)pyrimidin-4-yl)amino)bicyclo[2.2.2]octane-2-carboxylate (150 mg, 0.19 mmol) in DCM (6 mL) were added Et$_3$SiH (0.40 mL, 2.50 mmol) and TFA (0.20 mL, 2.70 mmol). The mixture was stirred at rt overnight. The reaction was stopped, and the mixture was added into saturated aqueous sodium carbonate (20 mL). The resulting mixture was extracted with dichloromethane (20 mL×3). The combined organic layers were washed with saturated brine (50 mL), dried over anhydrous sodium sulfate, and filtered. The filtrate was concentrated in vacuo to remove the solvent to give the title compound as black oil, which was used in the next step without further purification.

MS (ESI, pos. ion) m/z: 545.1 [M+H]$^+$.

Step 5: (+/−)-trans-3-((6-(benzo[b]thiophen-2-yl)-2-(5-chloro-1H-pyrazolo[3,4-b]pyridin-3-yl)pyrimidin-4-yl)amino)bicyclo[2.2.2]octane-2-carboxylic Acid To a solution of (+/−)-trans-methyl 3-((6-(benzo[b]thiophen-2-yl)-2-(5-chloro-1H-pyrazolo[3,4-b]pyridin-3-yl)pyrimidin-4-yl)amino)bicyclo[2.2.2]octane-2-carboxylate (112 mg, 0.21 mmol) in THF/MeOH/H$_2$O v/v/v=2 mL/2 mL/2 mL) was added NaOH (85 mg, 2.13 mmol). The mixture was stirred at rt overnight. To the reaction mixture was added saturated brine (20 mL), and the mixture was acidified with diluted hydrochloric acid (1 M) to pH about 6. The resulting mixture was extracted with 2-MeTHF (20 mL×3). The combined organic layers were washed with saturated brine (50 mL), dried over anhydrous sodium sulfate, and filtered. The filtrate was concentrated in vacuo to remove the solvent, and to the residue was added MeOH/EtOAc (v/v=1 mL/1 mL). The mixture was stirred at rt for 30 min, then there was a solid precipitated out. The mixture was filtered by suction, and the filter cake was washed with MeOH (2 mL) to give the title compound as light yellow solid (30 mg, two steps yield of step 4 and step 5: 27%).

MS (ESI, pos. ion) m/z: 531.2 [M+H]$^+$;

HRMS (ESI, pos. ion) m/z: 531.1374 [M+H]$^+$, (C$_{27}$H$_{24}$ClN$_6$O$_2$S) [M+H]$^+$ theoretical value: 531.1370;

$^1$H NMR (400 MHz, DMSO-d$_6$) δ (ppm): 8.95 (s, 1H), 8.57 (s, 1H), 8.05 (dd, J=5.6, 3.1 Hz, 1H), 7.97 (dd, J=5.5, 3.1 Hz, 1H), 7.60 (s, 1H), 7.48-7.35 (m, 2H), 6.96 (s, 1H), 4.69 (s, 1H), 3.60 (s, 1H), 2.41 (m, 1H), 1.99 (s, 2H), 1.89-1.61 (m, 5H), 1.55-1.41 (m, 2H).

Example 12: (R)-3-((2-(5-chloro-1H-pyrazolo[3,4-b]pyridin-3-yl)-6-(furan-2-yl)pyrimidin-4-yl)amino)-4,4-dimethylpentanoic Acid

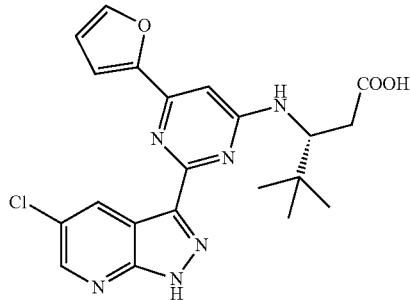 [SMILES: CC(C)(C)[C@@H](CC(=O)O)Nc1cc(-c2ccco2)nc(-c2n[nH]c3ncc(Cl)cc23)n1]

Step 1: 2,4-dichloro-6-(furan-2-yl)pyrimidine

To a solution of 2,4,6-trichloropyrimidine (100 mg, 0.55 mmol) in THF (4 mL) were added tetrakis(triphenylphosphine)palladium (43 mg, 0.05 mmol), furan-2-ylboronic acid (61 mg, 0.55 mol) and aqueous sodium bicarbonate solution (1 M, 64 mL, 64 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (42 mg, 36%).

$^1$H NMR (400 MHz, CDCl$_3$) δ (ppm): 7.67 (s, 1H), 7.58 (s, 1H), 7.44 (d, J=3.5 Hz, 1H), 6.65 (dd, J=3.3, 1.5 Hz, 1H).

Step 2: (R)-methyl 3-((2-chloro-6-(furan-2-yl)pyrimidin-4-yl)amino)-4,4-dimethylpentanoate To DMF (6 mL) were added 2,4-dichloro-6-(furan-2-yl) pyrimidine (0.29 g, 1.33 mmol), (R)-methyl 3-amino-4,4-dimethylpentanoate (0.43 g, 1.60 mmol) and K$_2$CO$_3$ (0.56 g, 3.99 mmol). The reaction mixture was stirred at 60° C. overnight. To the reaction mixture was added H$_2$O (20 mL), and the resulting mixture was extracted with ethyl acetate (20 mL×3). The combined organic layers were washed with saturated brine (40 mL), dried over anhydrous sodium sulfate and filtered. The filtrate was concentrated in vacuo and the residue was purified by silica gel column chromatography (PE/EtOAc (v/v)=10/1) to give the title compound as light yellow oil (0.47 g, 35%).

MS (ESI, pos. ion) m/z: 338.2 [M+H]$^+$;

$^1$H NMR (400 MHz, CDCl$_3$) δ (ppm): 7.57 (s, 1H), 7.23 (s, 1H), 6.81 (s, 1H), 6.56 (s, 1H), 5.31 (s, 1H), 3.64 (s, 3H), 2.74 (d, J=14.0 Hz, 1H), 2.40 (dd, J=15.3, 9.6 Hz, 1H), 1.28 (s, 1H), 1.00 (s, 9H).

Step 3: (R)-methyl 3-((2-(5-chloro-1-trityl-1H-pyrazolo[3,4-b]pyridin-3-yl)-6-(furan-2-yl) pyrimidin-4-yl)amino)-4,4-dimethylpentanoate To a mixed solvent of 1,4-dioxane (10 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (500 mg, 0.96 mmol), K$_2$CO$_3$ (156 mg, 1.13 mmol), PdCl$_2$(dppf) (85 mg, 0.12 mmol) and (R)-methyl 3-((2-chloro-6-(furan-2-yl)pyrimidin-4-yl)amino)-4,4-dimethylpentanoate (190 mg, 0.56 mmol). The air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (233 mg, 59%).

MS (ESI, pos. ion) m/z: 697.2 [M+H]$^+$.

Step 4: (R)-methyl 3-((2-(5-chloro-1H-pyrazolo[3,4-b]pyridin-3-yl)-6-(furan-2-yl)pyrimidin-4-yl) amino)-4,4-dimethylpentanoate To a solution of (R)-methyl 3-((2-(5-chloro-1-trityl-1H-pyrazolo[3,4-b]pyridin-3-yl)-6-(furan-2-yl)pyrimidin-4-yl) amino)-4,4-dimethylpentanoate (233 mg, 0.33 mmol) in DCM (10 mL) were added Et$_3$SiH (0.65 mL, 4.10 mmol) and TFA (0.30 mL, 4.00 mmol). The mixture was stirred at rt overnight. The reaction was stopped, and the mixture was added into saturated aqueous sodium bicarbonate (15 mL). The resulting mixture was extracted with dichloromethane (15 mL×3). The combined organic layers were washed with saturated brine (30 mL), dried over anhydrous sodium sulfate, and filtered. The filtrate was concentrated in vacuo to remove the solvent to give the title compound as black oil, which was used in the next step without further purification.

MS (ESI, pos. ion) m/z: 455.2 [M+H]$^+$.

Step 5: (R)-3-((2-(5-chloro-1H-pyrazolo[3,4-b]pyridin-3-yl)-6-(furan-2-yl)pyrimidin-4-yl)amino)-4,4-dimethylpentanoic Acid To a solution of (R)-methyl 3-((2-(5-chloro-1H-pyrazolo [3,4-b]pyridin-3-yl)-6-(furan-2-yl)pyrimidin-4-yl)amino)-4,4-dimethylpentanoate (170 mg, 0.37 mmol) in THF/MeOH/H$_2$O (v/v/v=4 mL/4 mL/2 mL) was added a solution of NaOH (151 mg, 3.78 mmol) in H$_2$O (2 mL). The mixture was stirred at rt overnight, then saturated brine (20 mL) was added. The resulting mixture was acidified with diluted hydrochloric acid (1 M) to pH about 6. The resulting mixture was extracted with 2-methyl tetrahydrofuran (20 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (24 mg, two steps yield of step 4 and step 5: 15%).

MS (ESI, pos. ion) m/z: 441.1 [M+H]$^+$;
HRMS (ESI, pos. ion) m/z: 441.1461[M+H]$^+$, ($C_{21}H_{22}ClN_6O_3$)[M+H]$^+$ theoretical value: 441.1442;
$^1$H NMR (400 MHz, DMSO-d$_6$) δ (ppm): 9.05 (s, 1H), 8.62 (s, 1H), 7.91 (s, 1H), 7.64 (d, J=9.1 Hz, 1H), 7.20 (s, 1H), 6.81 (s, 1H), 6.71 (s, 1H), 4.83 (s, 1H), 3.93 (s, 1H), 2.68 (m, 1H), 2.38-2.24 (m, 1H), 0.97 (s, 9H).

Example 13: (+/−)-trans-3-((2-(5-chloro-1H-pyrazolo[3,4-b]pyridin-3-yl)-6-(4-cyanophenyl) pyrimidin-4-yl)amino)bicyclo[2.2.2]octane-2-carboxylic Acid

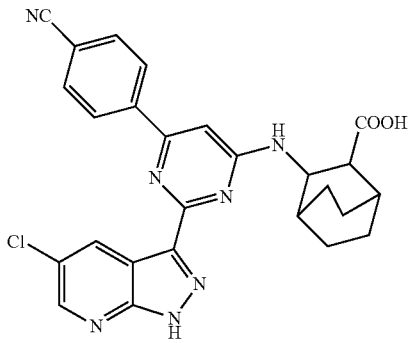 [SMILES: N#Cc1ccc(-c2cc(NC3C4CCC(CC4)C3C(=O)O)nc(-c3n[nH]c4ncc(Cl)cc34)n2)cc1]

Step 1: 4-(2,6-dichloropyrimidin-4-yl)benzonitrile

To a solution of 2,4,6-trichloropyrimidine (1.38 g, 7.52 mmol) in THF (20 mL) were added palladium acetate (0.16 g, 0.70 mmol), (4-cyanophenyl)boronic acid (1.02 g, 6.94 mmol) and aqueous sodium carbonate solution (1 M, 20.5 mL, 20.5 mmol). The mixture was stirred at 70° C. for 6 h under nitrogen protection. To the reaction mixture was added water (30 mL), and the resulting mixture was extracted with ethyl acetate (30 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=20/1) to give the title compound as a white solid (0.80 g, 46%).

$^1$H NMR (400 MHz, CDCl$_3$) δ (ppm): 8.22 (d, J=8.5 Hz, 2H), 7.86 (d, J=8.5 Hz, 2H), 7.74 (s, 1H).

Step 2: (+/−)-trans-methyl 3-((2-chloro-6-(4-cyanophenyl)pyrimidin-4-yl)amino) bicyclo[2.2.2]octane-2-carboxylate (+/−)-trans-Methyl 3-aminobicyclo[2.2.2]octane-2-carboxylate (0.58 g, 3.20 mmol) and 4-(2,6-dichloropyrimidin-4-yl)benzonitrile (0.79 g, 3.20 mmol) were dissolved in DMF (10 mL), then potassium carbonate (0.88 g, 6.40 mmol) was added. The mixture was stirred at rt overnight. To the reaction mixture was added water (20 mL), and the resulting mixture was extracted with ethyl acetate (25 mL×3). The combined organic layers were washed with saturated brine (70 mL×3), dried over anhydrous sodium sulfate and filtered. The filtrate was concentrated in vacuo and the residue was purified by silica gel column chromatography (PE/EtOAc (v/v)=10/1) to give the title compound as a white solid (0.67 g, 53%).

MS (ESI, pos. ion) m/z: 397.2 [M+H]$^+$;
$^1$H NMR (400 MHz, CDCl$_3$) δ (ppm): 8.12 (d, J=7.8 Hz, 2H), 7.78 (d, J=8.3 Hz, 2H), 6.89 (s, 1H), 4.36 (s, 1H), 3.76 (s, 3H), 2.41 (d, J=3.9 Hz, 1H), 2.11 (s, 1H), 1.88 (d, J=2.4 Hz, 1H), 1.69 (m, 5H), 1.62 (s, 1H), 1.51 (m, 2H), 1.28 (m, 1H).

Step 3: (+/−)-trans-methyl 3-((2-(5-chloro-1-trityl-1H-pyrazolo[3,4-b]pyridin-3-yl)-6-(4-cyanophenyl) pyrimidin-4-yl)amino)bicyclo[2.2.2]octane-2-carboxylate To a mixed solvent of 1,4-dioxane (10 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (500 mg, 0.96 mmol), K$_2$CO$_3$ (140 mg, 1.01 mmol), Pd(dppf)Cl$_2$ (75 mg, 0.10 mmol) and ((+/−)-trans-methyl 3-((2-chloro-6-(4-cyanophenyl)pyrimidin-4-yl)amino)bicyclo[2.2.2]octane-2-carboxylate (201 mg, 0.51 mmol). The air in the mixture was exchanged with nitrogen by bubbling for 10 min. The mixture in the sealed tub was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as a colorless oil (128 mg, 33%).

Step 4: (+/−)-trans-methyl 3-((2-(5-chloro-1H-pyrazolo[3,4-b]pyridin-3-yl)-6-(4-cyanophenyl) pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(4-cyanophenyl) pyrimidin-4-yl)amino)bicyclo[2.2.2]octane-2-carboxylate (128 mg, 0.17 mmol) in DCM (4 mL) were added Et$_3$SiH (0.35 mL, 2.50 mmol) and TFA (0.20 mL, 2.70 mmol). The mixture was stirred at rt overnight. The reaction was stopped, and the mixture was added into saturated aqueous sodium bicarbonate (10 mL). The resulting mixture was extracted with dichloromethane (10 mL×3). The combined organic layers were washed with saturated brine (30 mL), dried over anhydrous sodium sulfate, and filtered. The filtrate was concentrated in vacuo to remove the solvent to give the title compound as black oil, which was used in the next step without further purification.

MS (ESI, pos. ion) m/z: 514.1 [M+H]$^+$.

Step 5: (+/−)-trans-3-((2-(5-chloro-1H-pyrazolo[3,4-b]pyridin-3-yl)-6-(4-cyanophenyl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(4-cyanophenyl)pyrimidin-4-yl)amino)bicyclo[2.2.2]octane-2-carboxylate (87 mg, 0.17 mmol) in THF/MeOH/H$_2$O (v/v/v=4 mL/4 mL/2 mL) was added a solution of NaOH (71 mg, 1.78 mmol) in H$_2$O (2 mL). The mixture was stirred at rt overnight, then saturated brine (20 mL) was added. The resulting mixture was acidified with diluted hydrochloric acid (1 M) to pH about 6. The resulting mixture was extracted with 2-MeTHF (20 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=15/1) to give the title compound as a light yellow solid (42 mg, yield in two steps of step 4 and step 5: 49%).

MS (ESI, pos. ion) m/z: 500.1 [M+H]⁺;
HRMS (ESI, pos. ion) m/z: 500.1602 [M+H]⁺, ($C_{26}H_{23}ClN_7O_2$)[M+H]⁺ theoretical value: 500.1602;
¹H NMR (400 MHz, DMSO-$d_6$) δ (ppm): 8.91 (s, 1H), 8.63 (s, 1H), 8.26 (d, J=7.1 Hz, 2H), 8.03 (d, J=8.0 Hz, 2H), 7.16 (s, 1H), 7.02 (s, 1H), 4.76 (s, 1H), 2.58 (d, J=3.1 Hz, 1H), 2.01 (m, 2H), 1.58 (m, 9H), 1.21 (s, 1H);
¹³C NMR (101 MHz, DMSO-$d_6$) δ (ppm): 175.68, 163.31, 159.84, 158.83, 148.24, 141.97, 133.23, 131.06, 128.98, 127.88, 125.09, 119.09, 114.98, 112.91, 101.67, 50.79, 49.30, 28.72, 25.90, 24.27, 21.42, 19.46.

Example 14: (+/−)-trans-3-((6-(benzofuran-2-yl)-2-(5-chloro-1H-pyrazolo[3,4-b]pyridin-3-yl)pyrimidin-4-yl)amino)bicyclo[2.2.2]octane-2-carboxylic Acid

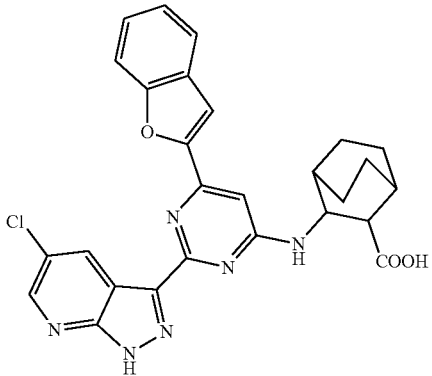 [SMILES: O=C(O)C1C2CCC(CC2)C1Nc1cc(-c2cc3ccccc3o2)nc(-c2n[nH]c3ncc(Cl)cc23)n1]

Step 1: 4-(benzofuran-2-yl)-2,6-dichloropyrimidine

To a solution of 2,4,6-trichloropyrimidine (2.02 g, 11.01 mmol) in THF (10 mL) were added tetrakis(triphenylphosphine)palladium (1.11 g, 0.99 mmol), furan-2-ylboronic acid (1.61 g, 9.94 mmol) and sodium bicarbonate solution (2.52 g, 30.00 mmol). The mixture was stirred at 80° C. for 4 h under nitrogen protection. The reaction mixture was filtered through a celite pad, and the filter cake was washed with ethyl acetate (20 mL). The filtrate was concentrated in vacuo to dry, and the residue was purified by silica gel column chromatography (PE) to give the title compound as a white solid (1.36 g, 52%).

¹H NMR (400 MHz, CDCl₃) δ (ppm): 8.21 (s, 1H), 8.06 (s, 1H), 7.83 (d, J=7.7 Hz, 1H), 7.75 (d, J=8.4 Hz, 1H), 7.53 (t, J=7.8 Hz, 1H), 7.39 (t, J=7.5 Hz, 1H).

Step 2: (+/−)-trans-methyl 3-((6-(benzo[b]furan-2-yl)-2-chloropyrimidin-4-yl)amino) bicyclo[2.2.2]octane-2-carboxylate (+/−)-trans-Methyl 3-aminobicyclo[2.2.2]octane-2-carboxylate (0.85 g, 4.60 mmol) and 4-(benzofuran-2-yl)-2,6-dichloropyrimidine (1.11 g, 4.19 mmol) were dissolved in DMF (10 mL), then potassium carbonate (1.18 g, 8.54 mmol) was added. The mixture was stirred at rt overnight. To the reaction mixture was added water (20 mL), and the resulting mixture was extracted with ethyl acetate (20 mL×3). The combined organic layers were washed with saturated brine (50 mL×3), dried over anhydrous sodium sulfate and filtered. The filtrate was concentrated in vacuo and the residue was purified by silica gel column chromatography (PE/EtOAc (v/v)=10/1) to give the title compound as a white solid (1.40 g, 81%).

MS (ESI, pos. ion) m/z: 412.3 [M+H]⁺;
¹H NMR (400 MHz, CDCl₃) δ (ppm): 7.67 (d, J=7.7 Hz, 1H), 7.59 (s, 1H), 7.56 (d, J=7.8 Hz, 1H), 7.43-7.36 (m, 2H), 6.90 (s, 1H), 5.59 (s, 1H), 4.36 (s, 1H), 3.77 (s, 3H), 2.41 (d, J=5.2 Hz, 1H), 1.91-1.78 (m, 4H), 1.69 (m, 6H), 1.49 (m, 1H).

Step 3: (+/−)-trans-methyl 3-((6-(benzo[b]furan-2-yl)-2-(5-chloro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (10 mL) and H₂O (0.5 mL) were added 5-chloro-3-(4,4,5,5-tetramethyl-1,3,2-dioxaborolan-2-yl)-1-trityl-1H-pyrazolo[3,4-b]pyridine (998 mg, 0.96 mmol, 50%), K₂CO₃ (135 mg, 0.98 mmol), Pd(dppf)Cl₂ (73 mg, 0.10 mmol) and (+/−)-trans-methyl 3-((6-(benzo[b]furan-2-yl)-2-chloropyrimidin-4-yl)amino)bicyclo[2.2.2]octane-2-carboxylate (200 mg, 0.49 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as a colorless oil (330 mg, 88%).

Step 4: (+/−)-trans-methyl 3-((6-(benzo[b]furan-2-yl)-2-(5-chloro-1H-pyrazolo[3,4-b]pyridin-3-yl)pyrimidin-4-yl)amino)bicyclo[2.2.2]octane-2-carboxylate To a solution of (+/−)-trans-methyl 3-((6-(benzo[b]furan-2-yl)-2-(5-chloro-1-trityl-1H-pyrazolo[3,4-b]pyridin-3-yl)pyrimidin-4-yl)amino)bicyclo[2.2.2]octane-2-carboxylate (330 mg, 0.43 mmol) in DCM (6 mL) were added Et₃SiH (0.85 mL, 5.30 mmol) and TFA (0.40 mL, 5.40 mmol). The mixture was stirred at rt overnight. The reaction was stopped, and the mixture was added into saturated aqueous sodium bicarbonate (10 mL). The resulting mixture was extracted with dichloromethane (10 mL×3). The combined organic layers were washed with saturated brine (30 mL), dried over anhydrous sodium sulfate, and filtered. The filtrate was concentrated in vacuo to remove the solvent to give the title compound as black oil, which was used in the next step without further purification.

MS (ESI, pos. ion) m/z: 529.3 [M+H]⁺.

Step 5: (+/−)-trans-3-((6-(benzo[b]furan-2-yl)-2-(5-chloro-1H-pyrazolo[3,4-b]pyridin-3-yl)pyrimidin-4-yl)amino)bicyclo[2.2.2]octane-2-carboxylic Acid To a solution of (+/−)-trans-methyl 3-((6-(benzo[b]furan-2-yl)-2-(5-chloro-1H-pyrazolo[3,4-b]pyridin-3-yl)pyrimidin-4-yl)amino)bicyclo[2.2.2]octane-2-carboxylate (230 mg, 0.43 mmol) in THF/MeOH/H₂O (v/v/v=4 mL/4 mL/2 mL) was added a solution of NaOH (179 mg, 4.48 mmol) in H₂O (2 mL). The mixture was stirred at rt overnight, then saturated brine (20 mL) was added. The resulting mixture was acidified with diluted hydrochloric acid (1 M) to pH about 6. The resulting mixture was extracted with 2-MeTHF (20 mL×3). The combined organic layers were washed with saturated brine (40 mL), dried over anhydrous sodium sulfate and filtered. The filtrate was concentrated in vacuo to remove the solvent and the residue was purified by silica gel column chromatography MeOH/EtOAc (v/v=1 mL/1 mL) to give the title compound as a light yellow solid (30 mg, yield in two steps of step 4 and step 5: 13%).

MS (ESI, pos. ion) m/z: 515.3 [M+H]$^+$;
HRMS (ESI, pos. ion) m/z: 515.1632 [M+H]$^+$, ($C_{27}H_{24}ClN_6O_3$)[M+H]$^+$ theoretical value: 515.1598;
$^1$H NMR (600 MHz, DMSO-d$_6$) δ (ppm): 8.94 (s, 1H), 8.61 (d, J=2.0 Hz, 1H), 7.91 (d, J=6.8 Hz, 1H), 7.79 (d, J=7.6 Hz, 1H), 7.67 (d, J=7.1 Hz, 2H), 7.42 (t, J=7.5 Hz, 1H), 7.35-7.30 (m, 1H), 7.02 (s, 1H), 4.74 (s, 1H), 2.43 (s, 1H), 2.03 (s, 1H), 1.92-1.49 (m, 8H), 1.38 (m, 2H);
$^{13}$C NMR (101 MHz, DMSO-d$_6$) δ (ppm): 176.34, 163.03, 160.12, 155.18, 154.46, 148.05, 131.19, 129.49, 128.80, 128.53, 126.71, 126.41, 124.91, 123.98, 122.68, 114.99, 111.88, 106.98, 99.73, 51.46, 50.59, 28.82, 26.25, 25.41, 24.39, 21.64, 19.68.

Example 15: (2S,3S)-3-((6-(5-cyclopropylfuran-2-yl)-2-(5-fluoro-1H-pyrazolo[3,4-b]pyridin-3-yl)pyrimidin-4-yl)amino)bicyclo[2.2.2]octane-2-carboxylic Acid

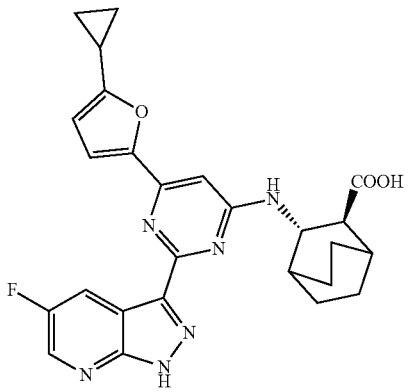 [SMILES: O=C(O)[C@H]1C2CCC(CC2)[C@@H]1Nc1cc(-c2ccc(C3CC3)o2)nc(-c2n[nH]c3ncc(F)cc23)n1]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: 4-(5-bromofuran-2-yl)-2,6-dichloropyrimidine

To a stirred solution of 2,4-dichloro-6-(furan-2-yl)pyrimidine (200 mg, 0.93 mmol) in DMF (8 mL) was added slowly NBS (198 mg, 1.12 mmol). The mixture was stirred at rt for 2 h, then added dropwise into water (50 mL) to quench the reaction. The mixture was extracted with ethyl acetate (50 mL×3). The combined organic layers were washed with saturated brine (80 mL), dried over anhydrous sodium sulfate and filtered. The filtrate was concentrated in vacuo and the residue was purified by silica gel column chromatography (PE/EA (v/v)=10/1) to give the title compound as yellow powder (187 mg, 68%).

$^1$H NMR (400 MHz, CDCl$_3$) δ (ppm): 7.54 (s, 1H), 7.38 (d, J=3.6 Hz, 1H), 6.57 (d, J=3.6 Hz, 1H).

Step 3: (2S,3S)-ethyl 3-((6-(5-bromofuran-2-yl)-2-chloropyrimidin-4-yl)amino)bicyclo[2.2.2]octane-2-carboxylate A suspension of 4-(5-bromofuran-2-yl)-2,6-dichloropyrimidine (188 mg, 0.64 mmol), (2S,3S)-ethyl 3-aminobicyclo[2.2.2]octane-2-carboxylate hydrochloride (180 mg, 0.77 mmol) and K$_2$CO$_3$ (266 mg, 1.92 mmol) in DMF (10 mL) was stirred at rt overnight. To the reaction mixture was added H$_2$O (100 mL) to quench the reaction, and the resulting mixture was extracted with ethyl acetate (50 mL×3). The combined organic layers were washed with saturated brine (80 mL×3), dried over anhydrous sodium sulfate and filtered. The filtrate was concentrated in vacuo and the residue was purified by silica gel column chromatography (PE/EtOAc (v/v)=5/1) to give the title compound as a white solid (210 mg, 75%).

MS (ESI, pos. ion) m/z: 442.2 [M+H]$^+$;
$^1$H NMR (400 MHz, CDCl$_3$) δ (ppm): 7.18 (d, J=3.3 Hz, 1H), 6.64 (s, 1H), 6.49 (d, J=3.4 Hz, 1H), 4.30 (s, 1H), 3.79 (s, 3H), 2.38 (d, J=4.9 Hz, 1H), 2.06 (s, 1H), 1.87 (d, J=2.4 Hz, 1H), 1.70-1.46 (m, 9H).

Step 4: (2S,3S)-ethyl 3-((2-chloro-6-(5-cyclopropylfuran-2-yl)pyrimidin-4-yl)amino) bicyclo[2.2.2]octane-2-carboxylate To a mixed solvent of toluene (8 mL) and H$_2$O (1 mL) were added (2S,3S)-ethyl 3-((6-(5-bromofuran-2-yl)-2-chloropyrimidin-4-yl)amino)bicyclo[2.2.2]octane-2-carboxylate (550 mg, 1.21 mmol), K$_3$PO$_4$ (770 mg, 3.63 mmol), Pd(OAc)$_2$ (28 mg, 0.12 mmol) and cyclopropylboronic acid (125 mg, 1.45 mmol). The mixture was stirred at 115° C. for 5 h. The mixture was filtered to remove the solid impurity, and the filtrate was concentrated to remove the solvent. The residue was purified by silica gel column chromatography (PE/EtOAc (v/v)=10/1-5/1) to give the title compound as a yellow solid (188 mg, 37%).

MS (ESI, pos. ion) m/z: 416.3 [M+H]$^+$.

Step 5: (2S,3S)-ethyl 3-((6-(5-cyclopropylfuran-2-yl)-2-(5-fluoro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (8 mL) and H$_2$O (1 mL) were added 5-fluoro-3-(4,4,5,5-tetramethyl-1,3,2-dioxaborolan-2-yl)-1-trityl-1H-pyrazolo[3,4-b]pyridine (476 mg, 0.47 mmol, 50%), K$_2$CO$_3$ (180 mg, 1.27 mmol), PdCl$_2$(dppf) (33 mg, 0.04 mmol) and (2S,3S)-ethyl 3-((2-chloro-6-(5-cyclopropylfuran-2-yl)pyrimidin-4-yl)amino)bicyclo[2.2.2]octane-2-carboxylate (175 mg, 0.42 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a yellow solid (194 mg, 62%).

Step 6: (2S,3S)-ethyl 3-((6-(5-cyclopropylfuran-2-yl)-2-(5-fluoro-1H-pyrazolo[3,4-b]pyridin-3-yl)pyrimidin-4-yl)amino)bicyclo[2.2.2]octane-2-carboxylate To a solution of (2S,3S)-ethyl 3-((6-(5-cyclopropylfuran-2-yl)-2-(5-fluoro-1-trityl-1H-pyrazolo[3,4-b]pyridin-3-yl)

pyrimidin-4-yl)amino)bicyclo[2.2.2]octane-2-carboxylate (194 mg, 0.26 mmol) in DCM (5 mL) were added trifluoroacetic acid (0.20 mL, 2.56 mmol) and triethyl silicane (0.42 mL, 2.56 mmol). The mixture was stirred at rt overnight. The reaction was stopped, and the reaction mixture was added into saturated aqueous sodium bicarbonate (30 mL). The resulting mixture was extracted with dichloromethane (100 mL×3). The combined organic layers were washed with saturated brine (180 mL), dried over anhydrous sodium sulfate, and filtered. The filtrate was concentrated in vacuo to remove the solvent, and the residue was purified by silica gel column chromatography (PE/EA (v/v)=1/1) to give the title compound as a light yellow solid (120 mg, 91%).

MS (ESI, pos. ion) m/z: 517.3 [M+H]$^+$.

Step 7: (2S,3S)-3-((6-(5-cyclopropylfuran-2-yl)-2-(5-fluoro-1H-pyrazolo[3,4-b]pyridin-3-yl)pyrimidin-4-yl)amino)bicyclo[2.2.2]octane-2-carboxylic Acid To a solution of (2S,3S)-ethyl 3-((6-(5-cyclopropylfuran-2-yl)-2-(5-fluoro-1H-pyrazolo[3,4-b]pyridin-3-yl)pyrimidin-4-yl)amino)bicyclo[2.2.2]octane-2-carboxylate (120 mg, 0.23 mmol) in THF/MeOH (5 mL/5 mL) was added a solution of NaOH (95 mg, 0.09 mmol) in water (0.5 mL). The mixture was stirred at rt overnight, then acidified with diluted with hydrochloric acid (1 M) to pH about 6. The resulting mixture was extracted with 2-methyl tetrahydrofuran (15 mL×3). The combined organic layers were washed with saturated brine (40 mL), dried over anhydrous sodium sulfate and filtered. The filtrate was concentrated in vacuo to remove the solvent and the residue was purified by silica gel column chromatography (DCM/MeOH (v/v)=10/1-5/1) to give the title compound as a white solid (18 mg, 16%).

MS (ESI, pos. ion) m/z: 489.20 [M+H]$^+$;
$^1$H NMR (600 MHz, DMSO-d$_6$) δ (ppm): 8.67 (s, 1H), 8.57 (s, 1H), 7.95 (s, 1H), 7.22 (s, 1H), 6.71 (s, 1H), 6.36 (d, J=3.1 Hz, 1H), 4.72 (s, 1H), 2.09 (s, 1H), 2.03-1.93 (m, 3H), 1.59 (m, 8H), 1.23 (s, 4H), 1.01 (d, J=7.8 Hz, 1H).

Example 16: (+/−)-trans-3-((2-(5-chloro-1H-pyrazolo[3,4-b]pyridin-3-yl)-6-phenylpyrimidin-4-yl)amino)bicyclo[2.2.2]octane-2-carboxylic Acid

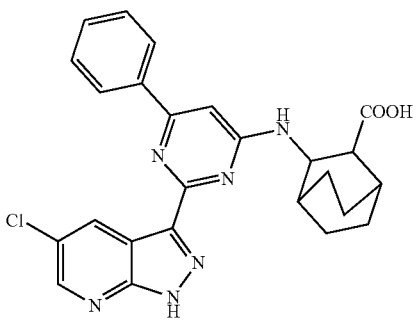 [SMILES: O=C(O)C1C2CCC(CC2)C1Nc1cc(-c2ccccc2)nc(-c2n[nH]c3ncc(Cl)cc23)n1]

Step 1: 2,4-dichloro-6-phenylpyrimidine

To a solution of 2,4,6-trichloropyrimidine (0.29 mL, 2.5 mmol) in THF (5 mL) were added palladium acetate (8 mg, 0.035 mmol), triphenylphosphine (18 mg, 0.065 mmol), benzeneboronic acid (0.20 g, 1.6 mmol) and aqueous sodium carbonate solution (1 M, 3.3 mL, 3.3 mmol). The mixture was stirred at 60° C. for 6 h under nitrogen protection. After the reaction was completed, the mixture was cooled to rt, and concentrated in vacuo. To the residue was added H$_2$O (10 mL), and the mixture was extracted with ethyl acetate (10 mL×3). The combined organic layers were washed with saturated brine (10 mL), dried over anhydrous sodium sulfate, filtered and concentrated in vacuo. The residue was purified by silica gel column chromatography (PE) to give the title compound as a white solid (0.225 g, 61%).

MS (ESI, pos. ion) m/z: 225.0 [M+H]$^+$;
$^1$H NMR (400 MHz, CDCl$_3$) δ (ppm): 8.15-8.04 (m, 2H), 7.70 (s, 1H), 7.63-7.50 (m, 3H).

Step 2: (+/−)-trans-methyl 3-((2-chloro-6-phenylpyrimidin-4-yl)amino)bicyclo[2.2.2]octane-2-carboxylate To a solution of 2,4-dichloro-6-phenylpyrimidine (1.52 g, 6.7 mmol) and (+/−)-trans-methyl 3-aminobicyclo[2.2.2]octane-2-carboxylate (1.84 g, 10.0 mmol) in N,N-dimethylformamide (10 mL) was added potassium carbonate (0.92 g, 6.7 mmol). The mixture was stirred at rt overnight. After the reaction was completed, to the reaction mixture was added water (50 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (n-hexane/EtOAc (v/v)=20/1-10/1) to give the title compound as a white solid (1.65 g, 66%).

MS (ESI, pos. ion) m/z: 372.2 [M+H]$^+$;
$^1$H NMR (400 MHz, CDCl$_3$) δ (ppm): 8.04-7.91 (m, 2H), 7.51-7.41 (m, 3H), 6.78 (s, 1H), 5.41 (s, 1H), 4.32 (s, 1H), 3.73 (s, 3H), 2.38 (d, J=5.1 Hz, 1H), 2.07 (s, 1H), 1.86 (m, 1H), 1.73 (m, 1H), 1.70-1.60 (m, 4H), 1.57 (m, 2H), 1.51-1.41 (m, 1H).

Step 3: (+/−)-trans-methyl 3-((2-(5-chloro-1-trityl-1H-pyrazolo[3,4-b]pyridin-3-yl)-6-phenylpyrimidin-4-yl)amino)bicyclo[2.2.2]octane-2-carboxylate To a mixed solvent of 1,4-dioxane (5 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (240 mg, 0.23 mmol, 50%), K$_2$CO$_3$ (96 mg, 0.69 mmol), PdCl$_2$(dppf) (20 mg, 0.02 mmol) and (+/−)-trans-methyl 3-((2-chloro-6-phenylpyrimidin-4-yl)amino)bicyclo[2.2.2]octane-2-carboxylate (95 mg, 0.25 mmol). The air in the mixture was exchanged with nitrogen by bubbling for 10 min. The mixture in the sealed tub was stirred for 1.5 h at 110° C. The mixture was filtered to remove the solid impurity, and the filtrate was concentrated to remove the solvent. The residue was purified by silica gel column chromatography (PE/EtOAc (v/v)=10/1-5/1) to give a white solid (56 mg, 50%).

Step 4: (+/−)-trans-methyl 3-((2-(5-chloro-1H-pyrazolo[3,4-b]pyridin-3-yl)-6-phenylpyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-phenylpyrimidin-4-yl)amino)bicyclo[2.2.2]octane-2-carboxylate (101 mg, 0.14 mmol) in DCM (5 mL) were added trifluoroacetic acid (163 mg, 1.43 mmol) and triethyl silicane (170 mL, 1.46 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (56 mg, 83%).

MS (ESI, pos. ion) m/z: 490.10 [M+H]$^+$.

Step 5: (+/−)-trans-3-((2-(5-chloro-1H-pyrazolo[3,4-b]pyridin-3-yl)-6-phenylpyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-phenylpyrimidin-4-yl)amino)bicyclo[2.2.2]octane-2-carboxylate (56 mg, 0.11 mmol) in THF/MeOH (v/v=5 mL/5 mL) was added a solution of sodium hydroxide (48 mg, 1.15 mmol) in water (1 mL). The mixture was stirred at rt overnight. To the reaction mixture was added water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (33 mg, 61%).

MS (ESI, pos. ion) m/z: 475.1 [M+H]$^+$;
HRMS (ESI, pos. ion) m/z: 475.1648 [M+H]$^+$, ($C_{25}H_{24}ClN_6O_2$) [M+H]$^+$ theoretical value: 475.1649;
$^1$H NMR (600 MHz, DMSO-$d_6$) δ (ppm): 12.43 (s, 1H), 8.94 (s, 1H), 8.64 (s, 1H), 8.09 (s, 1H), 7.87 (s, 1H), 7.56 (s, 2H), 7.24 (s, 1H), 7.07 (s, 1H), 6.93 (s, 1H), 4.75 (s, 1H), 2.78 (d, J=3.8 Hz, 1H), 2.02 (d, J=20.8 Hz, 2H), 1.90-1.69 (m, 3H), 1.62-1.38 (m, 4H).

Example 17: (+/−)-trans-3-((2-(5-chloro-1H-pyrazolo[3,4-b]pyridin-3-yl)-6-(1-methyl-1H-pyrrol-3-yl)pyrimidin-4-yl)amino)bicyclo[2.2.2]octane-2-carboxylic Acid

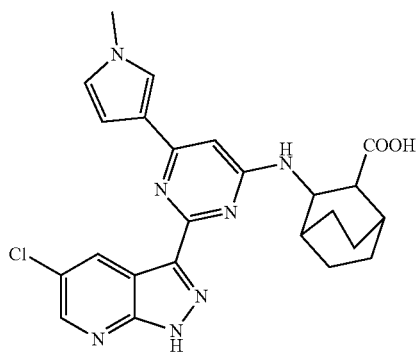 [SMILES: Cn1ccc(-c2cc(NC3C4CCC(CC4)C3C(=O)O)nc(-c3n[nH]c4ncc(Cl)cc34)n2)c1]

Step 1:
2,4-dichloro-6-(1-methyl-1H-pyrrol-3-yl)pyrimidine

To a solution of 2,4,6-trichloropyrimidine (545 mg, 2.97 mmol) in THF (20 mL) were added tetrakis(triphenylphosphine)palladium (320 mg, 0.27 mmol), (1-methyl-1H-pyrrol-3-yl)boronic acid (560 mg, 2.70 mmol) and sodium bicarbonate (682 mg, 8.11 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (406 mg, 66%).

MS (ESI, pos. ion) m/z: 228.1 [M+H]$^+$.

Step 2: (+/−)-trans-methyl 3-((2-chloro-6-(1-methyl-1H-pyrrol-3-yl)pyrimidin-4-yl) amino)bicyclo[2.2.2]octane-2-carboxylate (+/−)-trans-Methyl 3-aminobicyclo[2.2.2]octane-2-carboxylate (425 mg, 2.14 mmol) and 2,4-dichloro-6-(1-methyl-1H-pyrrol-3-yl)pyrimidine (406 mg, 1.78 mmol) were dissolved in DMF (10 mL), then potassium carbonate (492 mg, 3.56 mmol) was added. The mixture was stirred at rt overnight. To the reaction mixture was added water (40 mL), and the resulting mixture was extracted with ethyl acetate (40 mL×3). The combined organic layers were washed with saturated brine (50 mL 3), dried over anhydrous sodium sulfate and filtered. The filtrate was concentrated in vacuo and the residue was purified by silica gel column chromatography (PE/EtOAc (v/v)=5/1) to give the title compound as a white solid (123 mg, 18%).

MS (ESI, pos. ion) m/z: 375.3 [M+H]$^+$.

Step 3: (+/−)-trans-methyl 3-((2-(5-chloro-1-trityl-1H-pyrazolo[3,4-b]pyridin-3-yl)-6-(1-methyl-1H-pyrrol-3-yl)pyrimidin-4-yl)amino)bicyclo[2.2.2]octane-2-carboxylate To a mixed solvent of 1,4-dioxane (5 mL) and $H_2O$ (1 mL) were added 5-chloro-3-(4,4,5,5-tetramethyl-1,3,2-dioxaborolan-2-yl)-1-trityl-1H-pyrazolo[3,4-b]pyridine (307 mg, 0.29 mmol, 50%), $K_2CO_3$ (110 mg, 0.78 mmol), $PdCl_2$(dppf) (24 mg, 0.03 mmol) and (+/−)-trans-methyl 3-((2-chloro-6-(1-methyl-1H-pyrrol-3-yl)pyrimidin-4-yl)amino)bicyclo[2.2.2]octane-2-carboxylate (98 mg, 0.26 mmol). The air in the mixture was exchanged with nitrogen by bubbling for 10 min. The mixture in a sealed-tub was stirred for 1.5 h at 110° C. The mixture was filtered to remove the solid impurity, and the filtrate was concentrated to remove the solvent. The residue was purified by silica gel column chromatography (PE/EtOAc (v/v)=10/1-5/1) to give a white solid (183 mg, 95%).

$^1$H NMR (400 MHz, CDCl$_3$) δ (ppm): 8.98 (d, J=2.3 Hz, 1H), 8.18 (d, J=2.3 Hz, 1H), 7.41 (s, 1H), 7.31 (d, J=1.5 Hz, 5H), 7.26 (s, 10H), 6.72-6.67 (m, 2H), 6.52 (s, 1H), 4.30 (s, 1H), 3.76 (s, 3H), 3.70 (s, 3H), 2.44 (d, J=4.9 Hz, 1H), 1.91 (s, 3H), 1.77-1.49 (m, 8H).

Step 4: (+/−)-trans-methyl 3-((2-(5-chloro-1H-pyrazolo[3,4-b]pyridin-3-yl)-6-(1-methyl-1H-pyrrol-3-yl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(1-methyl-1H-pyrrol-3-yl)pyrimidin-4-yl)amino)bicyclo[2.2.2]octane-2-carboxylate (183 mg, 0.25 mmol) in DCM (5 mL) were added trifluoroacetic acid (0.4 mL, 2.08 mmol) and triethyl silicane (0.20 mL, 2.08 mmol). The mixture was stirred at rt overnight. The reaction mixture was added into saturated aqueous sodium bicarbonate (100 mL). The resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent to give the title compound as black oil (89 mg, 73%), which was used directly in the next step without further purification.

MS (ESI, pos. ion) m/z: 492.1 [M+H]$^+$.

Step 5: (+/−)-trans-3-((2-(5-chloro-1H-pyrazolo[3,4-b]pyridin-3-yl)-6-(1-methyl-1H-pyrrol-3-yl)pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(1-methyl-1H-pyrrol-3-yl)pyrimidin-4-yl)amino)bicyclo[2.2.2]octane-2-carboxylate (89 mg, 0.18 mmol) in THF/MeOH (v/v=5 mL/5 mL) was added a solution of sodium hydroxide (72 mg, 1.81 mmol) in water (1 mL). The mixture was stirred at rt overnight. To the reaction mixture was added water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (30 mg, 35%).

MS (ESI, pos. ion) m/z: 478.3 [M+H]$^+$;
HRMS (ESI, pos. ion) m/z: 478.1755 [M+H]$^+$, ($C_{25}H_{25}ClN_7O_2$) [M+H]$^+$ theoretical value: 478.1758;
$^1$H NMR (400 MHz, CDCl$_3$) δ (ppm): 15.17 (s, 1H), 8.76 (s, 2H), 7.86 (s, 1H), 6.96 (s, 1H), 6.89 (s, 1H), 6.65 (s, 1H), 4.85 (s, 1H), 3.74 (s, 3H), 2.75 (s, 1H), 2.07 (s, 1H), 1.95 (s, 1H), 1.80-1.44 (m, 9H);
$^{13}$C NMR (151 MHz, DMSO-d$_6$) δ(ppm): 175.35, 162.09, 154.27, 151.57, 149.48, 136.22, 130.19, 126.33, 125.53, 124.99, 114.88, 114.78, 108.84, 107.84, 97.33, 51.65, 48.59, 36.89, 29.35, 28.50, 25.62, 24.31, 21.29, 19.43.

Example 18: (2S,3S)-3-((6-(5-cyclopropylfuran-2-yl)-5-fluoro-2-(5-fluoro-1H-pyrazolo[3,4-b]pyridin-3-yl)pyrimidin-4-yl)amino)bicyclo[2.2.2]octane-2-carboxylic Acid

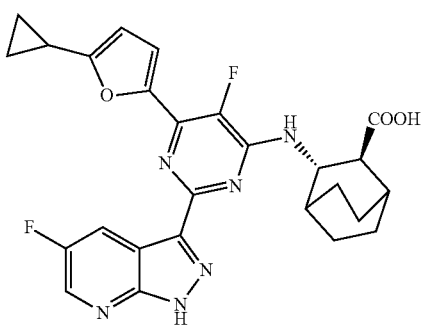 [SMILES: O=C(O)[C@H]1C2CCC(CC2)[C@@H]1Nc1nc(-c2n[nH]c3ncc(F)cc23)nc(-c2ccc(C3CC3)o2)c1F]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: (2S,3S)-ethyl 3-((2,6-dichloro-5-fluoropyrimidin-4-yl)amino)bicyclo[2.2.2]octane-2-carboxylate A suspension of 2,4,6-trichloro-5-fluoropyrimidine (1.54 g, 7.65 mmol), (2S,3S)-ethyl 3-aminobicyclo[2.2.2]octane-2-carboxylate hydrochloride (1.79 g, 7.65 mmol) and K$_2$CO$_3$ (2.64 g, 19.12 mmol) in DMF (15 mL) was stirred at rt overnight. Water (50 mL) was added to quench the reaction, and the resulting mixture was extracted with EtOAc (50 mL×3). The combined organic phases were washed with saturated brine (100 mL×3), dried over anhydrous Na$_2$SO$_4$, filtered, and the filtrate was concentrated in vacuo. The residue was purified by silica gel chromatograph (PE/EtOAc (v/v)=5/1) to give the title compound as a light yellow solid (0.69 g, 25%).

MS (ESI, pos. ion) m/z: 362.1 [M+H]$^+$;
$^1$H NMR (400 MHz, CDCl$_3$) δ (ppm): 5.38 (d, J=4.2 Hz, 1H), 4.53 (t, J=5.0 Hz, 1H), 4.22 (q, J=7.1 Hz, 2H), 2.38 (d, J=5.8 Hz, 1H), 2.04 (d, J=2.2 Hz, 1H), 1.89 (s, 1H), 1.80 (m, 1H), 1.61 (m, 4H), 1.47 (m, 1H), 1.28 (t, J=7.1 Hz, 4H).

Step 3: (2S,3S)-ethyl 3-((2-chloro-5-fluoro-6-(furan-2-yl)pyrimidin-4-yl)amino) bicyclo[2.2.2]octane-2-carboxylate Furan-2-ylboric acid (0.21 g, 1.90 mmol), K$_2$CO$_3$ (0.79 g, 5.70 mmol), PdCl$_2$(dppf) (0.14 g, 0.19 mmol) and (2S,3S)-ethyl 3-((2,6-dichloro-5-fluoropyrimidin-4-yl)amino) bicyclo[2.2.2]octane-2-carboxylate (0.69 g, 1.90 mmol) were mixed in THF (8 mL). To the mixture was added H$_2$O (0.5 mL), and the air in the mixture was exchanged with nitrogen by bubbling emptying. The mixture in a tube was sealed, and stirred at 100° C. for 4 h. The mixture was filtered to remove the solid impurity, and the filtrate was concentrated to remove the solvent. The residue was purified by silica gel column chromatography (PE/EtOAc (v/v)=10/1-5/1) to give the title compound as a light yellow solid (315 mg, 66%).

MS (ESI, pos. ion) m/z: 394.1 [M+H]$^+$;
$^1$H NMR (400 MHz, CDCl$_3$) δ (ppm): 7.66 (s, 1H), 7.19-7.13 (m, 1H), 6.59 (dd, J=3.3, 1.6 Hz, 1H), 5.35 (d, J=3.9 Hz, 1H), 4.54 (s, 1H), 4.24 (q, J=7.2 Hz, 2H), 2.41 (d, J=5.8 Hz, 1H), 1.91 (s, 1H), 1.84 (m, 1H), 1.68 (m, 5H), 1.46 (m, 1H), 1.28 (m, 5H).

Step 4: (2S,3S)-ethyl 3-((6-(5-bromofuran-2-yl)-2-chloro-5-fluoropyrimidin-4-yl)amino) bicyclo[2.2.2] octane-2-carboxylate To a solution of (2S,3S)-ethyl 3-((2-chloro-5-fluoro-6-(furan-2-yl) pyrimidin-4-yl)amino)bicyclo[2.2.2]octane-2-carboxylate (715 mg, 1.82 mmol) in 2-methylfuran (20 mL) was added NBS (388 mg, 2.18 mmol) in portions, and the mixture was stirred at rt for 1 h. To the reaction mixture was added saturated aqueous sodium thiosulfate (30 mL), and the resulting mixture was extracted with ethyl acetate (40 mL×3). The combined organic layers were washed with saturated brine (100 mL), dried over anhydrous sodium sulfate and filtered. The filtrate was concentrated in vacuo and the residue was purified by silica gel column chromatography (PE/EtOAc (v/v)=10/1) to give the title compound as colorless oil (678 mg, 79%).

MS (ESI, pos. ion) m/z: 472.0 [M+H]$^+$;

$^1$H NMR (400 MHz, CDCl$_3$) δ (ppm): 7.12 (d, J=1.7 Hz, 1H), 6.52 (d, J=3.4 Hz, 1H), 4.53 (s, 1H), 4.24 (q, J=7.0 Hz, 2H), 2.40 (d, J=5.7 Hz, 1H), 2.04 (s, 1H), 1.91 (s, 1H), 1.82 (m, 1H), 1.68 (m, 4H), 1.47 (m, 1H), 1.28 (m, 6H).

Step 5: (2S,3S)-ethyl 3-((2-chloro-6-(5-cyclopropyl-furan-2-yl)-5-fluoropyrimidin-4-yl) amino)bicyclo[2.2.2]octane-2-carboxylate To a reaction flask were added (2S,3S)-ethyl 3-((6-(5-bromofuran-2-yl)-2-chloro-5-fluoropyrimidin-4-yl)amino)bicyclo[2.2.2]octane-2-carboxylate (648 mg, 1.43 mmol), palladium acetate (33 mg, 0.14 mmol), triphenylphosphine (77 mg, 0.29 mmol), potassium phosphate (1.46 g, 4.31 mmol) and cyclopropylboronic acid (0.15 g, 1.70 mmol), then to the mixture were added toluene (15 mL) and water (0.3 mL). The mixture was stirred at 115° C. for 5 h under nitrogen protection. The reaction was stopped, and the reaction mixture was filtered through a celite pad. The filter cake was washed with EA (20 mL), and the filtrate was concentrated in vacuo. The residue was purified by silica gel column chromatography (PE/EtOAc (v/v)=10/1) to give the title compound as light yellow oil (426 mg, 68%).

MS (ESI, pos. ion) m/z: 434.2 [M+H]$^+$;

$^1$H NMR (600 MHz, CDCl$_3$) δ (ppm): 7.07 (dd, J=3.0, 2.0 Hz, 1H), 6.11 (d, J=3.4 Hz, 1H), 5.28 (d, J=4.5 Hz, 1H), 4.52 (t, J=5.6 Hz, 1H), 4.24 (m, 2H), 2.39 (d, J=5.7 Hz, 1H), 1.91 (d, J=2.5 Hz, 1H), 1.84 (m, 1H), 1.74-1.65 (m, 5H), 1.45 (m, 1H), 1.28 (m, 6H), 1.02-0.97 (m, 2H), 0.89 (m, 2H).

Step 6: (2S,3S)-ethyl 3-((6-(5-cyclopropylfuran-2-yl)-5-fluoro-2-(5-fluoro-1-trityl-1H-pyrazolo[3,4-b]pyridin-3-yl)pyrimidin-4-yl)amino)bicyclo[2.2.2]octane-2-carboxylate To 1,4-dioxane (20 mL) were added 5-fluoro-3-(4,4,5,5-tetramethyl-1,3,2-dioxaborolan-2-yl)-1-trityl-1H-pyrazolo[3,4-b]pyridine (50%, 2.00 g, 1.98 mmol), K$_2$CO$_3$ (285 mg, 2.06 mmol), PdCl$_2$(dppf) (155 mg, 0.21 mmol) and (2S,3S)-ethyl 3-((2-chloro-6-(5-cyclopropylfuran-2-yl)-5-fluoropyrimidin-4-yl)amino)bicyclo[2.2.2]octane-2-carboxylate (426 mg, 0.98 mmol). Then H$_2$O (0.5 mL) was added to the mixture, and the air in the mixture was exchanged with nitrogen by bubbling emptying for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1) to give the title compound as light yellow oil (654 mg, 86%).

Step 7: (2S,3S)-ethyl 3-((6-(5-cyclopropylfuran-2-yl)-5-fluoro-2-(5-fluoro-1H-pyrazolo[3,4-b]pyridin-3-yl)pyrimidin-4-yl)amino)bicyclo[2.2.2]octane-2-carboxylate To a solution of (2S,3S)-ethyl 3-((6-(5-cyclopropylfuran-2-yl)-5-fluoro-2-(5-fluoro-1-trityl-1H-pyrazolo[3,4-b]pyridin-3-yl)pyrimidin-4-yl)amino)bicyclo[2.2.2]octane-2-carboxylate (654 mg, 0.84 mmol) in DCM (20 mL) were added Et$_3$SiH (1.65 mL, 10.30 mmol) and TFA (0.78 mL, 11.00 mmol). The mixture was stirred at rt overnight. The reaction was stopped, then the reaction mixture was added into saturated aqueous sodium bicarbonate (30 mL), and the resulting mixture was extracted with dichloromethane (30 mL×3). The combined organic layers were washed with saturated brine (100 mL), dried over anhydrous sodium sulfate, and filtered. The filtrate was concentrated to remove the solvent, and the residue was purified by silica gel column chromatography (PE/EtOAc (v/v)=2/1) to give the title compound as light yellow oil (200 mg, 44%).

MS (ESI, pos. ion) m/z: 535.3 [M+H]$^+$.

Step 8: (2S,3S)-3-((6-(5-cyclopropylfuran-2-yl)-5-fluoro-2-(5-fluoro-1H-pyrazolo[3,4-b]pyridin-3-yl)pyrimidin-4-yl)amino)bicyclo[2.2.2]octane-2-carboxylic Acid To a solution of (2S,3S)-ethyl 3-((6-(5-cyclopropylfuran-2-yl)-5-fluoro-2-(5-fluoro-1H-pyrazolo[3,4-b]pyridin-3-yl)pyrimidin-4-yl)amino)bicyclo[2.2.2]octane-2-carboxylate (200 mg, 0.37 mmol) in THF/MeOH/H$_2$O (v/v/v=2 mL/2 mL/1 mL) was added a solution of NaOH (0.14 g, 3.80 mmol) in water (1 mL). The mixture was stirred at rt overnight. To the reaction mixture was added saturated brine (10 mL), and the mixture was acidified with diluted hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=15/1) to give the title compound as a light yellow solid (100 mg, 53%).

MS (ESI, pos. ion) m/z: 507.3 [M+H]$^+$;

HRMS (ESI, pos. ion) m/z: 507.1937[M+H]$^+$, (C$_{26}$H$_{25}$F$_2$N$_6$O$_3$)[M+H]$^+$ theoretical value: 507.1956;

$^1$H NMR (400 MHz, DMSO-d$_6$) δ (ppm): 14.21 (s, 1H), 8.63 (s, 1H), 8.60 (dd, J=8.7, 2.5 Hz, 1H), 7.66 (d, J=5.0 Hz, 1H), 7.12 (s, 1H), 6.40 (d, J=3.0 Hz, 1H), 4.80 (s, 1H), 3.18-3.13 (m, 1H), 2.69 (d, J=7.5 Hz, 1H), 2.15-2.08 (m, 1H), 2.01-1.95 (m, 1H), 1.92 (s, 1H), 1.75 (s, 3H), 1.52-1.31 (m, 4H), 1.02 (m, 2H), 0.88 (m, 2H).

Example 19: (2S,3S)-3-((2-(5-fluoro-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylic Acid

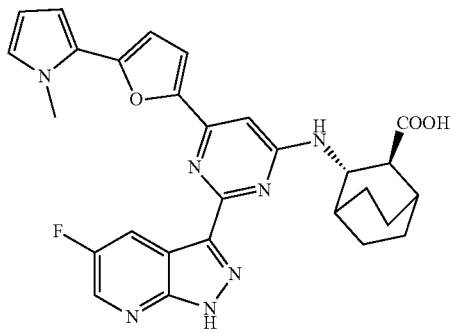 [SMILES: Cn1cccc1-c1ccc(-c2cc(N[C@H]3C4CCC(CC4)[C@@H]3C(=O)O)nc(-c3n[nH]c4ncc(F)cc34)n2)o1]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: 2,4-dichloro-6-(furan-2-yl)pyrimidine

To a solution of 2,4,6-trichloropyrimidine (100 mg, 0.55 mmol) in THF (4 mL) were added tetrakis(triphenylphosphine)palladium (43 mg, 0.05 mmol), furan-2-ylboronic acid (61 mg, 0.55 mol) and aqueous sodium bicarbonate solution (1 M, 64 mL, 1.64 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (42 mg, 36%).

MS (ESI, pos. ion) m/z: 215.0 [M+H]$^+$;

$^1$H NMR (400 MHz, CDCl$_3$) δ (ppm): 7.67 (d, J=0.7 Hz, 1H), 7.58 (s, 1H), 7.43 (d, J=3.4 Hz, 1H), 6.65 (dd, J=3.4, 1.6 Hz, 1H).

Step 3: 4-(5-bromofuran-2-yl)-2,6-dichloropyrimidine 2,4-Dichloro-6-(furan-2-yl)pyrimidine (200 mg, 0.93 mmol) was added into DMF (8 mL), and the mixture was stirred at rt, then NBS (198 mg, 1.12 mmol) was added in portions into the mixture. The resulting mixture was stirred at rt for 2 h. The reaction mixture was added dropwise into water (50 mL) to quench the reaction, and the resulting mixture was extracted with EtOAc (50 mL×3). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=10/1) to give the title compound as yellow powder (187 mg, 68%).

$^1$H NMR (400 MHz, CDCl$_3$) δ (ppm): 7.54 (s, 1H), 7.38 (d, J=3.6 Hz, 1H), 6.57 (d, J=3.6 Hz, 1H).

Step 4: (2S,3S)-ethyl 3-((6-(5-bromofuran-2-yl)-2-chloropyrimidin-4-yl)amino) bicyclo[2.2.2]octane-2-carboxylate A suspension of 2,4-dichloro-6-(5-bromofuran-2-yl)pyrimidine (188 mg, 0.64 mmol), (2S,3S)-trans-ethyl 3-aminobicyclo[2.2.2]octane-2-carboxylate hydrochloride (180 mg, 0.77 mmol) and K$_2$CO$_3$ (221 mg, 1.60 mmol) in DMF (10 mL) was stirred at rt overnight. To the reaction mixture was added H$_2$O (100 mL), and the mixture was extracted with EtOAc (50 mL×3). The combined organic layers were washed with saturated brine (80 mL), dried over anhydrous sodium sulfate, and filtered. The filtrate was concentrated, and the residue was purified by silica gel column chromatography (PE/EtOAc (v/v)=5/1) to give the title compound as a white solid (210 mg, 75%).

$^1$H NMR (400 MHz, CDCl$_3$) δ (ppm): 7.18 (d, J=3.3 Hz, 1H), 6.64 (s, 1H), 6.49 (d, J=3.4 Hz, 1H), 4.30 (s, 1H), 3.79 (s, 3H), 2.38 (d, J=4.9 Hz, 1H), 2.06 (s, 1H), 1.87 (d, J=2.4 Hz, 1H), 1.70-1.46 (m, 9H).

Step 5: (2S,3S)-ethyl 3-((2-chloro-6-(5-(1-methyl-1H-pyrrol-2-yl)furan-2-yl)pyrimidin-4-yl)amino)bicyclo[2.2.2]octane-2-carboxylate (2S,3S)-Ethyl 3-((6-(5-bromofuran-2-yl)-2-chloropyrimidin-4-yl)amino)bicyclo[2.2.2]octane-2-carboxylate (0.50 g, 1.10 mmol), K$_3$PO$_4$ (0.71 g, 3.30 mmol), palladium acetate (27 mg, 0.12 mmol), triphenylphosphine (59 mg, 0.22 mmol) and (1-methyl-1H-pyrrol-2-yl)boronic acid (0.17 g, 1.40 mmol) were mixed in toluene (15 m), then H$_2$O (0.5 mL) was added into the mixture. The resulting mixture was refluxed under nitrogen protection for 5 h. After the reaction was completed, the mixture was filtered to remove the solid impurity, and the filtrate was concentrated to remove the solvent. The residue was purified by silica gel column chromatography (PE/EtOAc (v/v)=15/1) to give the title compound as light yellow solid (236 mg, 47%).

MS (ESI, pos. ion) m/z: 455.1 [M+H]$^+$;

$^1$H NMR (400 MHz, CDCl$_3$) δ (ppm): 7.26 (d, J=3.5 Hz, 1H), 7.13 (s, 1H), 6.71 (s, 1H), 6.63 (s, 1H), 6.48 (s, 1H), 6.39 (d, J=3.5 Hz, 1H), 4.32 (s, 1H), 4.21 (dd, J=9.3, 4.6 Hz, 2H), 3.73 (s, 3H), 2.37 (s, 1H), 2.08 (s, 1H), 1.89 (d, J=3.6 Hz, 1H), 1.76 (m, 2H), 1.69 (m, 6H), 1.30-1.26 (m, 4H).

Step 5: (2S,3S)-ethyl 3-((2-(5-fluoro-1-trityl-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylate To a mixed solvent of 1,4-dioxane (20 mL) and H$_2$O (1 mL) were added 5-fluoro-3-(4,4,5,5-tetramethyl-1,3,2-dioxaborolan-2-yl)-1-trityl-1H-pyrazolo[3,4-b]pyridine (3.00 g, 2.97 mmol, 50%), K$_2$CO$_3$ (439 mg, 3.18 mmol), PdCl$_2$(dppf) (230 mg, 0.31 mmol) and (2S,3S)-ethyl 3-((2-chloro-6-(5-(1-methyl-1H-pyrrol-2-yl)furan-2-yl)pyrimidin-4-yl)amino) bicyclo[2.2.2]octane-2-carboxylate (700 mg, 1.54 mmol). The air in the mixture was exchanged with nitrogen by bubbling for 10 min. The mixture in a sealed-tube was stirred for 3 h at 110° C. The mixture was filtered to remove the solid impurity, and the filtrate was concentrated to remove the solvent. The residue was purified by silica gel column chromatography (PE/EtOAc (v/v)=10/1) to give the title compound as a light yellow solid (1.07 g, 87%).

Step 6: (2S,3S)-ethyl 3-((2-(5-fluoro-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylate (2S,3S)-Ethyl 3-((2-(5-fluoro-1-trityl-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylate (1.03 g, 1.32 mmol) was added into DCM (20 mL), then TFA (1.20 mL, 16.20 mmol) and triethyl silicane (2.55 mL, 16.00 mmol) were added into the mixture. The resulting mixture was stirred at rt overnight. The reaction was stopped, and the reaction mixture was added into saturated aqueous sodium bicarbonate (30 mL). The resulting mixture was extracted with dichloromethane (30 mL×3). The combined organic layers were washed with saturated brine (100 mL), dried over anhydrous sodium sulfate, and filtered. The filtrate was concentrated in vacuo, and the residue was purified by silica gel column chromatography (DCM/MeOH (v/v)=1/1) to give the title compound as a light yellow solid (130 mg, 18%).

MS (ESI, pos. ion) m/z: 556.3 [M+H]$^+$.

Step 7: (2S,3S)-3-((2-(5-fluoro-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylic Acid (2S,3S)-ethyl 3-((2-(5-fluoro-1H-pyrazolo[3,4-b]pyridin-3-yl)-6-(5-(1-methyl-1H-pyrrol-2-yl)furan-2-yl)pyrimidin-4-yl)amino)bicyclo[2.2.2]octane-2-carboxylate (130 mg, 0.23 mmol) was dissolved in THF/MeOH (v/v=2 mL/2 mL), then a solution of NaOH (95 mg, 2.38 mmol) in water (2 mL) was added into the mixture. The resulting mixture was stirred at rt overnight. The reaction mixture was acidified with hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a light yellow solid (11 mg, 9%).

MS (ESI, pos. ion) m/z: 528.2 [M+H]$^+$;
HRMS (ESI, pos. ion) m/z: 528.2146[M+H]$^+$, ($C_{28}H_{27}FN_7O_3$)[M+H]$^+$ theoretical value: 528.2159;
$^1$H NMR (400 MHz, DMSO-d$_6$) δ (ppm): 14.43 (s, 1H), 8.68 (s, 1H), 8.61 (s, 1H), 8.03 (s, 1H), 7.37 (s, 1H), 7.21 (s, 1H), 6.83 (s, 1H), 6.79 (s, 1H), 6.61 (s, 1H), 6.40 (s, 1H), 4.74 (s, 1H), 3.69 (s, 3H), 2.07-1.94 (m, 2H), 1.76 (s, 3H), 1.48 (m, 6H).

Example 20: (R)-3-((2-(5-fluoro-1H-pyrazolo[3,4-b]pyridin-3-yl)-7-methyl-7H-pyrrolo[2,3-d]pyrimidin-4-yl)amino)-4,4-dimethylpentanoic Acid

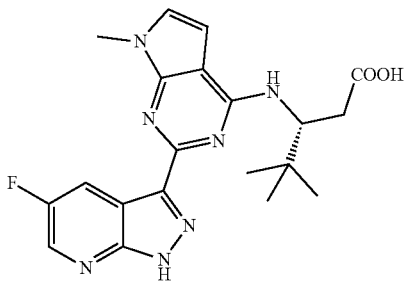 [SMILES: Cn1ccc2c(N[C@H](CC(=O)O)C(C)(C)C)nc(-c3n[nH]c4ncc(F)cc34)nc21]

Step 1: 2,4-dichloro-7-methyl-7H-pyrrolo[2,3-d]pyrimidine

A 0° C. solution of 2,4-dichloro-7H-pyrrolo[2,3-d]pyrimidine (1.00 g, 5.32 mmol) in THF (8 mL) was stirred for 5 min, then to the solution was added sodium hydroxide (255 mg, 6.38 mmol). The mixture was stirred for further 15 min, and iodomethane (8.50 g, 53.20 mmol) was added. The mixture was stirred at rt overnight. To the reaction mixture was added H$_2$O (100 mL), and the mixture was extracted with EtOAc (50 mL×3). The combined organic layers were washed with saturated brine (40 mL), dried over anhydrous sodium sulfate, and filtered. The filtrate was concentrated in vacuo to dry, and the residue was purified by silica gel column chromatography (PE/EtOAc (v/v)=10/1) to give the title compound as a white solid (1.00 g, 93%).

MS (ESI, pos. ion) m/z: 201.95 [M+H]$^+$.

Step 2: (R)-methyl 3-((2-chloro-7-methyl-7H-pyrrolo[2,3-d]pyrimidin-4-yl)amino)-4,4-dimethylpentanoate To a solution of 2,4-dichloro-7-methyl-7H-pyrrolo[2,3-d]pyrimidine (1.06 g, 5.25 mmol) in DMF (10 mL) were added (R)-methyl 3-amino-4,4-dimethylpentanoate (60%, 1.52 g, 5.73 mmol) and K$_2$CO$_3$ (1.45 g, 10.50 mmol). The mixture was stirred at 70° C. overnight. After the reaction was stopped, water (30 mL) was added to quench the reaction, and the resulting mixture was extracted with EtOAc (30 mL×3). The combined organic phases were washed with saturated brine (80 mL×3), dried over anhydrous Na$_2$SO$_4$, filtered, and the filtrate was concentrated in vacuo. The residue was purified by silica gel chromatograph (PE/EtOAc (v/v)=10/1) to give the title compound as a light yellow solid (315 mg, 18%).

MS (ESI, pos. ion) m/z: 325.2 [M+H]$^+$;
$^1$H NMR (400 MHz, CDCl$_3$) δ (ppm): 6.88 (s, 1H), 5.45 (s, 1H), 4.74 (s, 1H), 3.76 (s, 3H), 3.60 (s, 3H), 2.74 (dd, J=14.8, 4.0 Hz, 1H), 2.47 (dd, J=14.8, 8.8 Hz, 1H), 1.71 (s, 1H), 1.01 (s, 9H).

Step 3: (R)-methyl 3-((2-(5-fluoro-1-trityl-1H-pyrazolo[3,4-b]pyridin-3-yl)-7-methyl-7H-pyrrolo[2,3-d]pyrimidin-4-yl)amino)-4,4-dimethylpentanoate To a mixed solvent of 1,4-dioxane (10 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (1.00 g, 1.98 mmol, 50%), K$_2$CO$_3$ (129 mg, 0.93 mmol), PdCl$_2$(dppf) (70 mg, 0.09 mmol) and (R)-methyl 3-((2-chloro-7-methyl-7H-pyrrolo[2,3-d]pyrimidin-4-yl)amino)-4,4-dimethyl pentanoate (150 mg, 0.46 mmol). The air in the mixture was exchanged with nitrogen by bubbling for 10 min. The mixture in a sealed-tub was stirred for 3 h at 115° C. The mixture was filtered to remove the solid impurity, and the filtrate was concentrated to remove the solvent. The residue was purified by silica gel column chromatography (PE/EtOAc (v/v)=6/1) to give the title compound as light yellow oil (282 mg, 91%).

$^1$H NMR (400 MHz, CDCl$_3$) δ (ppm): 8.80 (d, J=6.8 Hz, 1H), 8.33 (s, 1H), 7.95 (s, 1H), 7.27 (m, 15H), 6.72 (d, J=3.1 Hz, 1H), 4.95 (s, 1H), 3.94 (s, 3H), 3.74 (s, 3H), 2.78 (m, 1H), 1.99 (s, 2H), 0.94 (s, 9H).

Step 4: (R)-methyl 3-((2-(5-fluoro-1H-pyrazolo[3,4-b]pyridin-3-yl)-7-methyl-7H-pyrrolo[2,3-d]pyrimidin-4-yl)amino)-4,4-dimethylpentanoate To a solution of (R)-methyl 3-((2-(5-fluoro-1-trityl-1H-pyrazolo[3,4-b]pyridin-3-yl)-7-methyl-7H-pyrrolo[2,3-d]pyrimidin-4-yl)amino)-4,4-dimethylpentanoate (282 mg, 0.42 mmol) in DCM (20 mL) were added Et$_3$SiH (0.60 mL, 3.80 mmol) and TFA (0.38 mL, 5.10 mmol). The mixture was stirred at rt overnight. The reaction was stopped, and the mixture was added into saturated aqueous sodium bicarbonate (30 mL). The resulting mixture was extracted with dichloromethane (30 mL×3). The combined organic layers were washed with saturated brine (80 mL), dried over anhydrous sodium sulfate, and filtered. The filtrate was concentrated to remove the solvent, and the residue was used in the next step without further purification.

MS (ESI, pos. ion) m/z: 426.1 [M+H]$^+$.

Step 5: (R)-3-((2-(5-fluoro-1H-pyrazolo[3,4-b]pyridin-3-yl)-7-methyl-7H-pyrrolo[2,3-d]pyrimidin-4-yl)amino)-4,4-dimethylpentanoic Acid To a solution of (R)-methyl 3-((2-(5-fluoro-1H-pyrazolo[3,4-b]pyridin-3-yl)-7-methyl-7H-pyrrolo[2,3-d]pyrimidin-4-yl)amino)-4,4-dimethylpentanoate (187 mg, 0.44 mmol) in THF/MeOH (v/v=2 mL/2 mL) was added a solution of sodium hydroxide (177 mg, 4.43 mmol) in water (2 mL). The mixture was stirred at rt overnight. To the reaction mixture was added saturated brine (10 mL), and the mixture was acidified with diluted hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=15/1) to give the title compound as a light yellow solid (13 mg, 7%).

MS (ESI, pos. ion) m/z: 412.3 [M+H]$^+$;
HRMS (ESI, pos. ion) m/z: 412.1893[M+H]$^+$, (C$_{20}$H$_{23}$FN$_7$O$_2$)[M+H]$^+$ theoretical value: 412.1897;
$^1$H NMR (400 MHz, DMSO-d$_6$) δ (ppm): 13.93 (s, 1H), 8.87 (s, 1H), 8.61 (s, 1H), 7.28 (d, J=9.0 Hz, 1H), 7.17 (s, 1H), 6.75 (s, 1H), 5.08 (s, 1H), 3.79 (s, 3H), 3.43 (s, 1H), 3.30 (m, 1H), 2.73 (m, 1H), 0.97 (s, 9H).

Example 21: (2S,3S)-3-((6-([2,2'-bifuran]-5-yl)-2-(5-fluoro-1H-pyrazolo[3,4-b]pyridin-3-yl)pyrimidin-4-yl)amino)bicyclo[2.2.2]octane-2-carboxylic Acid

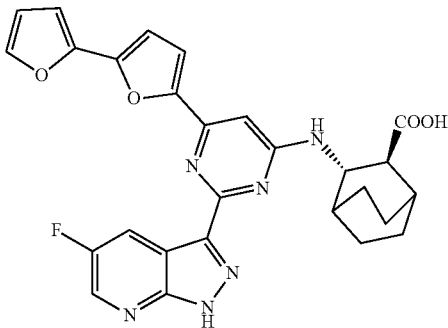 [SMILES: O=C(O)[C@H]1C2CCC(CC2)[C@@H]1Nc1cc(-c2ccc(-c3ccco3)o2)nc(-c2n[nH]c3ncc(F)cc23)n1]

Step 1: (2S,3S)-ethyl 3-((6-([2,2'-bifuran]-5-yl)-2-chloropyrimidin-4-yl)amino)bicyclo[2.2.2]octane-2-carboxylate (2S,3S)-Ethyl 3-((6-(5-bromofuran-2-yl)-2-chloropyrimidin-4-yl)amino) bicyclo[2.2.2]octane-2-carboxylate (1.52 g, 3.34 mmol), K$_3$PO$_4$ (3.36 g, 9.93 mmol), tetrakis(triphenylphosphine)palladium(0) (781 mg, 0.66 mmol) and furan-2-ylboronic acid (445 mg, 3.98 mmol) were mixed in a mixture of 1,4-dioxane (25 mL) and H$_2$O (0.5 mL). The resulting mixture was stirred at 105° C. overnight under nitrogen protection. The mixture was filtered to remove the solid impurity, and the filtrate was concentrated to remove the solvent. The residue was purified by silica gel column chromatography (PE/EtOAc (v/v)=10/1) to give the title compound as a light yellow solid (700 mg, 47%).

MS (ESI, pos. ion) m/z: 442.3 [M+H]$^+$;
$^1$H NMR (400 MHz, CDCl$_3$) δ (ppm): 7.50 (s, 1H), 7.30 (s, 1H), 6.84 (s, 1H), 6.77 (s, 1H), 6.70 (d, J=3.5 Hz, 1H), 6.54 (s, 1H), 4.34 (s, 1H), 4.22 (dd, J=14.2, 7.0 Hz, 2H), 2.37 (d, J=4.4 Hz, 1H), 2.09 (s, 1H), 1.89 (s, 1H), 1.80-1.65 (m, 5H), 1.51-1.44 (m, 1H), 1.30-1.23 (m, 6H).

Step 2: (2S,3S)-ethyl 3-((6-([2,2'-bifuran]-5-yl)-2-(5-fluoro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (20 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (3.00 g, 2.97 mmol, 50%), K$_2$CO$_3$ (439 mg, 3.18 mmol), PdCl$_2$(dppf) (237 mg, 0.32 mmol) and (2S,3S)-ethyl 3-((6-([2,2'-bifuran]-5-yl)-2-chloropyrimidin-4-yl)amino)bicyclo[2.2.2]octane-2-carboxylate (170 mg, 0.42 mmol). The air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a light yellow solid (1.01 g, 81%).

Step 3: (2S,3S)-ethyl 3-((6-([2,2'-bifuran]-5-yl)-2-(5-fluoro-1H-pyrazolo[3,4-b]pyridin-3-yl) pyrimidin-4-yl)amino)bicyclo[2.2.2]octane-2-carboxylate (2S,3S)-ethyl 3-((6-([2,2'-bifuran]-5-yl)-2-(5-fluoro-1-trityl-1H-pyrazolo[3,4-b]pyridin-3-yl)pyrimidin-4-yl)amino) bicyclo[2.2.2]octane-2-carboxylate (1.01 g, 1.29 mmol) was added into DCM (15 mL), then TFA (1.20 mL, 16.20 mmol) and triethyl silicane (2.50 mL, 15.70 mmol) were added into the mixture. The resulting mixture was stirred at rt overnight. To the reaction mixture was added saturated aqueous sodium bicarbonate (30 mL), and the mixture was extracted with dichloromethane (30 mL×3). The combined organic layers were washed with saturated brine (100 mL) one time, dried over anhydrous sodium sulfate and filtered. The filtrate was concentrated in vacuo, and the residue was purified by silica gel column chromatography (PE/EtOAc (v/v)=3/1) to give the title compound as a light yellow solid (245 mg, 35%).

MS (ESI, pos. ion) m/z: 543.2 [M+H]$^+$.

Step 4: (2S,3S)-3-((6-([2,2'-bifuran]-5-yl)-2-(5-fluoro-1H-pyrazolo[3,4-b]pyridin-3-yl) pyrimidin-4-yl)amino)bicyclo[2.2.2]octane-2-carboxylic Acid To a solution of (2S,3S)-ethyl 3-((6-([2,2'-bifuran]-5-yl)-2-(5-fluoro-1H-pyrazolo[3,4-b]pyridin-3-yl)pyrimidin-4-yl) amino)bicyclo[2.2.2]octane-2-carboxylate (245 mg, 0.45 mmol) in THF/MeOH (v/v=4 mL/4 mL) was added a solution of sodium hydroxide (183 mg, 4.58 mmol) in water (4 mL). The mixture was stirred at rt overnight. The reaction mixture was acidified with hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a light yellow solid (49 mg, 21%).

MS (ESI, pos. ion) m/z: 515.2 [M+H]$^+$;
HRMS (ESI, pos. ion) m/z: 515.1851, (C$_{27}$H$_{24}$FN$_6$O$_4$) [M+H]$^+$, theoretical value: 515.1843;
$^1$H NMR (400 MHz, DMSO-d$_6$) δ (ppm): 8.69 (s, 1H), 8.57 (d, J=7.3 Hz, 1H), 8.30 (s, 1H), 7.85 (s, 1H), 7.53 (s, 1H), 6.96 (s, 1H), 6.90 (s, 2H), 6.70 (s, 1H), 4.78 (s, 1H), 2.55 (s, 1H), 2.05 (s, 1H), 1.97 (s, 1H), 1.74 (m, 4H), 1.69-1.32 (m, 7H);
$^{13}$C NMR (151 MHz, DMSO-d$_6$) δ (ppm): 175.70, 162.62, 158.90, 158.65, 156.77, 155.14, 149.52, 147.80, 145.22, 144.36, 139.96, 139.76, 114.77, 114.28, 114.23, 112.69, 108.55, 107.99, 97.88, 50.74, 49.38, 28.78, 28.63, 25.85, 24.09, 21.30, 19.34.

Example 22: (2S,3S)-3-((2-(5-fluoro-1H-pyrazolo[3,4-b]pyridin-3-yl)-6-(5-(thiophen-2-yl) furan-2-yl) pyrimidin-4-yl)amino)bicyclo[2.2.2]octane-2-carboxylic Acid

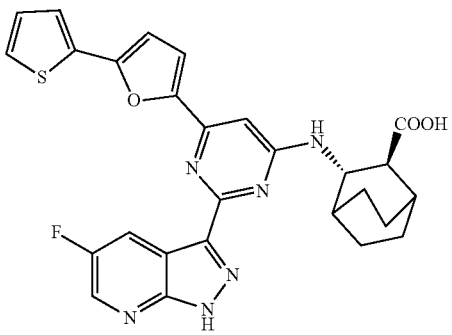 [SMILES: O=C(O)[C@H]1C2CCC(CC2)[C@@H]1Nc1cc(-c2ccc(-c3cccs3)o2)nc(-c2n[nH]c3ncc(F)cc23)n1]

Step 1: (2S,3S)-ethyl 3-aminobicyclo[2.2.2]octane-2-carboxylate Hydrochloride The title compound was prepared according to the synthetic method disclosed in patent application WO 2015073491.

Step 2: 2,4-dichloro-6-(5-(thiophen-2-yl)furan-2-yl)pyrimidine

To a −15° C. solution of thiophene (261 mg, 3.10 mmol) in anhydrous THF (15 mL) was added dropwise slowly n-butyl lithium (1.20 mL, 3.00 mmol, 2.5 mol/L), and the mixture was stirred for 1 h at −15° C. Then dichloro(N,N,N,N-tetramethylethylenediamine)zinc (258 mg, 1.02 mmol) was added. The mixture was stirred at rt for 1 h, then 4-(5-bromofuran-2-yl)-2,6-dichloropyrimidine (1.00 g, 3.40 mmol), triphenylphosphine (166 mg, 0.62 mmol) and palladium chloride (56 mg, 0.31 mmol) were added. The resulting mixture was stirred at 50° C. overnight. The reaction mixture was cooled to rt, and then filtered through a celite pad. The filtrate was concentrated in vacuo, and the residue was purified by silica gel column chromatography (PE/EtOAc (v/v)=15/1) to give the title compound as a light yellow solid (250 mg, 27%).

MS (ESI, pos. ion) m/z: 296.0 [M+H]$^+$.

Step 3: (2S,3S)-ethyl 3-((2-chloro-6-(5-(thiophen-2-yl)furan-2-yl)pyrimidin-4-yl)amino) bicyclo[2.2.2]octane-2-carboxylate A suspension of 2,4-dichloro-6-(5-(thiophen-2-yl)furan-2-yl)pyrimidine (250 mg, 0.84 mmol), (2S,3S)-trans-methyl 3-aminobicyclo[2.2.2]octane-2-carboxylate hydrochloride (197 mg, 0.84 mmol) and K$_2$CO$_3$ (291 mg, 2.10 mmol) in DMF (5 mL) was stirred at rt overnight. To the reaction mixture was added H$_2$O (30 mL), and the mixture was extracted with EtOAc (30 mL×3). The combined organic layers were washed with saturated brine (80 mL×3), dried over anhydrous sodium sulfate, and filtered. The filtrate was concentrated in vacuo, and the residue was purified by silica gel column chromatography (PE/EtOAc (v/v)=10/1) to give the title compound as a white solid (205 mg, 53%).

MS (ESI, pos. ion) m/z: 458.0 [M+H]$^+$;

$^1$H NMR (400 MHz, CDCl$_3$) δ (ppm): 7.49 (s, 1H), 7.34 (d, J=5.0 Hz, 1H), 7.29 (s, 1H), 7.13-7.10 (m, 1H), 6.77 (s, 1H), 6.65 (d, J=3.5 Hz, 1H), 4.34 (s, 1H), 4.23 (m, 2H), 2.38 (d, J=4.9 Hz, 1H), 2.09 (s, 1H), 1.90 (d, J=2.5 Hz, 1H), 1.80-1.65 (m, 6H), 1.49 (m, 1H), 1.38-1.31 (m, 2H), 1.24 (t, J=6.8 Hz, 3H).

Step 4: (2S,3S)-ethyl 3-((2-(5-fluoro-1-trityl-1H-pyrazolo[3,4-b]pyridin-3-yl)-6-(5-(thiophen-2-yl) furan-2-yl)pyrimidin-4-yl)amino)bicyclo[2.2.2]octane-2-carboxylate To a mixed solvent of 1,4-dioxane (10 mL) and H$_2$O (0.5 mL) were added 5-fluoro-3-(4,4,5,5-tetramethyl-1,3,2-dioxaborolan-2-yl)-1-trityl-1H-pyrazolo[3,4-b]pyridine (1.00 g, 0.99 mmol, 50%), K$_2$CO$_3$ (121 mg, 0.88 mmol), PdCl$_2$(dppf) (66 mg, 0.09 mmol) and (2S,3S)-ethyl 3-((2-chloro-6-(5-(thiophen-2-yl)furan-2-yl)pyrimidin-4-yl)amino) bicyclo[2.2.2]octane-2-carboxylate (200 mg, 0.44 mmol). The air in the mixture was exchanged with nitrogen by bubbling for 10 min. The mixture in a sealed-tube was stirred for 3 h at 115° C. After the reaction was completed, the mixture was filtered to remove the solid impurity, and the filtrate was concentrated to remove the solvent. The residue was purified by silica gel column chromatography (PE/EtOAc (v/v)=10/1) to give the title compound as a light yellow solid (300 mg, 85%).

Step 5: (2S,3S)-ethyl 3-((2-(5-fluoro-1H-pyrazolo[3,4-b]pyridin-3-yl)-6-(5-(thiophen-2-yl) furan-2-yl)pyrimidin-4-yl)amino)bicyclo[2.2.2]octane-2-carboxylate (2S,3S)-ethyl 3-((2-(5-fluoro-1-trityl-1H-pyrazolo[3,4-b]pyridin-3-yl)-6-(5-(thiophen-2-yl) furan-2-yl)pyrimidin-4-yl)amino)bicyclo[2.2.2]octane-2-carboxylate (300 mg, 0.37 mmol) was added into DCM (8 mL), then TFA (0.34 mL, 4.60 mmol) and triethyl silicane (0.72 mL, 4.50 mmol) were added into the mixture. The resulting mixture was stirred at rt overnight. The reaction was stopped, and the reaction mixture was added into saturated aqueous sodium bicarbonate (15 mL), and the resulting mixture was extracted with dichloromethane (10 mL×3). The combined organic layers were washed with saturated brine (30 mL), dried over anhydrous sodium sulfate, and filtered. The filtrate was concentrated in vacuo, and the residue was purified by silica gel column chromatography (PE/EtOAc (v/v)=1/1) to give the title compound as a light yellow solid (38 mg, 18%).

MS (ESI, pos. ion) m/z: 559.3 [M+H]$^+$.

Step 6: (2S,3S)-3-((2-(5-fluoro-1H-pyrazolo[3,4-b]pyridin-3-yl)-6-(5-(thiophen-2-yl) furan-2-yl)pyrimidin-4-yl)amino)bicyclo[2.2.2]octane-2-carboxylic Acid To a solution of (2S,3S)-ethyl 3-((2-(5-fluoro-1H-pyrazolo[3,4-b]pyridin-3-yl)-6-(5-(thiophen-2-yl)furan-2-yl)pyrimidin-4-yl)amino)bicyclo[2.2.2]octane-2-carboxylate (38 mg, 0.07 mmol) in THF/MeOH (v/v=2 mL/2 mL) was added a solution of sodium hydroxide (30 mg, 0.75 mmol) in water (2 mL). The mixture was stirred at rt overnight. The reaction mixture was acidified with hydrochloric acid (1 M) to pH about 6. The resulting mixture was extracted with 2-methyltetrahydrofuran (15 mL×3). The combined organic layers were washed with saturated brine (20 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a light yellow solid (30 mg, 83%).

MS (ESI, pos. ion) m/z: 531.2 [M+H]$^+$;

HRMS (ESI, pos. ion) m/z: 531.1613, ($C_{27}H_{24}FN_6O_3S$) [M+H]$^+$, theoretical value: 531.1615;

$^1$H NMR (400 MHz, DMSO-$d_6$) δ (ppm): 8.68 (d, J=1.0 Hz, 1H), 8.61 (d, J=7.1 Hz, 1H), 8.07 (d, J=5.0 Hz, 1H), 7.67 (d, J=4.8 Hz, 1H), 7.57 (s, 1H), 7.43 (s, 1H), 7.23-7.19 (m, 1H), 7.04 (d, J=3.3 Hz, 1H), 6.85 (s, 1H), 4.75 (s, 1H), 2.04 (s, 1H), 1.98 (s, 1H), 1.81-1.71 (m, 3H), 1.69-1.50 (m, 4H), 1.50-1.37 (m, 3H).

Example 23: (2S,3S)-3-((2-(5-fluoro-1H-pyrazolo[3,4-b]pyridin-3-yl)thieno[2,3-d]pyrimidin-4-yl)amino)bicyclo[2.2.2]octane-2-carboxylic Acid

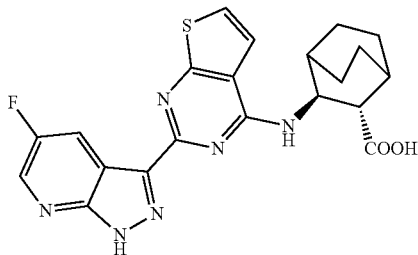 [SMILES: O=C(O)[C@H]1C2CCC(CC2)[C@@H]1Nc1nc(-c2n[nH]c3ncc(F)cc23)nc2sccc12]

Step 1: (2S,3S)-ethyl 3-aminobicyclo[2.2.2]octane-2-carboxylate Hydrochloride

The title compound can be prepared according to the synthetic method disclosed in patent application WO 2015073491.

Step 2: (2S,3S)-ethyl 3-((2-chlorothieno[2,3-d]pyrimidin-4-yl)amino)bicyclo[2.2.2]octane-2-carboxylate 2,4-dichlorothieno[2,3-d]pyrimidine (1.01 g, 4.93 mmol), (2S,3S)-ethyl 3-aminobicyclo[2.2.2]octane-2-carboxylate hydrochloride (0.98 g, 4.93 mmol) were dissolved in DMF (20 mL), then $K_2CO_3$ (1.70 g, 12.33 mmol) was added into the mixture. The resulting mixture was stirred at rt overnight. To the reaction mixture was added $H_2O$ (50 mL) to quench the reaction, and the mixture was extracted with EtOAc (50 mL×3). The combined organic layers were washed with saturated brine (150 mL×3), dried over anhydrous sodium sulfate, and filtered. The filtrate was concentrated in vacuo, and the residue was purified by silica gel column chromatography (PE/EtOAc (v/v)=5/1) to give the title compound as a light yellow solid (1.25 g, 69%).

MS (ESI, pos. ion) m/z: 366.0 [M+H]$^+$;

$^1$H NMR (400 MHz, CDCl$_3$) δ (ppm): 7.26 (d, J=6.0 Hz, 1H), 7.16 (d, J=5.8 Hz, 1H), 4.64 (t, J=5.3 Hz, 1H), 4.25 (q, J=7.1 Hz, 2H), 2.45 (d, J=5.7 Hz, 1H), 2.03 (d, J=2.4 Hz, 1H), 1.96 (d, J=2.7 Hz, 1H), 1.89-1.82 (m, 1H), 1.75-1.63 (m, 6H), 1.46 (m, 1H), 1.28 (t, J=7.1 Hz, 4H).

Step 3: (2S,3S)-ethyl 3-((2-(5-fluoro-1-trityl-1H-pyrazolo[3,4-b]pyridin-3-yl) thieno[2,3-d]pyrimidin-4-yl)amino)bicyclo[2.2.2]octane-2-carboxylate To a mixed solvent of 1,4-dioxane (10 mL) and $H_2O$ (0.5 mL) were added 5-fluoro-3-(4,4,5,5-tetramethyl-1,3,2-dioxaborolan-2-yl)-1-trityl-1H-pyrazolo[3,4-b]pyridine (50%, 4.40 g, 2.18 mmol), $K_2CO_3$ (320 mg, 2.32 mmol), PdCl$_2$(dppf) (172 mg, 0.23 mmol), (2S,3S)-ethyl 3-((2-chlorothieno[2,3-d]pyrimidin-4-yl)amino)bicyclo[2.2.2]octane-2-carboxylate (420 mg, 1.15 mmol). A stream of nitrogen was bubbled through the mixture for 10 min to remove air, then the mixture in a sealed-tube was stirred at 115° C. for 3 h. The mixture was filtered to remove the solid impurity, and the filtrate was concentrated to remove the solvent. The residue was purified by silica gel column chromatography (PE/EtOAc (v/v)=10/1) to give the title compound as light yellow oil (739 mg, 90%).

Step 4: (2S,3S)-ethyl 3-((2-(5-fluoro-1H-pyrazolo[3,4-b]pyridin-3-yl)thieno[2,3-d]pyrimidin-4-yl)amino)bicyclo[2.2.2]octane-2-carboxylate To a solution of (2S,3S)-ethyl 3-((2-(5-fluoro-1-trityl-1H-pyrazolo[3,4-b]pyridin-3-yl)thieno[2,3-d]pyrimidin-4-yl)amino)bicyclo[2.2.2]octane-2-carboxylate (739 mg, 1.02 mmol) in DCM (20 mL) were added Et$_3$SiH (1.95 mL, 12.20 mmol) and TFA (0.91 mL, 12.00 mmol). The mixture was stirred at rt overnight. The reaction was stopped, and the reaction mixture was added into saturated aqueous sodium bicarbonate (30 mL), and the resulting mixture was extracted with dichloromethane (30 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (PE/EtOAc (v/v)=3/1) to give the title compound as light yellow oil (105 mg, 22%).

MS (ESI, pos. ion) m/z: 467.1 [M+H]$^+$.

Step 5: (2S,3S)-3-((2-(5-fluoro-1H-pyrazolo[3,4-b]pyridin-3-yl)thieno[2,3-d]pyrimidin-4-yl)amino)bicyclo[2.2.2]octane-2-carboxylic Acid To a solution of (2S,3S)-ethyl 3-((2-(5-fluoro-1H-pyrazolo[3,4-b]pyridin-3-yl) thieno[2,3-d]pyrimidin-4-yl)amino)bicyclo[2.2.2]octane-2-carboxylate (105 mg, 0.23 mmol) in THF/MeOH/H$_2$O (v/v/v=2 mL/2 mL/1 mL) was added a solution of sodium hydroxide (91 mg, 2.28 mmol) in water (1 mL). The mixture was stirred at rt overnight. To the reaction mixture was added saturated brine (10 mL), and the resulting mixture was acidified with diluted hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=15/1) to give the title compound as a light yellow solid (45 mg, 46%).

MS (ESI, pos. ion) m/z: 439.1 [M+H]$^+$;

HRMS (ESI, pos. ion) m/z: 439.1364[M+H]$^+$, ($C_{21}H_{20}FN_6O_2S$)[M+H]$^+$ theoretical value: 439.1352

$^1$H NMR (400 MHz, DMSO-$d_6$) δ (ppm): 8.71 (s, 1H), 8.61 (d, J=7.2 Hz, 1H), 8.22 (s, 1H), 7.84 (s, 1H), 7.66 (d, J=5.0 Hz, 1H), 4.97 (s, 1H), 2.88 (d, J=6.4 Hz, 1H), 2.09 (s, 1H), 2.03 (s, 1H), 1.80 (m, 3H), 1.71-1.38 (m, 5H).

Example 24: (+/−)-trans-3-((6-([1,1'-biphenyl]-4-yl)-2-(5-chloro-1H-pyrazolo[3,4-b]pyridin-3-yl)pyrimidin-4-yl)amino)bicyclo[2.2.2]octane-2-carboxylic Acid

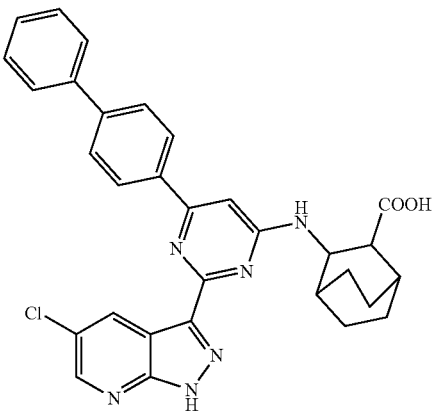 [SMILES: O=C(O)C1C2CCC(CC2)C1Nc1cc(-c2ccc(-c3ccccc3)cc2)nc(-c2n[nH]c3ncc(Cl)cc23)n1]

Step 1: 4-([1,1'-biphenyl]-4-yl)-2,6-dichloropyrimidine

To a solution of 2,4,6-trichloropyrimidine (1.05 g, 5.72 mmol) in THF (20 mL) were added palladium acetate (0.12 g, 0.52 mmol), triphenylphosphine (0.27 g, 1.03 mmol), [1,1'-biphenyl]-4-ylboronic acid (1.02 g, 5.15 mmol) and aqueous sodium carbonate solution (2 M, 7.73 mL, 15.45 mmol). The mixture was stirred at 70° C. for 6 h. The mixture was filtered through a celite pad, and the filter cake was washed with EA (20 mL). The filtrate was concentrated in vacuo, and the residue was purified by silica gel column chromatography (PE) to give the title compound as a white solid (0.98 g, 63%).

$^1$H NMR (400 MHz, CDCl$_3$) δ (ppm): 8.18 (d, J=8.3 Hz, 2H), 7.77 (d, J=8.3 Hz, 2H), 7.73 (s, 1H), 7.68 (d, J=7.2 Hz, 2H), 7.51 (t, J=7.4 Hz, 2H), 7.44 (t, J=7.3 Hz, 1H).

Step 2: (+/−)-trans-methyl 3-((6-([1,1'-biphenyl]-4-yl)-2-chloropyrimidin-4-yl)amino) bicyclo[2.2.2]octane-2-carboxylate (+/−)-trans-Methyl 3-aminobicyclo[2.2.2]octane-2-carboxylate (0.58 g, 3.17 mmol) and 4-([1,1'-biphenyl]-4-yl)-2,6-dichloropyrimidine (0.95 g, 3.15 mmol) were dissolved in DMF (10 mL), then potassium carbonate (0.88 g, 6.33 mmol) was added. The mixture was stirred at rt overnight. To the reaction mixture was added water (20 mL), and the resulting mixture was extracted with ethyl acetate (25 mL×3). The combined organic layers were washed with saturated brine (50 mL×3), dried over anhydrous sodium sulfate and filtered. The filtrate was concentrated in vacuo and the residue was purified by silica gel column chromatography (PE/EtOAc (v/v)=10/1) to give the title compound as a light yellow solid (1.11 g, 79%).

MS (ESI, pos. ion) m/z: 448.15 [M+H]$^+$;

$^1$H NMR (400 MHz, CDCl$_3$) δ (ppm): 8.09 (d, J=8.0 Hz, 2H), 7.71 (d, J=8.3 Hz, 2H), 7.66 (d, J=7.3 Hz, 2H), 7.48 (t, J=7.5 Hz, 2H), 7.39 (dd, J=5.5, 2.0 Hz, 1H), 6.85 (s, 1H), 5.54 (s, 1H), 4.36 (s, 1H), 3.76 (s, 3H), 2.42 (d, J=4.7 Hz, 1H), 2.08 (s, 1H), 1.89 (d, J=2.5 Hz, 1H), 1.78 (m, 3H), 1.68 (m, 3H), 1.60 (s, 1H), 1.53-1.44 (m, 1H).

Step 3: (+/−)-trans-methyl 3-((6-([1,1'-biphenyl]-4-yl)-2-(5-chloro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (10 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (500 mg, 0.55 mmol, 55%), K$_2$CO$_3$ (125 mg, 0.90 mmol), PdCl$_2$(dppf) (66 mg, 0.09 mmol), (+/−)-trans-methyl 3-((6-([1,1'-biphenyl]-4-yl)-2-chloropyrimidin-4-yl)amino) bicyclo[2.2.2]octane-2-carboxylate (200 mg, 0.45 mmol). A stream of nitrogen was bubbled through the mixture for 10 min to remove air, then the mixture in a sealed-tube was stirred at 115° C. for 3 h. The mixture was filtered to remove the solid impurity, and the filtrate was concentrated to remove the solvent. The residue was purified by silica gel column chromatography (PE/EtOAc (v/v)=10/1) to give the title compound as light yellow oil (303 mg, 84%).

Step 4: (+/−)-trans-methyl 3-((6-([1,1'-biphenyl]-4-yl)-2-(5-chloro-1H-pyrazolo[3,4-b]pyridin-3-yl)pyrimidin-4-yl)amino)bicyclo[2.2.2]octane-2-carboxylate To a solution of (+/−)-trans-methyl 3-((6-([1,1'-biphenyl]-4-yl)-2-(5-chloro-1-trityl-1H-pyrazolo[3,4-b]pyridin-3-yl)pyrimidin-4-yl)amino)bicyclo[2.2.2]octane-2-carboxylate (303 mg, 0.38 mmol) in DCM (6 mL) were added Et$_3$SiH (0.75 mL, 4.70 mmol) and TFA (0.35 mL, 4.70 mmol). The mixture was stirred at rt overnight. The reaction was stopped, and the reaction mixture was concentrated in vacuo to remove the solvent, and the residue was dissolved in 2-methyltetrahydrofuran (20 mL). The mixture was added into saturated aqueous sodium bicarbonate (15 mL). The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent to give the title compound as black oil, which was used in the next step without further purification.

MS (ESI, pos. ion) m/z: 565.1 [M+H]$^+$.

Step 5: (+/−)-trans-3-((6-([1,1'-biphenyl]-4-yl)-2-(5-chloro-1H-pyrazolo[3,4-b]pyridin-3-yl)pyrimidin-4-yl)amino)bicyclo[2.2.2]octane-2-carboxylic Acid To a solution of (+/−)-trans-methyl 3-((6-([1,1'-biphenyl]-4-yl)-2-(5-chloro-1H-pyrazolo[3,4-b]pyridin-3-yl)pyrimidin-4-yl)amino)bicyclo[2.2.2]octane-2-carboxylate (285 mg, 0.50 mmol) in THF/MeOH/H$_2$O (v/v/v=4 mL/4 mL/2 mL) was added a solution of NaOH (210 mg, 5.25 mmol) in water (1 mL). The mixture was stirred at rt overnight. The reaction mixture was acidified with diluted hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (23 mg, 8%).

MS (ESI, pos. ion) m/z: 551.10 [M+H]$^+$;

$^1$H NMR (400 MHz, DMSO-d$_6$) δ (ppm): 8.96 (s, 1H), 8.63 (d, J=2.0 Hz, 1H), 8.20 (d, J=7.2 Hz, 2H), 7.87 (d, J=8.2 Hz, 2H), 7.78 (d, J=7.4 Hz, 2H), 7.51 (t, J=7.5 Hz, 2H), 7.42 (t, J=7.2 Hz, 1H), 7.06 (s, 1H), 6.47 (s, 1H), 4.78 (s, 1H), 3.60 (s, 1H), 2.80 (s, 1H), 2.02-1.93 (m, 4H), 1.87 (m, 2H), 1.79-1.72 (m, 2H), 1.64 (s, 1H), 1.46-1.42 (m, 1H).

Example 25: (2S,3S)-3-((2-(5-fluoro-1H-pyrazolo[3,4-b]pyridin-3-yl)-7-methyl-7H-pyrrolo[2,3-d]pyrimidin-4-yl)amino)bicyclo[2.2.2]octane-2-carboxylic Acid

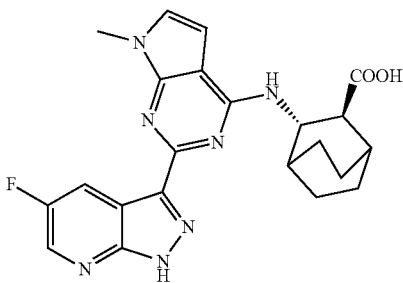 [SMILES: Cn1ccc2c(N[C@H]3C4CCC(CC4)[C@@H]3C(=O)O)nc(-c3n[nH]c4ncc(F)cc34)nc21]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: (2S,3S)-ethyl 3-((2-chloro-7-methyl-7H-pyrrolo[2,3-d]pyrimidin-4-yl)amino) bicyclo[2.2.2]octane-2-carboxylate (2S,3S)-ethyl 3-aminobicyclo[2.2.2]octane-2-carboxylate hydrochloride (1.26 g, 5.40 mmol) and 2,4-dichloro-7-methyl-7H-pyrrolo[2,3-d]pyrimidine (1.10 g, 5.40 mmol) were dissolved in DMF (5 mL), then potassium carbonate (1.50 g, 11.00 mmol) was added. The mixture was stirred at rt overnight. Water (50 mL) was added to quench the reaction, and the resulting mixture was extracted with EtOAc (50 mL×2). The combined organic phases were washed with saturated brine (80 m), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (979 mg, 50%).

MS (ESI, pos. ion) m/z: 363.2 [M+H]$^+$;

$^1$H NMR (400 MHz, $CDCl_3$) δ (ppm): 6.87 (d, J=3.4 Hz, 1H), 6.41 (s, 1H), 5.32 (s, 1H), 4.63 (s, 1H), 4.21 (q, J=7.1 Hz, 2H), 3.76 (s, 3H), 2.39 (d, J=4.9 Hz, 1H), 1.96-1.52 (m, 10H), 1.26 (t, J=7.0 Hz, 3H).

Step 3: (2S,3S)-ethyl 3-((2-(5-fluoro-1-trityl-1H-pyrazolo[3,4-b]pyridin-3-yl)-7-methyl-7H-pyrrolo[2,3-d]pyrimidin-4-yl)amino)bicyclo[2.2.2]octane-2-carboxylate To a mixed solvent of 1,4-dioxane (20 mL) and $H_2O$ (0.5 mL) were added 5-fluoro-3-(4,4,5,5-tetramethyl-1,3,2-dioxaborolan-2-yl)-1-trityl-1H-pyrazolo[3,4-b]pyridine (220 mg, 0.45 mmol), $K_2CO_3$ (160 mg, 1.24 mmol), PdCl$_2$(dppf) (30 mg, 0.04 mmol), (2S,3S)-ethyl 3-((2-chloro-7-methyl-7H-pyrrolo[2,3-d]pyrimidin-4-yl)amino)bicyclo[2.2.2]octane-2-carboxylate (150 mg, 0.41 mmol). A stream of nitrogen was bubbled through the mixture for 10 min to remove air, then the mixture was stirred at 115° C. for 3 h in a sealed-tube. The mixture was filtered to remove the solid impurity, and the filtrate was concentrated to remove the solvent. The residue was purified by silica gel column chromatography (PE/EtOAc (v/v)=10/1) to give the title compound as light yellow oil (170 mg, 58%).

$^1$H NMR (400 MHz, $CDCl_3$) δ (ppm): 8.71 (d, J=5.9 Hz, 1H), 8.33 (d, J=1.9 Hz, 1H), 7.42 (d, J=6.8 Hz, 1H), 7.32-7.24 (m, 15H), 6.66 (s, 1H), 4.83 (s, 1H), 4.04 (m, 2H), 3.75 (s, 3H), 2.81 (d, J=6.4 Hz, 1H), 1.99 (s, 1H), 1.93 (s, 1H), 1.84-1.41 (m, 9H), 1.23 (d, J=2.6 Hz, 3H).

Step 4: (2S,3S)-ethyl 3-((2-(5-fluoro-1H-pyrazolo[3,4-b]pyridin-3-yl)-7-methyl-7H-pyrrolo[2,3-d]pyrimidin-4-yl)amino)bicyclo[2.2.2]octane-2-carboxylate (2S,3S)-Ethyl 3-((2-(5-fluoro-1-trityl-1H-pyrazolo[3,4-b]pyridin-3-yl)-7-methyl-7H-pyrrolo[2,3-d]pyrimidin-4-yl)amino)bicyclo[22.2.2]octane-2-carboxylate (170 mg, 0.24 mmol) was dissolved in DCM (5 mL), then Et$_3$SiH (0.30 mL, 2.41 mmol) and TFA (0.20 mL, 2.41 mmol) were added into the mixture. The resulting mixture was stirred at rt overnight. The reaction mixture was added into saturated aqueous sodium bicarbonate (30 mL), and the resulting mixture was extracted with dichloromethane (30 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=2/1) to give the title compound as light yellow oil (96 mg, 86%).

MS (ESI, pos. ion) m/z: 464.2 [M+H]$^+$.

Step 5: (2S,3S)-3-((2-(5-fluoro-1H-pyrazolo[3,4-b]pyridin-3-yl)-7-methyl-7H-pyrrolo[2,3-d]pyrimidin-4-yl)amino)bicyclo[2.2.2]octane-2-carboxylic Acid To a solution of (2S,3S)-ethyl 3-((2-(5-fluoro-1H-pyrazolo[3,4-b]pyridin-3-yl)-7-methyl-7H-pyrrolo[2,3-d]pyrimidin-4-yl)amino)bicyclo[2.2.2]octane-2-carboxylate (97 mg, 0.21 mmol) in THF/MeOH/H$_2$O (v/v/v=2 mL/2 mL/1 mL) was added a solution of sodium hydroxide (85 mg, 2.09 mmol) in water (1 mL). The mixture was stirred at rt overnight. To the reaction mixture was added saturated brine (20 mL), and the mixture was acidified with hydrochloric acid (1 M) to pH about 6. The resulting mixture was extracted with 2-methyltetrahydrofuran (20 mL×3). The combined organic layers were washed with saturated brine (40 mL), dried over anhydrous sodium sulfate, and filtered. The filtrate was concentrated in vacuo to remove the solvent, and the residue was purified by preparative thin-layer chromatography (DCM/MeOH (v/v)=15/1) to give the title compound as a light yellow solid (36 mg, 40%).

MS (ESI, pos. ion) m/z: 436.3 [M+H]$^+$;

HRMS (ESI, pos. ion) m/z: 436.1887[M+H]$^+$, ($C_{22}H_{23}FN_7O_2$) [M+H]$^+$ theoretical value: 436.1897;

$^1$H NMR (400 MHz, DMSO-$d_6$) δ (ppm): 13.98 (s, 1H), 8.74 (s, 1H), 8.62 (s, 1H), 7.43 (s, 1H), 7.21 (s, 1H), 6.68 (s, 1H), 4.87 (s, 1H), 3.80 (s, 3H), 2.77 (d, J=5.6 Hz, 1H), 2.03 (d, J=12.2 Hz, 2H), 1.86-1.33 (m, 9H).

Example 26: (2S,3S)-3-((2-(5-fluoro-1H-pyrazolo[3,4-b]pyridin-3-yl)-6-(5-phenylfuran-2-yl)pyrimidin-4-yl)amino)bicyclo[2.2.2]octane-2-carboxylic Acid

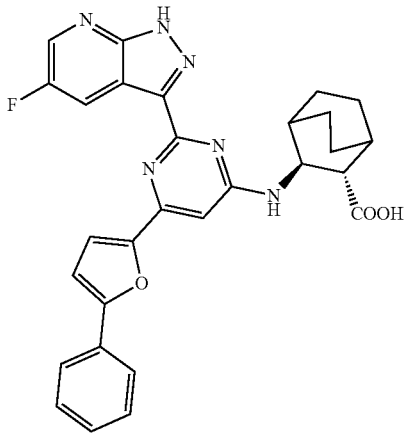 [SMILES: O=C(O)[C@H]1C2CCC(CC2)[C@@H]1Nc1cc(-c2ccc(-c3ccccc3)o2)nc(-c2n[nH]c3ncc(F)cc23)n1]

Step 1: (2S,3S)-ethyl 3-((2-chloro-6-(5-phenylfuran-2-yl)pyrimidin-4-yl)amino) bicyclo[2.2.2]octane-2-carboxylate To a mixed solvent of toluene (8 mL) and H₂O (1 mL) were added (2S,3S)-ethyl 3-((6-(5-bromofuran-2-yl)-2-chloropyrimidin-4-yl)amino)bicyclo[2.2.2]octane-2-carboxylate (200 mg, 0.45 mmol), K₃PO₄ (290 mg, 1.36 mmol), Pd(OAc)₂ (12 mg, 0.05 mmol) and phenylboronic acid (68 mg, 0.54 mmol). The mixture was stirred at 115° C. for 5 h. The mixture was filtered to remove the solid impurity, and the filtrate was concentrated to remove the solvent. The residue was purified by silica gel column chromatography (PE/EtOAc (v/v)=10/1-5/1) to give the title compound as a yellow solid (82 mg, 41%).

MS (ESI, pos. ion) m/z: 438.3 [M+H]⁺.

Step 2: (2S,3S)-ethyl 3-((2-(5-fluoro-1-trityl-1H-pyrazolo[3,4-b]pyridin-3-yl)-6-(5-phenylfuran-2-yl)pyrimidin-4-yl)amino)bicyclo[2.2.2]octane-2-carboxylate To a mixed solvent of 1,4-dioxane (8 mL) and H₂O (1 mL) were added 5-fluoro-3-(4,4,5,5-tetramethyl-1,3,2-dioxaborolan-2-yl)-1-trityl-1H-pyrazolo[3,4-b]pyridine (110 mg, 0.20 mmol), K₂CO₃ (80 mg, 0.55 mmol), PdCl₂(dppf) (15 mg, 0.02 mmol), (2S,3S)-ethyl 3-((2-chloro-6-(5-phenylfuran-2-yl)pyrimidin-4-yl)amino)bicyclo[2.2.2]octane-2-carboxylate (80 mg, 0.18 mmol). A stream of nitrogen was bubbled through the mixture for 10 min to remove air, then the mixture was stirred at 115° C. for 3 h in a sealed-tube. The mixture was filtered to remove the solid impurity, and the filtrate was concentrated to remove the solvent. The residue was purified by silica gel column chromatography (PE/EtOAc (v/v)=10/1-5/1) to give a yellow solid (102 mg, 72%).

Step 3: (2S,3S)-ethyl 3-((2-(5-fluoro-1H-pyrazolo[3,4-b]pyridin-3-yl)-6-(5-phenylfuran-2-yl) pyrimidin-4-yl)amino)bicyclo[2.2.2]octane-2-carboxylate (2S,3S)-Ethyl 3-((2-(5-fluoro-1-trityl-1H-pyrazolo[3,4-b]pyridin-3-yl)-6-(5-phenylfuran-2-yl)pyrimidin-4-yl)amino)bicyclo[2.2.2]octane-2-carboxylate (102 mg, 0.13 mmol) was added into DCM (5 mL), then TFA (0.10 mL, 1.31 mmol) and triethyl silicane (0.22 mL, 1.31 mmol) were added into the mixture. The resulting mixture was stirred at rt overnight. The reaction was stopped, and the mixture was added into saturated aqueous sodium bicarbonate (30 mL), and the resulting mixture was extracted with dichloromethane (100 mL×3). The combined organic layers were washed with saturated brine (120 mL), dried over anhydrous sodium sulfate, and filtered. The filtrate was concentrated in vacuo to remove the solvent, and the residue was purified by silica gel column chromatography (PE/EtOAc (v/v)=1/1) to give the title compound as a light yellow solid (61 mg, 87%).

MS (ESI, pos. ion) m/z: 539.2 [M+H]⁺.

Step 4: (2S,3S)-3-((2-(5-fluoro-1H-pyrazolo[3,4-b]pyridin-3-yl)-6-(5-phenylfuran-2-yl) pyrimidin-4-yl)amino)bicyclo[2.2.2]octane-2-carboxylic Acid To a solution of (2S,3S)-ethyl 3-((2-(5-fluoro-1H-pyrazolo[3,4-b]pyridin-3-yl)-6-(5-phenylfuran-2-yl)pyrimidin-4-yl)amino)bicyclo[2.2.2]octane-2-carboxylate (61 mg, 0.11 mmol) in THF/MeOH (v/v=5 mL/5 mL) was added a solution of sodium hydroxide (50 mg, 1.13 mmol) in water (0.5 mL). The mixture was stirred at rt overnight. The reaction mixture was acidified with hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (20 mg, 34%).

MS (ESI, pos. ion) m/z: 525.1 [M+H]⁺;

HRMS (ESI, pos. ion) m/z: 525.2038[M+H]⁺, (C₂₉H₂₆FN₆O₃) [M+H]⁺ theoretical value: 525.2050;

¹H NMR (600 MHz, DMSO-d₆) δ (ppm): 14.19 (s, 1H), 8.66 (s, 2H), 7.86 (d, J=6.3 Hz, 2H), 7.80 (d, J=7.2 Hz, 1H), 7.51 (t, J=7.6 Hz, 2H), 7.43-7.32 (m, 2H), 7.21 (s, 1H), 6.92 (s, 1H), 4.74 (s, 1H), 2.03 (s, 1H), 1.98 (s, 1H), 1.78-1.40 (m, 10H).

Example 27: (+/−)-trans-3-((2-(5-chloro-1H-pyrazolo[3,4-b]pyridin-3-yl)-5-fluoro-6-phenylpyrimidin-4-yl)amino)bicyclo[2.2.2]octane-2-carboxylic Acid

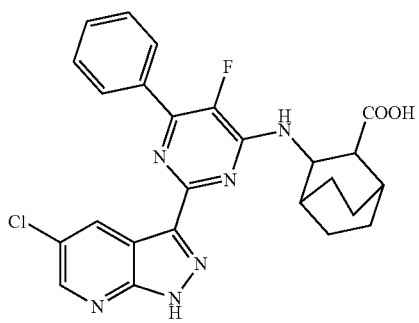 [SMILES: O=C(O)C1C2CCC(CC2)C1Nc1nc(-c2n[nH]c3ncc(Cl)cc23)nc(-c2ccccc2)c1F]

Step 1: (+/−)-trans-methyl 3-((2,6-dichloro-5-fluoropyrimidin-4-yl)amino)bicyclo[2.2.2]octane-2-carboxylate To a reaction flask were added 2,4,6-trichloro-5-fluoropyrimidine (10.00 g, 49.65 mmol), potassium carbonate (21.00 g, 148.90 mmol), (+/−)-trans-methyl 3-aminobicyclo[2.2.2]octane-2-carboxylate (10.00 g, 54.61 mmol) and DMF (50 mL). The mixture was stirred at rt for 5 h. To the reaction mixture was added water (100 mL), and the mixture was extracted with ethyl acetate (100 mL×3). The combined organic layers were washed with saturated brine (50 mL) one time, dried over anhydrous sodium sulfate and filtered. The filtrate was concentrated in vacuo, and the residue was purified by silica gel column chromatography (PE/EtOAc (v/v)=20/1) to give the title compound as a light yellow solid (12.00 g, 50.0%).

MS (ESI, pos. ion) m/z: 348.10[M+H]$^+$.

Step 2: (+/−)-trans-methyl 3-((2-chloro-5-fluoro-6-phenylpyrimidin-4-yl)amino) bicyclo[2.2.2]octane-2-carboxylate To a mixed solvent of acetonitrile (100 mL) and H$_2$O (5 mL) were added (+/−)-trans-methyl 3-((2,6-dichloro-5-fluoropyrimidin-4-yl)amino)bicyclo[2.2.2]octane-2-carboxylate (2.00 g, 5.74 mmol), phenylboronic acid (0.70 g, 5.74 mmol), potassium acetate (1.70 g, 17.2 mmol) and Pd(dppf)Cl$_2$ (0.50 g, 0.57 mmol). The resulting mixture was sirred at 80° C. for 12 h under nitrogen protection. The mixture was filtered to remove the solid impurity, and the filtrate was concentrated to remove the solvent. The residue was purified by silica gel column chromatography (PE/EtOAc (v/v)=20/1) to give the title compound as a yellow solid (430 mg, 19%).

MS (ESI, pos. ion) m/z: 390.1[M+H]$^+$.

Step 3: (+/−)-trans-methyl 3-((2-(5-chloro-1-trityl-1H-pyrazolo[3,4-b]pyridin-3-yl)-5-fluoro-6-phenylpyrimidin-4-yl)amino)bicyclo[2.2.2]octane-2-carboxylate To a mixed solvent of 1,4-dioxane (5 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (290 mg, 0.55 mmol), K$_2$CO$_3$ (214 mg, 1.56 mmol), PdCl$_2$(dppf) (30 mg, 0.03 mmol), (+/−)-trans-methyl 3-((2-chloro-5-fluoro-6-phenylpyrimidin-4-yl)amino)bicyclo[2.2.2]octane-2-carboxylate (196 mg, 0.52 mmol). A stream of nitrogen was bubbled through the mixture for 5 min to remove air, then the mixture in a sealed-tube was stirred at 115° C. for 3 h. The mixture was filtered to remove the solid impurity, and the filtrate was concentrated to remove the solvent. The residue was purified by silica gel column chromatography (PE/EtOAc (v/v)=10/1-5/1) to give the title compound as a white solid (196 mg, 52%).

Step 4: (+/−)-trans-methyl 3-((2-(5-chloro-1H-pyrazolo[3,4-b]pyridin-3-yl)-5-fluoro-6-phenylpyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-5-fluoro-6-phenylpyrimidin-4-yl)amino)bicyclo[2.2.2]octane-2-carboxylate (120 mg, 0.16 mmol) in DCM (5 mL) were added trifluoroacetic acid (0.20 mL, 2.62 mmol) and triethyl silicane (0.42 mL, 2.62 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (130 mg, 98%).

MS (ESI, pos. ion) m/z: 507.1 [M+H]$^+$.

Step 5: (+/−)-trans-3-((2-(5-chloro-1H-pyrazolo[3,4-b]pyridin-3-yl)-5-fluoro-6-phenyl pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-5-fluoro-6-phenylpyrimidin-4-yl)amino)bicyclo[2.2.2]octane-2-carboxylate (130 mg, 0.26 mmol) in THF/MeOH (v/v=5 mL/5 mL) was added a solution of sodium hydroxide (103 mg, 2.56 mmol) in water (1 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (39 mg, 31%).

MS (ESI, pos. ion) m/z: 493.3 [M+H]$^+$;
HRMS (ESI, pos. ion) m/z: 493.1556 [M+H]$^+$, (C$_{26}$H$_{25}$FClN$_6$O$_2$) [M+H]$^+$ theoretical value: 493.1555;
$^1$H NMR (400 MHz, CDCl$_3$) δ (ppm): 8.87 (s, 1H), 8.63 (s, 1H), 8.05 (d, J=7.1 Hz, 2H), 7.91 (d, J=6.4 Hz, 1H), 7.64-7.52 (m, 3H), 4.80 (s, 1H), 2.96 (d, J=7.1 Hz, 1H), 2.05 (s, 1H), 1.99 (s, 1H), 1.85-1.35 (m, 9H);
$^{13}$C NMR (151 MHz, DMSO-d$_6$) δ(ppm): 175.96, 154.82, 153.17, 153.09, 148.22, 148.08, 145.59, 143.29, 141.51, 134.20, 130.90, 130.49, 130.07, 129.09, 124.91, 114.78, 51.24, 47.85, 28.90, 28.80, 25.67, 24.45, 21.60, 19.52.

Example 28: (+/−)-trans-3-((2-(5-chloro-1H-pyrazolo[3,4-b]pyridin-3-yl)-6-(oxazol-2-yl)pyrimidin-4-yl)amino)bicyclo[2.2.2]octane-2-carboxylic Acid

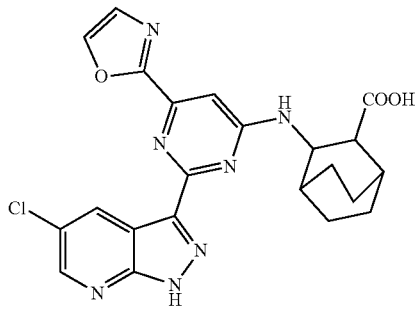 [SMILES: O=C(O)C1C2CCC(CC2)C1Nc1cc(-c2ncco2)nc(-c2n[nH]c3ncc(Cl)cc23)n1]

Step 1: 2-(2,6-dichloropyrimidin-4-yl)oxazole 2,4,6-trichloropyrimidine (67 mg, 0.37 mmol) was dissolved in DMF (8 mL), then bis(triphenylphosphine)palladium(II) chloride (25 mg, 0.03 mmol) and 2-(tributylstannyl)oxazole (120 mg, 0.34 mmol) were added into the mixture. The resulting mixture was stirred at 90° C. under nitrogen protection overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (33 mg, 46%).

MS (ESI, pos. ion) m/z: 215.9 [M+H]$^+$.

Step 2: (+/−)-trans-methyl 3-((2-chloro-6-(oxazol-2-yl)pyrimidin-4-yl)amino)bicyclo[2.2.2]octane-2-carboxylate (+/−)-trans-Methyl 3-aminobicyclo[2.2.2]octane-2-carboxylate (140 mg, 0.70 mmol) and 2-(2,6-dichloropyrimidin-4-yl)oxazole (126 mg, 0.58 mmol) were dissolved in DMF (10 mL), then potassium carbonate (161 mg, 1.17 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (115 mg, 54%).

MS (ESI, pos. ion) m/z: 363.1 [M+H]$^+$.

Step 3: (+/−)-trans-methyl 3-((2-(5-chloro-1-trityl-1H-pyrazolo[3,4-b]pyridin-3-yl)-6-(oxazol-2-yl)pyrimidin-4-yl)amino)bicyclo[2.2.2]octane-2-carboxylate To a mixed solvent of 1,4-dioxane (12 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (180 mg, 0.34 mmol), K$_2$CO$_3$ (130 mg, 0.93 mmol), PdCl$_2$(dppf) (22 mg, 0.03 mmol), (+/−)-trans-methyl 3-((2-chloro-6-(oxazol-2-yl)pyrimidin-4-yl)amino)bicyclo[2.2.2]octane-2-carboxylate (112 mg, 0.31 mmol). A stream of nitrogen was bubbled through the mixture for 10 min to remove air, then the mixture in a sealed-tube was stirred at 115° C. for 3 h under a sealed condition. The mixture was filtered to remove the solid impurity, and the filtrate was concentrated to remove the solvent. The residue was purified by silica gel column chromatography (PE/EtOAc (v/v)=10/1-4/1) to give the title compound as a white solid (45 mg, 20%).

Step 4: (+/−)-trans-methyl 3-((2-(5-chloro-1H-pyrazolo[3,4-b]pyridin-3-yl)-6-(oxazol-2-yl) pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(oxazol-2-yl)pyrimidin-4-yl)amino)bicyclo[2.2.2]octane-2-carboxylate (45 mg, 0.06 mmol) in DCM (5 mL) were added trifluoroacetic acid (0.05 mL, 0.62 mmol) and triethyl silicane (0.10 mL, 0.62 mmol). The mixture was stirred at rt overnight. The reaction mixture was added into saturated aqueous sodium bicarbonate (100 mL). The resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent to give the title compound as brown oil (28 mg, 94%), which was used directly in the next step without further purification.

MS (ESI, pos. ion) m/z: 480.3 [M+H]$^+$.

Step 5: (+/−)-trans-3-((2-(5-chloro-1H-pyrazolo[3,4-b]pyridin-3-yl)-6-(oxazol-2-yl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(oxazol-2-yl)pyrimidin-4-yl)amino)bicyclo[2.2.2]octane-2-carboxylate (28 mg, 0.06 mmol) in THF/MeOH (v/v=5 mL/5 mL) was added a solution of sodium hydroxide (25 mg, 0.58 mmol) in water (1 mL). The mixture was stirred at rt overnight. To the reaction mixture was added water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (11 mg, 40%).

MS (ESI, pos. ion) m/z: 466.1 [M+H]$^+$;
HRMS (ESI, pos. ion) m/z: 466.1391[M+H]$^+$, (C$_{22}$H$_{21}$ClN$_7$O$_3$) [M+H]$^+$ theoretical value: 466.1394;
$^1$H NMR (400 MHz, CDCl$_3$) δ (ppm): 14.32 (s, 1H), 8.96 (s, 1H), 8.63 (s, 1H), 8.39 (s, 1H), 8.01 (s, 1H), 7.52 (s, 1H), 7.17 (s, 1H), 4.74 (s, 1H), 1.80-1.43 (m, 12H).

Example 29: (+/−)-trans-3-((2-(5-chloro-1H-pyrazolo[3,4-b]pyridin-3-yl)-6-(thiophen-2-yl)pyrimidin-4-yl)amino)bicyclo[2.2.2]octane-2-carboxylic Acid

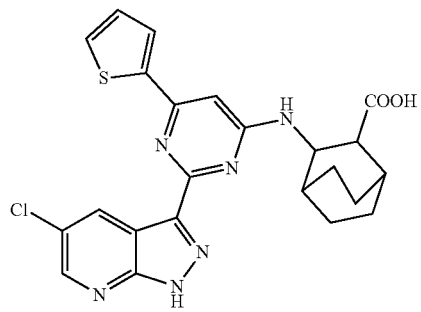 [SMILES: O=C(O)C1C2CCC(CC2)C1Nc1cc(-c2cccs2)nc(-c2n[nH]c3ncc(Cl)cc23)n1]

Step 1: 2,4-dichloro-6-(thiophen-2-yl)pyrimidine

To a solution of thiophene (500 mg, 5.94 mmol) in anhydrous tetrahydrofuran (20 mL) was added n-butyl-lithium (2.4 mL, 6.0 mmol, 2.5 mol/L) at −15° C., and the mixture was stirred for 1 h at −15° C. Then to the mixture was added ZnCl$_2$-TMEDA (495 mg, 1.96 mmol), and the resulting mixture was stirred for 1 h. Then palladium dichloride (105 mg, 0.59 mmol), triphenylphosphine (658 mg, 1.19 mmol) and 2,4,6-trichloropyrimidine (1.09 g, 5.94 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (616 mg, 45%).

MS (ESI, pos. ion) m/z: 230.2 [M+H]$^+$;

$^1$H NMR (400 MHz, CDCl$_3$) δ (ppm): 7.86 (d, J=3.7 Hz, 1H), 7.66 (d, J=4.9 Hz, 1H), 7.51 (s, 1H), 7.24-7.17 (m, 1H).

Step 2: (+/−)-trans-methyl 3-((2-chloro-6-(thiophen-2-yl)pyrimidin-4-yl)amino)bicyclo[2.2.2]octane-2-carboxylate (+/−)-trans-Methyl 3-aminobicyclo[2.2.2]octane-2-carboxylate (586 mg, 3.20 mmol) and 2,4-dichloro-6-(thiophen-2-yl)pyrimidine (616 mg, 2.67 mmol) were dissolved in DMF (6 mL), then potassium carbonate (1.11 g, 8.00 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=10/1) to give the title compound as a white solid (180 mg, 18%).

MS (ESI, pos. ion) m/z: 378.1 [M+H]$^+$;

$^1$H NMR (400 MHz, CDCl$_3$) δ (ppm): 7.74 (d, J=3.1 Hz, 1H), 7.50 (d, J=4.9 Hz, 1H), 7.17-7.10 (m, 1H), 6.68 (s, 1H), 5.47 (s, 1H), 4.30 (s, 1H), 3.76 (s, 3H), 2.39 (d, J=4.6 Hz, 1H), 2.08 (s, 1H), 1.87 (d, J=2.5 Hz, 1H), 1.82-1.65 (m, 8H).

Step 3: (+/−)-trans-methyl 3-((2-(5-chloro-1-trityl-1H-pyrazolo[3,4-b]pyridin-3-yl)-6-(thiophen-2-yl)pyrimidin-4-yl)amino)bicyclo[2.2.2]octane-2-carboxylate To a mixed solvent of 1,4-dioxane (12 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (299 mg, 0.57 mmol), K$_2$CO$_3$ (214 mg, 1.55 mmol), PdCl$_2$(dppf) (52 mg, 0.05 mmol), (+/−)-trans-methyl 3-((2-chloro-6-(thiophen-2-yl)pyrimidin-4-yl)amino)bicyclo[2.2.2]octane-2-carboxylate (195 mg, 0.52 mmol). A stream of nitrogen was bubbled through the mixture for 10 min to remove air, then the mixture in a sealed-tube was stirred at 115° C. for 1.5 h under a sealed condition. The mixture was filtered to remove the solid impurity, and the filtrate was concentrated to remove the solvent. The residue was purified by silica gel column chromatography (PE/EtOAc (v/v)=10/1-5/1) to give a white solid (365 mg, 96%).

Step 4: (+/−)-trans-methyl 3-((2-(5-chloro-1H-pyrazolo[3,4-b]pyridin-3-yl)-6-(thiophen-2-yl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(thiophen-2-yl)pyrimidin-4-yl)amino)bicyclo[2.2.2]octane-2-carboxylate (365 mg, 0.50 mmol) in DCM (5 mL) were added trifluoroacetic acid (0.80 mL, 4.95 mmol) and triethyl silicane (0.38 mL, 4.95 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (241 mg, 98%).

MS (ESI, pos. ion) m/z: 496.20 [M+H]$^+$.

Step 5: (+/−)-trans-3-((2-(5-chloro-1H-pyrazolo[3,4-b]pyridin-3-yl)-6-(thiophen-2-yl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(thiophen-2-yl)pyrimidin-4-yl)amino)bicyclo[2.2.2]octane-2-carboxylate (241 mg, 0.49 mmol) in THF/MeOH (v/v=5 mL/5 mL) was added a solution of sodium hydroxide (195 mg, 0.19 mmol) in water (4 mL). The mixture was stirred at rt overnight. To the reaction mixture was added water (20 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (103 mg, 44%).

MS (ESI, pos. ion) m/z: 481.2 [M+H]$^+$;

HRMS (ESI, pos. ion) m/z: 481.1238[M+H]$^+$, (C$_{23}$H$_{22}$ClN$_6$O$_2$S) [M+H]$^+$ theoretical value: 481.1213;

$^1$H NMR (400 MHz, CDCl$_3$) δ (ppm): 8.96 (s, 1H), 8.60 (d, J=2.1 Hz, 1H), 7.73 (s, 3H), 7.23-7.20 (m, 1H), 6.84 (s, 1H), 4.70 (s, 1H), 2.39 (s, 1H), 2.01 (s, 1H), 1.84-1.35 (m, 10H).

Example 30: (+/−)-trans-3-((2-(5-chloro-1H-pyrazolo[3,4-b]pyridin-3-yl)-6-cyclopropylpyrimidin-4-yl)amino)bicyclo[2.2.2]octane-2-carboxylic Acid

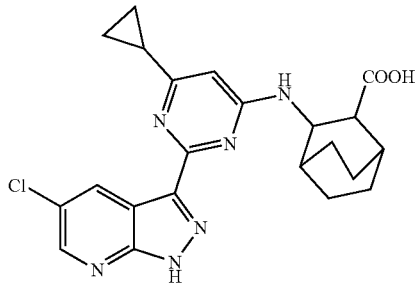 [SMILES: O=C(O)C1C2CCC(CC2)C1Nc1cc(C2CC2)nc(-c2n[nH]c3ncc(Cl)cc23)n1]

Step 1: (+/−)-trans-methyl 3-((2-chloro-6-cyclopropylpyrimidin-4-yl)amino)bicyclo[2.2.2]octane-2-carboxylate To a solution of (+/−)-trans-methyl 3-((2,6-dichloropyrimidin-4-yl)amino) bicyclo[2.2.2]octane-2-carboxylate (100 mg, 0.30 mmol) in tetrahydrofuran (5 mL) were added Pd(dppf)Cl$_2$ (25 mg, 0.03 mmol), potassium phosphate (160 mg, 0.75 mmol) and cyclopropylboronic acid (27 mg, 0.31 mmol). The mixture was refluxed overnight under nitrogen protection. The reaction mixture was cooled to rt and concentrated in vacuo. To the residue was added ethyl acetate (20 mL), and the mixture was washed with saturated aqueous sodium bicarbonate (20 mL) and saturated brine (20 mL). The organic layer was dried over anhydrous sodium sulfate, and filtered. The filtrate was concentrated in vacuo and the residue was purified by silica gel column chromatography (PE/EA (v/v)=5/1) to give the title compound as colorless oil (59 mg, 58%).

MS (ESI, pos. ion) m/z: 336.2 [M+H]$^+$;

$^1$H NMR (400 MHz, CDCl$_3$) δ (ppm): 6.18 (s, 1H), 5.37-5.13 (m, 1H), 4.17 (d, J=19.1 Hz, 1H), 3.76-3.73 (m, 3H), 2.35-2.31 (m, 1H), 2.07-2.03 (m, 1H), 1.84-1.79 (m, 2H), 1.70 (d, J=7.3 Hz, 2H), 1.65 (d, J=7.0 Hz, 2H), 1.54 (d, J=10.7 Hz, 2H), 1.46 (d, J=7.3 Hz, 1H), 1.36-1.23 (m, 1H), 1.08 (tt, J=9.1, 4.5 Hz, 2H), 1.02-0.96 (m, 2H).

Step 2: (+/−)-trans-methyl 3-((2-(5-chloro-1-trityl-1H-pyrazolo[3,4-b]pyridin-3-yl)-6-cyclopropylpyrimidin-4-yl)amino)bicyclo[2.2.2]octane-2-carboxylate To 1,4-dioxane (5 mL) were added 5-chloro-3-(4,4,5,5-tetramethyl-1,3,2-dioxaborolan-2-yl)-1-trityl-1H-pyrazolo[3,4-b]pyridine (210 mg, 0.39 mmol), K$_2$CO$_3$ (150 mg, 1.07 mmol), PdCl$_2$(dppf) (30 mg, 0.04 mmol) and (+/−)-trans-methyl 3-((2-chloro-6-cyclopropylpyrimidin-4-yl)amino)bicyclo[2.2.2]octane-2-carboxylate (120 mg, 0.36 mmol). Then H$_2$O (1 mL) was added to the mixture, and a stream of nitrogen was bubbled through the mixture to remove the air for 10 min. The mixture was stirred for 1.5 h at 110° C. in a sealed-tube. The mixture was filtered to remove the solid impurity, and the filtrate was concentrated to remove the solvent. The residue was purified by silica gel column chromatography (PE/EtOAc (v/v)=10/1-5/1) to give the title compound as a white solid (151 mg, 61%).

Step 3: (+/−)-trans-methyl 3-((2-(5-chloro-1H-pyrazolo[3,4-b]pyridin-3-yl)-6-cyclopropyl pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-cyclopropylpyrimidin-4-yl)amino)bicyclo[2.2.2]octane-2-carboxylate (151 mg, 0.22 mmol) in DCM (5 mL) were added trifluoroacetic acid (0.30 mL, 2.17 mmol) and triethyl silicane (0.60 mL, 2.17 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (81 mg, 82%).

MS (ESI, pos. ion) m/z: 453.2 [M+H]$^+$.

Step 4: (+/−)-trans-3-((2-(5-chloro-1H-pyrazolo[3,4-b]pyridin-3-yl)-6-cyclopropylpyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-cyclopropylpyrimidin-4-yl)amino)bicyclo[2.2.2]octane-2-carboxylate (81 mg, 0.18 mmol) in THF/MeOH (v/v=5 mL/5 mL) was added a solution of NaOH (75 mg, 0.07 mmol) in water (1 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (36 mg, 46%).

MS (ESI, pos. ion) m/z: 439.2 [M+H]$^+$;

HRMS (ESI, pos. ion) m/z: 439.1646[M+H]$^+$. (C$_{22}$H$_{24}$ClN$_6$O$_2$) [M+H]$^+$ theoretical value: 439.1649;

$^1$H NMR (400 MHz, CDCl$_3$) δ (ppm): 14.10 (s, 1H), 8.84 (s, 1H), 8.59 (s, 1H), 7.44 (s, 1H), 6.35 (s, 1H), 4.64 (s, 1H), 1.99 (s, 4H), 1.83-1.35 (m, 10H), 1.04 (s, 1H), 0.95 (s, 2H).

Example 31: (+/−)-trans-3-((2-(5-chloro-1H-pyrazolo[3,4-b]pyridin-3-yl)-6-(naphthalene-2-yl)pyrimidin-4-yl)amino)bicyclo[2.2.2]octane-2-carboxylic Acid

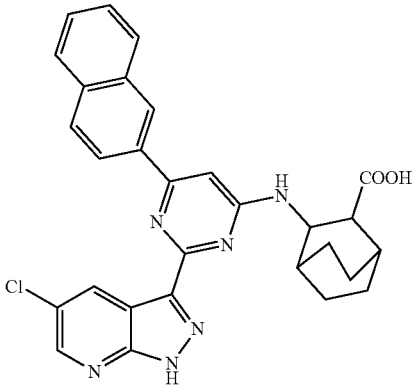 [SMILES: O=C(O)C1C2CCC(CC2)C1Nc1cc(-c2ccc3ccccc3c2)nc(-c2n[nH]c3ncc(Cl)cc23)n1]

Step 1: 2,4-dichloro-6-(naphthalen-2-yl)pyrimidine

To a solution of 2,4,6-trichloropyrimidine (500 mg, 2.73 mmol) in THF (8.18 mL) were added palladium acetate (63 mg, 0.27 mmol), triphenylphosphine (150 mg, 0.55 mmol), naphthalen-2-ylboronic acid (473 mg, 2.8 mmol) and aqueous sodium carbonate solution (1 M, 8.18 mL, 8.18 mmol). The mixture was stirred at 70° C. for 6 h. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (530 mg, 71%).

MS (ESI, pos. ion) m/z: 275.0[M+H]$^+$;

$^1$H NMR (400 MHz, CDCl$_3$) δ (ppm): 8.67 (s, 1H), 8.13 (dd, J=8.6, 1.7 Hz, 1H), 8.01 (t, J=8.0 Hz, 2H), 7.92 (d, J=7.7 Hz, 1H), 7.84 (s, 1H), 7.62 (dq, J=6.9, 5.7 Hz, 2H).

Step 2: (+/−)-trans-methyl 3-((2-chloro-6-(naphthalen-2-yl)pyrimidin-4-yl)amino) bicyclo[2.2.2]octane-2-carboxylate (+/−)-trans-Methyl 3-aminobicyclo[2.2.2]octane-2-carboxylate (388 mg, 2.12 mmol) and 2,4-dichloro-6-(naphthalen-2-yl)pyrimidine (530 mg, 1.93 mmol) were dissolved in DMF (5 mL), then potassium carbonate (789 mg, 5.71 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (n-hexane) to give the title compound as a white solid (330 mg, 41%).

MS (ESI, pos. ion) m/z: 422.0 [M+H]$^+$;

$^1$H NMR (400 MHz, CDCl$_3$) δ (ppm): 8.59 (s, 1H), 8.08-7.86 (m, 4H), 7.55 (p, J=6.9 Hz, 2H), 6.95 (s, 1H), 5.56 (s, 1H), 4.39 (s, 1H), 3.77 (s, 3H), 2.43 (d, J=4.6 Hz, 1H), 2.10 (s, 1H), 1.91 (s, 1H), 1.77-1.58 (m, 8H).

Step 3: (+/−)-trans-methyl 3-((2-(5-chloro-1-trityl-1H-pyrazolo[3,4-b]pyridin-3-yl)-6-(naphthalen-2-yl) pyrimidin-4-yl)amino)bicyclo[2.2.2]octane-2-carboxylate To a mixed solvent of 1,4-dioxane (5 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (220 mg, 0.42 mmol), K$_2$CO$_3$ (160 mg, 1.14 mmol), PdCl$_2$(dppf) (30 mg, 0.04 mmol), (+/−)-trans-methyl 3-((2-chloro-6-(naphthalen-2-yl)pyrimidin-4-yl)amino)bicyclo[2.2.2]octane-2-carboxylate (160 mg, 0.38 mmol). A stream of nitrogen was bubbled through the mixture for 10 min to remove air, then the mixture in a sealed-tube was stirred at 115° C. for 2 h. The mixture was filtered to remove the solid impurity, and the filtrate was concentrated to remove the solvent. The residue was purified by silica gel column chromatography (PE/EtOAc (v/v)=10/1-5/1) to give the title compound as a white solid (162 mg, 55%).

Step 4: (+/−)-trans-methyl 3-((2-(5-chloro-1H-pyrazolo[3,4-b]pyridin-3-yl)-6-(naphthalene-2-yl)pyrimidin-4-yl)amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(naphthalen-2-yl)pyrimidin-4-yl)amino)bicyclo[2.2.2]octane-2-carboxylate (162 mg, 0.21 mmol) in DCM (5 mL) were added trifluoroacetic acid (0.40 mL, 2.08 mmol) and triethyl silicane (0.40 mL, 2.08 mmol). The mixture was stirred at rt overnight. The reaction mixture was added into saturated aqueous sodium bicarbonate (60 mL). The resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent to give the title compound as brown oil (111 mg, 100%), which was used directly in the next step without further purification.

MS (ESI, pos. ion) m/z: 540.3 [M+H]$^+$.

Step 5: (+/−)-trans-3-((2-(5-chloro-1H-pyrazolo[3,4-b]pyridin-3-yl)-6-(naphthalen-2-yl) pyrimidin-4-yl)amino)bicyclo[2.2.2]octane-2-carboxylic Acid To a solution of (+/−)-trans-methyl 3-((2-(5-chloro-1H-pyrazolo[3,4-b]pyridin-3-yl)-6-(naphthalen-2-yl)pyrimidin-4-yl)amino)bicyclo[2.2.2]octane-2-carboxylate (152 mg, 0.28 mmol) in THF/MeOH (v/v=5 mL/5 mL) was added a solution of sodium hydroxide (120 mg, 2.82 mmol) in water (2 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (22 mg, 15%).

MS (ESI, pos. ion) m/z: 525.1 [M+H]$^+$;

HRMS (ESI, pos. ion) m/z: 525.1797[M+H]$^+$, (C$_{29}$H$_{26}$ClN$_6$O$_2$) [M+H]$^+$ theoretical value: 525.1806;

$^1$H NMR (400 MHz, CDCl$_3$) δ (ppm): 14.27 (s, 1H), 8.99 (s, 1H), 8.70 (s, 1H), 8.64 (s, 1H), 8.21 (s, 1H), 8.09 (d, J=8.1 Hz, 2H), 8.01 (s, 1H), 7.82 (s, 1H), 7.61 (s, 2H), 7.08 (s, 1H), 4.77 (s, 1H), 2.04 (s, 2H), 1.93-1.33 (m, 10H).

Example 32: (+/−)-trans-3-((2-(5-chloro-1H-pyrazolo[3,4-b]pyridin-3-yl)-6-(p-tolyl) pyrimidin-4-yl) amino)bicyclo[2.2.2]octane-2-carboxylic Acid

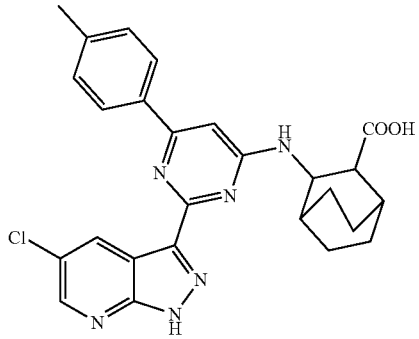 [SMILES: Cc1ccc(-c2cc(NC3C4CCC(CC4)C3C(=O)O)nc(-c3n[nH]c4ncc(Cl)cc34)n2)cc1]

Step 1: 2,4-dichloro-6-(p-tolyl)pyrimidine

To a solution of 2,4,6-trichloropyrimidine (1.48 g, 1.10 mmol) in THF (15 mL) were added palladium acetate (40 mg, 0.15 mmol), triphenylphosphine (81 mg, 0.29 mmol), p-methylbenzeneboronic acid (1.00 g, 7.36 mmol) and aqueous sodium carbonate solution (1 M, 15.00 mL, 14.71 mmol). The mixture was stirred at 65° C. overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a green solid (215 mg, 12%).

MS (ESI, pos. ion) m/z: 239.1 [M+H]$^+$;

$^1$H NMR (400 MHz, CDCl$_3$) δ (ppm): 7.99 (d, J=8.2 Hz, 2H), 7.66 (s, 1H), 7.34 (d, J=8.0 Hz, 2H), 2.46 (s, 3H).

Step 2: (+/−)-trans-methyl 3-((2-chloro-6-(p-tolyl) pyrimidin-4-yl)amino)bicyclo[2.2.2]octane-2-carboxylate (+/−)-trans-Methyl 3-aminobicyclo[2.2.2]octane-2-carboxylate (156 mg, 0.78 mmol) and 2,4-dichloro-6-(p-tolyl) pyrimidine (156 mg, 0.65 mmol) were dissolved in DMF (10 mL), then potassium carbonate (180 mg, 1.30 mmol) was added. The mixture was stirred at rt overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=5/1) to give the title compound as a white solid (103 mg, 41%).

MS (ESI, pos. ion) m/z: 386.3 [M+H]+.

Step 3: (+/−)-trans-methyl 3-((2-(5-chloro-1-trityl-1H-pyrazolo[3,4-b]pyridin-3-yl)-6-(p-tolyl)pyrimidin-4-yl)amino)bicyclo[2.2.2]octane-2-carboxylate To a mixed solvent of 1,4-dioxane (5 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (152 mg, 0.57 mmol), K$_2$CO$_3$ (214 mg, 1.56 mmol), PdCl$_2$(dppf) (30 mg, 0.03 mmol), (+/−)-trans-methyl 3-((2-chloro-6-(p-tolyl)pyrimidin-4-yl)amino)bicyclo[2.2.2]octane-2-carboxylate (200 mg, 0.52 mmol). A stream of nitrogen was bubbled through the mixture for 10 min to remove air, then the mixture in a sealed-tube was stirred at 115° C. for 1.5 h. The mixture was filtered to remove the solid impurity, and the filtrate was concentrated to remove the solvent. The residue was purified by silica gel column chromatography (PE/EtOAc (v/v)=10/1-5/1) to give the title compound as a white solid (122 mg, 32%).

Step 4: (+/−)-trans-methyl 3-((2-(5-chloro-1H-pyrazolo[3,4-b]pyridin-3-yl)-6-(p-tolyl) pyrimidin-4-yl) amino)bicyclo[2.2.2]octane-2-carboxylate To a solution of (+/−)-trans-methyl 3-((2-(5-chloro-1-trityl-1H-pyrazolo[3,4-b]pyridin-3-yl)-6-(p-tolyl)pyrimidin-4-yl)amino)bicyclo[2.2.2]octane-2-carboxylate (120 mg, 0.16 mmol) in DCM (5 mL) were added trifluoroacetic acid (0.15 mL, 1.65 mmol) and triethyl silicane (0.30 mL, 1.65 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (120 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (81 mg, 100%).

MS (ESI, pos. ion) m/z: 503.1 [M+H]+.

Step 5: (+/−)-trans-3-((2-(5-chloro-1H-pyrazolo[3,4-b]pyridin-3-yl)-6-(p-tolyl)pyrimidin-4-yl)amino) bicyclo[2.2.2]octane-2-carboxylic Acid To a solution of (+/−)-trans-methyl 3-((2-(5-chloro-1H-pyrazolo[3,4-b]pyridin-3-yl)-6-(p-tolyl)pyrimidin-4-yl) amino)bicyclo[2.2.2]octane-2-carboxylate (80 mg, 0.16 mmol) in THF/MeOH (v/v=5 mL/5 mL) was added a solution of sodium hydroxide (63 mg, 1.59 mmol) in water (2 mL). The mixture was stirred at rt overnight. To the reaction mixture was added water (10 mL), and the mixture was acidified with hydrochloric acid (1 M) to pH about 6. The resulting mixture was extracted with EtOAc (15 mL×3). The combined organic layers were washed with saturated brine (40 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (27 mg, 35%).

MS (ESI, pos. ion) m/z: 489.1 [M+H]+;
HRMS (ESI, pos. ion) m/z: 489.1817[M+H]+, (C$_{26}$H$_{26}$ClN$_6$O$_2$) [M+H]+ theoretical value: 489.1806;

$^1$H NMR (400 MHz, CDCl$_3$) δ (ppm): 14.22 (s, 1H), 12.37 (s, 1H), 8.95 (s, 1H), 8.62 (s, 1H), 8.00 (s, 1H), 7.71 (s, 1H), 7.37 (d, J=7.8 Hz, 2H), 6.88 (s, 1H), 4.72 (s, 1H), 2.40 (s, 3H), 2.03-1.36 (m, 12H).

Example 33: (+/−)-trans-3-((6-(4-(tert-butyl)phenyl)-2-(5-chloro-1H-pyrazolo[3,4-b]pyridin-3-yl) pyrimidin-4-yl)amino)bicyclo[2.2.2]octane-2-carboxylic Acid

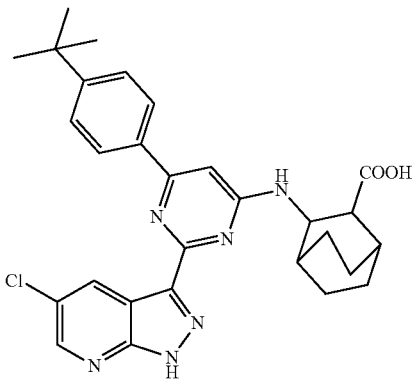 [SMILES: CC(C)(C)c1ccc(-c2cc(NC3C4CCC(CC4)C3C(=O)O)nc(-c3n[nH]c4ncc(Cl)cc34)n2)cc1]

Step 1:
4-(4-(tert-butyl)phenyl)-2,6-dichloropyrimidine

To a solution of 2,4,6-trichloropyrimidine (500 mg, 2.73 mmol) in THF (8.5 mL) were added palladium acetate (62 mg, 0.27 mmol), triphenylphosphine (150 mg, 0.56 mmol), (4-(tert-butyl)phenyl)boronic acid (490 mg, 2.75 mmol) and aqueous sodium carbonate solution (1 M, 8.18 mL, 8.18 mmol). The mixture was stirred at 70° C. for 6 h. The reaction mixture was cooled to rt and concentrated to remove the organic solvent, then to the residue was added water (30 mL). The resulting mixture was extracted with ethyl acetate (30 mL×3). The combined organic layers were washed with saturated brine (80 mL), dried over anhydrous sodium sulfate and filtered. The filtrate was concentrated in vacuo and the residue was purified by silica gel column chromatography (PE) to give the title compound as a white solid (593 mg, 77%). MS: (ESI, pos. ion) m/z: 281.0 [M+H]+;

$^1$H NMR (400 MHz, CDCl$_3$) δ (ppm): 8.03 (d, J=8.5 Hz, 2H), 7.67 (s, 1H), 7.56 (d, J=8.5 Hz, 2H), 1.39 (s, 9H).

Step 2: (+/−)-trans-methyl 3-((6-(4-(tert-butyl)phenyl)-2-chloropyrimidin-4-yl)amino) bicyclo[2.2.2] octane-2-carboxylate To a solution of 4-(4-(tert-butyl)phenyl)-2,6-dichloropyrimidine (590 mg, 2.10 mmol) and (+/−)-trans-methyl 3-aminobicyclo[2.2.2]octane-2-carboxylate (422 mg, 2.31 mmol) in N,N-dimethylformamide (10 mL) was added potassium carbonate (315 mg, 2.31 mmol). The mixture was stirred at rt overnight. To the reaction mixture was added water (200 mL) to dilute the mixture, and the resulting mixture was extracted with ethyl acetate (20 mL×3). The combined organic layers were washed with saturated brine (20 mL), dried over anhydrous sodium sulfate and filtered. The filtrate was concentrated in vacuo and the residue was purified by silica gel column chromatography (hexane/EtOAc (v/v)=20/1-5/1) to give the title compound as a white solid (593 mg, 66%).

MS: (ESI, pos. ion) m/z: 428.1 [M+H]$^+$;

$^1$H NMR (400 MHz, CDCl$_3$) δ (ppm): 7.94 (d, J=8.3 Hz, 2H), 7.50 (d, J=8.4 Hz, 2H), 6.78 (s, 1H), 5.42 (s, 1H), 4.33 (s, 1H), 3.76 (s, 3H), 2.40 (d, J=4.9 Hz, 1H), 2.07 (s, 1H), 1.88 (d, J=2.6 Hz, 1H), 1.76-1.60 (m, 6H), 1.58 (d, J=10.4 Hz, 2H), 1.37 (s, 9H).

Step 3: (+/−)-trans-methyl 3-((6-(4-(tert-butyl)phenyl)-2-(5-chloro-1-trityl-1H-pyrazolo[3,4-b]pyridin-3-yl)pyrimidin-4-yl)amino)bicyclo[2.2.2]octane-2-carboxylate To a mixed solvent of 1,4-dioxane (5 mL) and H$_2$O (1 mL) were added 5-chloro-3-(4,4,5,5-tetramethyl-1,3,2-dioxaborolan-2-yl)-1-trityl-1H-pyrazolo[3,4-b]pyridine (210 mg, 0.37 mmol), K$_2$CO$_3$ (151 mg, 1.02 mmol), PdCl$_2$(dppf) (30 mg, 0.03 mmol), (+/−)-trans-methyl 3-((6-(4-(tert-butyl)phenyl)-2-chloropyrimidin-4-yl)amino)bicyclo[2.2.2]octane-2-carboxylate (145 mg, 0.34 mmol). A stream of nitrogen was bubbled through the mixture for 10 min to remove air, then the mixture in a sealed-tube was stirred at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (130 mg, 49%).

Step 4: (+/−)-trans-methyl 3-((6-(4-(tert-butyl)phenyl)-2-(5-chloro-1H-pyrazolo[3,4-b]pyridin-3-yl)pyrimidin-4-yl)amino)bicyclo[2.2.2]octane-2-carboxylate To a solution of (+/−)-trans-methyl 3-((6-(4-(tert-butyl)phenyl)-2-(5-chloro-1-trityl-1H-pyrazolo[3,4-b]pyridin-3-yl)pyrimidin-4-yl)amino)bicyclo[2.2.2]octane-2-carboxylate (130 mg, 0.17 mmol) in DCM (5 mL) were added trifluoroacetic acid (0.15 mL, 1.65 mmol) and triethyl silicane (0.30 mL, 1.65 mmol). The mixture was stirred at rt overnight. The reaction mixture was added into saturated aqueous sodium bicarbonate (100 mL), and the resulting mixture was extracted with dichloromethane (50 mL×3). The combined organic layers were washed with saturated brine (100 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (55 mg, 62%).

MS (ESI, pos. ion) m/z: 546.2 [M+H]$^+$.

Step 5: (+/−)-trans-3-((6-(4-(tert-butyl)phenyl)-2-(5-chloro-1H-pyrazolo[3,4-b]pyridin-3-yl)pyrimidin-4-yl)amino)bicyclo[2.2.2]octane-2-carboxylic Acid To a solution of (+/−)-trans-methyl 3-((6-(4-(tert-butyl)phenyl)-2-(5-chloro-1H-pyrazolo[3,4-b]pyridin-3-yl)pyrimidin-4-yl)amino)bicyclo[2.2.2]octane-2-carboxylate (65 mg, 0.12 mmol) in THF/MeOH (v/v=5 mL/5 mL) was added a solution of NaOH (60 mg, 1.20 mmol) in water (1 mL). The mixture was stirred at rt overnight. To the reaction mixture was added water (30 mL), and the mixture was acidified with hydrochloric acid (1 M) to pH about 6. The resulting mixture was extracted with EtOAc (30 mL×3). The combined organic layers were washed with saturated brine (80 mL), dried over anhydrous sodium sulfate, and filtered.

The filtrate was concentrated in vacuo to remove the solvent, and the residue was purified by silica gel column chromatography (DCM/MeOH (v/v)=10/1-5/1) to give the title compound as a white solid (38 mg, 60%).

MS (ESI, pos. ion) m/z: 531.30 [M+H]$^+$;

HRMS (ESI, pos. ion) m/z: 531.2272 [M+H]$^+$, (C$_{29}$H$_{32}$ClN$_6$O$_2$) [M+H]$^+$ theoretical value: 531.2275;

$^1$H NMR (400 MHz, CDCl$_3$) δ (ppm): 14.23 (s, 1H), 8.95 (s, 1H), 8.62 (s, 1H), 8.04 (s, 2H), 7.73 (s, 1H), 7.58 (d, J=7.5 Hz, 2H), 6.89 (s, 1H), 4.73 (s, 1H), 2.01 (d, J=14.2 Hz, 2H), 1.87-1.45 (m, 8H), 1.34 (s, 9H), 1.20 (d, J=19.0 Hz, 2H).

Example 34: (2S,3S)-3-((2-(5-fluoro-1H-pyrazolo[3,4-b]pyridin-3-yl)-7-isopropyl-7H-pyrrolo[2,3-d]pyrimidin-4-yl)amino)bicyclo[2.2.2]octane-2-carboxylic Acid

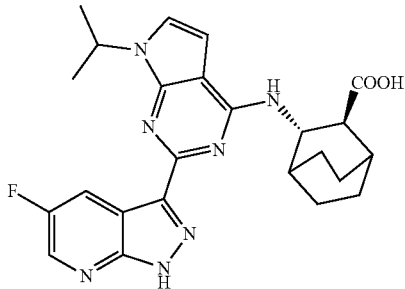 [SMILES: CC(C)n1ccc2c(N[C@H]3C4CCC(CC4)[C@@H]3C(=O)O)nc(-c3n[nH]c4ncc(F)cc34)nc21]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: 2,4-dichloro-7-isopropyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (130 mg, 3.19 mmol) at 0° C., and the mixture was stirred at this temperature for 30 min. Then 2-iodopropane (904 mg, 5.32 mmol) was added to the mixture, and the resulting mixture was stirred at rt overnight. Water (50 mL) was added to quench the reaction, and the resulting mixture was extracted with EtOAc (50 mL×2). The combined organic phases were washed with saturated brine (80 mL), dried over anhydrous Na$_2$SO$_4$, filtered, and the filtrate was concentrated in vacuo. The residue was purified by silica gel chromatograph (PE/EtOAc (v/v)=10/1) to give the title compound as a yellow solid (356 mg, 58%).

MS (ESI, pos. ion) m/z: 231.05 [M+H]$^+$.

Step 3: (2S,3S)-ethyl 3-((2-chloro-7-isopropyl-7H-pyrrolo[2,3-d]pyrimidin-4-yl)amino) bicyclo[2.2.2]octane-2-carboxylate (+/−)-trans-Ethyl 3-aminobicyclo[2.2.2]octane-2-carboxylate hydrochloride (459 mg, 1.96 mmol) and 2,4-dichloro7-isopropyl-7H-pyrrolo[2,3-d]pyrimidine (410 mg, 1.78 mmol) were dissolved in tetrahydrofuran (5 mL), then potassium carbonate (615 mg, 4.45 mmol) was added. The mixture was stirred at rt overnight. Water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (333 mg, 50%).

MS (ESI, pos. ion) m/z: 425.15 $[M+H]^+$;

$^1$H NMR (400 MHz, $CDCl_3$) δ (ppm): 7.39 (d, J=4.2 Hz, 1H), 7.02 (d, J=3.6 Hz, 1H), 6.43 (s, 1H), 5.25 (s, 1H), 5.04 (dt, J=13.5, 6.8 Hz, 1H), 4.62 (s, 1H), 3.76 (s, 3H), 2.42 (d, J=5.4 Hz, 1H), 2.02 (s, 1H), 1.95 (d, J=2.3 Hz, 1H), 1.88-1.74 (m, 2H), 1.64 (d, J=17.2 Hz, 5H), 1.47 (dd, J=6.7, 1.5 Hz, 6H).

Step 4: (2S,3S)-ethyl 3-((2-(5-fluoro-1-trityl-1H-pyrazolo[3,4-b]pyridin-3-yl)-7-isopropyl-7H-pyrrolo[2,3-d]pyrimidin-4-yl)amino)bicyclo[2.2.2]octane-2-carboxylate To a mixed solvent of 1,4-dioxane (20 mL) and $H_2O$ (0.5 mL) were added 5-fluoro-3-(4,4,5,5-tetramethyl-1,3,2-dioxaborolan-2-yl)-1-trityl-1H-pyrazolo[3,4-b]pyridine (220 mg, 0.42 mmol), $K_2CO_3$ (160 mg, 0.16 mmol), $PdCl_2$(dppf) (30 mg, 0.04 mmol), (2S,3S)-ethyl 3-((2-chloro-7-isopropyl-7H-pyrrolo[2,3-d]pyrimidin-4-yl)amino)bicyclo[2.2.2]octane-2-carboxylate (426 mg, 0.98 mmol). A stream of nitrogen was bubbled through the mixture for 10 min to remove air, then the mixture in a sealed-tube was stirred at 115° C. for 3 h. The mixture was filtered to remove the solid impurity, and the filtrate was concentrated to remove the solvent. The residue was purified by silica gel column chromatography (PE/EtOAc (v/v)=10/1) to give the title compound as light yellow oil (240 mg, 85%).

Step 5: (2S,3S)-ethyl 3-((2-(5-fluoro-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (2S,3S)-Ethyl 3-((2-(5-fluoro-1-trityl-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (240 mg, 0.33 mmol) was dissolved in DCM (5 mL), then $Et_3SiH$ (1.65 mL, 10.30 mmol) and TFA (0.78 mL, 11.00 mmol) were added into the mixture. The resulting mixture was stirred at rt overnight. The reaction mixture was added into saturated aqueous sodium bicarbonate (30 mL), and the resulting mixture was extracted with dichloromethane (30 mL×3). The combined organic layers were washed with saturated brine (100 mL), dried over anhydrous sodium sulfate, and filtered. The filtrate was concentrated to remove the solvent, and the residue was purified by silica gel column chromatography (PE/EtOAc (v/v)=2/1) to give the title compound as light yellow oil (153 mg, 61%).

MS (ESI, pos. ion) m/z: 492.4 $[M+H]^+$.

Step 6: (2S,3S)-3-((2-(5-fluoro-1H-pyrazolo[3,4-b]pyridin-3-yl)-7-isopropyl-7H-pyrrolo[2,3-d]pyrimidin-4-yl)amino)bicyclo[2.2.2]octane-2-carboxylic Acid To a solution of (2S,3S)-ethyl 3-((2-(5-fluoro-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (157 mg, 0.32 mmol) in THF/MeOH/$H_2O$ (v/v/v=2 mL/2 mL/2 mL) was added NaOH (127 mg, 3.19 mmol). The mixture was stirred at rt overnight. To the reaction mixture was added saturated brine (20 mL), and the mixture was acidified with hydrochloric acid (1 M) to pH about 6. The resulting mixture was extracted with 2-methyltetrahydrofuran (15 mL×3). The combined organic layers were washed with saturated brine (40 mL), dried over anhydrous sodium sulfate, and filtered. The filtrate was concentrated in vacuo to remove the solvent, and the residue was purified by preparative thin-layer chromatography (DCM/MeOH (v/v) =15/1) to give the title compound as a light yellow solid (66 mg, 45%).

MS (ESI, pos. ion) m/z: 464.3 $[M+H]^+$;

HRMS (ESI, pos. ion) m/z: 464.2202 $[M+H]^+$, $(C_{24}H_{27}FN_7O_2)$ $[M+H]^+$ theoretical value: 464.2210;

$^1$H NMR (400 MHz, DMSO-$d_6$) δ (ppm): 13.96 (s, 1H), 8.69 (s, 1H), 8.62 (s, 1H), 7.41 (s, 1H), 7.35 (d, J=2.8 Hz, 1H), 6.71 (s, 1H), 5.13-5.02 (m, 1H), 4.87 (s, 1H), 2.77 (d, J=6.3 Hz, 1H), 2.02 (d, J=11.7 Hz, 3H), 1.79 (s, 4H), 1.67-1.55 (m, 3H), 1.50-1.38 (m, 6H).

Example 35: (2S,3S)-ethyl 3-((2-(5-chloro-1H-pyrazolo[3,4-b]pyridin-3-yl)-7-isopropyl-7H-pyrrolo[2,3-d]pyrimidin-4-yl)amino)bicyclo[2.2.2]octane-2-carboxylate

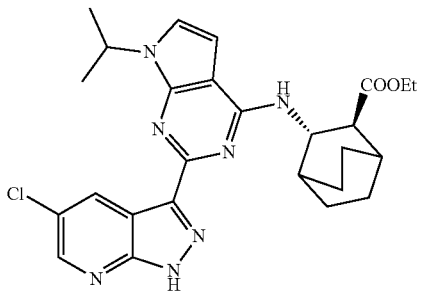 [SMILES: CCOC(=O)[C@H]1C2CCC(CC2)[C@@H]1Nc1nc(-c2n[nH]c3ncc(Cl)cc23)nc2c1ccn2C(C)C]

Step 1: (2S,3S)-ethyl 3-aminobicyclo[2.2.2]octane-2-carboxylate Hydrochloride

The title compound was prepared according to the synthetic method disclosed in patent application WO 2015073491.

Step 2: 2,4-dichloro-7-isopropyl-7H-pyrrolo[2,3-d]pyrimidine

To a solution of 2,4-dichloro-7H-pyrrolo[2,3-d]pyrimidine (500 mg, 2.66 mmol) in DMF (5 mL) was added NaH (60%, 130 mg, 3.19 mmol) at 0° C., and the mixture was stirred at this temperature for 30 min. Then 2-iodopropane (904 mg, 5.32 mmol) was added to the mixture, and the resulting mixture was stirred at rt overnight. Water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (460 mg, 75%).

MS (ESI, pos. ion) m/z: 232.0 $[M+H]^+$.

Step 3: (2S,3S)-ethyl 3-((2-chloro-7-isopropyl-7H-pyrrolo[2,3-d]pyrimidin-4-yl)amino) bicyclo[2.2.2]octane-2-carboxylate (+/−)-trans-Ethyl 2-aminobicyclo[2.2.2]octane-2-carboxylate (1.27 g, 5.40 mmol) and 2,4-dichloro-7-isopropyl-7H-pyrrolo[2,3-d]pyrimidine (1.10 g, 5.40 mmol) were added into in tetrahydrofuran (5 mL), then potassium carbonate (1.50 g, 11.00 mmol) was added. The mixture was stirred at rt overnight. Water (50 mL) was added to quench the reaction, and the resulting mixture was extracted with EtOAc (50 mL×2). The combined organic phases were washed with saturated brine (80 mL), dried over anhydrous $Na_2SO_4$, filtered, and the filtrate was concentrated in vacuo. The residue was purified by silica gel chromatograph (PE/EtOAc (v/v)=10/1) to give the title compound as a yellow solid (979 mg, 50%).

MS (ESI, pos. ion) m/z: 391.1 [M+H]$^+$.

Step 4: (2S,3S)-ethyl 3-((2-(5-chloro-1-trityl-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (2S,3S)-Ethyl 3-((2-chloro-7-isopropyl-7H-pyrrolo[2,3-d]pyrimidin-4-yl)amino) bicyclo[2.2.2]octane-2-carboxylate (100 mg, 0.25 mmol), $K_2CO_3$ (150 mg, 1.03 mmol), $PdCl_2$(dppf) (40 mg, 0.05 mmol) and 5-chloro-3-(4,4,5,5-tetramethyl-1,3,2-dioxaborolan-2-yl)-1-trityl-1H-pyrazolo[3,4-b]pyridine (160 mg, 0.31 mmol) were mixed in 1,4-dioxane (12 mL), then $H_2O$ (1 mL) was added into the mixture. A stream of nitrogen was bubbled through the mixture to remove the air for 10 min, then the mixture in a sealed-tube was stirred at 115° C. for 3 h. The mixture was filtered to remove the solid impurity, and the filtrate was concentrated to remove the solvent. The residue was purified by silica gel column chromatography (PE/EtOAc (v/v)=10/1-5/1) to give the title compound as a white solid (190 mg, 98%).

MS (ESI, pos. ion) m/z: 750.2 [M+H]$^+$.

Step 5: (2S,3S)-ethyl 3-((2-(5-chloro-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (2S,3S)-Ethyl 3-((2-(5-chloro-1-trityl-1H-pyrazolo[3,4-b]pyridin-3-yl)-7-isopropyl-7H-pyrrolo[2,3-d]pyrimidin-4-yl)amino)bicyclo[2.2.2]octane-2-carboxylate (190 mg, 0.25 mmol) was dissolved in DCM (10 mL), then $Et_3SiH$ (1.0 mL, 6.26 mmol) and TFA (1.0 mL, 13.46 mmol) were added into the mixture. The resulting mixture was stirred at r overnight. The reaction mixture was added into saturated aqueous sodium bicarbonate (50 mL), and the resulting mixture was extracted with dichloromethane (60 mL×3). The combined organic layers were washed with saturated brine (80 mL), dried over anhydrous sodium sulfate, and filtered. The filtrate was concentrated in vacuo to remove the solvent, and the residue was purified by silica gel column chromatography (DCM/MeOH (v/v)=10/1) to give the title compound as a white solid (60 mg, 46%).

MS (ESI, pos. ion) m/z: 508.1 [M+H]$^+$;
HRMS (ESI, pos. ion) m/z: 508.2207 [M+H]$^+$, ($C_{26}H_{31}ClN_7O_2$) [M+H]$^+$ theoretical value: 508.2228;
$^1$H NMR (400 MHz, $CDCl_3$) δ (ppm): 10.29 (d, J=7.1 Hz, 1H), 8.47 (s, 1H), 8.42 (s, 1H), 7.28 (s, 1H), 6.95 (s, 1H), 5.17 (dt, J=13.3, 6.7 Hz, 1H), 4.89 (s, 1H), 4.25-4.14 (m, 2H), 2.95 (d, J=4.3 Hz, 1H), 2.23 (s, 1H), 1.99 (m, 3H), 1.76 (dd, J=20.9, 10.7 Hz, 2H), 1.65 (m, 6H), 1.55 (s, 3H), 1.27 (t, J=7.1 Hz, 3H).

Example 36: (2S,3S)-ethyl 3-((2-(5-chloro-1H-pyrazolo[3,4-b]pyridin-3-yl)-6-phenyl pyrimidin-4-yl)amino)bicyclo[2.2.2]octane-2-carboxylate

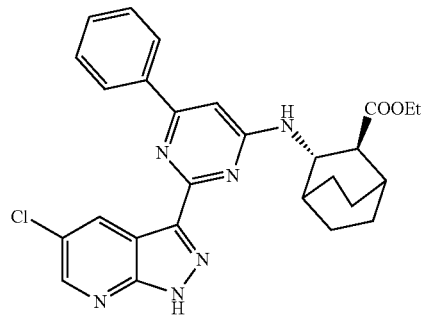 [SMILES: CCOC(=O)[C@H]1C2CCC(CC2)[C@@H]1Nc1cc(-c2ccccc2)nc(-c2n[nH]c3ncc(Cl)cc23)n1]

Step 1: (2S,3S)-ethyl 3-aminobicyclo[2.2.2]octane-2-carboxylate Hydrochloride The title compound was prepared according to the synthetic method disclosed in patent application WO 2015073491.

Step 2: 2,4-dichloro-6-phenylpyrimidine

To a solution of 2,4,6-trichloropyrimidine (1.00 g, 5.45 mmol) in THF (15 mL) were added tetrakis(triphenylphosphine)palladium (430 mg, 0.50 mmol), benzeneboronic acid (0.66 g, 5.45 mol) and aqueous sodium carbonate solution (1 M, 15 mL, 15 mmol). The mixture was stirred at 80° C. overnight under nitrogen protection. To the reaction mixture was added water (50 mL), and the resulting mixture was extracted with ethyl acetate (50 mL×3). The combined organic layers were washed with saturated brine (100 mL), dried over anhydrous sodium sulfate and filtered. The filtrate was concentrated in vacuo and the residue was purified by silica gel column chromatography (PE) to give the title compound as a green solid (0.76 g, 62%).

Step 3: (2S,3S)-ethyl 3-((2-chloro-6-phenylpyrimidin-4-yl)amino)bicyclo[2.2.2]octane-2-carboxylate 2,4-Dichloro-6-phenylpyrimidine (0.76 g, 3.40 mmol), potassium carbonate (0.93 g, 6.80 mmol) and (2S,3S)-ethyl 3-aminobicyclo[2.2.2]octane-2-carboxylate hydrochloride (0.96 g, 4.10 mmol) were suspended in DMF (10 ml). The mixture was heated to 80° C. and stirred for 24 h. To the reaction mixture was added water (40 mL), and the resulting mixture was extracted with ethyl acetate (30 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=15/1) to give the title compound as a pale solid (0.70 g, 50%).

MS (ESI, pos. ion) m/z: 386.1[M+H]$^+$.

Step 4: (2S,3S)-ethyl 3-((2-(5-chloro-1-trityl-1H-pyrazolo[3,4-b]pyridin-3-yl)-6-phenyl pyrimidin-4-yl)amino)bicyclo[2.2.2]octane-2-carboxylate To a mixed solvent of THF (10 mL) and H₂O (0.5 mL) were added 5-chloro-3-(4,4,5,5-tetramethyl-1,3,2-dioxaborolan-2-yl)-1-trityl-1H-pyrazolo[3,4-b]pyridine (162 mg, 0.31 mmol), potassium carbonate (143 mg, 1.03 mmol), palladium acetate (12 mg, 0.05 mmol), X-Phos (49 mg, 0.10 mmol) and (2S,3S)-ethyl 3-((2-chloro-6-phenylpyrimidin-4-yl)amino)bicyclo[2.2.2]octane-2-carboxylate (100 mg, 0.26 mmol). The mixture was heated to 80° C. and stirred for 12 h. The mixture was filtered through a celite pad to remove the solid impurity. The filtrate was concentrated in vacuo, and the residue was purified by silica gel column chromatography (PE/EtOAc (v/v)=8/1) to give the title compound as a light yellow solid (190 mg, 98%).

Step 5: (2S,3S)-ethyl 3-((2-(5-chloro-1H-pyrazolo[3,4-b]pyridin-3-yl)-6-phenylpyrimidin-4-yl)amino)bicyclo[2.2.2]octane-2-carboxylate To a reaction flask were added (2S,3S)-ethyl 3-((2-(5-chloro-1-trityl-1H-pyrazolo[3,4-b]pyridin-3-yl)-6-phenylpyrimidin-4-yl)amino)bicyclo[2.2.2]octane-2-carboxylate (190 mg, 0.37 mmol), triethylsilicane (780 mg, 6.26 mmol), trifluoroacetic acid (1500 mg, 13.46 mmol) and DCM (4 mL). The mixture was stirred at rt overnight. To the reaction mixture was added water (20 mL), and the resulting mixture was adjusted with saturated aqueous potassium carbonate to pH about 7 to 8. The mixture was extracted with dichloromethane (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (PE/EA (v/v)=4/1) to give the title compound as a white solid (120 mg, 93%).

MS (ESI, pos. ion) m/z: 503.3 [M+H]⁺;
HRMS (ESI, pos. ion) m/z: 503.1935 [M+H]⁺, ($C_{27}H_{28}ClN_6O_2$) [M+H]⁺ theoretical value: 503.1962;
¹H NMR (400 MHz, CDCl₃) δ (ppm): 13.47 (s, 1H), 8.90 (s, 1H), 8.54-8.38 (m, 1H), 8.14 (s, 2H), 7.55 (s, 3H), 6.77 (s, 1H), 4.22-4.14 (m, 2H), 2.48 (s, 1H), 2.07 (m, 2H), 1.74 (m, 9H), 1.20 (t, J=7.1 Hz, 3H).

Example 37: 3-((2-(5-chloro-1H-pyrazolo[3,4-b]pyridin-3-yl)-5-fluoro-6-(thiophen-2-yl) pyrimidin-4-yl)amino)-4-methyl-4-(pyridin-2-yl)pentanoic Acid

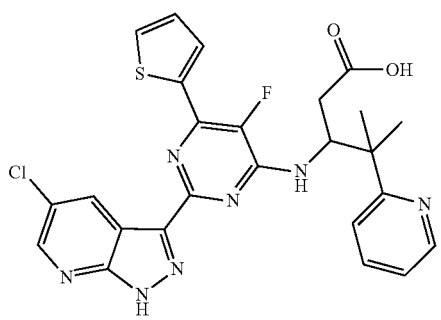 [SMILES: CC(C)(c1ccccn1)C(CC(=O)O)Nc1nc(-c2n[nH]c3ncc(Cl)cc23)nc(-c2cccs2)c1F]

Step 1: 2,4-dichloro-5-fluoro-6-(thiophen-2-yl)pyrimidine

To a solution of thiophene (300 mg, 3.57 mmol) in anhydrous tetrahydrofuran (20 mL) was added n-butyllithium (1.4 mL, 3.57 mmol, 2.5 mol/L) at −15° C., and the mixture was stirred for 1 h at −15° C. Then to the mixture was added ZnCl₂-TMEDA (300 mg, 1.18 mmol), and the resulting mixture was stirred for 1 h. Then palladium dichloride (65 mg, 0.36 mmol), triphenylphosphine (188 mg, 0.71 mmol) and 5-fluoro-2,4,6-trichloropyrimidine (790 mg, 3.92 mmol) were added to the mixture in turn. The resulting mixture was heated to 55° C. under nitrogen protection, and then stirred at this temperature overnight. To the reaction mixture was added water (50 mL), and the resulting mixture was extracted with ethyl acetate (50 mL×3). The combined organic layers were washed with saturated brine (50 mL), dried over anhydrous sodium sulfate and filtered. The filtrate was concentrated in vacuo and the residue was purified by silica gel column chromatography (PE) to give the title compound as a white solid (366 mg, 41%).

MS (ESI, pos. ion) m/z: 272.0 [M+Na]⁺.

Step 2: ethyl 3-((2-chloro-5-fluoro-6-(thiophen-2-yl)pyrimidin-4-yl)amino)-4-methyl-4-(pyridin-2-yl)pentanoate Ethyl 3-amino-4-methyl-4-(pyridin-2-yl)pentanoate (2.50 g, 10.4 mmol) and 2,4-dichloro-5-fluoro-6-(thiophen-2-yl)pyrimidine (2.00 g, 8.03 mmol) were dissolved in THF (20 mL). Then DIPEA (406 mg, 2.94 mmol) was added into the mixture. The mixture was refluxed overnight. To the reaction mixture was added water (40 mL), and the resulting mixture was extracted with ethyl acetate (40 mL×3). The combined organic layers were washed with saturated brine (50 mL), dried over anhydrous sodium sulfate and filtered. The filtrate was concentrated in vacuo and the residue was purified by silica gel column chromatography (PE/EtOAc (v/v)=20/1) to give the title compound as a white solid (3.42 g, 94%).

MS (ESI, pos. ion) m/z: 449.3 [M+H]⁺.

Step 3: ethyl 3-((2-bromo-5-fluoro-6-(thiophen-2-yl)pyrimidin-4-yl)amino)-4-methy-4-(pyridin-2-yl)pentanoate Ethyl 3-((2-chloro-5-fluoro-6-(thiophen-2-yl)pyrimidin-4-yl)amino)-4-methyl-4-(pyridin-2-yl)pentanoate (3.40 g 7.57 mol) was suspended in a solution of hydrobromic acid in acetic acid (40 mL, 33%), and the mixture was stirred for 1 h. The reaction mixture was poured into ice-water (30 mL), and the mixture was extracted with DCM (30 mL×3). The combined organic layers were washed with saturated aqueous sodium bicarbonate (50 mL×3) and saturated brine (50 mL) in turn, dried over anhydrous sodium bicarbonate, the filtered. The filtrate was concentrated in vacuo to give the title compound as a light yellow solid (3.30 g, 88%).

MS (ESI, pos. ion) m/z: 495.0 [M+H]⁺.

Step 4: ethyl 3-((2-(5-chloro-1-trityl-1H-pyrazolo[3,4-b]pyridin-3-yl)-5-fluoro-6-(thiophen-2-yl)pyrimidin-4-yl)amino)-4-methyl-4-(pyridin-2-yl)pentanoate To a mixed solvent of 1,4-dioxane (5 mL) and H₂O (0.5 mL) were added 5-chloro-3-(4,4,5,5-tetramethyl-1,3,2-dioxaborolan-2-yl)-1-trityl-1H-pyrazolo[3,4-b]pyridine (465 mg, 0.44 mmol, 50%), K₂CO₃ (230 mg, 1.62 mmol), PdCl₂(dppf) (60 mg, 0.08 mmol) and ethyl 3-((2-bromo-5-fluoro- 6-(thiophen-2-yl)pyrimidin-4-yl)amino)-4-methyl-4-(pyridin-2-yl) pentanoate (200 mg, 0.40 mmol). Then a stream of nitrogen was bubbled through the mixture for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (290 mg, 88%).

MS (ESI, pos. ion) m/z: 806.9 [M+H]$^+$.

Step 5: ethyl 3-((2-(5-chloro-1H-pyrazolo[3,4-b]pyridin-3-yl)-5-fluoro-6-(thiophen-2-yl) pyrimidin-4-yl)amino)-4-methyl-4-(pyridin-2-yl)pentanoate Ethyl 3-((2-(5-chloro-1-trityl-1H-pyrazolo[3,4-b]pyridin-3-yl)-5-fluoro-6-(thiophen-2-yl)pyrimidin-4-yl)amino)-4-methyl-4-(pyridin-2-yl)pentanoate (290 mg, 0.27 mmol) was dissolved in DCM (10 mL), then Et$_3$SiH (1 mL, 6.26 mmol) and TFA (1.0 mL, 13.46 mmol) were added into the mixture. The mixture was stirred at rt overnight. The reaction mixture was added into saturated aqueous sodium bicarbonate (30 mL), and the resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (100 mg, 49%).

MS (ESI, pos. ion) m/z: 564.8 [M+H]$^+$.

Step 6: 3-((2-(5-chloro-1H-pyrazolo[3,4-b]pyridin-3-yl)-5-fluoro-6-(thiophen-2-yl) pyrimidin-4-yl)amino)-4-methyl-4-(pyridin-2-yl)pentanoic Acid Ethyl 3-((2-(5-chloro-1H-pyrazolo[3,4-b]pyridin-3-yl)-5-fluoro-6-(thiophen-2-yl) pyrimidin-4-yl)amino)-4-methyl-4-(pyridin-2-yl)pentanoate (100 mg, 0.17 mmol) was dissolved in ethanol (4 mL) and THF (4 mL), then a solution of NaOH (35 mg, 0.88 mmol) in water (2 mL) was added into the mixture. The mixture was stirred at rt for 2 h. To the reaction mixture was added water (20 mL), and the mixture was acidified with hydrochloric acid (1 M) to pH about 6. The resulting mixture was extracted with EtOAc (20 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (85 mg, 89%).

MS (ESI, pos. ion) m/z: 538.0 [M+H]$^+$;
HRMS (ESI, pos. ion) m/z: 538.1230 [M+H]$^+$. (C$_{25}$H$_{22}$ClFN$_7$O$_2$S) [M+H]$^+$ theoretical value: 538.1228;

$^1$H NMR (600 MHz, DMSO-d$_6$) δ (ppm): 14.29 (s, 1H), 9.13 (s, 1H), 8.65 (d, J=2.2 Hz, 1H), 8.59 (d, J=4.2 Hz, 1H), 7.88 (dd, J=19.5, 7.2 Hz, 4H), 7.60 (s, 1H), 7.31 (dd, J=10.2, 5.6 Hz, 2H), 5.53 (s, 1H), 2.61 (dd, J=15.6, 11.4 Hz, 1H), 2.31 (s, 1H), 1.43 (d, J=27.6 Hz, 6H).

Example 38: 3-((2-(5-chloro-1H-pyrazolo[3,4-b]pyridin-3-yl)-5-fluoro-6-(thiophen-2-yl) pyrimidin-4-yl)amino)-4-methyl-4-(thiazol-2-yl)pentanoic Acid

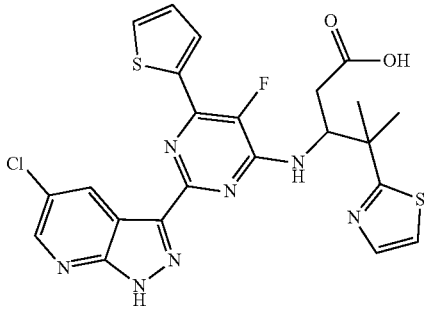 [SMILES: CC(C)(c1nccs1)C(CC(=O)O)Nc1nc(-c2n[nH]c3ncc(Cl)cc23)nc(-c2cccs2)c1F]

Step 1: ethyl 3-((2-chloro-5-fluoro-6-(thiophen-2-yl) pyrimidin-4-yl)amino)-4-methyl-4-(thiazol-2-yl) pentanoate Ethyl 3-amino-4-methyl-4-(thiazol-2-yl)pentanoate (1.56 g, 6.3 mmol) and 2,4-dichloro-5-fluoro-6-(thiophen-2-yl)pyrimidine (1.20 g, 4.80 mmol) were dissolved in THF (10 mL). Then DIPEA (1.20 g, 9.6 mmol) was added into the mixture. The mixture was heated and refluxed overnight. To the reaction mixture was added water (40 mL), and the resulting mixture was extracted with ethyl acetate (30 mL×3). The combined organic layers were washed with saturated brine (80 mL), dried over anhydrous sodium sulfate and filtered. The filtrate was concentrated in vacuo and the residue was purified by silica gel column chromatography (PE/EtOAc (v/v)=20/1) to give the title compound as a white solid (1.82 g, 83%).

MS (ESI, pos. ion) m/z: 455.2 [M+H]$^+$.

Step 2: ethyl 3-((2-bromo-5-fluoro-6-(thiophen-2-yl)pyrimidin-4-yl)amino)-4-methy-4-(thiazol-2-yl) pentanoate Ethyl 3-((2-chloro-5-fluoro-6-(thiophen-2-yl)pyrimidin-4-yl)amino)-4-methyl-4-(thiazol-2-yl)pentanoate (1.82 g, 4.00 mol) was suspended in a solution of hydrobromic acid in acetic acid (20 mL, 109 mmol, 33%). The mixture was stirred at rt for 1 h, then poured into ice-water (30 mL). The mixture was extracted with DCM (30 mL×3). The combined organic layers were washed with saturated aqueous sodium bicarbonate (60 mL×3) and saturated brine (80 mL), dried over anhydrous sodium sulfate and filtered. The filtrate was concentrated in vacuo to remove the solvent and give the title compound as a light yellow solid (1.89 g, 94%).

MS (ESI, pos. ion) m/z: 498.9 [M+H]$^+$.

Step 3: ethyl 3-((2-(5-chloro-1-trityl-1H-pyrazolo[3,4-b]pyridin-3-yl)-5-fluoro-6-(thiophen-2-yl)pyrimidin-4-yl)amino)-4-methyl-4-(thiazol-2-yl)pentanoate To a mixed solvent of 1,4-dioxane (5 mL) and H$_2$O (0.5 mL) were added 5-chloro-3-(4,4,5,5-tetramethyl-1,3,2-dioxaborolan-2-yl)-1-trityl-1H-pyrazolo[3,4-b]pyridine (413 mg, 0.33 mmol, 40%), K$_2$CO$_3$ (170 mg, 1.20 mmol), PdCl$_2$(dppf) (43 mg, 0.06 mmol) and ethyl 3-((2-bromo-5-fluoro-6-(thiophen-2-yl)pyrimidin-4-yl)amino)-4-methyl-4-(thiazol-2-yl) pentanoate (150 mg, 0.30 mmol). Then the air in the mixture was exchanged with nitrogen by bubbling for 10 min. The mixture in a sealed-tube was stirred for 3 h at 115° C. The mixture was filtered to remove the solid impurity, and the filtrate was concentrated to remove the solvent. The residue was purified by silica gel column chromatography (PE/EtOAc (v/v)=10/1-5/1) to give the title compound as a white solid (220 mg, 89%).

MS (ESI, pos. ion) m/z: 814.2[M+H]$^+$.

Step 4: ethyl 3-((2-(5-chloro-1H-pyrazolo[3,4-b]pyridin-3-yl)-5-fluoro-6-(thiophen-2-yl) pyrimidin-4-yl)amino)-4-methyl-4-(thiazol-2-yl)pentanoate Ethyl 3-((2-(5-chloro-1-trityl-1H-pyrazolo[3,4-b]pyridin-3-yl)-5-fluoro-6-(thiophen-2-yl) pyrimidin-4-yl)amino)-4-methyl-4-(thiazol-2-yl)pentanoate (220 mg, 0.27 mmol) was dissolved in DCM (10 mL), then a solution of Et$_3$SiH (1 mL, 6.26 mmol) and TFA (1.0 mL, 13.46 mmol) were added into the mixture. The mixture was stirred at rt overnight. The reaction mixture was added into saturated aqueous sodium bicarbonate (30 mL), and the resulting mixture was extracted with dichloromethane (30 mL×3). The combined organic layers were washed with saturated brine (80 mL), dried over anhydrous sodium sulfate, and filtered. The filtrate was concentrated in vacuo, and the residue was purified by silica gel column chromatography (DCM/MeOH (v/v)=10/1) to give the title compound as a white solid (70 mg, 45%).

MS (ESI, pos. ion) m/z: 572.0 [M+H]$^+$.

Step 5: 3-((2-(5-chloro-1H-pyrazolo[3,4-b]pyridin-3-yl)-5-fluoro-6-(thiophen-2-yl)pyrimidin-4-yl)amino)-4-methyl-4-(thiazol-2-yl)pentanoic Acid Ethyl 3-((2-(5-chloro-1H-pyrazolo[3,4-b]pyridin-3-yl)-5-fluoro-6-(thiophen-2-yl) pyrimidin-4-yl)amino)-4-methyl-4-(thiazol-2-yl)pentanoate (70 mg, 0.17 mmol) was dissolved in a mixed solvent of ethanol (4 mL) and THF (4 mL), then a solution of NaOH (35 mg, 0.87 mmol) in water (2 mL) was added into the mixture. The mixture was stirred at rt for 2 h. To the reaction mixture was added water (30 mL), and the mixture was acidified with hydrochloric acid (1 M) to pH about 6. The resulting mixture was extracted with EtOAc (30 mL×3). The combined organic layers were washed with saturated brine (50 mL), dried over anhydrous sodium sulfate, and filtered. The filtrate was concentrated in vacuo to remove the solvent, and the residue was purified by silica gel column chromatography (DCM/MeOH (v/v)=10/1-5/1) to give the title compound as a white solid (62 mg, 93%).

MS (ESI, pos. ion) m/z: 544.0 [M+H]$^+$;
HRMS (ESI, pos. ion) m/z: 544.0780 [M+H]$^+$, ($C_{23}H_{20}ClFN_7O_2S_2$) [M+H]$^+$ theoretical value: 544.0792;
$^1$H NMR (600 MHz, DMSO-d$_6$) δ (ppm): 14.26 (s, 1H), 12.10 (s, 1H), 9.11 (d, J=1.7 Hz, 1H), 8.64 (d, J=1.8 Hz, 1H), 7.90 (t, J=9.8 Hz, 3H), 7.76 (d, J=3.1 Hz, 1H), 7.63 (d, J=3.2 Hz, 1H), 7.35-7.29 (m, 1H), 5.48 (t, J=9.6 Hz, 1H), 2.68 (dd, J=15.9, 11.1 Hz, 1H), 2.39 (d, J=15.1 Hz, 1H), 1.51 (s, 3H), 1.44 (s, 3H).

Examples of Biological Assay

Using parts of the compounds of the invention as examples, the inventors have detected antiviral and cytotoxicity activities of the compounds of the invention and pharmacokinetic properties in the following examples.

Example A: Cytopathic Effect Assay (CPE Assay)

Detection the inhibitory effect of the compound against cytopathic effect (CPE) of virus H1N1 A/Weiss/43 in vitro.

Scheme: MDCK cells (Madin-Daby canine kidney cells) were seeded in a 384-well plate with 2000 cells per well and cultured at 37° C. under 5% CO$_2$ condition overnight. Next day, cell culture medium was replenished with fresh medium containing relevant concentrations of test compounds and virus H1N1 A/Weiss/43 at a multiplicity of infection to yield 80-95% CPE (or the titer was 1 TCID90/well). The top concentration of the test compounds was 50 μM and then diluted by 3-fold serially for a total of 8 concentrations at 50 nM, 16.67 nM, 5.56 nM, 1.85 nM, 0.62 nM, 0.21 nM, 0.069 nM, 0.023 nM. The test condition of cytotoxicity test group was the same as described above, except that the cell culture medium of cytotoxicity test group didn't contain influenza virus. A virus control group without drug and a no virus infected cell control group without drug were set at the same time. Each group was set in duplicate, and incubated at 37° C. under 5% CO$_2$ condition for 5 days. The cell activity was detected by using CCK-8 kits, and the data were used for calculating the antiviral effect and cytotoxicity against virus-infected cell of the compound. Data were analyzed by using GraphPad Prism software, and the CPE inhibition ratio and cell survival ratio were calculated. EC$_{50}$ and CC$_{50}$ values were obtained according to the curve fitting.

CPE inhibition ratio=(abosorbance of dosing well–abosorbance of virus control well)/(abosorbance of cell control well–abosorbance of virus control well)×100% cell survival ratio=(abosorbance of dosing well–abosorbance of medium control well)/(abosorbance of cell control well–abosorbance of medium control well)×100%

Table 1 shows inhibitory activities of parts of the compounds in the invention against influenza virus (A/Weiss/43 (H1N1)).

TABLE 1

| Example No. | EC$_{50}$ (nM) |
|---|---|
| Example 1 | 0.059 |
| Example 2 | 0.054 |
| Example 3 | 0.39 |
| Example 4 | 0.075 |
| Example 14 | 0.696 |
| Example 15 | 0.303 |
| Example 16 | 0.14 |
| Example 29 | 0.203 |
| Example 30 | 0.35 |
| Example 31 | 0.513 |
| Example 34 | 0.227 |

Table 1 shows that the compounds of the invention have good anti-influenza virus activity.

Example B: Pharmacokinetic Evaluation after Administering a Certain Amount of the Compounds of the Invention by Intravenous or Oral Pharmacokinetic characteristics of the compounds of the invention in SD rat were evaluated. The compounds disclosed herein were administered in form of a saline solution containing 5% DMSO, 5% Kolliphor HS 15 and 90% Saline. For intravenous administration (iv), the animals were administered with a dose of 1 mg/kg, and blood samples (0.3 mL) were collected at the time points of 0.083, 0.25, 0.5, 1.0, 2.0, 5.0, 7.0 and 24 h after drug administration, then each blood sample was processed to separate plasma by centrifugation at 3000 rpm or 4000 rpm for 10 minutes. For oral administration (po), the animals were administered with a dose of 5 mg/kg, and blood samples (0.3 mL) were collected at the time points of 0.25, 0.5, 1.0, 2.0, 5.0, 7.0 and 24 h after drug administration, then each blood sample was processed to separate plasma by centrifugation at 3000 rpm or 4000 rpm for 10 minutes. Plasma samples were collected and stored at −20° C. or −70° C. until LC/MS/MS analysis.

Table 2 shows the pharmacokinetic data of parts of the compounds in the invention in SD rats.

TABLE 2

| Test compound | Administration route | dosage mg/kg | $AUC_{last}$ hr*ng/mL | $AUC_{INF}$ hr*ng/mL | CL L/h/Kg |
|---|---|---|---|---|---|
| Example 2 | iv | 1 | 909 | 910 | 18.5 |
| | po | 5 | 1060 | 1060 | N/A |

The assay shows that the compounds of the invention have high exposure level and good absorption, the compounds of the invention have good pharmacokinetic properties.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples. In addition, those skilled in the art can integrate and combine different embodiments or examples of the specification or the features of them as long as they are not contradictory to one another.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A compound having Formula (I) or a stereoisomer, a tautomer, an N-oxide, or a pharmaceutically acceptable salt thereof,

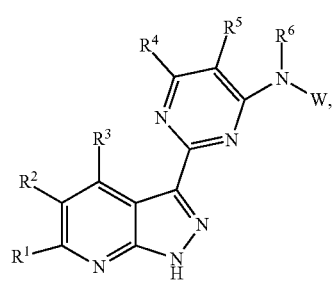

(I)

wherein,
each of $R^1$, $R^2$ and $R^3$ is independently H, D, F, Cl, Br, CN, $NO_2$, —C(=O)$R^a$, —C(=O)$OR^b$, —C(=O)NR$^c$R$^d$, —OR$^b$, —NR$^c$R$^d$, $R^b$O—C$_{1-4}$ alkylene, $R^d$R$^c$N—C$_{1-4}$ alkylene, C$_{1-6}$ alkyl, C$_{2-6}$ alkenyl or C$_{2-6}$ alkynyl; or, $R^1$ and $R^2$, together with the carbon atoms to which they are attached, form a C$_{3-6}$ carbocyclic ring, 5- to 6-membered heterocyclic ring, C$_{6-10}$ aromatic ring or 5- to 6-membered heteroaromatic ring, and wherein each of C$_{1-6}$ alkyl, C$_{2-6}$ alkenyl, C$_{2-6}$ alkynyl, C$_{3-6}$ carbocyclic ring, 5- to 6-membered heterocyclic ring, C$_{6-10}$ aromatic ring and 5- to 6-membered heteroaromatic ring is independently unsubstituted or substituted with 1, 2, 3 or 4 substituents independently selected from D, F, Cl, Br, CN, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;
$R^4$ is C$_{2-6}$ alkynyl, C$_{3-12}$ carbocyclyl 3- to 12- membered heterocyclyl, C$_{6-10}$ aryl, or 5- to 16-membered heteroaryl, and wherein each of C$_{2-6}$ alkynyl, C$_{3-12}$ carbocyclyl, 3- to 12-membered heterocyclyl, C$_{6-10}$ aryl and 5- to 16-membered heteroaryl is independently unsubstituted or substituted with 1, 2, 3, 4 or 5 R';
$R^5$ is H, D, F, Cl, Br, CN, $NO_2$, —C(=O)R$^a$, —C(=O)OR$^b$, —C(=O)NR$^c$R$^d$, —OR$^b$, —NR$^c$R$^d$, R$^b$O—C$_{1-4}$ alkylene, R$^d$R$^c$N—C$_{1-4}$ alkylene, C$_{1-6}$ alkyl, C$_{2-6}$ alkenyl, C$_{2-6}$ alkynyl, C$_{3-12}$ cycloalkyl, C$_{3-12}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene, and wherein each of C$_{1-6}$ alkyl, C$_{2-6}$ alkenyl, C$_{2-6}$alkynyl, C$_{3-12}$ cycloalkyl, C$_{3-12}$ cycloalkyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl and (5- to 10-membered heteroaryl)-C$_{1-4}$ alkylene is independently unsubstituted or substituted with 1, 2, 3, 4 or 5 R';
or, $R^4$ and $R^5$, together with the carbon atoms to which they are attached, form a C$_{3-12}$carbocyclic ring, 3- to 12-membered heterocyclic ring, C$_{6-10}$ aromatic ring or 5- to 10-membered heteroaromatic ring, and wherein each of C$_{3-12}$ carbocyclic ring, 3- to 12-membered heterocyclic ring, C$_{6-10}$ aromatic ring and 5- to 10-membered heteroaromatic ring is independently unsubstituted or substituted with 1, 2, 3, 4 or 5 R';
each R' is independently D, F, Cl, Br, CN, $NO_2$, —OR$^b$, —NR$^c$R$^d$, R$^b$O—C$_{1-4}$ alkylene, R$^d$R$^c$N—C$_{1-4}$ alkylene, —C(=O)R$^a$, —C(=O)OR$^b$, —C(=O)NR$^c$R$^d$, C$_{1-12}$ alkyl, C$_{1-6}$ haloalkyl, C$_{3-6}$ cycloalkyl, C$_{3-6}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene; or, two adjacent R', together with the carbon atoms to which they are attached, form a C$_{3-6}$ carbocyclic ring, 5- to 6-membered heterocyclic ring, C$_{6-10}$ aromatic ring or 5- to 6-membered heteroaromatic ring, and wherein each of C$_{1-12}$ alkyl, C$_{1-6}$ haloalkyl, C$_{3-6}$ cycloalkyl, C$_{3-6}$ cycloalkyl-C$_{1-4}$ alkylene, 3- to 8-membered heterocyclyl, (3- to 8-membered heterocyclyl)-C$_{1-4}$ alkylene, C$_{6-10}$ aryl, C$_{6-10}$ aryl-C$_{1-4}$ alkylene, 5- to 10-membered heteroaryl, (5- to 10-membered heteroaryl)-C$_{1-4}$ alkylene, C$_{3-6}$ carbocyclic ring, 5- to 6-membered heterocyclic ring, C$_{6-10}$ aromatic ring and 5- to 6-membered heteroaromatic ring is independently unsubstituted or substituted with 1, 2, 3 or 4 substituents independently selected from D, F, Cl, Br, CN, NO$_2$, —OR$^b$, —NR$^c$R$^d$, C$_{1-6}$ alkyl, C$_{1-6}$ haloalkyl, R$^b$O—C$_{1-4}$ alkylene or R$^d$R$^c$N—C$_{1-4}$ alkylene;

R$^6$ is H, D or C$_{1-6}$ alkyl, and wherein C$_{1-6}$ alkyl is optionally substituted with 1, 2, 3 or 4 substituents independently selected from D, F, Cl, Br, CN, NO$_2$ or —OR$^b$;

W is C$_{1-8}$ alkyl, C$_{3-12}$ carbocyclyl or 3- to 12-membered heterocyclyl, and wherein each of C$_{1-8}$ alkyl, C$_{3-12}$ carbocyclyl and 3- to 12-membered heterocyclyl is independently unsubstituted or substituted with 1, 2, 3 or 4 R$^w$;

each R$^w$ is independently D, F, Cl, Br, CN, NO$_2$, —C(═O)R$^a$, —C(═O)OR$^b$, —C(═O)NR$^c$R$^d$, —NR$^e$C(═O)R$^a$, —NR$^e$C(═O)NR$^c$R$^d$, —S(═O)$_2$R$^f$, —S(═O)$_2$NR$^e$C(═O)R$^a$, —S(═O)$_2$NR$^c$R$^d$, (R$^b$O)$_2$P(═O)—C$_{0-2}$ alkylene, —OR$^b$, R$^b$O—C$_{1-2}$ alkylene, R$^d$R$^c$N—C$_{1-2}$ alkylene, C$_{1-6}$ alkyl, 5- to 6-membered heteroaryl or 5- to 6-membered heterocyclyl, and wherein each of C$_{1-6}$ alkyl, 5- to 6-membered heteroaryl and 5- to 6-membered heterocyclyl is independently unsubstituted or substituted with 1, 2, 3 or 4 substituents independently selected from D, F, Cl, Br, CN, N$_3$, ═O, NO$_2$, —OR$^b$, C$_{1-6}$ alkyl or C$_{1-6}$ haloalkyl;

each R$^a$, R$^b$, R$^c$, R$^d$, R$^e$ and R$^f$ is independently H, D, hydroxy, C$_{1-6}$ haloalkyl, C$_{1-6}$ alkyl, C$_{1-6}$ alkoxy, C$_{2-6}$ alkenyl, C$_{2-6}$ alkynyl, C$_{3-6}$ carbocyclyl, C$_{3-6}$ carbocyclyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl or (5- to 10-membered heteroaryl)-C$_{1-4}$ alkylene; wherein each of C$_{1-6}$ alkyl, C$_{1-6}$ alkoxy, C$_{2-6}$ alkenyl, C$_{2-6}$ alkynyl, C$_{3-6}$ carbocyclyl, C$_{3-6}$carbocyclyl-C$_{1-4}$ alkylene, 3- to 12-membered heterocyclyl, (3- to 12-membered heterocyclyl)-C$_{1-4}$ alkylene, C$_{6-10}$ aryl, C$_{6-10}$ aryl-C$_{1-4}$ alkylene, 5- to 10-membered heteroaryl and (5- to 10-membered heteroaryl)-C$_{1-4}$ alkylene is independently unsubstituted or substituted with 1, 2, 3 or 4 substituents independently selected from D, F, Cl, CN, OH, NH$_2$, C$_{1-6}$ alkyl, C$_{1-6}$ haloalkyl, C$_{1-6}$ alkoxy or C$_{1-6}$ alkylamino;

or, R$^c$ and R$^d$, together with the nitrogen atom to which they are attached, form 3- to 8-membered heterocyclyl or 5- to 8-membered heteroaryl, and wherein each of 3- to 8-membered heterocyclyl and 5- to 8-membered heteroaryl is independently unsubstituted or substituted with 1, 2, 3 or 4 substituents independently selected from D, F, Cl, CN, OH, NH$_2$, C$_{1-6}$ alkyl, C$_{1-6}$ haloalkyl, C$_{1-6}$ alkoxy or C$_{1-6}$ alkylamino.

2. The compound of claim 1 having Formula (II),

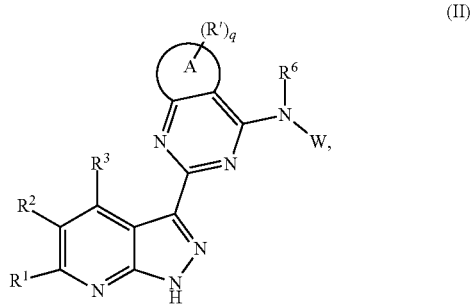

(II)

wherein A is a C$_{3-12}$ carbocyclic ring, 3- to 12-membered heterocyclic ring, C$_{6-10}$ aromatic ring or 5- to 10-memebered heteroaromatic ring; and q is 0, 1, 2, 3, 4, or 5.

3. The compound of claim 1, wherein W is C$_{1-8}$ alkyl, C$_{3-8}$ carbocyclyl or 3- to 12-membered heterocyclyl, and wherein each of C$_{1-8}$ alkyl, C$_{3-8}$ carbocyclyl and 3- to 12-membered heterocyclyl is independently unsubstituted or substituted with 1, 2, 3 or 4 R$^w$.

4. The compound of claim 2, wherein A is a C$_{3-6}$ carbocyclic ring, 3-to 6-membered heterocyclic ring, C$_{6-10}$ aromatic ring or 5- to 6-memebered heteroaromatic ring.

5. The compound of claim 2, wherein A is a C$_{3-6}$ carbocyclic ring, 3-to 6-membered heterocyclic ring, benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline.

6. The compound of claim 1, wherein R$^4$ is C$_{2-4}$ alkynyl, C$_{3-6}$ carbocyclyl, 5- to 10-membered heterocyclyl, C$_{6-10}$ aryl, or 5- to 10-membered heteroaryl, and wherein each of C$_{2-4}$ alkynyl, C$_{3-6}$ carbocyclyl, 5- to 10-membered heterocyclyl, C$_{6-10}$ aryl, and 5- to 10-membered heteroaryl is independently unsubstituted or substituted with 1, 2, 3, 4 or 5 R';

R$^5$ is H, D, F, Cl, Br, CN, NO$_2$, —C(═O)R$^a$, —C(═O)OR$^b$, —C(═O)NR$^c$R$^d$, —OR$^b$, —NR$^c$R$^d$, C$_{1-3}$ alkyl, C$_{2-4}$ alkenyl, C$_{2-4}$ alkynyl, C$_{3-6}$ cycloalklyl, C$_{3-6}$ cycloalkyl-C$_{1-4}$ alkylene, 5- to 6-membered heterocyclyl, (5- to 6-membered heterocyclyl)-C$_{1-4}$ alkylene, C$_{6-10}$ aryl, C$_{6-10}$ aryl-C$_{1-4}$ alkylene, 5- to 6-membered heteroaryl or (5- to 6-membered heteroaryl)-C$_{1-4}$ alkylene, and wherein each of C$_{1-3}$ alkyl, C$_{2-4}$ alkenyl, C$_{2-4}$ alkynyl, C$_{3-6}$ cycloalkyl, C$_{3-6}$ cycloalkyl-C$_{1-4}$ alkylene, 5- to 6-membered heterocyclyl, (5- to 6-membered heterocyclyl)-C$_{1-4}$ alkylene, C$_{6-10}$ aryl, C$_{6-10}$ aryl-C$_{1-4}$ alkylene, 5- to 6-membered heteroaryl and (5- to 6-membered heteroaryl)-C$_{1-4}$ alkylene is independently unsubstituted or substituted with 1, 2, 3, 4 or 5 R';

or, R$^4$ and R$^5$, together with the carbon atoms to which they are attached, form a C$_{3-6}$ carbocyclic ring, 3- to 6-membered heterocyclic ring, C$_{6-10}$ aromatic ring or 5- to 10-membered heteroaromatic ring, and wherein each of C$_{3-6}$ carbocyclic ring, 3- to 6-membered heterocyclic ring, C$_{6-10}$ aromatic ring and 5- to 10-membered heteroaromatic ring is independently unsubstituted or substituted with 1, 2, 3, 4 or 5 R'.

7. The compound of claim 1, wherein R$^4$ and R$^5$, together with the carbon atoms to which they are attached, form a C$_{3-6}$ carbocyclic ring, 3- to 6-membered heterocyclic ring, C$_{6-10}$ aromatic ring or 5- to 6-membered heteroaromatic ring, and wherein each of C$_{3-6}$ carbocyclic ring, 3- to 6-membered heterocyclic ring, C$_{6-10}$ aromatic ring and 5- to 6-membered heteroaromatic ring is independently unsubstituted or substituted with 1, 2, 3, 4 or 5 R'.

8. The compound of claim 1, wherein R$^4$ is ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imdazolyl, benzimdazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl or dibenzofuryl, and wherein each of ethynyl, propinyl, cyclopropyl, cyclobutyl, cyclopentyl, pyrrolidinyl, pyrazolidinyl, imidazolidinyl, tetrahydrofuryl, tetrahydrothienyl, tetrahydropyranyl, tetrahydrothiopyranyl, piperidinyl, morpholinyl, thiomorpholinyl, piperazinyl, 4,5,6,7-tetrahydrobenzofuryl, 1,2,3,4-tetrahydroisoquinolyl, phenyl, naphthyl, furyl, benzofuryl, pyrrolyl, pyridyl, pyrazolyl, imdazolyl, benzimdazolyl, triazolyl, tetrazolyl, oxazolyl, isoxazolyl, oxadiazolyl, 1,3,5-triazinyl, thiazolyl, thienyl, benzothienyl, pyrazinyl, pyridazinyl, pyrimidinyl, indolyl, purinyl, quinolyl, isoquinolyl, phenoxathiinyl and dibenzofuryl is independently unsubstituted or substituted with 1, 2, 3, 4 or 5 R';

$R^5$ is H, D, F, Cl, Br, CN, $NO_2$, methyl, ethyl, n-propyl or i-propyl;

or, $R^4$ and $R^5$, together with the carbon atoms to which they are attached, form benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline or isoquinoline, and wherein each of benzene, naphthalene, furan, benzofuran, pyrrole, pyridine, pyrazole, imidazole, benzimidazole, triazole, tetrazole, oxazole, oxadiazole, 1,3,5-triazine, thiazole, thiophene, benzothiophene, pyrazine, pyridazine, pyrimidine, indole, purine, quinoline and isoquinoline is independently unsubstituted or substituted with 1, 2, 3, 4 or 5 R'.

9. The compound of claim 1, wherein each of $R^1$, $R^2$ and $R^3$ is independently H, D, F, Cl, Br, CN, $NO_2$, —C(=O)$R^a$, —C(=O)O$R^b$, —C(=O)N$R^cR^d$, —O$R^b$, —N$R^cR^d$, methyl, ethyl, n-propyl or i-propyl; or, $R^1$ and $R^2$, together with the carbon atoms to which they are attached, form a $C_{5-6}$ carbocyclic ring, 5- to 6-membered heterocyclic ring, benzene ring or 5-to 6-membered heteroaromatic ring, and wherein each of methyl, ethyl, n-propyl i-propyl, $C_{5-6}$ carbocyclic ring, 5- to 6-membered heterocyclic ring, benzene ring and 5- to 6-membered heteroaromatic ring is independently unsubstituted or substituted with 1, 2, 3 or 4 substituents independently selected from D, F, Cl, Br, CN, —O$R^b$, —N$R^cR^d$ or $C_{1-3}$ haloalkyl.

10. The compound of claim 1, wherein each R' is independently D, F, Cl, Br, CN, $NO_2$, —O$R^b$, —N$R^cR^d$, —C(=O)$R^a$, —C(=O)O$R^b$, —C(=O)N$R^cR^d$, $C_{1-9}$ alkyl, $C_{1-3}$ haloalkyl, $C_{3-6}$ cycloalkyl, 5- to 6-membered heterocyclyl, phenyl, pheny-$C_{1-2}$ alkylene or 5- to 6-memberd heteroaryl; or two adjacent R', together with the carbon atoms to which they are attached, form a $C_{5-6}$ carbocyclic ring or benzene ring, and wherein each of $C_{1-9}$ alkyl, $C_{1-3}$ haloalkyl, $C_{3-6}$ cycloalkyl, 5- to 6-membered heterocyclyl, phenyl, pheny-$C_{1-2}$ alkylene, 5- to 6-memberd heteroaryl, $C_{5-6}$ carbocyclic ring and benzene ring is independently unsubstituted or substituted with 1, 2, 3 or 4 substituents independently selected from D, F, Cl, Br, CN, $NO_2$, —O$R^b$, —NR'$R^d$, methyl, ethyl, n-propyl or i-propyl.

11. The compound of claim 1, wherein each R' is independently D, F, Cl, Br, CN, $NO_2$, OH, —$OCH_3$, —$OCH_2CH_3$, —N$R^cR^d$, —C(=O)$R^a$, —C(=O)OH, —C(=O)O$CH_2CH_3$, —C(=O)O$CH_3$, —C(=O)$NH_2$, methyl, ethyl, n-propyl, i-propyl, n-butyl, i-butyl, t-butyl, trifluoromethyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, and wherein each of methyl, ethyl, n-propyl, i-propyl, n-butyl, i-butyl, t-butyl, difluoromethyl, monofluoromethyl, 2,2-difluoroethyl, 1,2-difluoroethyl, trifluoroethyl, 1-fluoroethyl, 2-fluoroethyl, cyclopropyl, cyclobutyl, cyclopentyl, cyclohexyl, pyrrolidyl, tetrahydrofuranyl, tetrahydrothienyl, tetrahydropyranyl, tetrahydrothiapyranyl, piperidyl, morpholinyl, thiomorpholinyl, piperazinyl, phenyl, furyl, pyrrolyl, pyridinyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with 1, 2, 3 or 4 substituents independently selected from D, F, Cl, Br, CN, $NO_2$, OH, —$NH_2$, methyl, ethyl, n-propyl or i-propyl.

12. The compound of claim 1, wherein $R^6$ is H, D, $CF_3$, methyl, ethyl, n-propyl or i-propyl.

13. The compound of claim 1, wherein W is $C_{1-6}$ alkyl, $C_{5-8}$ carbocyclyl or 5- to 8-membered heterocyclyl, and wherein each of $C_{1-6}$ alkyl, $C_{5-8}$ carbocyclyl and 5- to 8-membered heterocyclyl is independently unsubstituted or substituted with 1, 2, 3 or 4 $R^W$.

14. The compound of claim 1, wherein each $R^W$ is independently D, F, Cl, Br, CN, $NO_2$, —C(=O)$OCH_3$, —C(=O)O$CH_2CH_3$, —C(=O)OH, —C(=O)N$R^cR^d$, —NHC(=O)$R^a$, —NHC(=O)N$R^cR^d$, —S(=O)$_2R^f$, —S(=O)$_2$NHC(=O)$R^a$, —S(=O)$_2$N$R^cR^d$, $(R^bO)_2$P(=O)—$C_{0-2}$ alkylene, —O$R^b$, methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl or 5- to 6-membered heterocyclyl, and wherein each of methyl, ethyl, n-propyl, i-propyl, furyl, pyrrolyl, pyridyl, pyrazolyl, imdazolyl, triazolyl, tetrazolyl, oxazolyl, oxadiazolyl, 1,3,5-triazinyl, thiazolyl, thienyl, pyrazinyl, pyridazinyl, pyrimidyl and 5- to 6-membered heterocyclyl is independently unsubstituted or substituted with 1, 2, 3 or 4 substituentes independently selected from D, F, Cl, Br, CN, $N_3$, =O, $NO_2$, —$OCH_3$, $C_{1-3}$ alkyl or $C_{1-3}$ haloalkyl.

15. The compound of claim 1, wherein each $R^a$, $R^b$, $R^c$, $R^d$, $R^e$ and $R^f$ is independently H, D, hydroxy, trifluoromethyl, methyl, ethyl, i-propyl, n-propyl, n-butyl, t-butyl, methoxy, ethoxy, cyclopropyl, $C_{3-6}$ carbocyclyl, 5- to 6-membered heterocyclyl, phenyl, 5- to 6-membered heteroaryl or (5- to 6-membered heteroaryl)-$C_{1-4}$ alkylene, and wherein each of methyl, ethyl, i-propyl, n-propyl, n-butyl, t-butyl, methoxy, ethoxy, cyclopropyl, $C_{3-6}$ carbocyclyl, 5- to 6-membered heterocyclyl, phenyl, 5- to 6-membered heteroaryl and (5- to 6-membered heteroaryl)-$C_{1-4}$ alkylene is independently unsubstituted or substituted with 1, 2, 3 or 4 sustituents independently selected from D, F, Cl, CN, OH, $NH_2$, $C_{1-3}$ alkyl, $C_{1-3}$ haloalkyl or methoxy;

or, $R^C$ and $R^d$, together with the nitrogen atom to which they are attached, form 5- to 6-membered heterocyclyl or 5- to 6-membered heteroaryl, and wherein each of 5- to 6-membered heterocyclyl and 5- to 6-membered heteroaryl is independently unsubstituted or substituted with 1, 2, 3 or 4 sustituents independently selected from D, F, Cl, CN, OH, $NH_2$, $C_{1-3}$ alkyl, $C_{1-3}$ haloalkyl or methoxy.

16. The compound of claim 1, wherein W is one of the following sub-formulae:
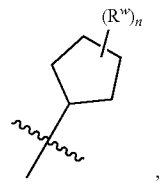
(W-1)
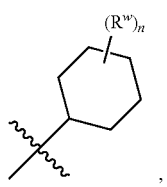
(W-2)
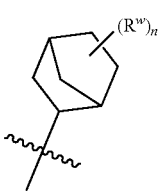
(W-3)
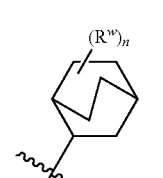
(W-4)
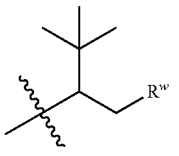
(W-5)
or
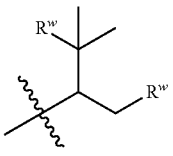
(W-6)
wherein n is 0, 1, 2, 3 or 4.
17. The compound of claim 1 having Formula (III), (IV), (V), (VI), (VII), (VIII), (IX) or (X),
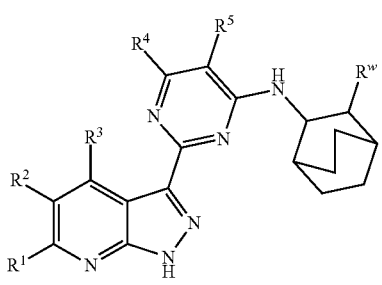
(III)
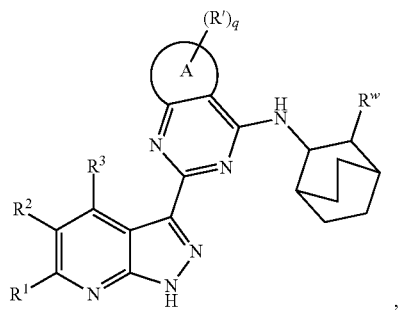
(IV)
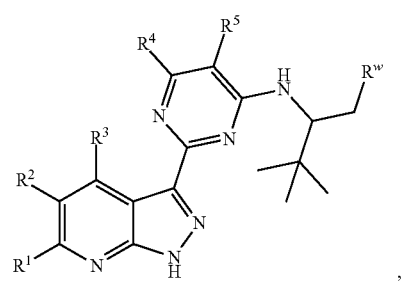
(V)
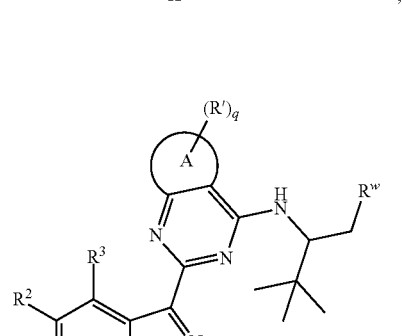
(VI)
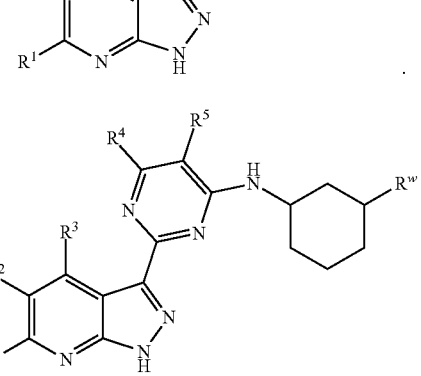
(VII)
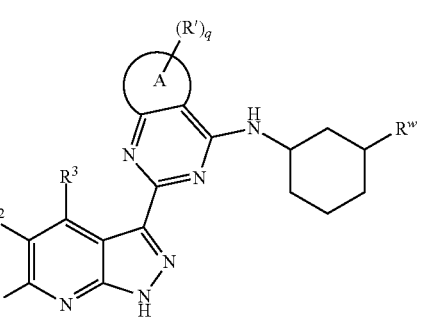
(VIII)

-continued
(IX)
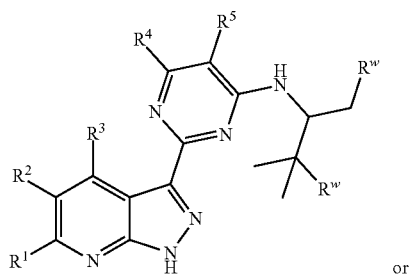
or
(X)
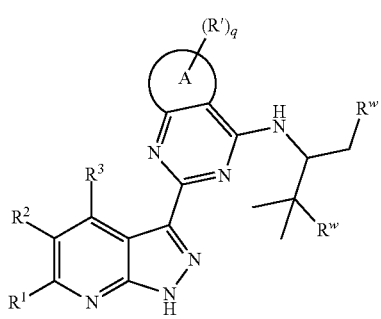
wherein A is a $C_{3-12}$ carbocyclic ring, 3- to 12-membered heterocyclic ring, $C_{6-10}$ aromatic ring or 5- to 10-memebered heteroaromatic ring; and
q is 0, 1, 2, 3, 4, or 5.
18. The compound of claim 1 having Formula (XI), (XII), (XIII) or (XIV),
(XI)
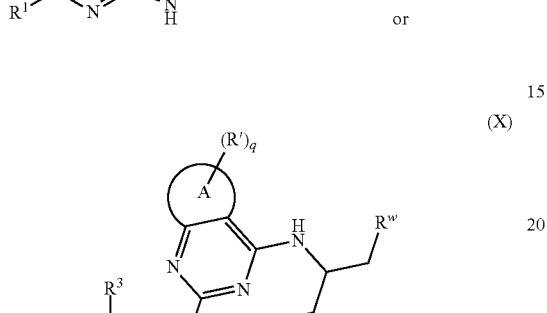
,
(XII)
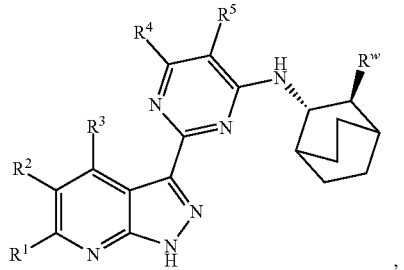
,
-continued
(XIII)
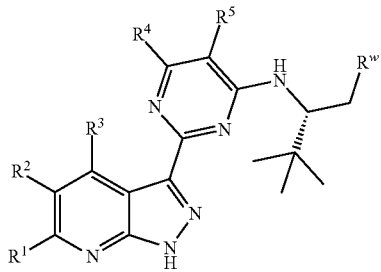
or
(XIV)
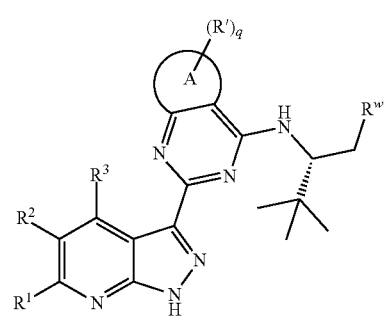
.
19. The compound of claim 1 having one of the following structures:
(1)
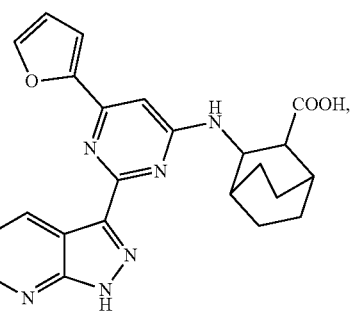
(2)
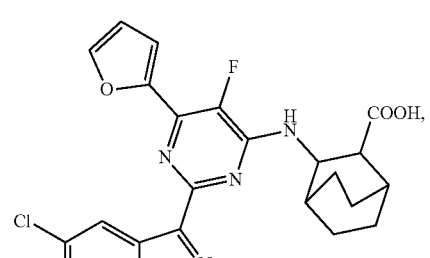
(3)
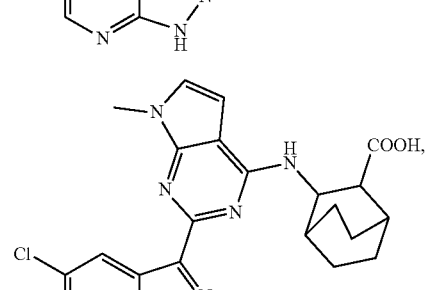

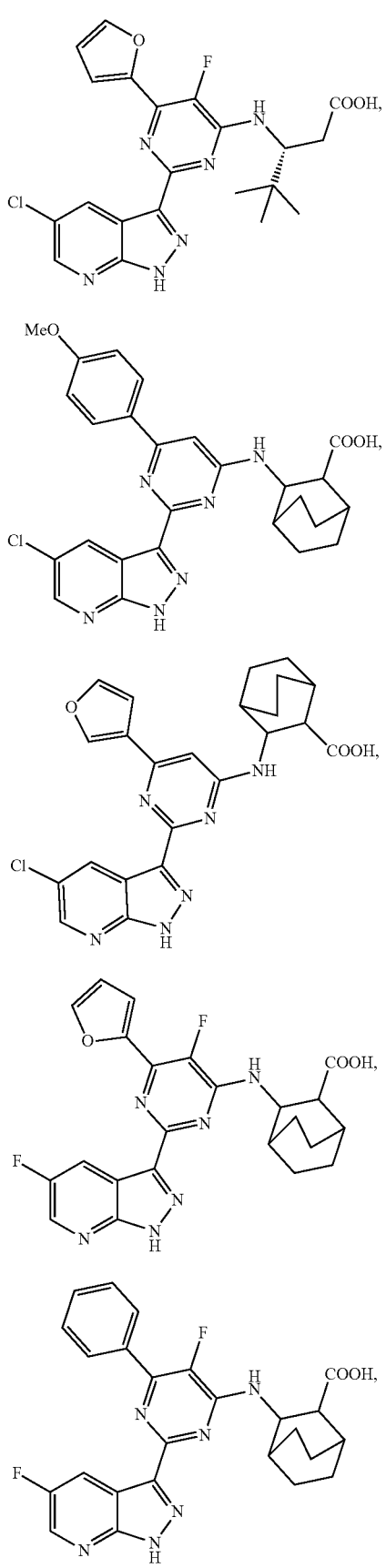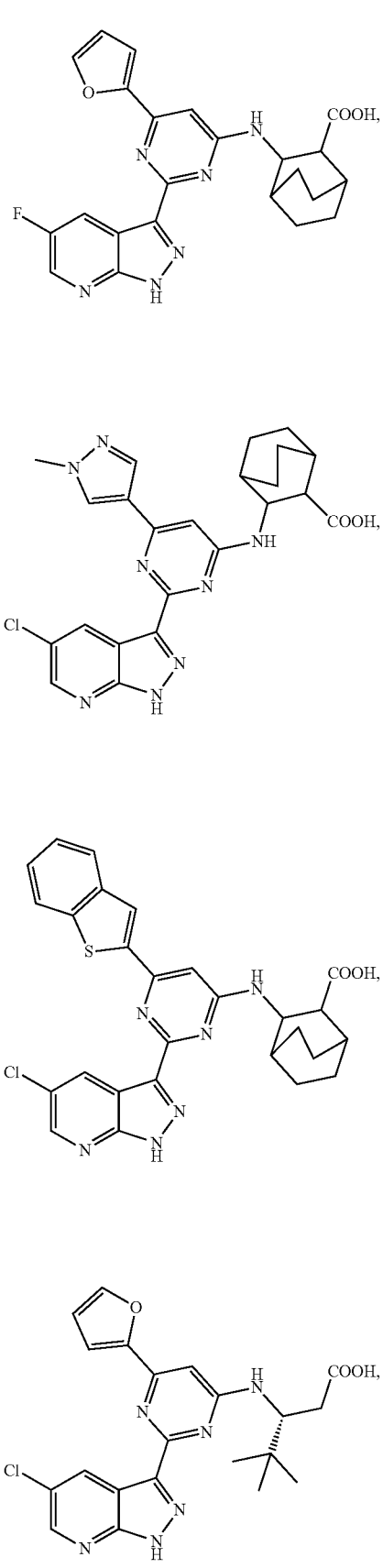

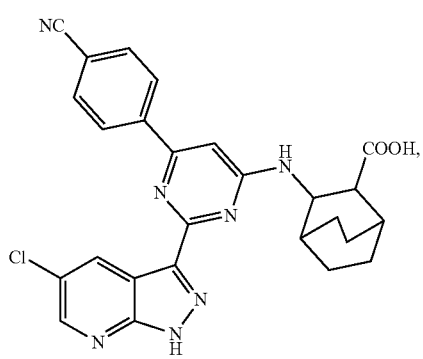
(13)
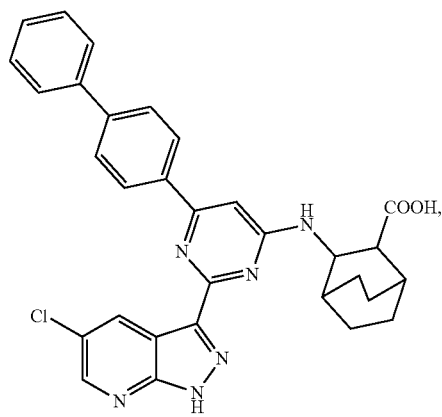
(17)
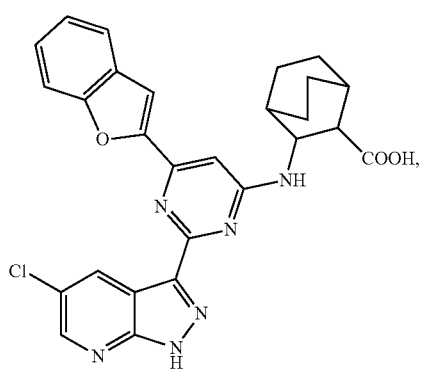
(14)
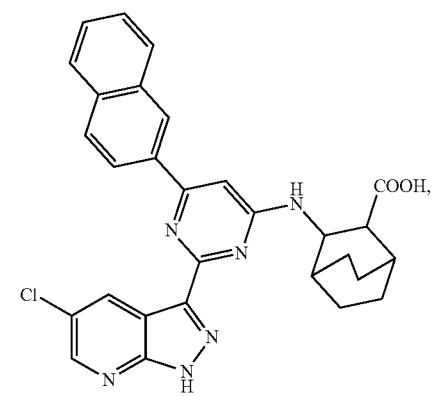
(18)
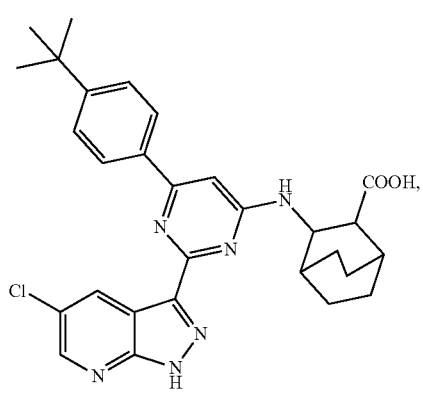
(15)
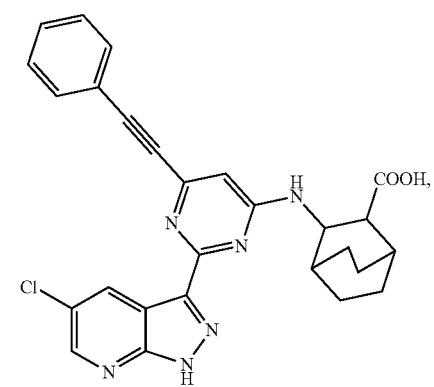
(19)
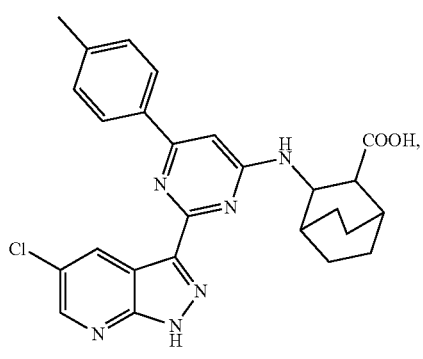
(16)
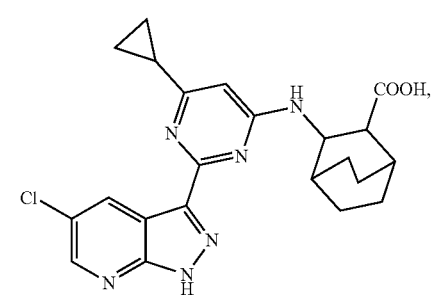
(20)

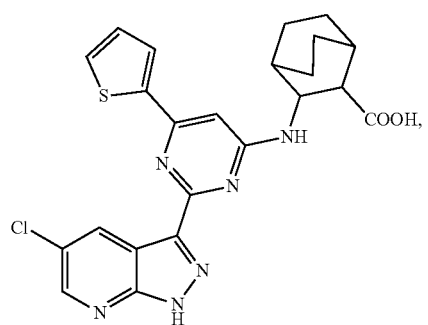
(21)
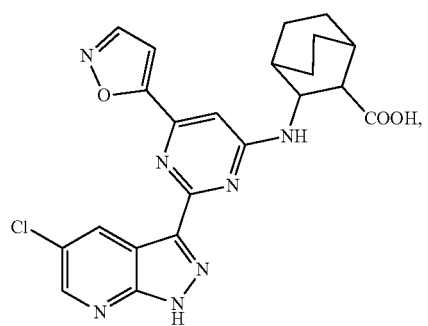
(22)
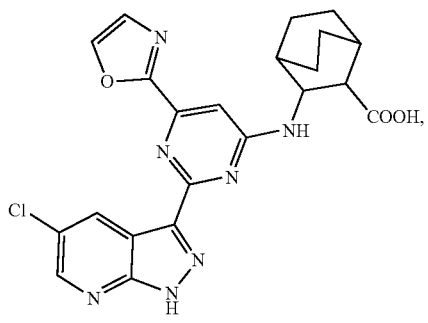
(23)
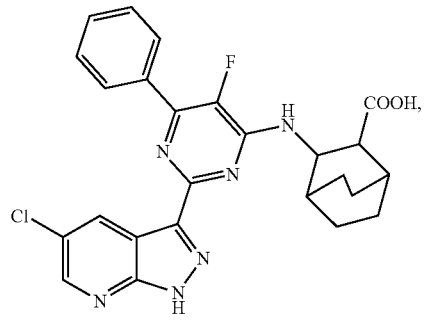
(24)
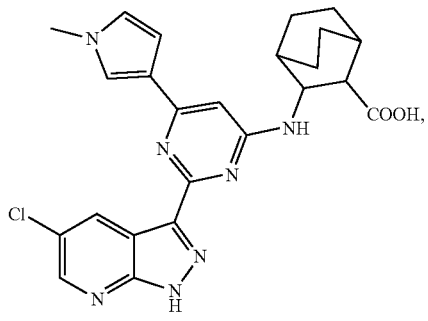
(25)
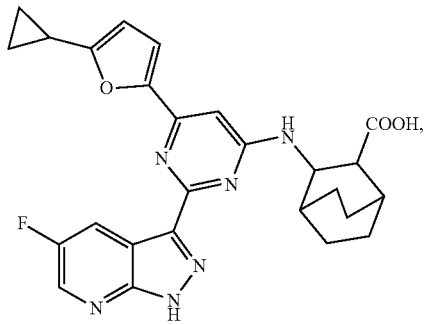
(26)
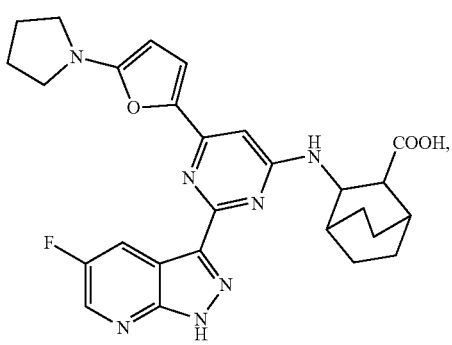
(27)
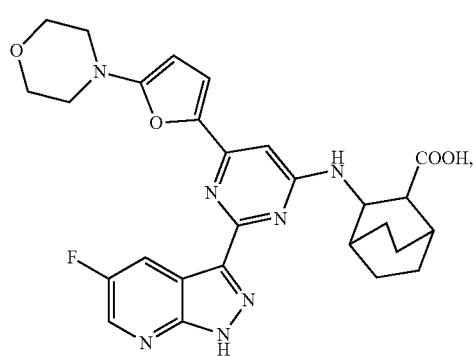
(28)
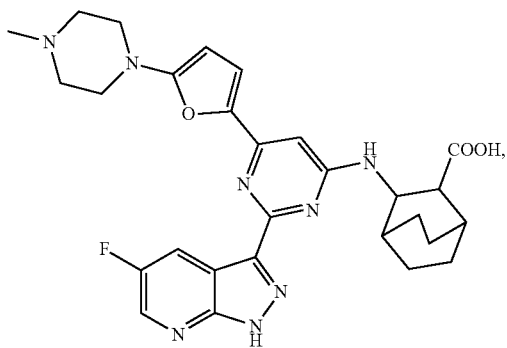
(29)

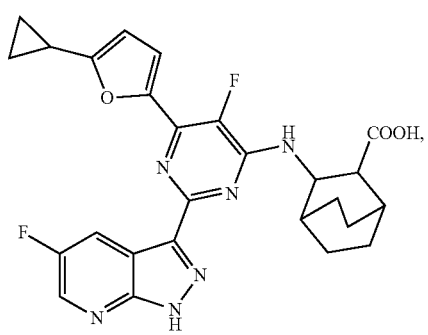
(30)
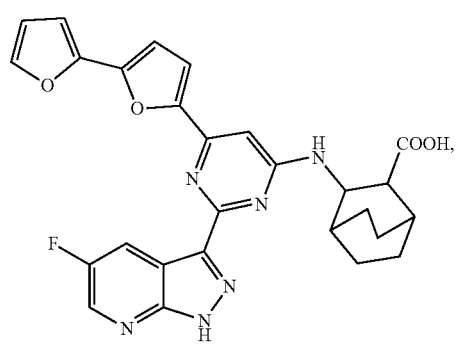
(31)
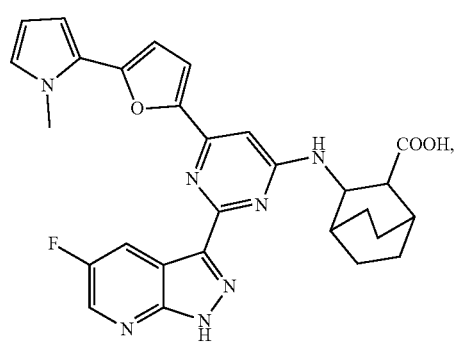
(32)
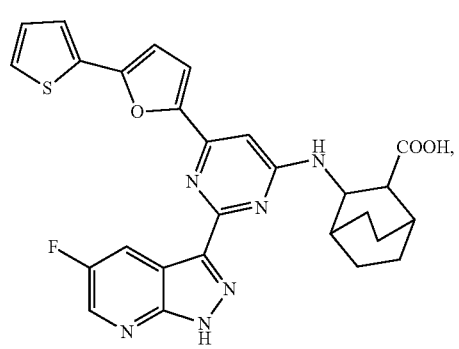
(33)
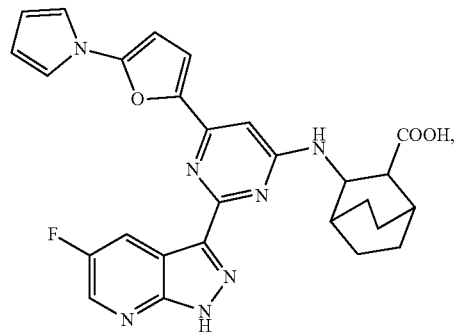
(34)
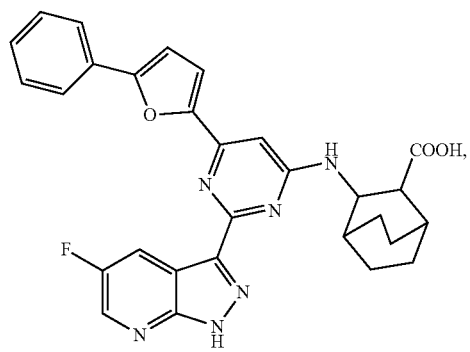
(35)
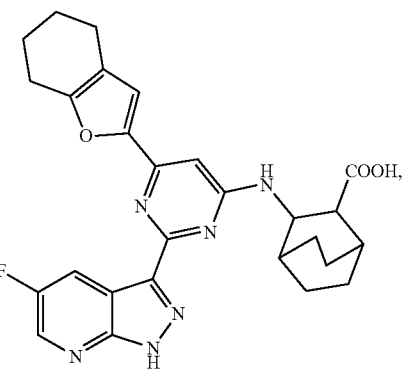
(36)
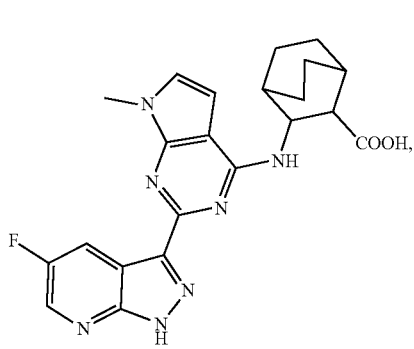
(37)

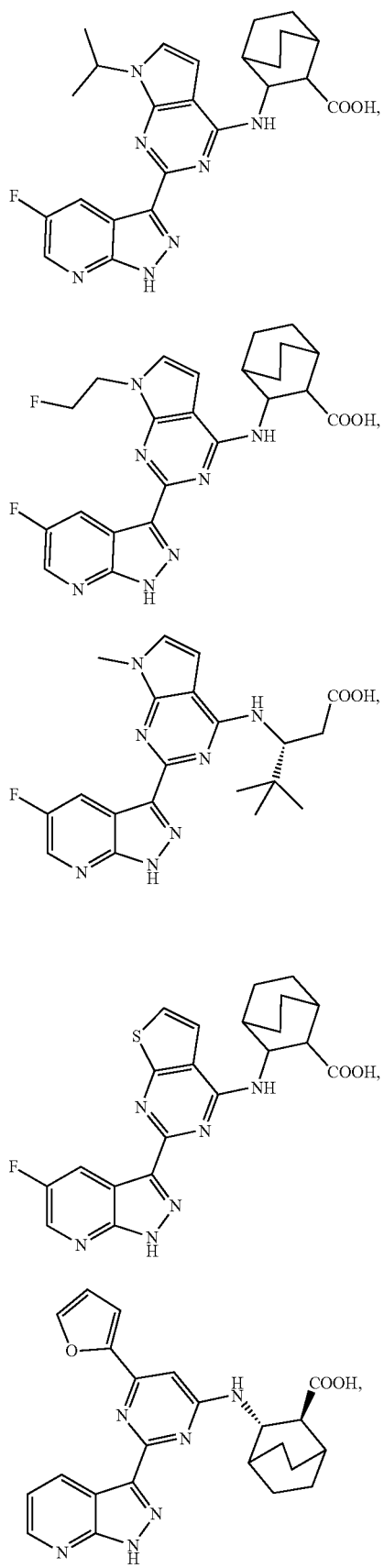
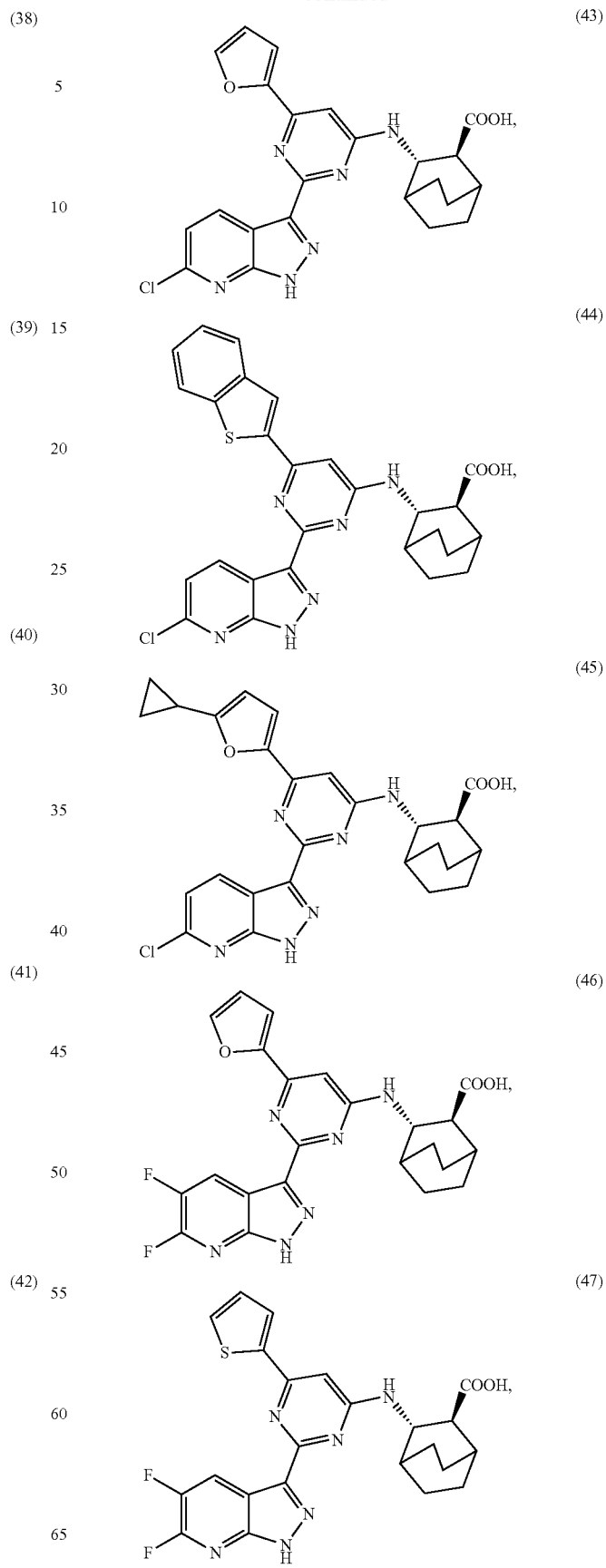

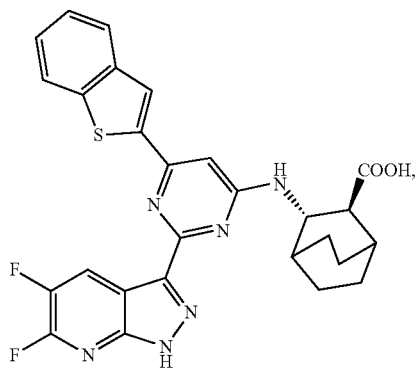
(48)
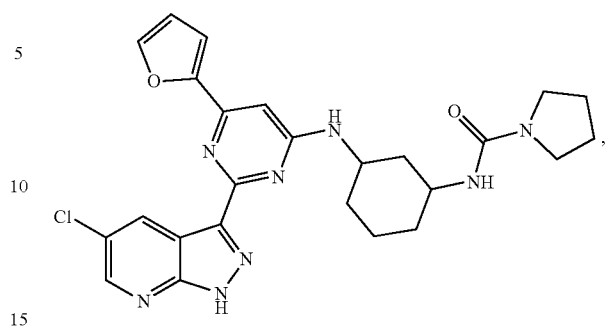
(52)
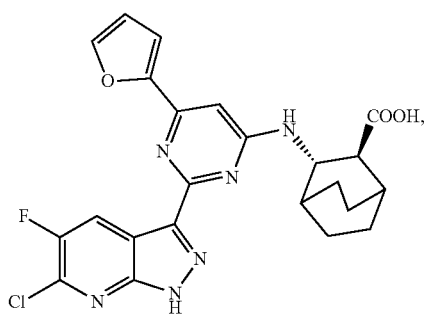
(49)
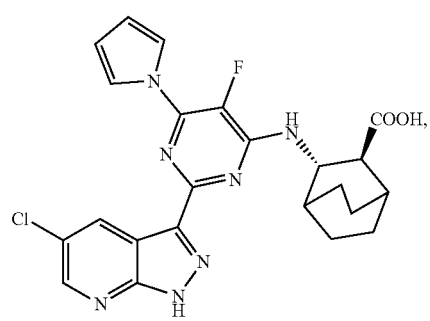
(53)
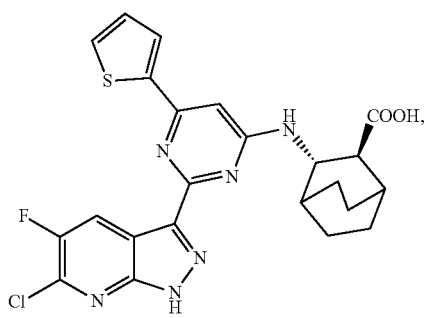
(50)
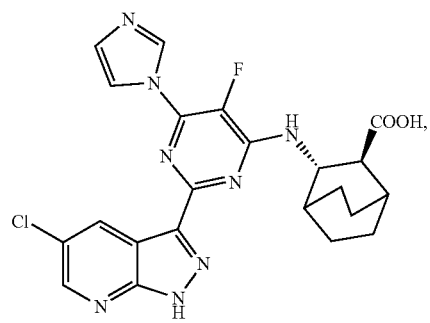
(54)
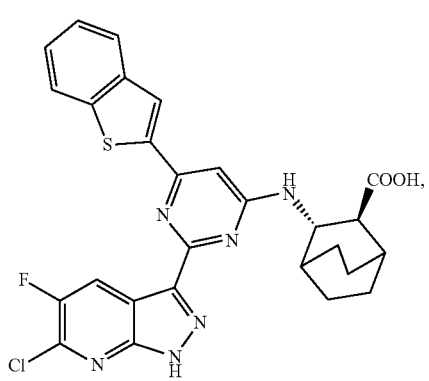
(51)
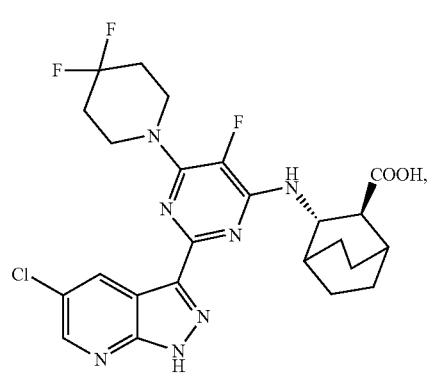
(55)

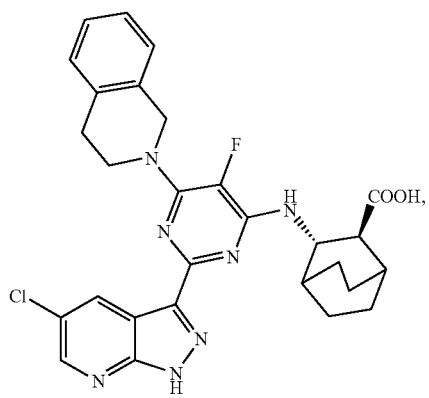
(56)
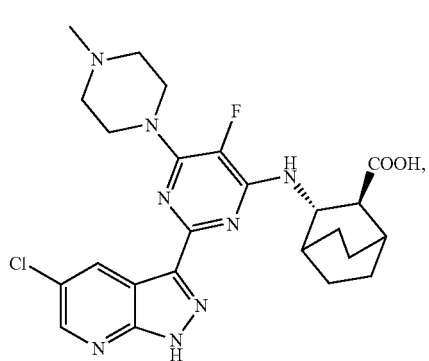
(57)
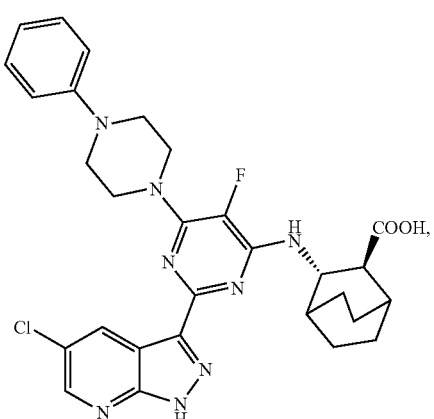
(58)
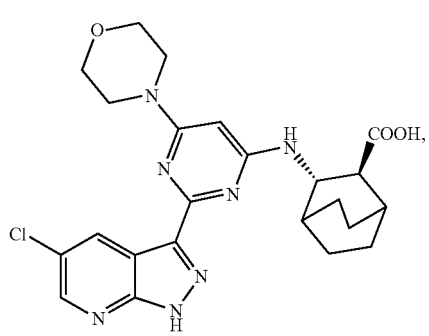
(59)
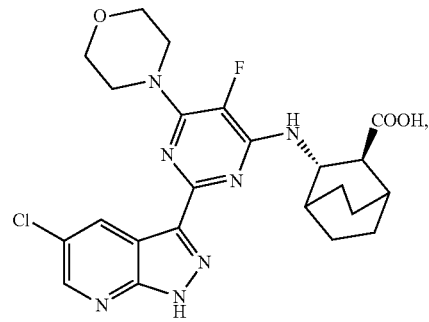
(60)
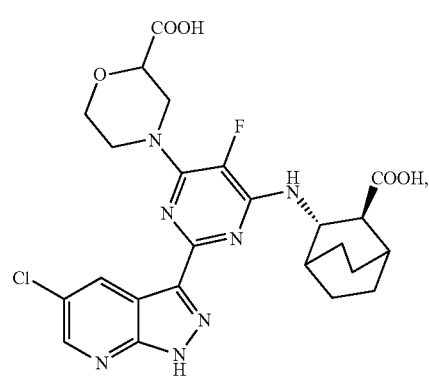
(61)
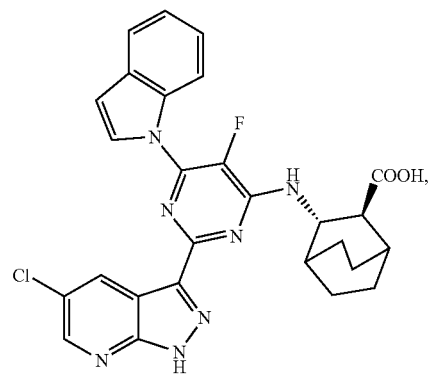
(64)
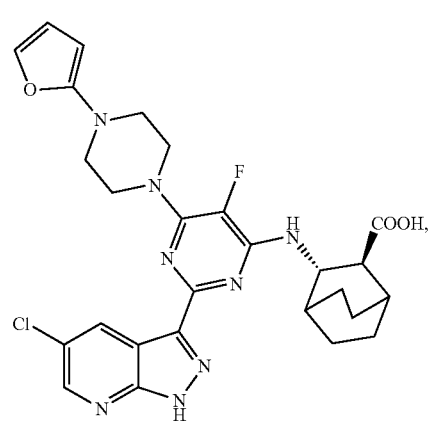
(66)

(67) 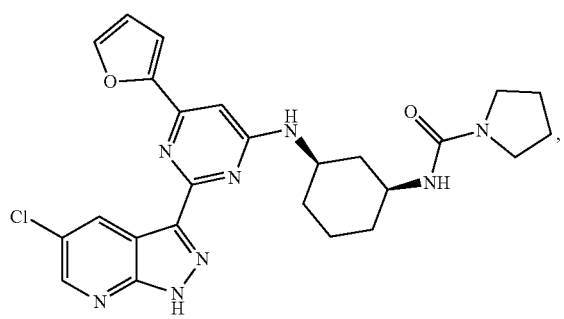
(68) 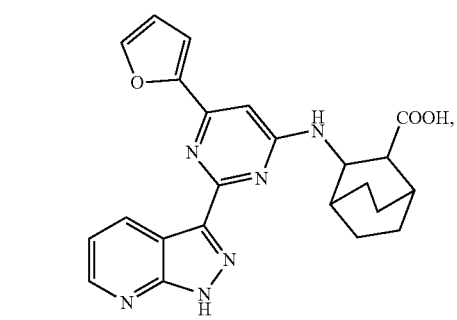
(69) 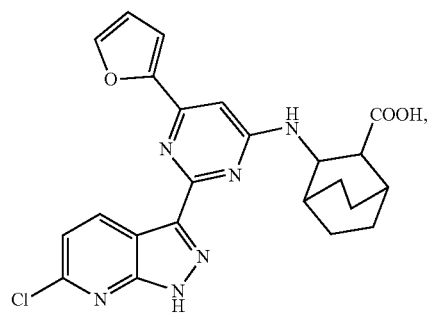
(70) 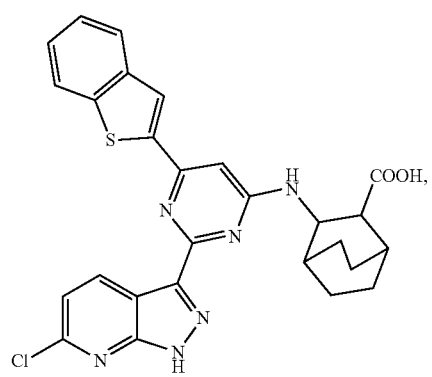
(71) 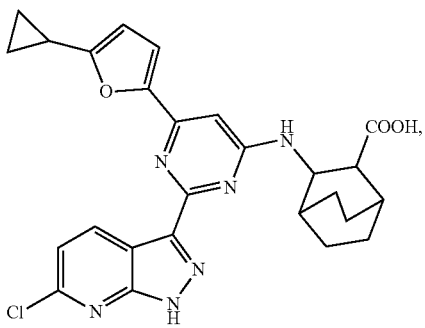
(72) 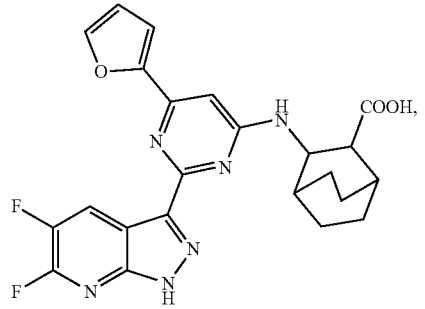
(73) 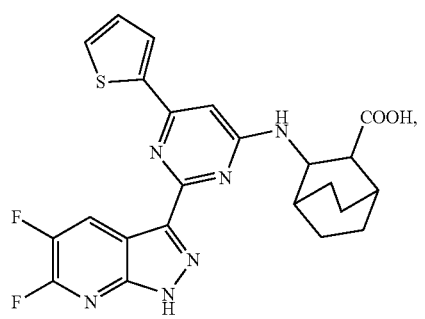
(74) 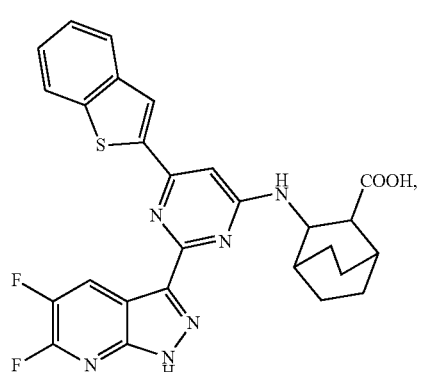
(75) 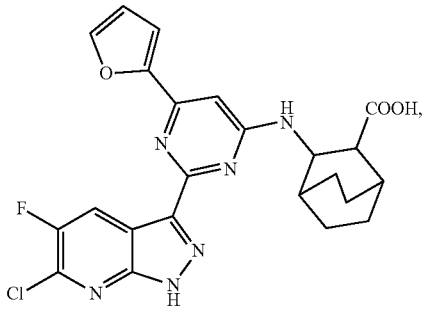

(76) 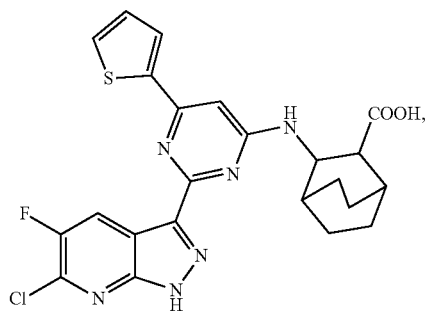
(77) 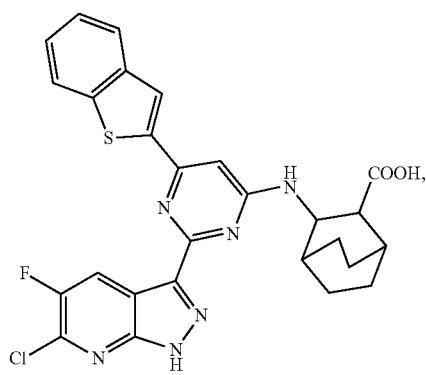
(78) 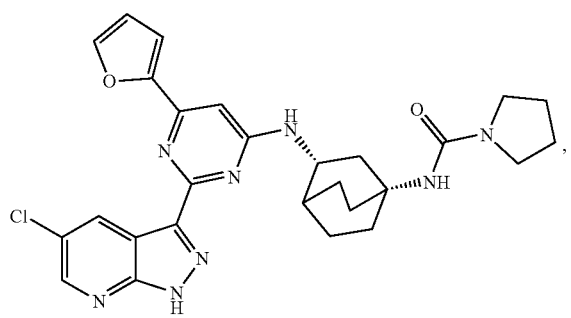
(79) 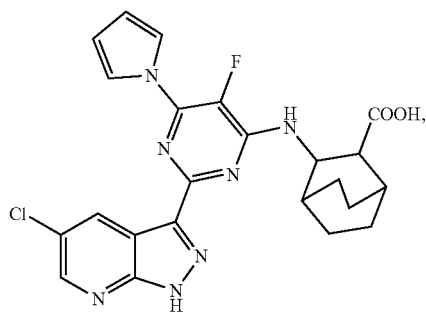
(80) 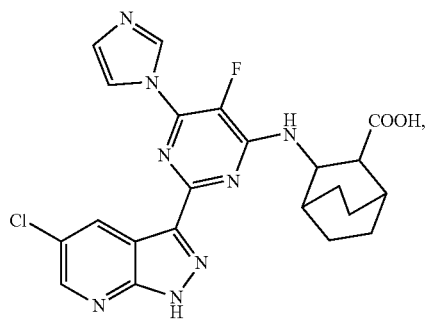
(81) 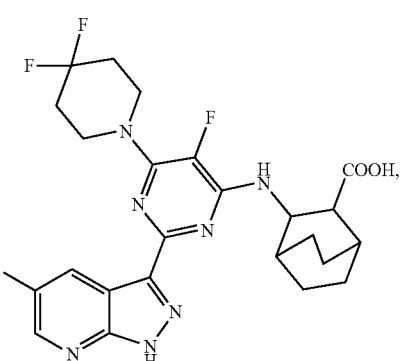
(82) 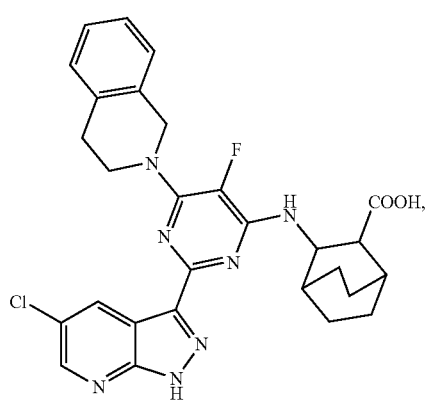
(83) 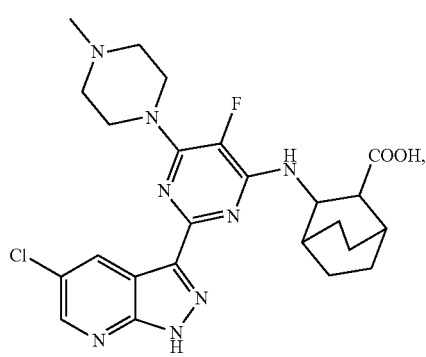

(84)
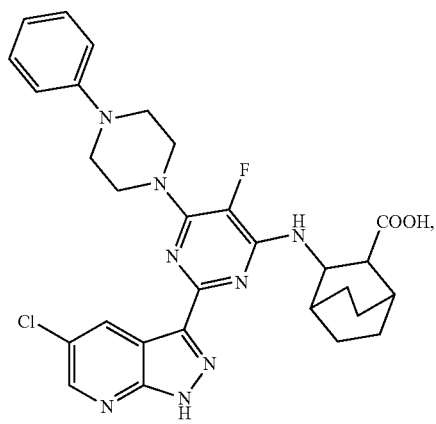
(85)
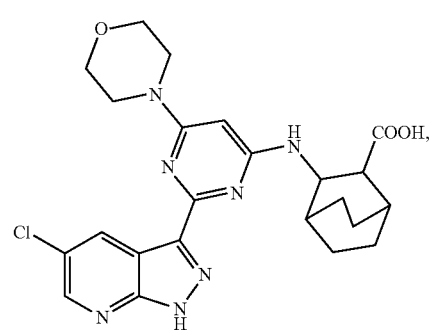
(86)
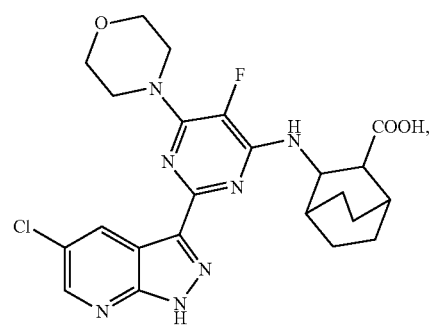
(87)
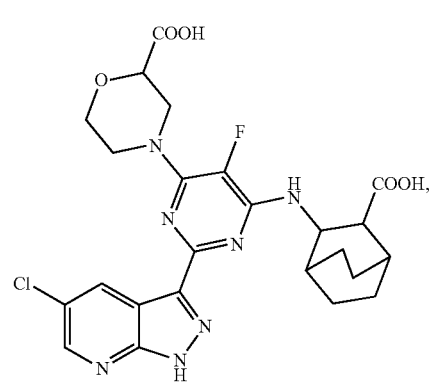
(90)
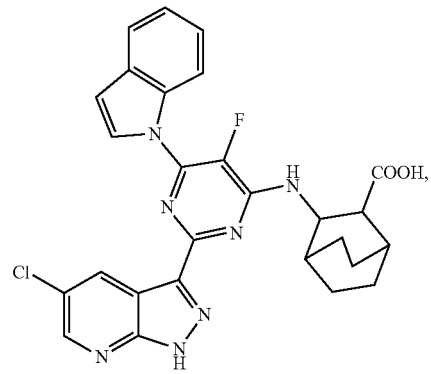
(92)
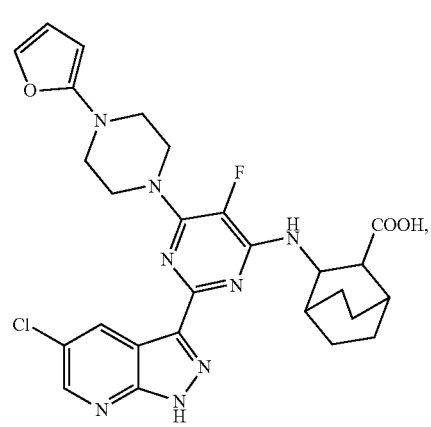
(93)
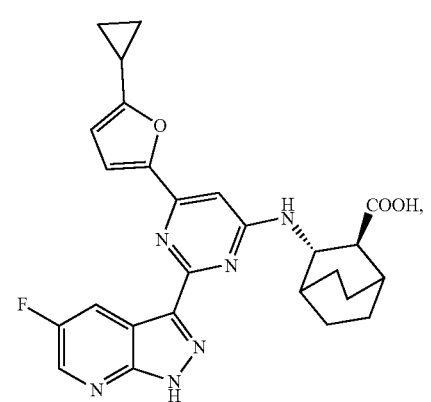
(94)
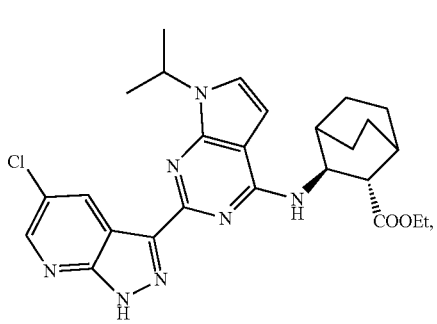

(95)
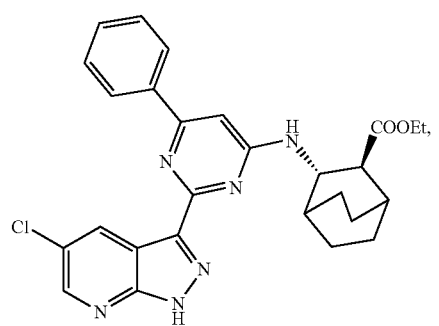
(96)
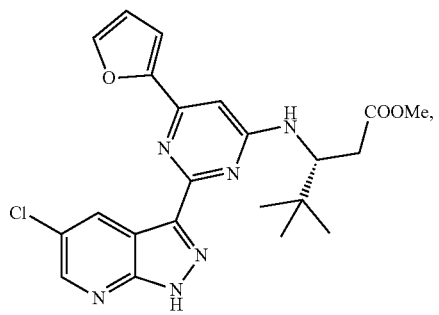
(97)
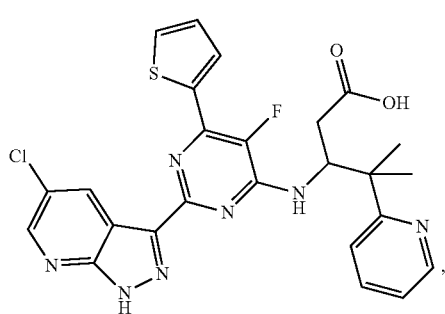
(98)
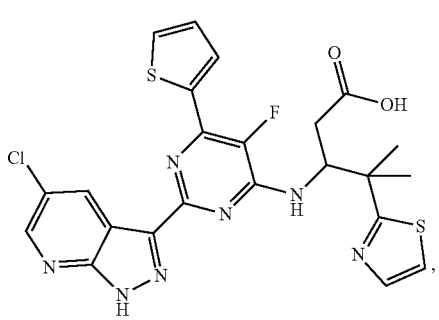
(99)
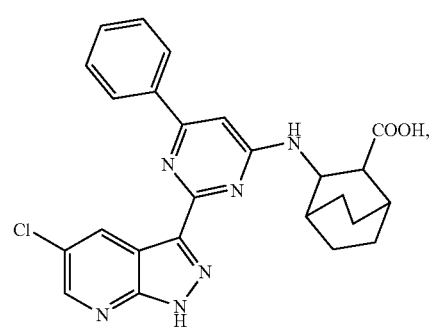
(100)
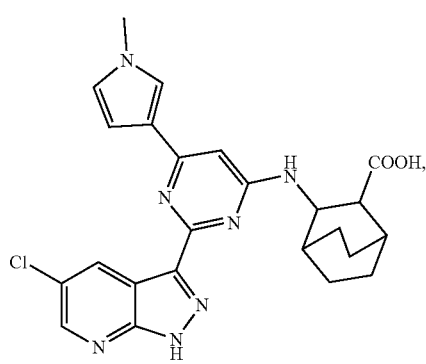
(101)
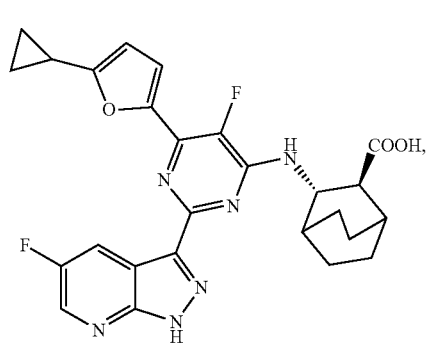
(102)
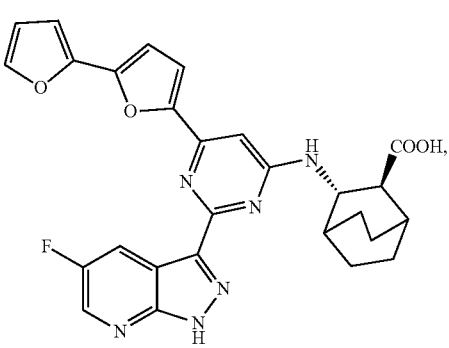
(103)

-continued

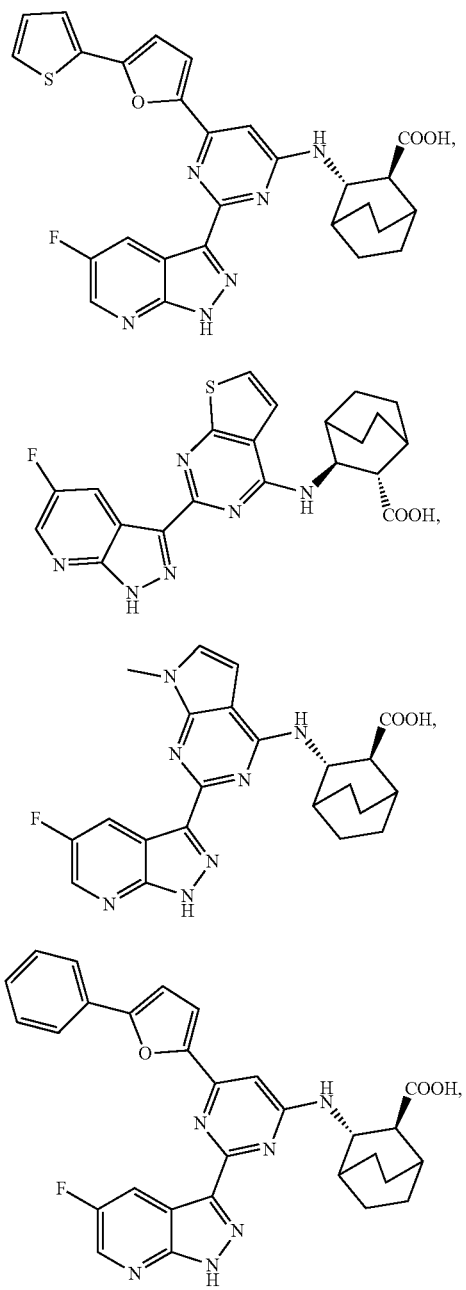

(104)

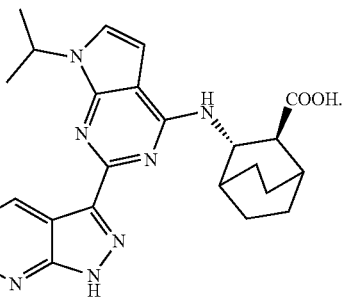

(105)

(106)

(107)

-continued (108)

or a stereoisomer, a tautomer, an N-oxide, or a pharmaceutically acceptable salt thereof.

20. A pharmaceutical composition comprising the compound of claim 1; optionally, further comprising a pharmaceutically acceptable carrier, excipient, vehicle or a combination thereof.

21. The pharmaceutical composition of claim 20 further comprising one or more other therapeutic agents, and wherein the other therapeutic agent is an anti-influenza virus agent or anti-influenza virus vaccine.

22. The pharmaceutical composition of claim 21, wherein the other therapeutic agent is amantadine, rimantadine, oseltamivir, zanamivir, peramivir, laninamivir, laninamivir octanoate hydrate, favipiravir, arbidol, ribavirin, stachyflin, ingavirin, fludase, CAS no.1422050-75-6, JNJ-872, S-033188, an influenza vaccine or a combination thereof.

23. A method of treating or lessening a disorder or disease caused by a virus infection in a subject, comprising administering to the subject a therapeutically effective amount of the compound of claim 1, wherein the virus infection is influenza virus infection.

24. A method of inhibiting virus in a subject, comprising administering to the subject a therapeutically effective amount of the compound of claim 1, wherein inhibiting virus is realized by inhibiting influenza virus RNA polymerase.

25. A method of treating or lessening a disorder or disease caused by a virus infection in a subject, comprising administering to the subject a therapeutically effective amount of the pharmaceutical composition of claim 20, wherein the virus infection is influenza virus infection.

26. A method of inhibiting virus in a subject, comprising administering to the subject a therapeutically effective amount of the pharmaceutical composition of claim 20, wherein inhibiting virus is realized by inhibiting influenza virus RNA polymerase.

* * * * *